US006319716B1

(12) United States Patent
Tikoo et al.

(10) Patent No.: US 6,319,716 B1
(45) Date of Patent: Nov. 20, 2001

(54) BOVINE ADENOVIRUS TYPE 3 GENOME AND VECTOR SYSTEMS DERIVED THEREFROM

(75) Inventors: Suresh Kumar Tikoo; Lorne A. Babiuk, both of Saskatoon (CA); Police Seshidhar Reddy, Gaithersburg, MD (US); Alexandre Zakhartchouk; Mohit Baxi, both of Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 09/103,330

(22) Filed: Jun. 23, 1998

Related U.S. Application Data

(63) Continuation-in-part of application No. 08/880,234, filed on Jun. 23, 1997, now abandoned.

(51) Int. Cl.$^7$ .......................... C12N 15/181; C12N 15/64
(52) U.S. Cl. .......................... 435/471; 435/472; 435/475; 435/235.1; 435/320.1; 435/477; 424/199.1; 424/93.2
(58) Field of Search .............................. 435/235.1, 91.41, 435/463, 465, 475.477, 320.1, 471, 472; 424/199.1, 93.2

(56) References Cited

U.S. PATENT DOCUMENTS

| 3,962,424 | 6/1976 | Zygraich et al. . |
| 4,510,245 | 4/1985 | Cousens et al. . |
| 4,920,209 | 4/1990 | Davis et al. . |
| 5,024,939 | 6/1991 | Gorman . |
| 5,151,267 | 9/1992 | Babiuk et al. . |
| 5,756,086 | 5/1998 | McClelland et al. . |
| 5,770,442 | 6/1998 | Wickham et al. . |
| 5,820,868 | 10/1998 | Mittal et al. . |
| 5,846,782 | 12/1998 | Wickham et al. . |
| 5,871,727 | 2/1999 | Curiel . |
| 5,922,576 | 7/1999 | He et al. . |

FOREIGN PATENT DOCUMENTS

| 717253 | 8/1996 | (AU) . |
| 2012895 | 9/1990 | (CA) . |
| 185573 | 6/1986 | (EP) . |
| 0259149 | 3/1988 | (EP) . |
| 389286 | 9/1990 | (EP) . |
| 2 642 767 | 8/1990 | (FR) . |
| 2 657 880 | 8/1991 | (FR) . |
| WO 86/06409 | 11/1986 | (WO) . |
| WO 91/11525 | 8/1991 | (WO) . |
| WO 95/16048 | 6/1995 | (WO) . |
| WO 96/22378 A1 | 7/1996 | (WO) . |
| WO 98/59063 A2 | 12/1998 | (WO) . |

OTHER PUBLICATIONS

Lee, J.B. et al., (1998) "Genetic organization and DNA sequence of early region 4 of bovine adenovirus type 3" *Virus Genes* 17:99–100.

Amalfitano, A. et al., (Apr. 1996) "Improved adenovirus packaging cell lines to support the growth of replication–defective gene–delivery vectors" *Proc. Natl. Acad. Sci., USA*, Genetics 93(8):3352–3356.

Fallaux, F.J. et al., (Jan. 20, 1996) "Characterization of 911: a new helper cell line for the titration and propagation of early region 1–deleted adenoviral vectors" *Human Gene Therapy*, 7:215–222.

Reddy, P.S. et al., (Nov., 1999) "Replication–defective bovine adenovirus type 3 as an expression vector" *J. Virol.*, 73(11):9137–9144.

Fitzgerald et al., *Gene* 185:181–186 (Feb. 24, 1997).

Krougliak et al., *Human Gene Therapy* 6:1575–1586 (Dec. 1995).

Mittal, S.K. et al. "Pathogenesis and immunogenicity of Bovine Adenovirus Type 3 in Cotton rats (*Sigmodon hispidus*)" *Virology* 213(1) 131–139 (Jan. 1995).

Mittal, S.K. et al "Pathology and immunogenicitiy in the cotton rat (*Sigmodon hispidus*) model after infection with a bovine adenovirus type 3 recombinant virus expressing the firefly luciferase gene" *Journal of General Virology* 77(Part 1):1–9 (Jan. 1, 1996).

Ojkic, D. et al. "Sequence analysis of the coding regions for the terminal protein precursor of bovine adenovirus serotypes 2 and 3" *Abstract of the 97th General Meeting of the American Society for Microbiology* 97(0):532 (May 4–8, 1997).

Ojkic, D. et al. "Sequence analysis of the terminal protein precursor coding regions from bovine adenovirus serotypes 2 and 3" *Intervirology* 40(4):253–262 (Jul.–Aug. 1997).

Yagubi, A. et al. "Sequence analysis of the regional encoding the DNA polymerase of bovine adenovirus serotypes 2 and 3" *Abstract of the 97th General Meeting of the American Society for Microbiology* 97(0):532 (May 4–8, 1997).

(List continued on next page.)

Primary Examiner—Mary E. Mosher
(74) *Attorney, Agent, or Firm*—Morrison & Foerster LLP

(57) ABSTRACT

The present invention provides the complete nucleotide sequence of a bovine adenovirus. The invention further provides bovine adenovirus vectors and expression systems which can be used, among other things, for insertion of foreign sequences, for provision of DNA control sequences including transcriptional and translational regulatory sequences, for diagnostic purposes to detect the presence of viral nucleic acids or proteins encoded by these regions in a subject or biological sample, for provision of immunogenic polypeptides or fragments thereof, for vaccines and for gene therapy. Cell lines comprising the vectors of the invention, and methods for making bovine adenovirus vectors are also provided.

35 Claims, 94 Drawing Sheets

OTHER PUBLICATIONS

Alley et al., "The mucosal immune system" In: B–lymphocytes in human diseases (G. Bird and J. E. Calvert, Eds.), Oxford University Press, Oxford, Chapter 9:222–254 (1988).

Andersson et al., "Impaired intracellular transport of class I MHC antigens as a possible means for adenoviruses to evade immune surveillance" *Cell 43:*215–222 (1985).

Baca–Estrada et al., "Immunogenicity of bovine herpesvirus 1 glycoprotein D in mice: Effect of antigen form on the induction of cellular and humoral immune responses" *Viral Immunol. 9*(1):11–22 (1996).

Barbeau et al., "Quantitative analysis of regions of adenovirus E1A products involved in interactions with cellular proteins" *Biochem. Cell Biol. 70:*1123–1134 (1992).

Bartha, "Proposal for subgrouping of bovine adenoviruses" *Acta. Vet. Acad. Sci. Hung. 19*(3):319–321 (1969).

Baxi et al., "Characterization of bovine adenovirus type 3 early region 2B" *Virus Genes 16*(3):313–316 (1998).

Belák et al., "Subtypes of bovine adenovirus type 2 exhibit major differences in region E3" *Virol. 153:*262–271 (1986).

Bellett et al., "Functions of the two adenovirus early E1A proteins and their conserved domains in cell cycle alteration, actin reorganization, and gene activation in rat cells" *Virol. 63*(1):303–310 (1989).

Benkö et al., "Molecular cloning and physical mapping of the DNA of bovine adenovirus serotype 4; study of the DNA homology among bovine, and porcine adenoviruses" *J. Gen. Virol. 71:*465–469 (1990).

Berg, "Potential metal–binding domains in nucleic acid binding proteins" *Science 232:*485–487 (1986).

Berk et al., "Pre–early adenovirus 5 gene product regulates synthesis of early viral messenger RNAs" *Cell 17:*935–944 (1979).

Berk et al., "Structure of the adenovirus 2 early mRNAs" *Cell 14:*695–711 (1978).

Berk, "Adenovirus promotors and E1A transactivation" *Ann. Rev. Genet. 20:*45–79 (1986).

Berkner et al., "Expression of dihydrofolate reductase, and of the adjacent E1b region, in an Ad5–dihydrofolate reductase recombinant virus" *Nucl. Acids Res. 12*(4):1925–1941 (1984).

Berkner, "Development of adenovirus vectors for the expression of heterologous genes" *Biotechniques 6:*616–629 (1989).

Bett et al., "Packaging capacity and stability of human adenovirus type 5 vectors" *Virol. 67*(10):5911–5921 (1993).

Birnboim et al., "A rapid extraction procedure for screening recombinant plasmid DNA" *Nucl. Acids Res. 7*(6):1513–1523 (1978).

Boshart et al., "A very strong enhancer is located upstream of an immediate early gene of human cytomegalovirus" *Cell 41:*521–530 (1985).

Bostock, "Viruses as vectors" *Vet. Microbiol. 23:*55–71 (1990).

Boyle et al., "How do other poxviruses fit in as potential vectored vaccine substrates for animal immunizations?" *Res. Virol. 140:*483–491 (1989).

Boyle et al., "Recombinant fowlpox virus vaccines for poultry" *Immunol. Cell Biol. 71:*391–397 (1993).

Boyle et al., "Vectors for recombinant vaccine delivery" *Animal Parasite Control Utilizing Biotechnology*, ed. W. K. Yong CRC Press, Boca Raton, FL, pp. 25–47 (1992).

Branton et al., "Transformation by human adenoviruses" *Biochim. Biophys. Acta 780:*67–94 (1985).

Brennan et al., "Embryonic transcriptional activation of a Xenopus cytoskeletal actin gene does not require a serum response element" *Roux's Arch. Dev. Biol. 199:*89–96 (1990).

Bruder et al., "Nuclear factor EF–1A binds to the adenovirus E1A core enhancer element and to other transcriptional control regions" *Mol. Cell Biol. 9*(11):5143–5153 (1989).

Buge et al., "An adenovirus–simian immunodeficiency virus env vaccine elicits humoral, cellular, and mucosal immune responses in rhesus macaques and decreases viral burden following vaginal challenge" *J. Virol. 71*(11):8531–8541 (1997).

Burget et al., "An adenovirus type 2 glycoprotein blocks cell surface expression of human histocompatibility class I antigens" *Cell 41:*987–997 (1985).

Burget et al., "The E3/19K protein of adenovirus type 2 binds to the domains of histocompatibility antigens for CTL recognition" *EMBO J. 6*(7):2019–2026 (1987).

Cai et al., "Nucleotide and deduced amino acid sequence of the bovine adenovirus type 3 proteinase" *Nucl. Acids Res. 18:*5568 (1990).

Carlin et al., "Epidermal growth factor receptor is down–regulated by a 10,400 MW protein encoded by the E3 region of adenovirus" *Cell 57:*135–144 (1989).

Chanda et al., "High level expression of the envelope glycoproteins of the human immunodeficiency virus type 1 in presence of rev gene using helper–independent adenovirus type 7 recombinants" *Virol. 175:*535–547 (1990).

Chartier et al., "Efficient generation of recombinant adenovirus vectors by homologous recombination in *Escherichia coli*" *J. Virol. 70*(7):4805–4610 (1996).

Chroboczek et al., "The sequence of adenovirus fiber: Similarities and differences between serotypes 2 and 5" *Virol. 161:*549–554 (1987).

Chu et al., "Electroporation for the efficient transfection of mammalian cells with DNA" *Nucl. Acids Res. 15*(3):1311–1326 (1987).

Cladaras et al., "DNA sequence of the early E3 transcription unit of adenovirus 5" *Virol. 140:*28–43 (1985).

Conley et al., "Intravascular and mucosal immunoglobin A: Two separate but related systems of immune defense?" *Ann. Intern. Med. 106:*892–899 (1987).

Culp et al., "The 289–amino acid E1A protein of adenovirus binds zinc in a region that is important for trans–activation" *Proc. Natl. Acad. Sci. USA 85:*6450–6454 (1988).

Darbyshire et al., "A new adenovirus serotype of bovine origin" *J. Comp. Pathol. 75:*327–330 (1965).

Darbyshire et al., "The pathogenesis and pathology of infection in calves with a strain of bovine adenovirus type 3" *Res. Vet. Sci. 7:*81–93 (1966).

Darbyshire, "Oncogenicity of bovine adenovirus type 3 in hamsters" *Nature 211:*102 (1966).

Degryse, "In vivo intermolecular recombination in *Escherichia coli:* Application to plasmid constructions" *Gene 170:*45–50 (1996).

Dewar et al., "Synthesis and processing of human immunodeficiency virus type 1 envelope proteins encoded by a recombinant human adenovirus" *Virol. 63*(1):129–136 (1989).

De Wet et al., "Firefly luciferase gene: Structure and expression in mammalian cells" *Mol. Cell Biol. 7*(2):725–737 (1987).

Doronin et al., "Expression of the gene encoding secreted placental alkaline phosphatase (SEAP0 by a nondefective adenovirus vector" *Gene* 126:247–250 (1993).

Graham et al., "Adenovirus–based expression vectors and recombinant vaccines" In: Vaccines: New approaches to immunological problems, (R.W. Ellis ed.), Butterworth–Heineman, Stoneham, Chapter 16:363–390 (1992).

Green et al., "Evidence for a repeating cross–β sheet structure in the adenovirus fibre" *EMBO J.* 2(8):1357–1365 (1983).

Grunhaus et al., "Adenoviruses as cloning vectors" *Sem. in Virol.* 3:237–252 (1992).

Gunning et al., "A human β–actin expression vector system directs high–level accumulation of antisense transcripts" *Proc. Natl. Acad. Sci. USA* 84:4831–4835 (1987).

Haj–Ahmed et al., "Development of a helper–independent human adenovirus vector and its use in the transfer of the herpes simplex virus thymidine kinase gene" *Virol.* 57:267–274 (1986).

Harlow et al., "Association of adenovirus early–region 1A proteins with cellular polypeptides" *Mol. Cell Biol.* 6(5):1579–1589 (1986).

Hearing et al., "The adenovirus type 5 E1A enhancer contains two functionally distinct domains: One is specific for E1A and the other modulates all early units in cis" *Cell* 45:229–236 (*1986*).

Hérissé et al., "Nucleotide sequence of the EcoR1 D fragment of adenovirus 2 genome" *Nucl. Acids Res.* 8(10):2173–2192 (1980).

Hérissé et al., "Nucleotide sequence of the EcoR1 E fragment of adenovirus 2 genome" *Nucl. Acids Res.* 9(5):1229–1249 (1981).

Hirt, "Selective extraction of polyoma DNA from infected mouse cell cultures" *J. Mol. Biol.* 26:365–369 (1967).

Hong et al., "Characterization of the early region 3 and fiber genes of Ad7" *Virol.* 167:545–553 (1988).

Horton et al., "A protein serologically and functionally related to the group C E3 14,700–kilodalton protein if found in multiple adenovirus serotypes" *Virol.* 64(3):1250–1255 (1990).

Howe et al., "Retinoblastoma growth suppressor and a 300–kDa protein appear to regulate cellular DNA synthesis" *Proc. Natl. Acad. Sci. USA* 87:5883–5887 (1990).

Chanda et al., "High level expression of the envelope glycoproteins of the human immunodeficiency virus type 1 in presence of rev gene using helper–independent adenovirus type 7 recombinants" *Virol.* 175:535–547 (1990).

Chartier et al., "Efficient generation of recombinant adenovirus vectors by homologous recombination in *Escherichia coli*" *J. Virol.* 70(7):4805–4610 (1996).

Chroboczek et al., "The sequence of adenovirus fiber: Similarities and differences between serotypes 2 and 5" *Virol.* 161:549–554 (1987).

Chu et al., "Electroporation for the efficient transfection of mammalian cells with DNA" *Nucl. Acids Res.* 15(3):1311–1326 (1987).

Cladaras et al., "DNA sequence of the early E3 transcription unit of adenovirus 5" *Virol.* 140:28–43 (1985).

Conley et al., "Intravascular and mucosal immunoglobin A: Two separate but related systems of immune defense?" *Ann. Intern. Med.* 106:892–899 (1987).

Howe et al., "Effects of Ad5 E1A mutant viruses on the cell cycle in relation to the binding of cellular proteins including the retinoblastoma protein and cyclin A" *Virol.* 186:15–24 (1992).

Hu et al., "Restriction analysis and homology studies of the bovine adenovirus 7 genome" *Virol.* 51:880–883 (1984).

Hu et al., "Sequence homology between bovine and human adenoviruses" *Virol.* 49:604–608 (1984).

Hughes et al., "Functional and topographical analyses of epitopes on bovine herpesvirus type 1 glycoprotein IV" *Arch. Virol.* 103:47–60 (1988).

Idamakanti, "Molecular characterization of early region–3 of bovine adenovirus–3" M. Sci. Thesis, University of Saskatchewan, Saskatoon, Saskatchewan, p. ii–93 (1998).

Mattson et al., "Bovine adenovirus type–3 infection in feedlot calves" *J. Vet. Res.* 49(1):67–69 (1988).

McDermott et al., "Protection of mice against lethal challenge with herpes simplex virus by vaccination with an adenovirus vector expressing HSV glycoprotein B" *Virol.* 169:244–247 (1989).

McKnight et al., "Transcriptional control signals of a eukaryotic protein–coding gene" *Science* 217:316–322 (1982).

McLorie et al., "Individual adenovirus E1B proteins induce transformation independently but by additive pathways" *J. Gen. Virol.* 72:1467–1471 (1991).

Mittal et al., "Sequence analysis of bovine adenovirus type 3 early region 3 and fibre protein genes" *J. Gen. Virol.* 73:3295–3300 (1992).

Mittal et al., "Sequence analysis of bovine adenovirus type 3 early region 3 and fibre protein genes" *J. Gen. Virol.* 74:2825 (Corrections of Mittal, *J. Gen. Virol.* 73 1992) (1992).

Mittal et al., "Monitoring foreign gene expression by a human adenovirus–based vector using the firefly luciferase gene as a receptor" *Virus Res.* 28:67–90 (1993).

Mittal et al., "Development of a bovine adenovirus type 3–based expression vector" *J. Gen. Virol.* 76:93–102 (1995).

Mittal et al., "Induction of systemic and mucosal immune responses in cotton rats immunized with human adenovirus type 5 recombinants expressing the full truncated forms of bovine herpesvirus type 1 glycoprotein gD" *Virology* 222:299–309 (1996).

Morin et al., "Recombinant adenovirus induces antibody response to hepatitis B virus surface antigen in hamsters" *Proc. Natl. Acad. Sci. USA* 84:4626–4630 (1987).

Moss, "Recombinant DNA virus vectors for vaccination" *Semin. Immunol.* 2:317–327 (1990).

Motoi et al., "Neoplastic transformation of hamster cells in vitro by bovine adenovirus type–3" *Gann* 63:415–418 (1972).

Murphy, "Mucosal immunity to viruses" In: Handbook of mucosal immunity (P.L. Ogra, J. Mestecky, M.E. Lamm, W. Strober, J.R. McGhee and J. Bienstock ed.), Academic Press, San Diego, Chapter 29:333–339 (1994).

Nevins, "Induction of the synthesis of a 70,000 dalton mammalian heat shock protein by the adenovirus E1A gene product" *Cell* 29:913–919 (1982).

Nevins, "Mechanism of activation of early viral transcription by the adenovirus E1A gene product" *Cell* 26:213–220 (1981).

Niiyama et al., "Biochemical studies on bovine adenovirus type 3" *Virol.* 16(3):621–633 (1975).

Orkin et al., "Report and recommendations of the panel to assess the NIH investment in research on gene therapy (1995)" http://www.nih.gov/news/panelrep.html:1–31 (1999).

Papp et al., "Mucosal immunization with recombinant adenoviruses: induction of immunity and protection of cotton rats against respiratory bovine herpesvirus type 1 infection" *J. Gen. Virol.* 78:2933–2943 (1997).

Philipson, "Structure and assembly of adenoviruses" *Curr. Top. Microbiol. & Immunol.* 109:1–52 (1983).

Prevec et al., "A recombinant human adenovirus vaccine against rabies" *J. Inf. Dis.* 161:27–30 (1990).

Prevec et al., "Use of human adenovirus–based vectors for antigen expression in animals" *J. Gen. Virol.* 70:429–434 (1989).

Ragot et al., "Efficient adenovirus–mediated transfer of a human minidystrophin gene to skeletal muscle of mdx mice" *Nature* 361:647–650 (1993).

Raviprakash et al., "The mouse adenovirus type 1 contains an unusual E3 region" *Virol.* 63(12):5455–5458 (1989).

Reddy et al., "Nucleotide sequence, genome organization, and transcription map of bovine adenovirus type 3" *Virol* 72(2):1394–1402 (1998).

Rosenfeld et al., "Adenovirus–mediated transfer of a recombinant α1–antitrypsin gene to the lung epithelium in vivo" *Science* 252:431–434 (1991).

Rosenfeld et al., "In vivo transfer of the human cystic fibrosis transmembrane conductance regulator gene to the airway epithelium" *Cell* 68:141–155 (1992).

Rouse et al., "Host response to infectious bovine rhinotracheitis virus" *J. Immunol.* 113(5):1391–1398 (1974).

Sanger et al., "DNA sequencing with chain–terminating inhibitors" *Proc. Natl. Acad. Sci. USA* 74(12):5463–5467 (1977).

Schneider et al., "Expression of the glycoprotein of vesicular stomatitis virus by infectious adenovirus vectors" *J. Gen. Virol.* 70:417–427 (1989).

Shinagawa et al., "Phylogenetic relationships between adenoviruses as inferred from nucleotide sequences of inverted terminal repeats" *Gene* 55:85–93 (1987).

Signas et al., "Adenovirus 3 fiber polypeptide gene: Implications for the structure of the fiber protein" *Virol.* 53(2):672–678 (1985).

Signas et al., "Region E3 of human adenoviruses; Differences between the oncogenic adenovirus–3 and the non–oncogenic adenovirus–2" *Gene* 50:173–184 (1986).

Song et al., "Conservation of DNA sequence in the predicted major late promotor regions of selected mastadenoviruses" *Virol.* 220:390–401 (1996).

Southern et al., "Transformation of mammalian cells to antibiotic resistance with a bacterial gene under control of the SV40 early region promotor" *J. Mol. Appl. Genet.* 1:327–341 (1982).

Southern, "Detection of specific sequences among DNA fragments separated by gel electrophoresis" *J. Mol. Biol.* 98:503–517 (1975).

Spibey et al., "Identification and nucleotide sequence of the early region 1 from canine adenovirus types 1 and 2" *Virus. Res.* 14:241–256 (1989).

Stephens et al., "Differential splicing yields novel adenovirus 5 E1A mRNAs that encode 30 kd and 35kd proteins" *EMBO J.* 6(7):2027–2035 (1987).

Stratford–Perricaudet et al., "Evaluation of the transfer and expression in mice of an enzyme–encoding gene using a human adenovirus vector" *Hum. Gene Ther.* 1:241–256 (1990).

Subramani et al., "Analysis of gene expression using simian virus 40 vectors" *Anal. Biochem.* 135:1–15 (1983).

Thomsen et al., "Pseudorabies virus as a live virus vector for expression of foreign genes" *Gene* 5:261–265 (1987).

Tikoo et al., "Molecular cloning, sequencing, and expression of functional bovine herpesvirus 1 glycoprotein gIV in transfected bovine cells" *Virol.* 64:5132–5142 (1990).

Tikoo et al., "Analysis of bovine herpesvirus 1 glycoprotein gIV truncations and deletions expressed by recombinant vaccinia viruses" *Virol.* 67(4):2103–2109 (1993).

Tollefson et al., "The 10,4000– and 14,500–dalton proteins encoded by region E3 of adenovirus form a complex and function together to down–regulate the epidermal growth factor receptor" *Virol.* 65(6):3095–3105 (1991).

Tsukamoto et al., "Nonproductive infection and induction of cellular deoxyribonucleic acid synthesis by bovine adenovirus type 3 in a contact–inhibited mouse cell line" *Virol.* 9(3):465–473 (1972).

Verma et al., "Gene therapy–promises, problems and prospects" *Nature* 389:239–242 (1997).

Whyte et al., "Association between an oncogene and an anti–oncogene: The adenovirus E1A proteins bind to the retinoblastoma gene product" *Nature* 334:124–129 (1988).

Whyte et al., "Two regions of the adenovirus early region 1A proteins are required for transformation" *Virol.* 62(1):257–265 (1988).

Wold et al., "Adenovirus region E3 proteins that prevent cytolysis by cytotoxic T cells and tumor necrosis factor" *Mol. Biol. Med.* 6:433–452 (1989).

Wold et al., "Region E3 of adenovirus: A cassette of genes involved in host immunosurveillance and virus–cell interactions" *Virol.* 184:1–8 (1991).

Xu et al., "Investigation of promoter function in human and animal cells infected with human recombinant adenoviruses expressing rotoavirus antigen VP7sc" *J. Gene Virol* 76:1971–1980 (1995).

Xu et al., "Construction of ovine adenovirus recombinants by gene insertion or deletion of related terminal region sequences" *Virol.* 230:62–71 (1997).

Yanich–Peron et al., "Improved M13 phage cloning vectors and host strains: Nucleotide sequences of the M13mp18 and pUC19 vectors" *Gene* 33:103–109 (1985).

Yee et al., "Detection of cellular proteins associated with human adenovirus type 5 early region 1A polypeptides" *Virol.* 147:142–153 (1985).

Yuasa et al., "Preferential expression of the large hepatitis B virus surface antigen gene by an adenovirus–hepatitis B virus recombinant" *J. Gen. Virol.* 72:1927–1934 (1991).

Zerler et al., "Different functional domains of the adenovirus E1A gene are involved in regulation of host cell cycle products" *Mol. Cell Biol.* 7(2):821–929 (1987).

Zheng et al., "The E1 sequence of bovine adenovirus type 3 and complementation of human adenovirus type 5 E1A function in bovine cells" *Virus Res.* 31:163–186 (1994).

Zoller et al., "Oligonculeotide–directed mutagenesis using M13–derived vectors: An efficient and general procedure for the production of point mutations in any fragment of DNA" *Nucl. Acids Res.* 10(20):6487–6500 (1982).

Imler, "Adenovirus vectors as recombinant viral vaccines" *Vacci*

Alley et al., "The mucosal immune system" In: B–lymphocytes in human diseases (G. Bird and J. E. Calvert, Eds.), Oxford University Press, Oxford, Chapter 9:222–254 (1988).ne 13(13):1143–1151 (1995).

Jelsma et al., "Use of deletion and point mutants spanning the coding region of the adenovirus 5 E1A gene to define a domain that is essential for transcriptional activation" *Virol.* 163:494–502 (1988).

Johnson et al., "Abundant expression of herpes simplex virus glycoprotein gB using an adenovirus vector" *Virol.* 164:1–14 (1988).

Jones et al., "Isolation of adenovirus type 5 host range deletion mutants defective for transformation of rat embryo cells" *Cell* 16:683–689 (1979).

Kaledin, "Cloning and sequencing of EIA gene of bovine adenovirus 3 genome" *Sbornik Nauchnykh Trudov–Moskovskaya Veterinaria Akademiya* 159:78–82 (1988).

Kimelman et al., "E1a regions of the human adenoviruses and of the highly oncogenic simian adenovirus 7 are closely related" *Virol.* 53(2):399–409 (1985).

Kit et al., "Modified–live infectious bovine rhinotracheitis virus vaccine expressing monomer and dimer forms of foot–and–mouth disease capsid protein epitopes on surface of hybrid virus particles" *Arch. Virol.* 120:1–17 (1991).

Kovesdi et al., "Role of an adenovirus E2 promotor binding factor in E1A–mediated coordinated gene control" *Proc. Natl. Acad. Sci. USA* 84:2180–2184 (1987).

Kruglyak et al., "Cloning fragments of virrion DNA of cattle adenoviruses BAV 3 in pUC 19 plasmid" *Soviet Agricultural Sciences* 11:64–67 (1987).

Kurokawa et al., "Biochemical studies on bovine adenovirus type 3: III. Cleavage maps of viral DNA by restriction endonucleases EcoRI, BamHI, and HindIII" *Virol.* 28(1):212–218 (1978).

Laemmli et al., "Cleavage of structural proteins during the assembly of the head bacteriophage T4" *Nature* 227:680–685 (1970).

Lee et al., "Activation of transcription by two factors that bind promotor and enhancer sequences of the human metallothionein gene and SV40" *Nature* 325:368–372 (1987).

Lee et al., "Genetic organization and DNA sequence of early region 4 of bovine adenovirus type 3" *Virus Genes* 17(1):99–100 (1998).

Liang et al., "Identification and deletion mutagenesis of the bovine herpesvirus 1 dUTPase gene and a gene homologous to herpes simplex virus UL49.5" *Virol.* 195:42–50 (1993).

Lillie et al., "An adenovirus E1A protein region required for transformation and transcriptional repression" *Cell* 46:1043–1051 (1986).

Lillie et al., "Transcription activation by the adenovirus E1a protein" *Nature* 338:39–44 (1989).

Lubeck et al., "Immunogenicity and efficacy testing in chimpanzees of an oral hepatitis B vaccine based on live recombinant adenovirus" *Proc. Natl. Acad. Sci. USA* 86:6763–6767 (1989).

Kunkel et al., "Rapid and efficient site–specific mutagenesis without phenotypic selection" *Meth. Enzymol.* 154:367–382 (1987).

Dower et al., "High efficiency transformation of *E. coli* by high voltage electroporation" *Nucl. Acids Res.* 16(13):6127–6145 (1988).

Dragulev et al., "Sequence analysis of putative E3 and fiber genomic regions of two strains of canine adenovirus type 1" *Virol.* 183:298–305 (1991).

Dynan et al., "The promotor–specific transcription factor sp1 binds to upstream sequences in the SV40 early promotor" *Cell* 35:79–87 (1983).

Dyson et al., "Large T antigens of many polyomaviruses are able to form complexes with the retinoblastoma protein" *Virol.* 64(3):1353–1356 (1990).

Egan et al., "Binding of the Rb1 protein to E1A products is required for adenovirus transformation" *Oncogene* 4:383–388 (1989).

Elgadi et al., "Sequence and sequence analysis of E1 and pIX regions of the BAV3 genome" *Intervirol.* 36:113–120 (1993).

Esposito et al., "Infectious recombinant vectored virus vaccines" *Adv. Vet. Sci. Comp. Med.* 33:195–247 (1989).

Fejér et al., "Multiple enlargements in the right inverted terminal repeat of the DNA of canine adenovirus type 2" *Acta Microbiologica Hungarica* 39:159–168 (1992).

Fitzpatrick et al., Mapping of epitopes on bovine herpesvirus type 1 glycoproteins gI and gIII *Virol.* 176:145–157 (1990).

Flomenberg et al., "Sequence and genetic organization of adenovirus type 35 early region 3" *Virol.* 62(11):4431–4437 (1988).

Ghosh–Choudhury et al., "Protein IX, a minor component of the human adenovirus capsid, is essential for the packaging of full length genomes" *EMBO J.* 6:1733–1739 (1991).

Ginsberg et al., "Role or early region 3 (E3) in pathogenesis of adenovirus disease" *Proc. Natl. Acad. Sci. USA* 86:3823–3827 (1989).

Gooding et al., "A 14,700 MW protein from the E3 region of adenovirus inhibits cytolysis by tumor necrosis factor" *Cell* 53:341–346 (1988).

Graham et al., "A new technique for the assay of infectivity of human adenovirus 5 DNA" *Virology* 52:456–467 (1973).

Graham et al., "Characteristics of a human cell line transformed by DNA from human adenovirus type 5" *J. Gen. Virol.* 36:59–72 (1977).

Graham et al., "Cloning and expression of glycoprotein genes in human adenovirus vectors" *J. Cell. Biochem.* UCLA Symposium on Molecular and Cellular Biology, Suppl. 12B, Abstract F109 (1988).

Graham et al., "Infectious circular DNA of human adenovirus type 5: Regeneration of viral DNA termini from molecules lacking terminal sequences" *EMBO J.* 8:2077–2085 (1989).

Graham et al., "Manipulation of adenovirus vectors" In: Methods in Molecular Biology: Gene transfer and expression protocols, Edited by E. J. Murray, Clifton, N. J.; Humana Press, Chapter 11, 7:109–146 (1991).

Ertl et al., "Novel vaccine approaches" *J. Immunol.* 156:3579–3582 (1996).

```
         10         20         30         40         50         60
CATCATCAAT AATCTACAGT ACACTGATGG CAGCGGTCCA ACTGCCAATC ATTTTTGCCA 70         80         90        100        110        120
CGTCATTTAT GACGCAACGA CGGCGAGCGT GGCGTGCTGA CGTAACTGTG GGGCGGAGCG 130        140        150        160        170        180
CGTCGCGGGAG GCGGGCGGCGC TGGGCGGGGC TGAGGGGCGG GGGGCGGGCG CGCGGGGCGG 190        200        210        220        230        240
CGCGCGGGGC GGGGCGGAGGG GCGGAGTTCC GCACCCGCTA CGTCATTTTC AGACATTTTT 250        260        270        280        290        300
TAGCAAAATTT GCGCCTTTTG CAAGCATTTT TCTCACATTT CAGGTATTTA GAGGGCGGAT 310        320        330        340        350        360
TTTTGGTGTT CGTACTTCCG TGTCACATAG TTCACTGTCA ATCTTCATTA CGGCTTAGAC 370        380        390        400        410        420
AAATTTTCGG CGTCTTTTCC GGGTTTATGT CCCCGGTCAC CTTTATGACT GTGTGAAACA 430        440        450        460        470        480
CACCTGCCCA TTGTTTACCC TTGGTCAGTT TTTTCGTCTC CTAGGGTGGG AACATCAAGA
```

Fig. 1A

```
                490             500             510             520             530             540
         ACAAAATTGC CGAGTAATTG TGCACCTTTT TCCGCGGTTAG GACTGCGTTT CACACGTAGA 550             560             570             580             590             600
         CAGACTTTTT CTCATTTCT CACACTCCGT CGTCCGCTTC AGAGCTCTGC GTCTTCGCTG 610             620             630             640             650
         CCACC ATG AAG TAC CTG GTC CTC GTT CTC AAC GAC GGC ATG AGT CGA ATT GAA
               Met Lys Tyr Leu Val Leu Val Leu Asn Asp Gly Met Ser Arg Ile Glu 660             670             680             690             700
         AAA GCT CTC CTG TGC AGC GAT GGT GAG GTG GAT TTA GAG TGT CAT GAG GTA
         Lys Ala Leu Leu Cys Ser Asp Gly Glu Val Asp Leu Glu Cys His Glu Val 710             720             730             740             750
         CTT CCC CCT TCT CCC GCG CCT GTC CCC GCT TCT GTG TCA CCC GTG AGG AGT
         Leu Pro Pro Ser Pro Ala Pro Val Pro Ala Ser Val Ser Pro Val Arg Ser 760             770             780             790             800
         CCT CCT CCT CTG TCT CCG GTG TTT CCT CCG TCT CCG CCA GCC CCG CTT GTG
         Pro Pro Pro Leu Ser Pro Val Phe Pro Pro Ser Pro Pro Ala Pro Leu Val 810             820             830             840             850
         AAT CCA GAG GCG AGT TCG CTG CAG CAG TAT CGG AGA GAG CTG TTA GAG
         Asn Pro Glu Ala Ser Ser Leu Leu Gln Gln Tyr Arg Arg Glu Leu Leu Glu
```

Fig. 1B

```
860                         870                         880                         890                         900
AGG AGC CTG CTC CGA ACG GCC GAA GGT CAG CAG CGT GCA GTG TGT CCA TGT
Arg Ser Leu Leu Arg Thr Ala Glu Gly Gln Gln Arg Ala Val Cys Pro Cys 910                         920                         930                         940                         950
GAG CGG TTG CCC GTG GAA GAG GAT GAG TGT CTG AAT GCC GTA AAT TTG CTG
Glu Arg Leu Pro Val Glu Glu Asp Glu Cys Leu Asn Ala Val Asn Leu Leu 960                         970                         980                         990                         1000                        1010
TTT CCT GAT CCC TGG CTA AAT GCA GCT GAA AAT GGG GGT GAT ATT TTT AAG
Phe Pro Asp Pro Trp Leu Asn Ala Ala Glu Asn Gly Gly Asp Ile Phe Lys 1020                        1030                        1040                        1050                        1060
TCT CCG GCT ATG TCT CCA GAA CCG TGG ATA GAT TTG TCT AGC TAC GAT AGC
Ser Pro Ala Met Ser Pro Glu Pro Trp Ile Asp Leu Ser Ser Tyr Asp Ser 1070                        1080                        1090                        1100                        1110
GAT GTA GAA GAG GTG ACT AGT CAC TTT TTT CTG GAT TGC CCT GAA GAC CCC
Asp Val Glu Glu Val Thr Ser His Phe Phe Leu Asp Cys Pro Glu Asp Pro 1120                        1130                        1140                        1150                        1160
AGT CGG GAG TGT TCA TCT TGT GGG TTT CAT CAG GCT CAA AGC GGA ATT CCA
Ser Arg Glu Cys Ser Ser Cys Gly Phe His Gln Ala Gln Ser Gly Ile Pro
```

*Fig. 1C*

```
             1170            1180            1190            1200             1210
GGC ATT ATG TGC AGT TTG TGC TAC ATG CGC CAA ACC TAC CAT TGC ATC TAT
Gly Ile Met Cys Ser Leu Cys Tyr Met Arg Gln Thr Tyr His Cys Ile Tyr 1220            1230            1240            1250            1260            1270
A[GTAAG TACATTCTGT AAAAGAACAT CTTGGTGATT TCTAGGTATT GTTTAGGGAT
S 1280       1290       1300       1310       1320            1330
TAACTGGGTG GAGTGATCTT AATCCGGCAT AACCAAATAC ATGTTTTCAC AG]GT CCA GTT
                                                          er Pro Val 1340       1350       1360        1370           1380        1390
TCT GAA GAG GAA ATG TGAGT CATGTTGACT TTGGCGCGC A AGAGGAAATG TGAGTCATGT
Ser Glu Glu Glu Met End 1400       1410       1420       1430       1440           1450
TGACTTTGGC GCGCCCTACG GTGACTTTAA AGCAATTTGA GGATCACTTT TTTGTTAGTC 1460       1470            1480            1490            1500
GCTATAAAGT AGTCACGGAG TCTTC ATG GAT CAC TTA AGC GTT CTT TTG GAT TTG
                          Met Asp His Leu Ser Val Leu Leu Asp Leu 1510            1520            1530            1540            1550
AAG CTG CTT CGC TCT ATC GTA GCG GGG GCT TCA AAT CGC ACT GGA GTG TGG
Lys Leu Leu Arg Ser Ile Val Ala Gly Ala Ser Asn Arg Thr Gly Val Trp
```

Fig. 1D

```
1560                 1570                 1580                 1590                 1600
AAG AGG CGG CTG TGG CTG GGA CGC CTG ACT CAA CTG GTC CAT GAT ACC TGC
Lys Arg Arg Leu Trp Leu Gly Arg Leu Thr Gln Leu Val His Asp Thr Cys 1610                 1620                 1630                 1640                 1650
GTA GAG AAC GAG AGC ATA TTT CTC AAT TCT CTG CCA GGG AAT GAA GCT TTT
Val Glu Asn Glu Ser Ile Phe Leu Asn Ser Leu Pro Gly Asn Glu Ala Phe 1660                 1670                 1680                 1690                 1700
TTA AGG TTG CTT CGG AGC GGC TAT TTT GAA GTG TTT GAC GTG TTT GTG GTG
Leu Arg Leu Leu Arg Ser Gly Tyr Phe Glu Val Phe Asp Val Phe Val Val 1710                 1720                 1730                 1740                 1750
CCT GAG CTG CAT CTG GAC ACT CCG GGT CGA GTG GTC GCC GCT CTT GCT CTG
Pro Glu Leu His Leu Asp Thr Pro Gly Arg Val Val Ala Ala Leu Ala Leu 1760                 1770                 1780                 1790                 1800
CTG GTG TTC ATC CTC AAC GAT TTA GAC GCT AAT TCT GCT TCT TCA GGC TTT
Leu Val Phe Ile Leu Asn Asp Leu Asn Asp Ala Asn Ser Ala Ser Ser Gly Phe 1810                 1820                 1830                 1840                 1850                 1860
GAT TCA GGT TTT CTC GTG GAC CGT CTC TGC GTG CCG CTA TGG CTG AAG GCC
Asp Ser Gly Phe Leu Val Asp Arg Leu Cys Val Pro Leu Trp Leu Lys Ala
                                                                Met Ala Glu Gly
```

Fig. 1E

```
                  1870              1880              1890              1900              1910
          AGG GCG TTC AAG ATC ACC CAG AGC TCC AGG AGC ACT TCG CAG CCT TCC TCG
          Arg Ala Phe Lys Ile Thr Gln Ser Ser Arg Ser Thr Ser Gln Pro Ser Ser
          Gln Gly Val Asp His Pro Glu Leu Gln Glu His Phe Ala Ala Phe Leu
                  1920              1930              1940              1950              1960
          TCG CCC GAC AAG ACG ACC CAG ACT ACC AGC CAG TA GAC GGG GAC AGC CCA
          Ser Pro Asp Lys Thr Thr Gln Thr Thr Ser Gln End
          Val Ala Arg Gln Asp Asp Pro Asp Tyr Gln Pro Val Asp Gly Asp Ser Pro
                  1970              1980              1990              2000              2010
          CCC CGG GCT AGC CTG GAG GAG GCT GAA CAG AGC AGC ACT CGT TTC GAG CAC
          Pro Arg Ala Ser Leu Glu Glu Ala Glu Gln Ser Ser Thr Arg Phe Glu His
                  2020              2030              2040              2050              2060
          ATC AGT TAC CGA GAC GTG GTG GAT GAC TTC AAT AGA TGC CAT GAT GTT TTT
          Ile Ser Tyr Arg Asp Val Val Asp Asp Phe Asn Arg Cys His Asp Val Phe
                  2070              2080              2090              2100              2110
          TAT GAG AGG TAC AGT TTT GAG GAC ATA AAG AGC TAC GAG GCT TTG CCT GAG
          Tyr Glu Arg Tyr Ser Phe Glu Asp Ile Lys Ser Tyr Glu Ala Leu Pro Glu
```

*Fig. 1F*

```
      2120                 2130                2140                2150                 2160
GAC AAT TTG GAG CAG CTC ATA GCT ATG CAT GCT AAA ATC AAG CTG CCC
Asp Asn Leu Glu Gln Leu Ile Ala Met His Ala Lys Ile Lys Leu Pro 2170                2180                 2190                2200                 2210
GGT CGG GAG TAT GAG TTG ACT CAA CCT TTG AAC ATA ACA TCT TGC GCC TAT
Gly Arg Glu Tyr Glu Leu Thr Gln Pro Leu Asn Ile Thr Ser Cys Ala Tyr 2220                2230                 2240                2250                 2260
GTG CTC GGA AAT GGG GCT ACT ATT AGG GTA ACA GGG GAA GCC TCC CCG GCT
Val Leu Gly Asn Gly Ala Thr Ile Arg Val Thr Gly Glu Ala Ser Pro Ala 2270                2280                 2290                2300                 2310                 2320
ATT AGA GTG GGG GCC ATG GCC GTG GGT CCG TGT GTA ACA GGA ATG ACT GGG
Ile Arg Val Gly Ala Met Ala Val Gly Pro Cys Val Thr Gly Met Thr Gly 2330                2340                 2350                2360                 2370
GTG ACT TTT GTG AAT TGT AGG TTT GAG AGA GAG TCA ACA ATT AGG GGG TCC
Val Thr Phe Val Asn Cys Arg Phe Glu Arg Glu Ser Thr Ile Arg Gly Ser 2380                2390                 2400                2410                 2420
CTG ATA CGA GCT TCA ACT CAC GTG CTG TTT CAT GGC CTG TGT TAT TTT ATG GGA
Leu Ile Arg Ala Ser Thr His Val Leu Phe His Gly Cys Tyr Phe Met Gly
```

Fig. 1G

```
                2430              2440              2450              2460              2470
           ATT ATG GGC ACT TGT ATT GAG GTG GGG GCG GGA GCT TAC ATT CGG GGT TGT
           Ile Met Gly Thr Cys Ile Glu Val Gly Ala Gly Ala Tyr Ile Arg Gly Cys 2480              2490              2500              2510              2520
           GAG TTT GTG GGC TGT TAC CGG GGA ATC TGT TCT ACT TCT AAC AGA GAT ATT
           Glu Phe Val Gly Cys Tyr Arg Gly Ile Cys Ser Thr Ser Asn Arg Asp Ile 2530              2540              2550              2560              2570
           AAG GTG AGG CAG TGC AAC TTT GAC AAA TGC TTA CTG GGT ATT ACT TGT AAG
           Lys Val Arg Gln Cys Asn Phe Asp Lys Cys Leu Leu Gly Ile Thr Cys Lys 2580              2590              2600              2610              2620
           GGG GAC TAT CGT CTT TCG GGA AAT GTG TGT TCT GAG ACT TTC TGC TTT GCT
           Gly Asp Tyr Arg Leu Ser Gly Asn Val Cys Ser Glu Thr Phe Cys Phe Ala 2630              2640              2650              2660              2670
           CAT TTA GAG GGA GAG GGT TTG GTT AAA AAC AAC ACA GTC AAG TCC CCT AGT
           His Leu Glu Gly Glu Gly Leu Val Lys Asn Asn Thr Val Lys Ser Pro Ser 2680              2690              2700              2710              2720
           CGC TGG ACC AGC GAG TCT GGC TTT TCC ATG ATA ACT TGT GCA GAC GGC AGG
           Arg Trp Thr Ser Glu Ser Gly Phe Ser Met Ile Thr Cys Ala Asp Gly Arg
```

*Fig. 1H*

```
2730                2740                2750                2760                2770
GTT ACG CCT TTG GGT TCC CTC CAC ATT GTG GGC AAC CGT TGT AGG CGT TGG
Val Thr Pro Leu Gly Ser Leu His Ile Val Gly Asn Arg Cys Arg Arg Trp 2780                2790                2800                2810                2820                2830
CCA ACC ATG CAG GGG AAT GTG TTT ATC ATG TCT AAA CTG TAT CTG GGC AAC
Pro Thr Met Gln Gly Asn Val Phe Ile Met Ser Lys Leu Tyr Leu Gly Asn 2840                2850                2860                2870                2880
AGA ATA GGG ACT GTA GCC CTG CCC CAG TGT GCT TTC TAC AAG TCC AGC ATT
Arg Ile Gly Thr Val Ala Leu Pro Gln Cys Ala Phe Tyr Lys Ser Ser Ile 2890                2900                2910                2920                2930
TGT TTG GAG GAG AGG ACA AAC AAG CTG GTC TTG GCT TGT GCT TTT GAG
Cys Leu Glu Glu Arg Thr Asn Lys Leu Val Leu Ala Cys Ala Phe Glu 2940                2950                2960                2970                2980
AAT AAT GTA CTG GTG TAC AAA GTG CTG AGA CGG AGT CCC TCA ACC GTG
Asn Asn Val Leu Val Tyr Lys Val Leu Arg Arg Glu Ser Pro Ser Thr Val 2990                3000                3010                3020                3030
AAA ATG TGT GTT TGT GGG ACT TCT CAT TAT GCA AAG CCT TTG ACA CTG GCA
Lys Met Cys Val Cys Gly Thr Ser His Tyr Ala Lys Pro Leu Thr Leu Ala
```

Fig. 11

```
                                    3050                   3060                  3070              3080
ATT ATT TCT TCA GAT ATT CGG GCT AAT CGA TAC ATG TAC ACT GTG GAC TCA
Ile Ile Ser Ser Asp Ile Arg Ala Asn Arg Tyr Met Tyr Thr Val Asp Ser 3090                 3100                3110                3120                   3130                       3140
ACA GAG TTC ACT TCT GAC GAG GAT T AAAAGTGGGC GGGGCCAAGA GGGGTATAAA
Thr Glu Phe Thr Ser Asp Glu Asp End 3150                  3160                  3170                3180                  3190                 3200
TAGGTGGGGA GGTTGAGGGG AGCCGTAGTT TCTGTTTTTC CCAGACTGGG GGGGACAAAC ATG
                                                                                                                                                    Met 3210                 3220               3230                  3240                 3250
GCC GAG GAA GGG CGC ATT TAT GTG CCT TAT GTA ACT GCC CGC CTG CCC AAG
Ala Glu Glu Gly Arg Ile Tyr Val Pro Tyr Val Thr Ala Arg Leu Pro Lys 3260                3270              3280                   3290                   3300
TGG TCG GGT TCG GTG CAG GAT AAG ACG GGC TCG AAC ATG TTG GGG GGT GTG
Trp Ser Gly Ser Val Gln Asp Lys Thr Gly Ser Asn Met Leu Gly Gly Val 3310                3320              3330                 3340                    3350
GTA CTC CCT CCT AAT TCA CAG GCG CAC CGG ACG GAG ACC GTG GGC ACT GAG
Val Leu Pro Pro Asn Ser Gln Ala His Arg Thr Glu Thr Val Gly Thr Glu
```

Fig. 1J

```
3360                         3370                         3380                         3390                         3400
GCC ACC AGA GAC AAC CTG CAC GCC GAG GGA GCG CGT CCT GAG GAT CAG
Ala Thr Arg Asp Asn Leu His Ala Glu Gly Ala Arg Arg Pro Glu Asp Gln 3410                         3420                         3430                         3440                         3450
ACG CCC TAC ATG ATC TTG GTG GAG GAC TCT CTG GGA GGT TTG AAG AGG CGA
Thr Pro Tyr Met Ile Leu Val Glu Asp Ser Leu Gly Gly Leu Lys Arg Arg 3460                         3470                         3480                         3490                         3500
ATG GAC TTG CTG GAA GAA TCT AAT CAG CAG CTG GCA ACT CTC AAC CGT
Met Asp Leu Leu Glu Glu Ser Asn Gln Gln Leu Ala Thr Leu Asn Arg 3510                         3520                         3530                         3540                         3550
CTC CGT ACA GGA CTC GCT GCC TAT GTG CAG GCT AAC CTT GTG GGC GGC CAA
Leu Arg Thr Gly Leu Ala Ala Tyr Val Gln Ala Asn Leu Val Gly Gly Gln 3560                         3570                         3580                         3590                         3600                         3610
GTT AAC CCC TTT GTT TAAATA AAAATACACT CATACAGTTT ATTATGCTGT
Val Asn Pro Phe Val End 3620       3630       3640       3650       3660       3670
CAATAAAATT CTTTATTTTT CCTGTGATAA TACCGTGTCC AGCGTGCTCT GTCAATAAGG 3680       3690       3700       3710       3720       3730
GTCCTATGCA TCCTGAGAAG GGCCTCATAT ACCCATGGCA TGAATATTAA GATACATGGG
```

*Fig. 1K*

```
      3740       3750       3760       3770       3780       3790
CATAAGGCCC TCAGAAGGGT TGAGGTAGAG CCACTGCAGA CTTTCGTGGG GAGGTAAGGT 3800       3810       3820       3830       3840       3850
GTTGTAAATA ATCCAGTCAT ACTGACTGTG CTGGGCGTGG AAGGAAAAGA TGTCTTTTAG 3860       3870       3880       3890       3900       3910
AAGAAGGGTG ATTGGCAAAG GGAGGCTCTT AGTGTAGGTA TTGATAAATC TGTTCAGTTG 3920       3930       3940       3950       3960       3970
GGAGGGATGC ATTCGGGGGC TAATAAGGTG GAGTTTAGCC TGAATCTTAA GGTTGGCAAT 3980       3990       4000       4010       4020       4030
GTTGCCCCCT AGGTCTTTGC GAGGATTCAT GTTGTGCAGT ACCACAAAAA CAGAGTAGCC 4040       4050       4060
TGTGCATTTG GGGAATTTAT CATGAAGCT T
```

Fig. 1L

```
                          Rb BINDING SEQUENCE
         120                   132
Ad5      IleAspLeuThrCysHisGluAlaGlyPheProProSer
             ··    —     —              —
         ValAspLeuGluCysHisGluVal     LeuProProSer
BAV3     26                           37
```

Fig. 2B

```
Ad5    82                                                        100
       LeuAspPheSerThrProGlyArgAlaAlaAlaAlaValAlaAlaPheLeuSerPheIle
          |   |   |   |   |   |   |   |   |   |   |
       LeuAsp   ThrProGlyArgValValAlaAlaLeuAlaLeuValPheIle
BAV3   83                                                         99
```

*Fig. 3A*

```
Ad5         20                              26
            GlnSerSerAsnSerThrSer
               |   |   |   |   |
            GlnSerSerArgSerThrSer
BAV3       136                             142
```

*Fig. 3B*

```
Ad5  150  GlnLysTyrSerIleGluGlnLeuThrThrTyrTrpLeuGlnProGlyAspAspPheGlu
           :  |   |        |          :   |        |   |        |
BAV3  74  GluArgTyrSerPheGluAspIleLysSerTyrGluAlaLeuProGluAspAsnLeuGlu

170  GluAlaIleArgValTyrAlaLysValAlaLeuArgProAspCysLysTyrLysIleSer
              |   :   |   |   :   |   |           |       |   :   :
       94  GlnLeuIleAlaMetHisAlaLysIleLysLeuLeuProGlyArgGluTyrGluLeuThr

190  LysLeuValAsnIleArgAsnCysCysTyrIleSerGlyAsnGlyAlaGluValGluIle
              :   |   |           |       |   :   |   |   |   |   :   :
      114  GlnProLeuAsnIleThrSerCysAlaTyrValLeuGlyAsnGlyAlaThrIleArgVal

210  AspThrGluAspArgValAlaPheArgCysSerMetIleAsnMetTrpProGlyValLeu
              |               |       |           :   :       |   |
      134  ThrGlyGluAlaSerProAlaIleArgValGlyAlaMetAlaValGlyProCysValThr

230  GlyMetAspGlyValValIleMetAsnValArgPheThr   GlyProAsnPheSerGly
              |   |   |   |           :   |   |   |                   |
      154  GlyMetThrGlyValThrPheValAsnCysArgPheGluArgGluSerThrIleArgGly

249  ThrValPheLeuAlaAsnThrAsnLeuIleLeuHisGlyValSerPheTyr   GlyPhe
              :   :       |   |   :   :   |   |           :   :       |
      174  SerLeuIleArgAlaSerThrHisValLeuPheHisGlyCys   TyrPheMetGlyIle

268  AsnAsnThrCysValGluAlaTrpThrAspValArgValArgGlyCysAlaPheTyrCys
              |   |   :   |
      193  MetGlyThrCysIleGluValGlyAlaGlyAlaTyrIleArgGlyCysGluPheValGly

288  CysTrpLysGlyValValCysArgProLysSerArgAla   SerIleLysLysCysLeu
              |   :   |   :       |                               :   :   |
      213  CysTyrArgGlyIle   CysSerThrSerAsnArgAspIleLysValArgGlnCysAsn

307  PheGluArgCysThrLeuGlyIleLeuSerGluGlyAsnSerArgValArgHisAsnVal
              |   :   :   |       |   |   |           |       |   :       |   |
      232  PheAspLysCysLeuLeuGlyIleThrCysLysGlyAspTyrArgLeuSerGlyAsnVal

327  AlaSerAspCysGlyCysPheMetLeuValLysSerValAlaValIleLysHisAsnMet
              |   :           |   |       :                   :   :   |   |
      252  CysSerGluThrPheCysPheAlaHisLeuGluGlyGluGlyLeuValLysAsnAsnThr
```

FIG. 4A

```
347   Val   CysGlyAsn        CysGluAspArgAlaSerGlnMetLeuThrCysSerAsp
      |              :              |  :  |  |  :  |
272   ValLysSerProSerArgTrpThrSerGluSerGlyPheSerMetIleThrCysAlaAsp

364   GlyAsnCysHisLeuLeuLysThrIleHisVal   AlaSerHisSerArgLysAlaTrp
      |        |      :  |  :         :        |  :        |
292   GlyArgValThrProLeuGlySerLeuHisIleValGlyAsnArgCysArgArg    Trp

383   ProValPheGluHisAsnIleLeuHisArgCysSerLeuHisLeuGlyAsnArgArgGly
      |              |  :           |     |  |  |  |        |
311   ProThrMetGlnGlyAsnValPheIleMetSerLysLeuTyrLeuGlyAsnArgIleGly

403      ValPheLeuProTyrGlnCysAsnLeuSerHisThrLysIleLeuLeuGluProGlu
         |  |  |   |  |          :  :        |     |  |
331   ThrValAlaLeuPro    GlnCysAlaPheTyrLysSerSerIleCysLeuGluGluArg

422   SerMetSerLysValAsnLeuAsnGlyValPheAspMetThrMetLysIleTrpLysVal
      :        |  :        |           |  :        :  :  :  |  |
350   AlaThrAsnLysLeuValLeuAlaCysAlaPheGluAsnAsnValLeuValTyrLysVal

442   LeuArgTyrAspGluThrArgThrArgCysArgProCysGluCysGlyGlyLysHisIle
      |  |     :              |     :        |  |  |        |
370   LeuArgArgGluSerProSerThr     ValLysMetCysValCysGlyThrSerHisTyr

462   ArgAsnGlnProValMetLeuAspVal   ThrGluGluLeuArgProAspHisLeuVal
         |  :        |     :  :     :  :     |        :     :  :
389      AlaLysProLeuThrLeuAlaIleIleSerSerAspIleArgAlaAsnArgTyrMet

481   LeuAlaCysHisArgAlaGluPheGlySerSerAspGluAspThrAspEnd
         :           :  |  |        :  |  |  |  |
408      TyrThrValAspSerThrGluPhe   ThrSerAspGluAspEnd
```

FIG. 4B

```
Ad5   1    MetSerThrAsnSerPheAspGlySerIleValSerSerTyrLeuThrThrArgMetPro
                  ::                                    ::
BAV3  1    MetAla          GluGlyArgIleTyrValProTyrValThrAlaArgLeuPro

21   ProTrpAlaGlyValArgGlnAsnValMetGlySerSerIleAspGlyArgProValLeu
                                                  ::
      18   LysTrpSerGlyValGlnAspLysThrGlySerAsnMetLeuGlyGlyValValLeu

41   ProAlaAsnSerThrThrLeuThrTyrGluThrValSerGlyThrProLeuGluThrAla
                     ::
      38   ProProAsnSerGlnAlaHisArgThrGluThrVal     GlyThrGlu    AlaThr

61   AlaSerAlaAlaAlaSerAlaAlaAlaAlaThrAlaAlaArgGlyIleValThrAspPheAla

55               ArgAspAsnLeuHisAlaGluGlyAlaArg     ArgProGluAspGlnThr   Pro

81   PheLeuSerProLeuAlaSerSerAlaAlaSerArgSerAlaAlaArgAspSerAlaArgAspLysLeu
                  ::
      72   TyrMetIle          LeuValGluAspSerLeuGlyGlyLeuLysArgArgMetAspLeuLeu

101   ThrAlaLeuLeuAlaGlnLeu          AspSerLeuThrArgGluLeuAsnValValSerGln

91   GluGluSerAsnGlnGlnLeuGlnLeuAlaThrLeuAsnArg     LeuArgThr          Gly

120   GlnLeuLeuAspLeuArgGlnGlnValSerAlaAlaLeuLysAlaSerSerProProAsnAla
                       ::
     108   LeuAlaAlaTyr     ValGln          AlaAsnLeuValGlyGlyGlnValAsnProPhe

140   ValEnd

125   ValEnd
```

Fig. 5

```
                                           10                   20                   30                   40                   50
     C CTC ATC AAA CAA CCC GTG GGC ACC ACC CAC GTG GAA ATG CCT CGC AAC
ORF 1  Leu Ile Lys Gln Pro Val Gly Thr Thr His Val Glu Met Pro Arg Asn 60                   70                   80                   90                  100
     GAA GTC CTA GAA CAA CAT CTG ACC TCA CAT GGC GCT CAA ATC GCG GGC GGA
     Glu Val Leu Glu Gln His Leu Thr Ser His Gly Ala Gln Ile Ala Gly Gly 110                  120                  130                  140                  150
     GGC GCT GCG GGC GAT TAC TTT AAA AGC CCC ACT TCA GCT CGA ACC CTT ATC
     Gly Ala Ala Gly Asp Tyr Phe Lys Ser Pro Thr Ser Ala Arg Thr Leu Ile 160                  170                  180                  190                  200
     CCG CTC ACC GCC TCC TGC TTA AGA CCA GAT GGA GTC TTT CAA CTA GGA GGA
     Pro Leu Thr Ala Ser Cys Leu Arg Pro Asp Gly Val Phe Gln Leu Gly Gly 210                  220                  230                  240                  250
     GGC TCG CGT TCA TCT TTC AAC CCC CTG CAA ACA GAT TTT GCC TTC CAC GCC
     Gly Ser Arg Ser Ser Phe Asn Pro Leu Gln Thr Asp Phe Ala Phe His Ala 260                  270                  280                  290                  300
     CTG CCC TCC AGA CCG CGC CAC GGG GGC ATA GGA TCC AGG CAG TTT GTA GAG
     Leu Pro Ser Arg Pro Arg His Gly Gly Ile Gly Ser Arg Gln Phe Val Glu
```

Fig. 7A

```
310                    320                   330                   340                   350
GAA TTT GTG CCC GCC GTC TAC CTC AAC CCC TAC TCG GGA CCG CCG GAC TCT
Glu Phe Val Pro Ala Val Tyr Leu Asn Pro Tyr Ser Gly Pro Pro Asp Ser 360                    370                   380                   390                   400
TAT CCG GAC CAG TTT ATA CGC CAC TAC AAC GTG TAC AGC AAC TCT GTG AGC
Tyr Pro Asp Gln Phe Ile Arg His Tyr Asn Val Tyr Ser Asn Ser Val Ser
                                                             ORF 2   Ala 410                    420                   430                   440                   450                   460
GGT TAT AGC T GAG ATT GTA AGA CTC TCC TAT CTG TCT CTG TGC TGC TTT TCC
Gly Tyr Ser   Glu Ile Val Arg Leu Ser Tyr Leu Ser Leu Cys Cys Phe Ser
Val Ile Ala 470                   480                   490                   500                   510
GCT TCA AGC CCC ACA AGC ATG AAG GGG TTT CTG CTC ATC TTC AGC CTG CTT
Ala Ser Ser Pro Thr Ser Met Lys Gly Phe Leu Leu Ile Phe Ser Leu Leu
        ORF 3   Phe  Met Lys Gly Phe Leu Leu Ile Phe Ser Leu Leu 520                    530                   540                   550                   560
GTG CAT TGT CCC CTA ATT CAT GTT GGG ACC ATT AGC TTC TAT GCT GCA AGG
Val His Cys Pro Leu Ile His Val Gly Thr Ile Ser Phe Tyr Ala Ala Arg
```

Fig. 7B

```
      570                 580                 590                 600                 610
CCC GGG TCT GAG CCT AAC GCG ACT TAT GTT TGT GAC TAT GGA AGC GAG TCA
Pro Gly Leu Ser Leu Thr Arg Leu Met Phe Val Thr Met Glu Ala Ser Gln

Pro Gly Ser Glu Pro Asn Ala Thr Tyr Val Cys Asp Tyr Gly Ser Glu Ser
      620                 630                 640                 650                 660
GAT TAC AAC CCC ACC ACG GTT CTG TGG TTG GCT CGA GAG ACC GAT GGC TCC
Ile Thr Thr Pro Pro Arg Phe Cys Gly Trp Leu Ala Arg Pro Met Ala Pro

Asp Tyr Asn Pro Thr Thr Val Leu Trp Leu Ala Arg Glu Thr Asp Gly Ser
      670                 680                 690                 700                 710
TGG ATC TCT GTT CTT TTC CGT CAC AAC GGC TCC TCA ACT GCA GCC CCC GGG
Gly Ser Leu Phe Phe Ser Val Thr Thr Ala Pro Gln Leu Gln Pro Pro Gly

Trp Ile Ser Val Leu Phe Arg His Asn Gly Ser Ser Thr Ala Ala Pro Gly
      720                 730                 740                 750                 760
GTC GTC GCG CAC TTT ACT GAC CAC AAC AGC AGC ATT GTG GTG CCC CAG TAT
Ser Ser Arg Thr Leu Thr Asp His Asn Ser Ser Ile Val Val Pro Gln Tyr

Val Val Ala His Phe Thr Asp His Asn Ser Ser Ile Val Val Pro Gln Tyr
      770                 780                 790                 800                 810
TAC CTC CTC AAC AAC TCA CTC TCT AAG CTC TGC TGC TCA TAC CGG CAC AAC
Thr Ser Ser Thr His Ser Leu Ser Lys Leu Cys Cys Ser Ala His Thr Gly Thr Thr

Tyr Leu Leu Asn Asn Ser Leu Ser Lys Leu Cys Cys Ser Tyr Arg His Asn
```

*Fig. 7C*

```
820                830               840               850                860
GAG CGT TCT CAG TTT ACC TGC AAA CAA GCT GAC GTC CCT GAC GTC CCT ACC TGT CAC GAG
Ser Val Leu Ser Leu Pro Ala Asn Lys Leu Thr Ser Leu Pro Val Thr Ser
Glu Arg Ser Gln Phe Thr Cys Lys Gln Ala Asp Val Pro Thr Cys His Glu 870                880               890               900                910               920
CCC GGC AAG CCG CTC ACC CTC CGC GTC TCC CCC GCG CTG GGA ACT GCC CAC
Pro Ala Ser Arg Ser Pro Ser Ala Ser Pro Pro Arg Trp Glu Leu Pro Thr
Pro Gly Lys Pro Leu Thr Leu Arg Val Ser Pro Ala Leu Gly Thr Ala His 930               940               950               960                970
CAA GCA GTC ACT TGG TTT TTT CAA AAT GTA CCC ATA GCT ACT GTT TAC CGA
Lys Gln Ser Leu Gly Phe Phe Lys Met Tyr Pro
Gln Ala Val Thr Trp Phe Phe Gln Asn Val Pro Ile Ala Thr Val Tyr Arg 980              990              1000              1010              1020
CCT TGG GGC AAT GTA ACT TGG TTT CCT CCC TTC ATG TGT ACC TTT AAT
Pro Trp Gly Asn Val Thr Trp Phe Pro Pro Phe Met Cys Thr Phe Asn 1030             1040             1050             1060              1070
GTC AGC CTG AAC TCC CTA CTT ATT TAC AAC TTT TCT GAC AAA ACC GGG GGG
Val Ser Leu Asn Ser Leu Leu Ile Tyr Asn Phe Ser Asp Lys Thr Gly Gly
```

Fig. 7D

```
              1080                      1100                     1120
CAA TAC ACA GCT CTC ATG CAC TCC GGA CCT GCT TCC CTC TTT CAG CTC TTT
Gln Tyr Thr Ala Leu Met His Ser Gly Pro Ala Ser Leu Phe Gln Leu Phe 1130              1150                      1170
AAG CCA ACG ACT TGT GTC ACC AAG GTG GAG GAC CCG CCG TAT GCC AAC GAC
Lys Pro Thr Thr Cys Val Thr Lys Val Glu Asp Pro Pro Tyr Ala Asn Asp 1180                      1200                      1220
CCG GCC TCG CCT GTG TGG CGC CCA CTG CTT TTT GCC TTC GTC CTC TGC ACC
Pro Ala Ser Pro Val Trp Arg Pro Leu Leu Phe Ala Phe Val Leu Cys Thr 1230                      1250                      1270
GGC TGC GCG GTG TTG TTA ACC GCC TTC GGT CCA TCG ATT CTA TCC GGT ACC
                ORF 4   Pro Pro Ser Val His Arg Phe Tyr Pro Val Pro
Gly Cys Ala Val Leu Leu Thr Ala Phe Gly Pro Ser Ile Leu Ser Gly Thr 1280              1300                      1320
CGA AAG CTT ATC TCA GCC CGC TTT TGG AGT CCC GAG CCC TAT ACC ACC CTC
Glu Ser Leu Ser Gln Pro Ala Phe Gly Val Pro Ser Pro Ile Pro Pro Ser
Arg Lys Leu Ile Ser Ala Arg Phe Trp Ser Pro Glu Pro Tyr Thr Thr Leu
```

*Fig. 7E*

```
1330              1340              1350              1360              1370              1380
CAC T AAC AGT CCC CCC ATG GAG CCA GAC GGA GTT CAT GCC GAG CAG CAG TTT
Thr   Asn Ser Pro Pro Met Glu Pro Asp Gly Val His Ala Glu Gln Gln Phe
His 1390              1400              1410              1420              1430
ATC CTC AAT CAG ATT TCC TGC GCC AAC ACT GCC CTC CAG CGT CAA AGG GAG
Ile Leu Asn Gln Ile Ser Cys Ala Asn Thr Ala Leu Gln Arg Gln Arg Glu 1440              1450              1460              1470              1480
GAA CTA GCT TCC CTT GTC ATG TTG CAT GCC TGT AAG CGT GGC CTC TTT TGT
Glu Leu Ala Ser Leu Val Met Leu His Ala Cys Lys Arg Gly Leu Phe Cys

ORF 5   Leu Pro Leu Ser Cys Cys Met Pro Val Ser Val Ala Ser Phe Val 1490              1500              1510              1520              1530
CCA GTC AAA ACT TAC AAG CTC AGC CTC AAC GCC CTC AGC GAG CAC AGC
Pro Val Lys Thr Tyr Lys Leu Ser Leu <u>Asn Ala Ser</u> Ala Ser Glu His Ser

Gln Ser Lys Leu Thr Ser Ser Ala Ser Thr Pro Arg Pro Ala Ser Thr Ala 1540              1550              1560              1570              1580
CTG CAC TTT GAA AAA AGT CCC TCC CGA TTC ACC CTG GTC AAC ACT CAC GCC
Leu His Phe Glu Lys Ser Pro Ser Arg Phe Thr Leu Val Asn Thr His Ala

Cys Thr Leu Lys Lys Val Pro Pro Asp Ser Pro Trp Ser Pro Thr Leu Thr Pro
```

*Fig. 7F*

```
                1590            1600            1610            1620            1630
            GGA GCT TCT GTG CGA GTG GCC CTA CAC CAC CAG GGA GCT TCC GGC AGC ATC
            Gly Ala Ser Val Arg Val Ala Leu His His Gln Gly Ala Ser Gly Ser Ile
            Glu Leu Leu Cys Glu Trp Pro Tyr Thr Thr Arg Glu Leu Pro Ala Ala Ser 1640            1650            1660            1670            1680
            CGC TGT TCC TGT TCC CAC GCC GAG TGC CTC CCC GTC CTC CTC AAG ACC CTC
            Arg Cys Ser Cys His Ala Glu Cys Leu Pro Val Leu Leu Lys Thr Leu
            Ala Val Pro Val Pro Thr Pro Ser Ala Ser Pro Ser Ser Ser Arg Pro Ser 1690            1700            1710            1720            1730            1740
            TGT GCC TTT AAC TTT TTA GAT TAG CTGAAAGCAA ATATAAAATG GTGTGCTTAC
            Cys Ala Phe Asn Phe Leu Asp
            Val Pro Leu Thr Phe 1750            1760            1770            1780            1790
            CGTAATTCTG TTTTGACTTG TGTGCTTGA TTT CTC CCC CTG CGC CGT AAT CCA GTG 1800            1810            1820            1830            1840
            CCC CTC TTC AAA ACT CTC GTA ACT CTC CCC TAT GCG ATT CGC ATA GGC ATA TTT TCT 1850            1860            1870            1880            1890
            AAA AGC TCT GAA GTC AAC ATC ACT CTC AAA CAC TTC TCC GTT GTA GGT TAC
```

Fig. 7G

```
                                              1940              1950
1900          1910         1920          1930
TTT CAT CTA CAG ATA AAG TCA TCC ACC GGT T AAC ATC ATG AAG AGA AGT GTG
              ORF 6        Ser His Pro Val  Asn Ile Met Lys Arg Ser Val 1990              2000
              1960         1970          1980
CCC CAG GAC TTT AAT CTT GTG TAT CCG TAC AAG GCT AAG AGG CCC AAC ATC
Pro Gln Asp Phe Asn Leu Val Tyr Pro Tyr Lys Ala Lys Arg Pro Asn Ile 2040              2050
              2010         2020          2030
ATG CCG CCC TTT TTT GAC CGC AAT GGC TTT GTT GAA AAC CAA GAA GCC ACG
Met Pro Pro Phe Phe Asp Arg Asn Gly Phe Val Glu Asn Gln Glu Ala Thr 2090              2100
              2060         2070          2080
CTA GCC ATG CTT GTG GAA AAG CCG CTC ACG TTC GAC AAG GAA GGT GCG CTG
Leu Ala Met Leu Val Glu Lys Pro Leu Thr Phe Asp Lys Glu Gly Ala Leu 2140              2150
              2110         2120          2130
ACC CTG GGC GTC GGA CGC GGC ATC CGC ATT AAC CCC GCG GGG CTT CTG GAG
Thr Leu Gly Val Gly Arg Gly Ile Arg Ile Asn Pro Ala Gly Leu Leu Glu 2190              2200
              2160         2170          2180
ACA AAC GAC CTC GCG TCC GCT GTC TTC CCA CCG CTG GCC TCC GAT GAG GCC
Thr Asn Asp Leu Ala Ser Ala Val Phe Pro Pro Leu Ala Ser Asp Glu Ala
```

*Fig. 7H*

```
                    2220              2230              2240              2250
      2210   GGC AAC GTC ACG CTC AAC ATG TCT GAC GGG CTA TAT ACT AAG GAC AAC AAG
             Gly Asn Val Thr Leu Asn Met Ser Asp Gly Leu Tyr Thr Lys Asp Asn Lys 2260              2270              2280              2290              2300
             CTA GCT GTC AAA GTA GGT CCC GGG CTG TCC CTC GAC TCC AAT AAT GCT CTC
             Leu Ala Val Lys Val Gly Pro Gly Leu Ser Leu Asp Ser Asn Asn Ala Leu 2310              2320              2330              2340              2350
             CAG GTC CAC ACA GGC GAC GGG CTC ACG GTA ACC GAT GAC AAG GTG TCT CTA
             Gln Val His Thr Gly Asp Gly Leu Thr Val Thr Asp Asp Lys Val Ser Leu 2360              2370              2380              2390              2400
             AAT ACC CAA GCT CCC CTC TCG ACC ACC AGC GCG GGC CTC TCC CTA CTT CTG
             Asn Thr Gln Ala Pro Leu Ser Thr Thr Ser Ala Gly Leu Ser Leu Leu Leu 2410              2420              2430              2440              2450              2460
             GGT CCC AGC CTC CAC TTA GGT GAG GAG GAA CGA CTA AAC ACC GGA
             Gly Pro Ser Leu His Leu Gly Glu Glu Glu Arg Leu Asn Thr Gly 2470              2480              2490              2500              2510
             GCG GGC CTC CAA ATT AGC AAT AAC GCT CTG GCC GTA AAA GTA GGT TCA GGT
             Ala Gly Leu Gln Ile Ser Asn Asn Ala Leu Ala Val Lys Val Gly Ser Gly
```

Fig. 71

```
                                 2550                      2560
      2520          2530          2540           TCC CTG GGG GAC GGT CTA
ATC ACC GTA GAT GCT CAA AAC CAG CTC GCT GCA     Ser Leu Gly Asp Gly Leu
Ile Thr Val Asp Ala Gln Asn Gln Leu Ala Ala 2600                      2610
      2570          2580          2590           GGG CCC GGA CTT ACA ATA
GAA AGC AGA GAT AAT AAA ACT GTC GTT AAG GCT     Gly Pro Gly Leu Thr Ile
Glu Ser Arg Asp Asn Lys Thr Val Val Lys Ala 2650                      2660
      2620          2630          2640           CAG GTC AAC CCG
ACT AAT CAA GCT CTT ACT GTT GCT CTT CAG GGC AAC GGG CTT  Gln Val Asn Pro
Thr Asn Gln Ala Leu Thr Val Ala Leu Gln Gly Asn Gly Leu 2700                      2710
      2670          2680          2690           CTC AAC TTT GCA
GAA GGG CAA CTG CAG CTA AAC ATT ACT GCC GGT CAG GGC     Leu Asn Phe Ala
Glu Gly Gln Leu Gln Leu Asn Ile Thr Ala Gly Gln Gly 2750                      2760
      2720          2730          2740           CAT TTT CCC CCT GGC
AAC AAC AGC CTC GCC GTG GAG CTG GGC TCG GGC CTG     His Phe Pro Pro Gly
Asn Asn Ser Leu Ala Val Glu Leu Gly Ser Gly Leu 2800                      2810
      2770          2780          2790           GGA GAT ATA GAC ATC CGA GAT AAT
CAA AAC CAA GTA AGC CTT TAT CCC GGA GAT        Gly Asp Ile Asp Ile Arg Asp Asn
Gln Asn Gln Val Ser Leu Tyr Pro Gly Asp
```

Fig. 7J

```
2820                  2830                  2840                  2850                  2860
AGG GTG ACT GTG CCC GCT GGG CCA GGC CTG AGA ATG CTC AAC CAC CAA CTT
Arg Val Thr Val Pro Ala Gly Pro Gly Leu Arg Met Leu Asn His Gln Leu 2870                  2880                  2890                  2900                  2910
GCC GTA GCT TCC GGA GAC GGT TTA GAA GTC CAC AGC GAC ACC CTC CGG TTA
Ala Val Ala Ser Gly Asp Gly Leu Glu Val His Ser Asp Thr Leu Arg Leu 2920                  2930                  2940                  2950                  2960                  2970
AAG CTC TCC CAC GGC CTG ACA TTT GAA AAT GGC GCC GTA CGA GCA AAA CTA
Lys Leu Ser His Gly Leu Thr Phe Glu Asn Gly Ala Val Arg Ala Lys Leu 2980                  2990                  3000                  3010                  3020
GGA CCA GGA CTT GGC ACA GAC GAC TCT GGT CGG TCC GTG GTT CGC ACA GGT
Gly Pro Gly Leu Gly Thr Asp Asp Ser Gly Arg Ser Val Val Arg Thr Gly 3030                  3040                  3050                  3060                  3070
CGA GGA CTT AGA GTT GCA AAC GGC CAA GTC CAG ATC TTC AGC GGA AGA GGC
Arg Gly Leu Arg Val Ala Asn Gly Gln Val Gln Ile Phe Ser Gly Arg Gly 3080                  3090                  3100                  3110                  3120
ACC GCC ATC GGC GAT AGC AGC ACT CTC AAC ATC CGG GCG CCC CTA
Thr Ala Ile Gly Thr Asp Ser Ser Leu Thr Leu Asn Ile Arg Ala Pro Leu
```

Fig. 7K

```
      3130            3140             3150              3160             3170
CAA TTT TCT GGA CCC GCC TTG ACT GCT AGT TTG CAA GGC AGT GGT CCG ATT
Gln Phe Ser Gly Pro Ala Leu Thr Ala Ser Leu Gln Gly Ser Gly Pro Ile 3180            3190             3200              3210             3220
ACT TAC AAC AGC AAC AAT GGC ACT TTC GGT CTC TCT ATA GGC CCC GGA ATG
Thr Tyr Asn Ser Asn Asn Gly Thr Phe Gly Leu Ser Ile Gly Pro Gly Met 3230            3240             3250              3260             3270
TGG GTA GAC CAA AAC AGA CTT CAG GTA AAC CCA GGC GCT GGT TTA GTC TTC
Trp Val Asp Gln Asn Arg Leu Gln Val Asn Pro Gly Ala Gly Leu Val Phe 3280            3290             3300              3310             3320
CAA GGA AAC CTT GTC CCA AAC CTT GCG GAT CCG CTG GCT ATT TCC GAC
Gln Gly Asn Leu Val Pro Asn Leu Ala Asp Pro Leu Ala Ile Ser Asp 3330            3340             3350              3360             3370
AGC AAA ATT AGT CTC AGT CTC GGT CCC GGC CTG ACC CAA GCT TCC AAC GCC
Ser Lys Ile Ser Leu Ser Leu Gly Pro Gly Leu Thr Gln Ala Ser Asn Ala 3380            3390             3400              3410             3420
CTG ACT TTA AGT TTA GGA AAC GGG CTT GAA TTC TCC AAT CAA GCC GTT GCT
Leu Thr Leu Ser Leu Gly Asn Gly Leu Glu Phe Ser Asn Gln Ala Val Ala
```

*Fig. 7L*

```
3430          3440          3450          3460          3470          3480
ATA AAA GCG GGC CGG GGC TTA CGC TTT GAG TCT TCC TCA CAA GCT TTA GAG
Ile Lys Ala Gly Arg Gly Leu Arg Phe Glu Ser Ser Ser Gln Ala Leu Glu 3490          3500          3510          3520          3530
AGC AGC CTC ACA GTC GGA AAT GGC TTA ACG CTT ACC GAT ACT GTG ATC CGC
Ser Ser Leu Thr Val Gly Asn Gly Leu Thr Leu Thr Asp Thr Val Ile Arg 3540          3550          3560          3570          3580
CCC AAC CTA GGG GAC GGC CTA GAG GTC AGA GAC AAT AAA ATC ATT GTT AAG
Pro Asn Leu Gly Asp Gly Leu Glu Val Arg Asp Asn Lys Ile Ile Val Lys 3590          3600          3610          3620          3630
CTG GGC GCG AAT CTT CGT TTT GAA AAC GGA GCC GTA ACC GCC GGC ACC GTT
Leu Gly Ala Asn Leu Arg Phe Glu Asn Gly Ala Val Thr Ala Gly Thr Val 3640          3650          3660          3670          3680
AAC CCT TCT GCG CCC GAG GCA CCA ACT CTC ACT GCA GAA CCA CCC CTC
Asn Pro Ser Ala Pro Glu Ala Pro Thr Leu Thr Ala Glu Pro Pro Leu 3690          3700          3710          3720          3730
CGA GCC TCC AAC TCC CAT CTT CAA CTG TCC CTA TCG GAG GGC TTG GTT GTG
Arg Ala Ser Asn Ser His Leu Gln Leu Ser Leu Ser Glu Gly Leu Val Val
```

Fig. 7M

```
3740              3750              3760              3770              3780
CAT AAC AAC GCC CTT GCT CTC CAA CTG GGA GAC GGC ATG GAA GTA AAT CAG
His Asn Asn Ala Leu Ala Leu Gln Leu Gly Asp Gly Met Glu Val Asn Gln 3790              3800              3810              3820              3830
CAC GGA CTT ACT TTA AGA GTA GGC ACT TTG CAA ATG CGT GAC GGC ATT
His Gly Leu Thr Leu Arg Val Gly Ser Gly Leu Gln Met Arg Asp Gly Ile 3840              3850              3860              3870              3880
TTA ACA GTT ACA CCC AGC GGC ACT CCT ATT GAG CCC AGA CTG ACT GCC CCA
Leu Thr Val Thr Pro Ser Gly Thr Pro Ile Glu Pro Arg Leu Thr Ala Pro 3890              3900              3910              3920              3930
CTG ACT CAG ACA GAG AAT GGA ATC GGG CTC GCT CTC GGC GCC GGC TTG GAA
Leu Thr Gln Thr Glu Asn Gly Ile Gly Leu Ala Leu Gly Ala Gly Leu Glu 3940              3950              3960              3970              3980              3990
TTA GAC GAG AGC GCG CTC ACC CTG CAA GTA AAA GTT GGG CCC GGC ATG CGC CTG AAC
Leu Asp Glu Ser Ala Leu Thr Leu Gln Val Lys Val Gly Pro Gly Met Arg Leu Asn 4000              4010              4020              4030              4040
CCT GTA GAA AAG TAT GTA ACC CTG CTC CTG GGT CCT GGC CTT AGT TTT GGG
Pro Val Glu Lys Tyr Val Thr Leu Leu Leu Gly Pro Gly Leu Ser Phe Gly
```

*Fig. 7N*

```
                              4060                      4080                4090
     CAG CCG GCC AAC AGG ACA AAT TAT GAT GTG CGC GTT TCT GTG GAG CCC CCC
4050
     Gln Pro Ala Asn Arg Thr Asn Tyr Asp Val Arg Val Ser Val Glu Pro Pro 4110                      4130                4140
     ATG GTT TTC GGA CAG CGT GGT CAG CTC ACA TTT TTA GTG GGT CAC GGA CTA
4100
     Met Val Phe Gly Gln Arg Gly Gln Leu Thr Phe Leu Val Gly His Gly Leu 4160                      4180                4190
     CAC ATT CAA AAT TCC AAA CTT CAG CTC AAT TTG GGA CAA GGC CTC AGA ACT
4150
     His Ile Gln Asn Ser Lys Leu Gln Leu Asn Leu Gly Gln Gly Leu Arg Thr 4210                      4230                4240
     GAC CCC GTC ACC AAC CAG CTG GAA GTG CCC CTC GGT CAA GGT TTG GAA ATT
4200
     Asp Pro Val Thr Asn Gln Leu Glu Val Pro Leu Gly Gln Gly Leu Glu Ile 4260                      4280                4290
     GCA GAC GAA TCC CAG GTT AGG GTT AAA TTG GGC GAT GGC CTG CAG TTT GAT
4250
     Ala Asp Glu Ser Gln Val Arg Val Lys Leu Gly Asp Gly Leu Gln Phe Asp 4310                      4330                4340
     TCA CAA GCT CGC ATC ACT ACC GCT CCT AAC ATG GTC ACT GAA ACT CTG TGG
4300
     Ser Gln Ala Arg Ile Thr Thr Ala Pro Asn Met Val Thr Glu Thr Leu Trp
```

*Fig. 70*

```
4350                4360                4370            4380                4390
ACC GGA ACA GGC AGT AAT GCT AAT GTT ACA TGG CGG GGC TAC ACT GCC CCC
Thr Gly Thr Gly Ser Asn Ala Asn Val Thr Trp Arg Gly Tyr Thr Ala Pro 4400                4410                4420                4430                4440
GGC AGC AAA CTC TTT TTG AGT CTC ACT CGG TTC AGC ACT GGT CTA GTT TTA
Gly Ser Lys Leu Phe Leu Ser Leu Thr Arg Phe Ser Thr Gly Leu Val Leu 4450                4460                4470                4480                4490            4500
GGA AAC ATG ACT ATT GAC AGC AGC AAT GCA TCC TTT GGG CAA TAC ATT AAC GCG
Gly Asn Met Thr Ile Asp Ser Ser Asn Ala Ser Phe Gly Gln Tyr Ile Asn Ala 4510                4520                4530                4540                4550
GGA CAC GAA CAG ATC GAA TGC TTT ATA TTG GAC AAT CAG GGT AAC CTA
Gly His Glu Gln Ile Glu Cys Phe Ile Leu Leu Asp Asn Gln Gly Asn Leu 4560                4570                4580                4590                4600
AAA GAA GGA TCT AAC TTG CAA GGC ACT TGG GAA GTG AAG AAC AAC CCC TCT
Lys Glu Gly Ser Asn Leu Gln Gly Thr Trp Glu Val Lys Asn Asn Pro Ser 4610                4620                4630                4640                4650
GCT TCC AAA GCT GCT TTT TTG CCT TCC ACC GCC CTA TAC CCC ATC CTC AAC
Ala Ser Lys Ala Ala Phe Leu Pro Ser Thr Ala Leu Tyr Pro Ile Leu Asn
```

Fig. 7P

```
      4660                4670                4680                4690                4700
GAA AGC CGA GGG AGT CTT CCT GGA AAA AAT CTT GTG GGC ATG CAA GCC ATA
Glu Ser Arg Gly Ser Leu Pro Gly Lys Asn Leu Val Gly Met Gln Ala Ile 4710                4720                4730                4740                4750
CTG GGA GGC GGG GGC ACT TGC ACT GTG ATA GCC ACC CTC AAT GGC AGA CGC
Leu Gly Gly Gly Gly Thr Cys Thr Val Ile Ala Thr Leu Asn Gly Arg Arg 4760                4770                4780                4790                4800
AGC AAC AAC TAT CCC GCG GGC CAG TCC ATA ATT TTC GTG TGG CAA GAA TTC
Ser Asn Asn Tyr Pro Ala Gly Gln Ser Ile Ile Phe Val Trp Gln Glu Phe 4810                4820                4830                4840                4850
AAC ACC ATA GCC CGC CAA CCT CTG AAC CAC TCT ACA CTT ACT TTT TCT TAC
Asn Thr Ile Ala Arg Gln Pro Leu Asn His Ser Thr Leu Thr Phe Ser Tyr 4860                4870                4880                4890                4900
TGG ACT TA AAT AAG TTG GAA ATA AAG AGT TAA ACT GAA TGT TTA AGT GCA
Trp Thr 4910                4920                4930                4940                4950
ACA GAC TTT TAT TGG TTT TGG CTC ACA ACA AAT TAC AAC AGC ATA GAC AAG 4960                4970                4980                4990                5000
TCA TAC CGG TCA AAC AAC ACA GGC TCT CGA AAA CGG GCT AAC CGC TCC AAG
```

Fig. 7Q

```
5010      5020      5030           5040                    5050           5060
AAT CTG TCA CGC AGA CGA GCA AGT CCT AAA TGT TTT TTC ACT CTC TTC GGG
     5070           5080           5090                    5100
GCC AAG TTC AGC ATG TAT CGG ATT TTC TGC TTA CAC CTT T
```

Fig. 7R

```
Ad2    MSKEIPTPYMWSYQPQMGLAAGAAQDYSTRINYMSAGPHMISRVNGIRAH      50
BAV3           LIKQPVVGTTHV-----------------------EMPRNEVLEQH      23
              :. :  . ::                              .::   :
Ad2    RNRILLEQAAITTTPRNNLNPRSWPAALVYQESPAPTTVVLPRDAQAEVQ     100
BAV3   LTSHGAQIAGGG-----AAGDYFKSPTSARTLIPLTASCL------RPDG      62
        .:  :::.:::     . :           . :   .      ::::
Ad2    MTNSGAQLAGGFRHRVRSPGQGITHLKIRGRGIQLNDESVSSSLGLRPDG     150
BAV3   VFQLGGGSRSSFNPLQTDFAFHALPSRPRHGGIGSRQFVEEFVPAVYLNP     112
        :.:.::  ::::  :::: :..     :  ::  ::::. ::.:::::.:: ::
Ad2    TFQIGGAGRSSFTPRQAILTLQTSSSEPRSGGIGTLQFIEEFVPSVYFNP     200
BAV3   YSGPPDSYPDQFIRHYNVYSNSVSGYS       139
        .::::   :::::::   .       :   ::
Ad2    FSGPPGHYPDQFIPNFDAVKDSADGYD       227
```

FIG. 8A

```
BAV3    M------EPDGVHAEQQFILNQISCANTALQRQREELASLVMLHACKRGL         77
        :      : ::. .::  .       : .    ::    .: ::  ::::.
Ad5     MTDTLDLEMDGIITEQRLL--ERRRAAAEQQRMNQELQDMVNLHQCKRGI         48

BAV3    FCPVKTYKLSLNASASEHSLHFEKSPSRFTLVNTHAGASVRVALHHQGAS        127
        :: ::  :...  . .. : :  :   : ::          ... :   .
Ad5     FCLVKQAKVTYDSNTTGHRLSYKLPTKRQKLVVMVGEKPITITQHSVETE         98

BAV3    GSIRCSCSHAECLPVLLKTLCAFNFLD                               154
        :  :  :    : : :.:::.:     :
Ad5     GCIHSPCQGPEDLCTLIKTLCGLKDLIPFN                            128
```

FIG. 8B

```
BAV3  1 - MKRSVPQD--FNLVYPYKAKR-----PNIMPPFFDRNGFVENQEATLAML      -43
          ::::  :      :: :::::          :::    ::  :: :::
Ad2   1 - MKRARPSEDTFNPVYPYDTETGPPTVPFLTPPFVSPNGFQESPPGVLSLR      -50

BAV3  1 - VEKPLTFDKE-GALTLGVGRGIRINPAGLLETNDLASAVFPPLASDEAGN      -92
          :: ::  : :  :: :::  :::::::
Ad2   1 - VSEPL--DTSHGMLALKMGSGLTLDKAGNLTSQNVTTV------------      -86

BAV3  1 - VTLNMSDGLYTKDNKLAVKVGPGLSLDSNNALQVHTGDGLTVTDDKVSLN      -142
                    ::: ::::    :::::  :::  ::::  :
Ad2   1 - ----TQPLKKTKSNISLDTSAPLTI-TSGALTVATTAPLIVTSGALSVQ      -130

BAV3  1 - TQAPLSTTSAGLSLLLGPSLHLGEEERLTVNTGAGLQISNNALAVKVGSG      -192
            : :::
Ad2   1 - SQAPLT-------------VQDSKLSIATKGPITVSDGKLALQTSAP      -164

BAV3  1 - ITVDAQNQLAASLGDGLESRDNKTVVKAGPGLTITNQALTVATGNGLQVN      -242
                  :     :::       ::::
Ad2   1 - LSGSDSDTLTVT------------------ASPPLTTATGS-LGIN      -191

BAV3  1 - PEGQLQLNITAGQGLNFANNSLAVELGSGLHFPPGQNQVSLYPGDGIDIR      -292
                  :          :  ::
Ad2   1 - MEDPIYVN--------NGKIGIKISGPLQVAQ------      -215

BAV3  1 - DNRVTVPAGPGLRMLNHQLAVASGDGLEVHSDTLRLKLSHGLTFENGAVR      -342
                                    :::: :
Ad2   1 - ---------------------------NSDTLTVVTGPGVTVEQNSLR      -236
```

*Fig. 8C*

```
BAV3  - AKLGPGLGTDDSGRSVVRTGRGLRVANGQVQIFSGRGTAIGTDSSLTLNI  -392
              ::    :   ::    ::::   :
Ad2   - TKVAGAIGYDSSNNMEIKTGGGMRINNNL--LILDVDYPFDAQTKLRLKL  -284
                                       :
BAV3  - RAPLQFSGPALTASLQGSGPITYNSNNGTFGLSIGPGMWVDQNRLQVNPG  -442
         :  :: :     :
Ad2   - ----------GQGPLYINASHN---------------------LDINYN  -302

BAV3  - AGLVFQGNNLVPNLADPLAISDKISLSLGPGLTQASNALTLSLGNGLEF  -492
         ::      :: :::    :
Ad2   - RGLYL------------FNASNNTKKLEVSIKKSS--------GLNF   -329

BAV3  - SNQAVAIKAGRGLRFESSSQALESSLTVGNGLTLTDTVIRPNLGDGLEVR  -542
          :   :::  :::
Ad2   - DNTAIAINAGKGLEFDTNT------------------------------  -348

BAV3  - DNKIIVKLGANLRFENGAVTAGTVNPSAPEAPPTLTAEPPLRASNSHLQL  -592
Ad2   - -------------------------------------------------  -348

BAV3  - SLSEGLVVHNNALALQLGDGMEVNQHGLTLRVGSGLQMRDGILTVTPSGT  -642
          ::::   ::::
Ad2   - --------------------SESPDIN--PIKTKIGSGID------YNENGA  -372

BAV3  - PIEPRLTAPLTQTENGIGLALGAGLELDESALQVKVGPGMRLNPVEKYVT  -692
           ::::   :
Ad2   - ---------------KLGAGLSFDNSG----------------------  -387
```

Fig. 8D

```
BAV3  - LLLGPGLSFGQPANRTNYDVRVSVEPPMVFGQRGQLTFLVGHGLHIQNSK -742
              :   :   : :  :    : ::        :
Ad2   - -----AITIG-----NKNDDKLTLWTTPDPSP-----------------NCR -412

BAV3  - LQLNLGQGLRTDPVTNQLEVPLGQGLEIADESQVRVKLGDGLQFDSQARI -792
                                          ::
Ad2   - IHSD----------------------------------NDCKFTLVLT---KCGSQVLA -434

BAV3  - TTAPNMVTETLWTGTGSNANVTWRGYTAPGSKLFLSLTRFSTGLVLGNMT -842
         ::     :    :   :   :    : :   :
Ad2   - TVAALAVSGDLSSMTGTVASVS------------IFLRFDQ--NGVLMENSS -472

BAV3  - IDSNASFGQYINAGHEQIECFILLDNQGNLKEGSNLQGTWEVKNNPSASK -892
                                         ::
Ad2   - LKKHY-------------------------------WNFRNGNS------TNANPYTNA -494

BAV3  - AAFLPSTALYPILNESRGSLPGKNLVGMQAILGGGGTCTVIA-TLNGRRS -941
         ::                                  ::::
Ad2   - VGFMPNLLAYP---KTQSQTAKNNIVSQVYLHGDKTKPMILTITLNGTSE -541

BAV3  - NNYPAGQSII---FVWQ-EFNTIARQPLNHSTLTFSYWT -976
                       ::::
Ad2   - STETSEVSTYSMSFTWSWESGKYTTETFATNSYTFSYIAQE -582
```

Fig. 8E

CATCATCAAT AATCTACAGT ACACTGATGG CAGCGGTCCA ACTGCCAATC ATTTTTGCCA
60

CGTCATTTAT GACGCAACGA CGGCGAGCGT GGCGTGCTGA CGTAACTGTG GGGCGGAGCG
120

CGTCGCGGAG GCGGCGGCGC TGGGCGGGGC TGAGGGCGGC GGGGGCGGCG CGCGGGGCGG
180

CGCGCGGGGC GGGGCGAGGG GCGGAGTTCC GCACCCGCTA CGTCATTTTC AGACATTTTT
240

TAGCAAATTT GCGCCTTTTG CAAGCATTTT TCTCACATTT CAGGTATTTA GAGGGCGGAT
300

TTTTGGTGTT CGTACTTCCG TGTCACATAG TTCACTGTCA ATCTTCATTA CGGCTTAGAC
360

AAATTTTCGG CGTCTTTTCC GGGTTTATGT CCCCGGTCAC CTTTATGACT GTGTGAAACA
420

CACCTGCCCA TTGTTTACCC TTGGTCAGTT TTTTCGTCTC CTAGGGTGGG AACATCAAGA
480

ACAAATTTGC CGAGTAATTG TGCACCTTTT TCCGCGTTAG GACTGCGTTT CACACGTAGA
540

CAGACTTTTT CTCATTTTCT CACACTCCGT CGTCCGCTTC AGAGCTCTGC GTCTTCGCTG
600

CCACCATGAA GTACCTGGTC CTCGTTCTCA ACGACGGCAT GAGTCGAATT GAAAAAGCTC
660

TCCTGTGCAG CGATGGTGAG GTGGATTTAG AGTGTCATGA GGTACTTCCC CCTTCTCCCG
720

CGCCTGTCCC CGCTTCTGTG TCACCCGTGA GGAGTCCTCC TCCTCTGTCT CCGGTGTTTC
780

CTCCGTCTCC GCCAGCCCCG CTTGTGAATC CAGAGGCGAG TTCGCTGCTG CAGCAGTATC
840

GGAGAGAGCT GTTAGAGAGG AGCCTGCTCC GAACGGCCGA AGGTCAGCAG CGTGCAGTGT
900

GTCCATGTGA GCGGTTGCCC GTGGAAGAGG ATGAGTGTCT GAATGCCGTA AATTTGCTGT
960

TTCCTGATCC CTGGCTAAAT GCAGCTGAAA ATGGGGGTGA TATTTTTAAG TCTCCGGCTA
1020

TGTCTCCAGA ACCGTGGATA GATTTGTCTA GCTACGATAG CGATGTAGAA GAGGTGACTA
1080

GTCACTTTTT TCTGGATTGC CCTGAAGACC CCAGTCGGGA GTGTTCATCT TGTGGGTTTC
1140

ATCAGGCTCA AAGCGGAATT CCAGGCATTA TGTGCAGTTT GTGCTACATG CGCCAAACCT
1200

ACCATTGCAT CTATAGTAAG TACATTCTGT AAAAGAACAT CTTGGTGATT TCTAGGTATT
1260

Fig. 20A

```
GTTTAGGGAT TAACTGGGTG GAGTGATCTT AATCCGGCAT AACCAAATAC ATGTTTTCAC
1320

AGGTCCAGTT TCTGAAGAGG AAATGTGAGT CATGTTGACT TTGGCGCGCA AGAGGAAATG
1380

TGAGTCATGT TGACTTTGGC GCGCCCTACG GTGACTTTAA AGCAATTTGA GGATCACTTT
1440

TTTGTTAGTC GCTATAAAGT AGTCACGGAG TCTTCATGGA TCACTTAAGC GTTCTTTTGG
1500

ATTTGAAGCT GCTTCGCTCT ATCGTAGCGG GGGCTTCAAA TCGCACTGGA GTGTGGAAGA
1560

GGCGGCTGTG GCTGGGACGC CTGACTCAAC TGGTCCATGA TACCTGCGTA GAGAACGAGA
1620

GCATATTTCT CAATTCTCTG CCAGGGAATG AAGCTTTTTT AAGGTTGCTT CGGAGCGGCT
1680

ATTTTGAAGT GTTTGACGTG TTTGTGGTGC CTGAGCTGCA TCTGGACACT CCGGGTCGAG
1740

TGGTCGCCGC TCTTGCTCTG CTGGTGTTCA TCCTCAACGA TTTAGACGCT AATTCTGCTT
1800

CTTCAGGCTT TGATTCAGGT TTTCTCGTGG ACCGTCTCTG CGTGCCGCTA TGGCTGAAGG
1860

CCAGGGCGTT CAAGATCACC CAGAGCTCCA GGAGCACTTC GCAGCCTTCC TCGTCGCCCG
1920

ACAAGACGAC CCAGACTACC AGCCAGTAGA CGGGGACAGC CCACCCCGGG CTAGCCTGGA
1980

GGAGGCTGAA CAGAGCAGCA CTCGTTTCGA GCACATCAGT TACCGAGACG TGGTGGATGA
2040

CTTCAATAGA TGCCATGATG TTTTTTATGA GAGGTACAGT TTTGAGGACA TAAAGAGCTA
2100

CGAGGCTTTG CCTGAGGACA ATTTGGAGCA GCTCATAGCT ATGCATGCTA AAATCAAGCT
2160

GCTGCCCGGT CGGGAGTATG AGTTGACTCA ACCTTTGAAC ATAACATCTT GCGCCTATGT
2220

GCTCGGAAAT GGGGCTACTA TTAGGGTAAC AGGGGAAGCC TCCCCGGCTA TTAGAGTGGG
2280

GGCCATGGCC GTGGGTCCGT GTGTAACAGG AATGACTGGG GTGACTTTTG TGAATTGTAG
2340

GTTTGAGAGA GAGTCAACAA TTAGGGGGTC CCTGATACGA GCTTCAACTC ACGTGCTGTT
2400

TCATGGCTGT TATTTTATGG GAATTATGGG CACTTGTATT GAGGTGGGGG CGGGAGCTTA
2460

CATTCGGGGT TGTGAGTTTG TGGGCTGTTA CCGGGGAATC TGTTCTACTT CTAACAGAGA
2520
```

Fig. 20B

TATTAAGGTG AGGCAGTGCA ACTTTGACAA ATGCTTACTG GGTATTACTT GTAAGGGGA
2580

CTATCGTCTT TCGGGAAATG TGTGTTCTGA GACTTTCTGC TTTGCTCATT TAGAGGGAGA
2640

GGGTTTGGTT AAAAACAACA CAGTCAAGTC CCCTAGTCGC TGGACCAGCG AGTCTGGCTT
2700

TTCCATGATA ACTTGTGCAG ACGGCAGGGT TACGCCTTTG GGTTCCCTCC ACATTGTGGG
2760

CAACCGTTGT AGGCGTTGGC CAACCATGCA GGGGAATGTG TTTATCATGT CTAAACTGTA
2820

TCTGGGCAAC AGAATAGGGA CTGTAGCCCT GCCCCAGTGT GCTTTCTACA AGTCCAGCAT
2880

TTGTTTGGAG GAGAGGGCGA CAAACAAGCT GGTCTTGGCT TGTGCTTTTG AGAATAATGT
2940

ACTGGTGTAC AAAGTGCTGA GACGGGAGAG TCCCTCAACC GTGAAAATGT GTGTTTGTGG
3000

GACTTCTCAT TATGCAAAGC CTTTGACACT GGCAATTATT TCTTCAGATA TTCGGGCTAA
3060

TCGATACATG TACACTGTGG ACTCAACAGA GTTCACTTCT GACGAGGATT AAAAGTGGGC
3120

GGGGCCAAGA GGGGTATAAA TAGGTGGGGA GGTTGAGGGG AGCCGTAGTT TCTGTTTTTC
3180

CCAGACTGGG GGGGACAACA TGGCCGAGGA AGGGCGCATT TATGTGCCTT ATGTAACTGC
3240

CCGCCTGCCC AAGTGGTCGG GTTCGGTGCA GGATAAGACG GGCTCGAACA TGTTGGGGGG
3300

TGTGGTACTC CCTCCTAATT CACAGGCGCA CCGGACGGAG ACCGTGGGCA CTGAGGCCAC
3360

CAGAGACAAC CTGCACGCCG AGGGAGCGCG TCGTCCTGAG GATCAGACGC CCTACATGAT
3420

CTTGGTGGAG GACTCTCTGG GAGGTTTGAA GAGGCGAATG GACTTGCTGG AAGAATCTAA
3480

TCAGCAGCTG CTGGCAACTC TCAACCGTCT CCGTACAGGA CTCGCTGCCT ATGTGCAGGC
3540

TAACCTTGTG GGCGGCCAAG TTAACCCCTT TGTTTAAATA AAAATACACT CATACAGTTT
3600

ATTATGCTGT CAATAAAATT CTTTATTTTT CCTGTGATAA TACCGTGTCC AGCGTGCTCT
3660

GTCAATAAGG GTCCTATGCA TCCTGAGAAG GGCCTCATAT ACCATGGCAT GAATATTAAG
3720

ATACATGGGC ATAAGGCCCT CAGAAGGGTT GAGGTAGAGC CACTGCAGAC TTTCGTGGGG
3780

Fig. 20C

AGGTAAGGTG TTGTAAATAA TCCAGTCATA CTGACTGTGC TGGGCGTGGA AGGAAAAGAT
3840

GTCTTTTAGA AGAAGGGTGA TTGGCAAAGG GAGGCTCTTA GTGTAGGTAT TGATAAATCT
3900

GTTCAGTTGG GAGGGATGCA TTCGGGGCT AATAAGGTGG AGTTTAGCCT GAATCTTAAG
3960

GTTGGCAATG TTGCCCCCTA GGTCTTTGCG AGGATTCATG TTGTGCAGTA CCACAAAAAC
4020

AGAGTAGCCT GTGCATTTGG GGAATTTATC ATGAAGCTTG GAGGGAAGG CATGAAAAAA
4080

TTTTGAGATG GCTTTATGGC GCCCCAGGTC TTCCATGCAT TCGTCCATAA TAATAGCAAT
4140

AGGCCCGGTT TTGGCTGCCT GGGCAAACAC GTTCTGAGGG TGGGCGACAT CATAGTTGTA
4200

GTCCATGGTC AGGTCTTCAT AGGACATGAT CTTAAAGGCA GGTTTTAGGG TGCTGCTTTG
4260

AGGAACCAGA GTTCCTGTGG GGCCGGGGGT GTAGTTCCCT TCACAGATTT GGGTCTCCCA
4320

AGCAAGCAGT TCTTGCGGGG GTATCATGTC AACTTGGGGG ACTATAAAAA AAACAGTTTC
4380

GGGAGGTGGT TGAATGAGGC CCGTAGACAT AAGGTTTCTG AGGAGCTGGG ATTTTCCACA
4440

ACCGGTTGGT CCGTAGACCA CCCCAATAAC GGGTTGCATG GTAAAGTTTA AAGATTTGCA
4500

TGAACCGTCA GGGCGCAGAT ATGGCATGGT GGCATTCATG GCATCTCTTA TCGCCTGATT
4560

ATAGTCTGAG AGGGCATTGA GTAGGGTGGC GCCCCCCATA GCCAGTAGCT CGTCCAAGGA
4620

AGAAAAGTGT CTAAGAGGTT TGAGGCCTTC AGCCATGGGC ATGGACTCTA AGCACTGTTG
4680

CATGAGAGCA CATTTGTCCC AAAGCTCAGA GACGTGGTCT AGTACATCTC CATCCAGCAT
4740

AGCTCTTTGT TTCTTGGGTT GGGGTGGCTG TTGCTGTAGG GGGCGAGACG GTGACGGTCG
4800

ATGGCCCGCA GGGTGCGGTC TTTCCAGGGC CTGAGCGTCC TCGCCAGGGT CGTCTCGGTG
4860

ACCGTGAAGG GCTGCTGATG CGTCTGTCTG CTGACCAGCG AGCGCCTCAG GCTGAGCCTG
4920

CTGGTGCCGA ACTTTTCGTC GCCTAGCTGT TCAGTGGAAT AATAACAAGT CACCAGAAGG
4980

TCGTAGGAGA GTTGTGAGGT GGCATGGCCT TTGCTCGAAG TTTGCCAGAA CTCTCGGCGG
5040

Fig. 20D

```
CGGCAGCTTG GGCAGTAGAT GTTTTTAAGG GCATATAGTT TGGGGGCTAA GAAGACAGAT
5100

TCCTGGCTGT GGGCGTCTCC GTGGCAGCGG GGGCACTGGG TCTCGCATTC CACAAGCCAA
5160

GTCAGCTGAG GGTTGGTGGG ATCAAAGACC AGAGGACGGT TATTACCTTT CAGGCGGTGC
5220

TTGCCTCGGG TGTCCATGAG TTCCTTTCCC CTTTGGGTGA GAAACATGCT GTCCGTGTCT
5280

CCGTAGACAA ATTTGAGAAT CCGGTCTTCT AGGGGAGTGC CTCTGTCTTC TAAATAGAGG
5340

ATGTCTGCCC ATTCAGAGAC AAAGGCTCTA GTCCACGCGA GGACAAATGA AGCTATGTGT
5400

GAGGGGTATC TGTTATTAAA TATGAGAGAG GATTTTTTTT GCAAAGTATG CAGGCACAGG
5460

GCTGAGTCAT CAGCTTCCAG AAAGGTGATT GGTTTGTAAG TGTATGTCAC GTGATGGTTC
5520

TGGGGGTCTC CCAGGGTATA AAAGGGGGCG TCTTCGTCTG AGGAGCTATT GCTAGTGGGT
5580

GTGCACTGAC GGTGCTTCCG CGTGGCATCC GTTTGCTGCT TGACGGGTGA GTAGGTGATT
5640

TTTAGCTCTG CCATGACAGA GGAGCTCAGG TTGTCAGTTT CCACGAAGGC GGTGCTTTTG
5700

ATGTCGTAGG TGCCGTCTGA AATGCCTCTA ACATATTTGT CTTCCATTTG GTCAGAAAAG
5760

ACAGTGACTC TGTTGTCTAG CTTAGTGGCA AAGCTGCCAT ACAGGGCATT GGACAGCAGT
5820

TTGGCAATGC TTCTGAGAGT TTGGTTTTTC TCTTTATCCG CCCTTTCCTT GGGCGCAATG
5880

TTAAGTTGCA CGTAGTCTCT AGCCAGACAC TCCCACTGGG GAAATACTGT GGTGCGGGGG
5940

TCGTTGAGAA TTTGGACTCT CCAGCCGCGG TTATGAAGCG TGATGGCATC CAAACAAGTT
6000

ACCACTTCCC CCCGTAGTGT CTCGTTGGTC CAGCAGAGGC GACCTCCTTT TCTGGAGCAG
6060

AAGGGCGGTA TAACGTCCAA GAATGCTTCT GGGGGTGGGT CTGCATCAAT GGTGAATATC
6120

GCGGGCAGTA GGGTGCGATC AAAATAGTCA ATGGGTCTGT GCAACTGGGT TAGGCGGTCT
6180

TGCCAGTTTT TAATTGCAAG CGCTCGATCA AAGGGGTTCA AAGGTTTTCC CGCTGGGAAA
6240

GGATGGGTGA GGGCGCTGGC ATACATGCCG CAGATGTCAT ACACATAGAT GGCTTCTGTT
6300
```

*Fig. 20E*

AGGACGCCTA TGTAGGTAGG ATAGCATCGG CCGCCCCGAA TACTTTCTCT AACGTAATCA
6360

TACATTTCAT TGGAAGGGGC TAGTAGAAAG TTGCCCAGAG AGCTCCTGTT GGGACGCTGG
6420

GATCGGTAGA CTACCTGTCT GAAGATGGCA TGGGAATTGG AGCTGATGGT GGGCCTTTGG
6480

AGGACATTGA AATTGCAGTG GGGCAGCCCC ACTGACGTGT GAACAAAGTC CAAATAAGAT
6540

GCTTGGAGTT TTTTAACCAA TTCGGCCGTA ACCAGCACGT CCATAGCACA GTAGTCCAAG
6600

GTGCGTTGCA CAATATCATA GGCACCTGAA TTCTCTTGCA GCCAGAGACT CTTATTGAGA
6660

AGGTACTCCT CGTCGCTGGA CCAGTAGTCC CTCTGAGGAA AAGAATCTGC GTCGGTTCGG
6720

TAGGTACCTA ACATGTAAAA TTCATTTACA GCTTTGTAAG GGCAGCAGCC TTTTTCCACG
6780

GGTAAAGCGT AAGCGGCAGC TGCGTTCCTG AGACTCGTGT GCGTGAGAGC AAAGGTATCT
6840

CGGACCATGA ACTTCACAAA CTGAAATTTA TAGTCTGCTG AGGTGGGAGT GCCTTCCTCC
6900

CAGTCTTTGA AGTCTTTTCG AGCAGCATGT GTGGGGTTAG GCAGAGCAAA AGTTAAGTCA
6960

TTGAAAAGAA TCTTGCCACA ACGAGGCATG AAATTTCTAC TGACTTTAAA AGCAGCTGGA
7020

ATACCTTGTT TGTTGTTAAT GACTTGTGCG GCTAGAACAA TCTCATCAAA GCCGTTTATG
7080

TTGTGCCCTA CGACATAGAC TTCCAAGAAA GTCGGTTGCC CTTTGAGTTC AAGCGTACAC
7140

AGTTCCTCGA AAGGAATGTC GCTGGCATGG ACATAGCCCA GTTTGAGGCA GAGGTTTTCT
7200

AAGCACGGAT TATCTGCCAG GAACTGGCGC CAAAGCAAAG TGCTGGCAGC TTCTTGAAGG
7260

GCATCCCGAT ACTGTTTAAA CAAGCTGCCT ACTTTGTTTC TTTGCGGGTT GAGGTAGTAG
7320

AAGGTATTTG CTTGCTTTGG CCAGCTTGAC CACTTTTGCT TTTTAGCTAT GTTAACAGCC
7380

TGTTCGCATA GCTGCGCGTC ACCAAACAAA GTAAACACGA GCATAAAAGG CATGAGTTGC
7440

TTGCCAAAGC TACCGTGCCA AGTGTATGTT TCCACATCAT AGACGACAAA GAGGCGCCGG
7500

GTGTCGGGGT GAGCGGCCCA GGGGAAAAAC TTTATTTCTT CCCACCAGTC CGAAGATTGG
7560

Fig. 20F

```
GTGTTTATGT GGTGAAAGTA AAAGTCCCGG CGGCGAGTGC TGCAGGTGTG CGTCTGCTTA
7620

AAATACGAAC CGCAGTCGGC ACATCGCTGG ACCTCTGCGA TGGTGTCTAT GAGATAGAGC
7680

TTTCTCTTGT GAATAAGAAA GTTGAGGGGG AAGGGAAGGC GCGGCCTGTC AGCGCGGGCC
7740

GGGATGCTTG TAATTTTCAG CTTCCCCTTG TATGTTTTGT AAACGCACAT ATTTGCGTTG
7800

CAGAACCGGA CGAGCGTGTC TTGGAATGAA AGGATATTTT CTGGTTTTAA ATCAAATGGG
7860

CAGTGCTCCA AGTGCAGTTC AAAAAGGTTT CGGAGACTGC TGGAAACGTC TGCGTGATAC
7920

TTGACTTCCA GGGTGGTCCC GTCTTCAGTC TGACCGTGCA GCCGTAGGGT ACTGCGTTTG
7980

GCGACCAGGG GCCCCCTTGG GGCTTTCTTT AAAGGGGACG TCGAGGGCCG AGGGGCGGCC
8040

TTTGCCTTTC GGGCCTGAGG GGCGGTAGCT GGACCGGATC GTTGAGTTCG GCATGGGTT
8100

GCAGCTGTTG GCGCAGGTCT GATGCGTGCT GCACGACTCT GCGGTTGATT CTCTGAATCT
8160

CCGGGTGTTG GGTGAATGCT ACTGGCCCCG TCACTTTGAA CCTGAAAGAG AGGTCGACAG
8220

AGTTAATAGA TGCATCGTTA AGCTCCGCCT GTCTAATAAT TTCTTCCACG TCACCGCTGT
8280

GGTCTCGGTA AGCAATGTCT GTCATAAACC GTTCGATCTC TTCCTCGTCC AGTTCTCCGC
8340

GACCAGCTCG GTGGACCGTG GCTGCCAAGT CCGTGCTAAT GCGTCGCATG AGCTGGGAAA
8400

AGGCATTGGT TCCCGGTTCA TTCCACACTC TGCTGTATAT AACAGCGCCA TCTTCGTCTC
8460

GGGCTCGCAT GACCACCTGG CCCAAGTTTA GCTCCACGTG GCGAGCAAAG ACGGGGCTGA
8520

GGCGGAGGTG GTGGTGCAGA TAATTGAGAG TGGTGGCTAT GTGCTCCACG ATGAAGAAGT
8580

AGATGACCCA TCTGCGGATG GTCGACTCGT TAATGTTGCC CTCTCGCTCC AGCATGTTTA
8640

TGGCTTCGTA AAAGTCCACA GCGAAGTTAA AAAACTGCTC GTTGCGGGCG GAGACTGTCA
8700

GCTCTTCTTG CAGGAGACGA ATGACTTCGG CTACGGCGGC GCGGACTTCT TCGGCAAAGG
8760

AGCGCGGCGG CACGTCCTCC TCCTCCTCTT CTTCCCCCTC CAGCGGGGGC ATCTCCAGCT
8820
```

Fig. 20G

```
CTACCGGTTC CGGGCTGGGG GACAGGGAAG GCGGTGCGGG CCGAACGACC CGTCGGCGTC
8880

GGGTGGGCAA GGGGAGACTC TCTATGAATC GCTGCACCAT CTCGCCCCGG CGTATCCGCA
8940

TCTCCTGGGT AACGGCACGC CCGTGTTCTC GGGGTCGGAG CTCAAAAGCT CCGCCCCGCA
9000

GTTCGGTCAG AGGCCGCGCC GCGGGCTGGG GCAGGCTGAG TGCGTCAATA ACATGCGCCA
9060

CCACTCTCTC CGTAGAGGCG GCTGTTTCGA ACCGAAGAGA CTGAGCATCC ACGGGATCGC
9120

TGAAGCGTTG CACAAAAGCT TCTAACCAGT CGCAGTCACA AGGTAGGCTG AGCATAGGTG
9180

AGGCTCGCTC GGTGTTGTTT CTGTTTGGCG GCGGGTGGCT GAGGAGAAAA TTAAAGTACG
9240

CGCACCGCAG GCGCCGGATG GTTGTCAGTA TGATGAGATC CCTGCGACCC GCTTGTTGGA
9300

TTCTGATGCG GTTTGCAAAG CCCCAGGCTT GGTCTTGGCA TCGCCCAGGT TCATGCACTG
9360

TTCTTGGAGG AATCTCTCTA CGGGCACGTT GCGGCGCTGC GGGGGCAGGG TCAGCCATTT
9420

CGGTGCGTCC AAACCCACGC AATGGTTGGA TGAGAGCCAA GTCCGCTACT ACGCGCTCTG
9480

CTAGGACGGC TTGCTGGATC TGCCGCAGCG TTTCATCAAA GTTTTCCAAG TCAATGAAGC
9540

GGTCGTAGGG GCCCGCGTTT ATGGTGTAGG AGCAGTTTGC CATGGTGGAC CAGTCCACAA
9600

TCTGCTGATC TACCCGCACC GTTTCTCGGT ACACCAGTCG GCTATAGGCT CGCGTCTCGA
9660

AAACATAGTC GTTGCAAACG CGCACCACGT ATTGGTAGCC GATTAGGAAG TGCGGCGGCG
9720

GGTATAAGTA GAGCGGCCAG TTTTGCGTGG CCGGCTGTCT GGCGCCCAGA TTCCGTAGCA
9780

TGAGTGTGGG GTATCGGTAC ACGTGACGCG ACATCCAGGA GATGCCCGCG GCCGAAATGG
9840

CGGCCCTGGC GTACTCCCGG GCCCGGTTCC ATATATTCCT GAGAGGACGA AAGATTCCAT
9900

GGTGTGCAGG GTCTGCCCCG TAAGACGCGC GCAATCTCTC GCGCTCTGCA AAAACATAC
9960

AGATGAAACA TTTTTGGGGC TTTTCAGATG ATGCATCCCG CTTTACGGCA AATGAAGCCC
10020

AGATCCGCGG CAGTGGCGGG GGTTCCTGCT GCGGCCGCCG GCGCGAGCGT TGACTCAGGC
10080
```

Fig. 20H

GGTACTACCG CGCCCCCTGG TGTCGAGTGC GGCGAGGGGG AAGGGTTAGC TCGGCTGTAC
10140

GCGCACCCGG ACACACACCC GCGCGTGTGC GTGAAGCGCG ATGCGGCGGA GGCGTACGTT
10200

CCCCGGGAGA ACTTATTCCG CGACCGCAGC GGGGAGGAAC CCGAAGGGAG CCGAGACCTA
10260

AAGTACAAGG CCGGTCGGCA GTTGCGCGCC GGCATGCCCC GAAAGCGGGT GCTGACCGAA
10320

GGGGACTTTG AGGTGGATGA GCGCACTGGC ATCAGCTCAG CCAAAGCCCA CATGGAGGCG
10380

GCCGATCTAG TGCGGGCTTA CGAGCAAACG GTGAAGCAAG AGGCTAATTT TCAAAAGTCA
10440

TTTAATAACC ACGTGCGGAC ACTGATCTCC CGCGAGGAGA CCACCCTGGG TTTGATGCAC
10500

TTGTGGGACT TTGCGGAGGC ATACGCGCAG AACCCCGGCA GCAAGACCCT TACGGCCCAA
10560

GTCTTTCTCA TCGTGCAGCA CTTGCAAGAT GAGGGCATTT TTGGGGAAGC TTTCTTAAGC
10620

ATAGCAGAGC CCGAGGGACG ATGGATGCTA GATCTGCTAA ACATATTGCA GTCCATTGTG
10680

GTGCAAGAGC GCCAGCTTTC GCTATCTGAA AAGGTAGCCG CGGTGAACTA CTCCGTAGTT
10740

ACCCTGGGCA AACATTATGC CCGCAAGATC TTTAAGAGCC CCTTTGTGCC GCTTGACAAG
10800

GAGGTGAAGA TCAGTACATT TTATATGCGC GCGGTGCTTA AGGTCCTGGG TCTAAGTCAC
10860

GACCTGGGCA TGTACAGAAA CGAAAAGGTG GAGAAGCTAG CTAGCATAGG CAGGCGTTCG
10920

GGAGATGAGC GACGCGGAGC TGCTGTTCAA CCTCCGCCGC GCACTAACCA CTGGCGATTC
10980

TGAAGCATTC GATGAAGGCG GGGACTTTAC CTGGGCTCCG CCAACTCGCG CGACCGCGGC
11040

GGCCGCTTTG CCGGGGCCCG AGTTTGAGAG TGAAGAGACG GACGATGAAG TCGACGAATG
11100

AGTGATGCGG ACCCCCGTAT CTTTCAGCTG GTCAGTCGGC AAGAGACCGT AGCCATGGCC
11160

GAAGCGCCCC GAAGCCTGGG CCCCGCCCCT TCCAATCCTA GTTTGCAGGC TTTATTCCAA
11220

AGCCAGCCCA GCGCCGAGCA GGAGTGGCAC GGCGTGCTGG AGAGAGTCAT GGCCCTTAAC
11280

AAAAATGGAG ACTTTGGCTC GCAGCCCCAG GCGAACCGGT TTGGAGCCAT CCTCGAAGCC
11340

Fig. 20I

GTGGTGCCCC CGCGCTCCGA TCCCACCCAT GAAAAAGTGC TAGCTATTGT GAATGCGCTC
11400

TTGGAGACTC AGGCCATCCG TCGCGATGAG GCCGGACAGA TGTACACCGC GCTGTTGCAG
11460

CGGGTGGCCA GATACAACAG TGTGAATGTG CAGGGCAATT TGGACAGGCT GATTCAGGAC
11520

GTGAAGGAGG CTCTGGCGCA GCGCGAGCGC ACCGGGCCGG GGGCCGGCCT AGGGTCTGTG
11580

GTAGCCTTGA ATGCCTTCCT GAGCACACAG CCAGCGGTGG TGGAGAGGGG CCAGGAGAAC
11640

TATGTGGCCT TTGTGAGCGC CTTAAAACTC ATGGTGACCG AGGCGCCGCA GTCTGAGGTT
11700

TACCAGGCCG GACCTAGTTT CTTTTTTCAA ACCAGCCGGC ACGGTTCGCA GACGGTAAAC
11760

CTCAGTCAGG CCTTTGATAA CTTGCGACCC CTCTGGGGCG TGCGCGCGCC AGTACACGAG
11820

CGTACTACCA TCTCCTCTCT GCTCACACCA AACACCCGCT TGCTCTTGCT CCTCATTGCG
11880

CCCTTTACGG ACAGCGTGGG CATATCCCGG GACAGTTACC TGGGGCATCT GCTGACCCTT
11940

TACCGGGAGA CCATAGGTAA CACTCGAGTT GATGAGACCA CGTACAACGA GATCACGGAA
12000

GTGAGTCGGG CCCTGGGCGC CGAAGACGCG TCTAACTTGC AAGCCACTCT CAACTACTTA
12060

CTCACAAATA AGCAGAGCAA GTTGCCACAG GAGTTTTCTC TGAGTCCCGA AGAGGAGCGG
12120

GTGCTGCGCT ACGTGCAGCA ATCTGTCAGT TTATTTTTAA TGCAGGATGG ACACACGGCC
12180

ACCACTGCTC TAGATCAGGC TGCGGCCAAC ATAGCGCCCT CGTTTTACGC GTCCCACCGC
12240

GACTTTATAA ACCGACTGAT GGACTATTTC CAGCGAGCTG CGGCTATGGC CCCTGACTAC
12300

TTTTTACAGG CTGTTATGAA TCCCCACTGG CTCCCGCCGC CGGGTTTCTT TACTCAGGAG
12360

TTTGACTTTC CGGAGCCCAA CGGAGGCTTC CTGTGGGATG ATTTGGACAG CGCGCTCCTA
12420

CGCGCGCACG TAAAAGAAGA GGAGGATCAA GGAGCTGTGG CGGCACGCC GGCGGCTTCG
12480

GCGCCCGCGT CTCGCGCGCA CACACCACCG CCGCCGCCCG GTGCCGCGGA CCTCTTTGCT
12540

CCTAACGCCT TCCGCAATGT GCAAAATAAC GGCGTGGATG AACTTATTGA CGGCTTAAGC
12600

Fig. 20J

```
AGATGGAAGA CTTACGCCCA GGAGAGGCAG GAAGTCGTTG AGCGGCACAG GCGCAGAGAG
12660

GCGCGTCGCC GGGCGCGCGA GGCGCGTCTA GAGTCGAGCG ATGATGACGA CAGCGACCTA
12720

GGGCCGTTTC TACGGGGCAC GGGGCACCTC GTTCACAACC AGTTTATGCA TCTGAAGCCC
12780

CGGGGTCCCC GCCAGTTTTG GTAACCGCAC TGTATTAAGC TGTAAGTCCT CTCATTTGAC
12840

ACTTACCAAA GCCATGGTCT TGCTTCGCCT CTGACACTTT CTCTCCCCCC ACACGCGGCA
12900

CCCTACAGCC TAGGGGCGAT GCTCCAGCCC GAACTGCAGC CAATTCCGCT GTCCCGCCGC
12960

CGGCTTATGA GGCGGTGGTG GCTGGGGCCT TCCAGACGCT TTCTCTTCGA CGAGATCCAC
13020

GTCCCGCCGC GATATGCTGC CGCGTCTGCG GGGAGAAACA GTATCCGTTA TTCCATGCTG
13080

CCCCCGTTGT ATGACACCAC GAAGATATAC CTTATCGACA ACAAATCTTC AGACATCCAA
13140

ACTCTGAATT ACCAAAACGA CCACTCAGAT TACCTCACTA CCATCGTGCA GAACAGCGAC
13200

TTCACGCCCC TGGAGGCTAG CAACCACAGC ATCGAGCTAG ACGAGCGGTC CCGCTGGGGC
13260

GGAAACCTTA AAACCATCCT TTATACAAAC CTGCCTAATA TCACCCAGCA CATGTTTTCT
13320

AACTCTTTTC GGGTAAAGAT GATGGCCTCA AAAAAGACG GCGTGCCCCA GTACGAGTGG
13380

TTCCCCCTAA GGCTGCCCGA GGGTAACTTT TCTGAGACTA TGGTCATTGA CCTCATGAAC
13440

AATGCCATCG TAGAGCTGTA CTTGGCTTTG GGGCGCCAGG AGGGCGTGAA GGAAGAGGAC
13500

ATCGGGGTAA AGATCGATAC GCGCAACTTT AGTCTGGGCT ATGACCCGCA GACCCAGTTA
13560

GTGACGCCCG GCGTATACAC CAATGAAGCT ATGCATGCGG ACATCGTGTT GCTGCCGGGC
13620

TGTGCTATAG ACTTTACGCA CTCCCGATTA ACAACCTCT TGGGCATACG CAAGCGTTTT
13680

CCGTACCAAG AGGGCTTCGT CATCTCCTAT GAGGACCTTA AGGGGGGTAA CATCCCCGCT
13740

TTGATGGACG TGGAGGAGTT TAACAAGAGC AAGACGGTTC GAGCTTTGCG GGAGGACCCC
13800

AAGGGGCGCA GTTATCACGT GGGCGAAGAC CCAGAAGCCA GAGAAAACGA AACCGCCTAC
13860
```

Fig. 20K

CGCAGCTGGT ACCTGGCTTA CAATTACGGG GACCCAGAAA AAGGGGTGCG GGCCACCACA
13920

CTGCTGACTA CCGGCGACGT GACCTGCGGG GTGGAACAGA TCTACTGGAG CTTGCCGGAC
13980

ATGGCACTGG ACCCAGTCAC TTTCAAGGCT TCGCTGAAAA CTAGCAATTA CCCCGTGGTG
14040

GGCACAGAAC TTTTGCCACT GGTGCCGCGT AGCTTTTATA ACGCTCAGGC TGTGTACTCA
14100

CAGTGGATAC AAGAAAAAAC TAACCAGACC CACGTTTTCA ATCGCTTTCC CGAAAATCAG
14160

ATCTTGGTGC GGCCCCCTGC GCCTACCATC ACGTCCATAA GTGAAAATAA GCCCAGCTTG
14220

ACAGATCACG GAATCGTGCC GCTCCGGAAC CGCTTGGGGG GCGTGCAACG TGTGACTTTG
14280

ACTGACGCGC GGCGAAGATC CTGCCCCTAC GTCTACAAGA GCTTAGGCAT TGTGACGCCG
14340

CAAGTGCTAT CTAGCCGCAC GTTTTAAGCA GACAGGGGCA CAGCAGCCGT TTTTTTTTTT
14400

TTTTTTTCGC TCCACCAGGG ACTGTCAGGA ACATGGCCAT TCTAATCTCT CCTAGCAATA
14460

ACACGGGCTG GGGCCTGGGA TGCAATAAGA TGTACGGGGG CGCTCGCATA CGTTCAGACT
14520

TGCATCCAGT GAAGGTGCGG TCGCATTATC GGGCCGCCTG GGGCAGCCGC ACCGGTCGGG
14580

TGGGTCGCCG CGCAACCGCA GCTTTAGCCG ATGCCGTCGC GGCCACCGGT GATCCGGTGG
14640

CCGACACAAT CGAGGCGGTG GTGGCTGACG CCCGCCAGTA CCGGCGCCGC AGACGGCGAG
14700

GGGTGCGCCG AGTCAGAAGG TTGCGTCGGA GCCCCCGCAC TGCCCTGCAG CGACGGGTTC
14760

GTAGCGTACG CCGACAAGTG GCGAGGGCCC GCAGGGTGGG CCGGCGCGCG GCCGCTATCG
14820

CAGCAGACGC GGCCATGGCC ATGGCGGCGC CAGCTCGGCG ACGCCGTAAC ATCTACTGGG
14880

TACGCGATGC GGCAACCGGA GCCCGCGTTC CGGTGACAAC CCGGCCTACG GTCAGCAACA
14940

CCGTTTGAAA TGTCTGCTAC TTTTTTTTGC TTCAATAAAA GCCCGCCGAC TGATCAGCCA
15000

CACCTTGTCA CGCAGAATTC TTTCAAACCA TTGCGCTCTC AGCGCGCGCG CCGATAAACC
15060

CACTGTGATG GCCTCCTCTC GGTTGATTAA AGAAGAAATG TTAGACATCG TGGCGCCTGA
15120

Fig. 20L

```
GATTTACAAG CGCAAACGGC CCAGGCGAGA ACGCGCAGCA CCGTATGCTG TGAAGCAGGA
15180

GGAGAAGCCT TTAGTAAAGG CGGAGCGCAA AATTAAGCGC GGCTCCAGAA AGCGGGCCTT
15240

GTCAGGCGTT GACGTTCCTC TGCCCGATGA CGGCTTTGAG GACGACGAGC CCCACATAGA
15300

ATTTGTGTCT GCGCCGCGTC GGCCCTACCA GTGGAAGGGC AGGCGGGTGC GCCGGGTTTT
15360

GCGTCCCGGC GTGGCCGTTA GTTTCACGCC CGGCGCGCGC TCCCTCCGTC CGAGTTCCAA
15420

GCGGGTGTAT GACGAGGTGT ACGCAGACGA CGACTTCTTA GAAGCGGCCG CGGCCCGTGA
15480

GGGGGAGTTT GCTTACGGAA AGCGGGGACG CGAGGCGGCC CAGGCCCAGC TGCTACCGGC
15540

TGTGGCCGTG CCGGAACCGA CTTACGTAGT TTTGGATGAG AGCAACCCCA CCCCGAGCTA
15600

CAAGCCTGTA ACCGAGCAGA AAGTTATTCT TTCCCGCAAG CGGGGTGTGG GGAAGGTAGA
15660

GCCTACCATC CAGGTTTTAG CTAGCAAGAA GCGGCGCATG GCCGAGAATG AGGATGACCG
15720

CGGGGCCGGC TCCGTGGCCG AAGTGCAGAT GCGAGAAGTT AAACCGGTAA CCGCTGCCTT
15780

GGGTATTCAG ACCGTGGATG TTAGCGTGCC CGACCACAGC ACTCCCATGG AGGTCGTGCA
15840

GAGTCTCAGT CGGGCGGCTC AAGTAGCTCA ACGCCTGACC CAACAACAGG TGCGGCCTTC
15900

GGCTAAGATT AAAGTGGAGG CCATGGATCT TTCTGCTCCC GTAGACGCAA AGCCTCTTGA
15960

CTTAAAACCC GTGGACGTAA AGCCGACCCC GACCTTCGTG CTTCCCAGCT TTCGTTCACT
16020

CAGCACCCAA ACTGACTCTT TGCCCGCGGC AGTGGTCGTG CCGCGCAAGC CCCGCGTGCA
16080

CCGTGCTACT AGGCGTACTG CGCGCGGCTT GCTGCCCTAT TACCGCCTGC ATCCTAGCAT
16140

CACGCCGACA CCGGGTTACC GAGGATCTGT CTACACGAGC TCGGGTGTGC GCCTGCCCGC
16200

CGTCCGGGCG CCGCCGTCGC CGCCGTACCC GCAGGGCGAC TCCCCGCCTC AGCGCTGCCG
16260

CGGCCGCGGC GCTGCTGCCC GGCGTGCGCT ATCACCCTAG CATCCGCCAA GCGGCCACAG
16320

TAACCCGGCT CCGCCGTTAA GCGCTGTGAA ACTGCAACAA CAACAACAAA AATAAAAAAA
16380
```

Fig. 20M

```
AGTCTCCGCT CCACTGTGCA CCGTTGTCCA TCGGCTAATA AAGTCCCGCT TTGTGCGCCG
16440

CAGGAACCAC TATCCGTAAC CTGCGAAAAT GAGTCCCCGC GGAAATCTGA CTTACAGACT
16500

GAGAATACCG GTCGCCCTCA GTGGCCGGCG CCGGCGCCGA ACAGGCTTGC GAGGAGGGTC
16560

TGCGTACCTG CTCGGCCGCC GCAGAAGGCG CGCGGGCGGC GGCCGCCTGC GCGGGGCTT
16620

CCTTCCCCTC CTGGCTCCCA TCATTGCAGC CGCCATCGGC GCAATCCCCG GCATCGCATC
16680

AGTGGCCATT CAGGCGGCCC ACAACAAATA GGGACAGTGT AAAGAAAGCT CAATCTCAAT
16740

AAAACAAACC GCTCGATGTG CATAACGCTC TCGGCCTGCA ACTTCTGCTG CTTACGTCTT
16800

TGACCAAAGT CACTACTGTT TTCCTTTTAC CCAGAGCCGG CGCCAGCCCC ACACAGCTTG
16860

TTAACACGCC ATGGACGAAT ACAATTACGC GGCTCTTGCT CCCCGGCAAG GCTCCCGACC
16920

CATGCTGAGC CAGTGGTCCG GCATCGGCAC GCACGAAATG CACGGCGGAC GTTTTAATCT
16980

GGGCAGTTTG TGGAGCGGGA TCAGGAATGT GGGCAGCGCG TTAAGAACTG GGGCTCTCGG
17040

GCCTGGCACA GCAATGCGGG CAAGCGTTGC GCGCCCAGCT GAAAAAGACG GGCTTGCAAG
17100

AAAAGATATT GAGGGCGTTA GCGCCGGTAT CCACGGAGCC GTGGATCTGG GCCGTCAGCA
17160

GCTAGAGAAA GCTATTGAGC AGCGCCTAGA GCGTCGCCCC ACCGCTGCCG GTGTGGAAGA
17220

CCTTCCGCTT CCCCCGGGAA CAGTCTTAGA AGCTGATCGT TTACCGCCCT CCTACGCCGA
17280

AGCGGTGGCT GAGCGCCCGC CGCCGGCTGA CGTTCTCCTG CCCGCATCCT CAAAGCCGCC
17340

GGTGGCGGTG GTGACCTTGC CCCCGAAAAA GAGAGTGTCT GAAGAGCCTG TGGAGGAAGT
17400

TGTGATTCGT TCCTCCGCAC CGCCGTCGTA CGACGAGGTT ATGGCACCGC AGCCGACTCT
17460

GGTAGCCGAG CAGGGCGCCA TGAAAGCAGT GCCCGTGATT AAGCCGGCTC AACCTTTTAC
17520

CCCAGCTGTG CACGAAACGC AACGCATAGT GACCAACTTG CCAATCACCA CAGCTGTGAC
17580

ACGGCGACGC GGGTGGCAGG GCACTCTGAA TGACATCGTG GGCCTCGGCG TTCGTACCGT
17640
```

Fig. 20N

GAAGCGCCGG CGGTGCTATT GAGGGGGCGC GCAGCGGTAA TAAAGAGAAC ATAAAAAAGC
17700

AGGATTGTGT TTTTTGTTTA GCGGCCACTG ACTCTCCCTC TGTGTGACAC GTCCTCCGCC
17760

AGAGCGTGAT TGATTGACCG AGATGGCTAC CCCGTCGATG CTGCCGCAAT GGTCCTACTG
17820

CACATCGCCG GTCAGGACGC GTCCGAGTAC CTGTCCCCCG GCTTGGTGCA ATTCGCACAA
17880

GCCACCGAAT CCTACTTTAA CATTGGGAAC AAGTTTAGAA ACCCCACCGT CGCCCCGACG
17940

CACGATGTCA CCACGGAGCG TTCGCAGCGT CTGCAGCTCC GCTTCGTGCC CGTAGACCGG
18000

GAGGACACAC AGTACTCCTA CAAAACCCGC TTCCAGCTAG CCGTGGGCGA CAACCGGGTG
18060

CTGGACATGG CCAGCACGTA TTTTGACATC CGCGGTACGC TGGAGAGGGG CGCCAGTTTC
18120

AAGCCTTACA GCGGCACGGC CTACAACTCC TTTGCCCCCA ACAGTGCCCC TAACAATACG
18180

CAGTTTAGGC AGGCCAACAA CGGTCATCCT GCTCAGACCA TAGCTCAAGC TTCTTACGTG
18240

GCTACCATCG GCGGTGCCAA CAATGACTTG CAAATGGGTG TGGACGAGCG TCAGCAGCCG
18300

GTGTATGCGA ACACTACGTA CCAGCCGGAA CCTCAGCTCG GCATTGAAGG TTGGACAGCT
18360

GGATCCATGG CGGTCATCGA TCAAGCAGGC GGGCGGGTTC TCAGGAACCC TACTCAAACT
18420

CCCTGCTACG GGTCCTATGC TAAGCCGACT AACGAGCACG GGGGCATTAC TAAAGCAAAC
18480

ACTCAGGTGG AGAAAAAGTA CTACAGAACA GGGGACAACG GTAACCCGGA AACAGTGTTT
18540

TATACTGAAG AGGCTGACGT GCTAACGCCC GACACCCACC TTGTTCACGC GGTACCGGCC
18600

GCGGATCGGG CAAAGGTGGA GGGGCTATCT CAGCACGCAG CTCCCAACAG GCCGAACTTT
18660

ATCGGCTTTC GGGACTGCTT TGTAGGCTTG ATGTATTATA ACAGCGGGGG CAACCTGGGC
18720

GTCTTAGCGG GTCAATCCTC TCAGCTGAAT GCCGTGGTAG ACCTGCAAGA CCGCAACACT
18780

GAGCTTTCCT ATCAGATGCT TCTTGCAAAC ACGACGGACA GATCCCGCTA TTTTAGCATG
18840

TGGAACCAAG CCATGGACTC GTACGACCCG GAGGTCAGGG TGATAGATAA CGTGGGCGTA
18900

Fig. 20O

GAGGACGAGA TGCCTAATTA CTGCTTTCCG TTGTCGGGGG TTCAGATTGG AAACCGTAGC
18960

CACGAGGTTC AAAGAAACCA ACAACAGTGG CAAAATGTAG CTAATAGTGA CAACAATTAC
19020

ATAGGCAAGG GGAACCTACC GGCCATGGAG ATAAATCTAG CGGCCAATCT CTGGCGTTCC
19080

TTTTTGTACA GTAATGTGGC GTTGTACTTG CCAGACAACC TTAAATTCAC CCCTCACAAC
19140

ATTCAACTCC CGCCTAACAC GAACACCTAC GAGTACATGA ACGGGCGAAT CCCCGTTAGC
19200

GGCCTTATTG ATACGTACGT AAATATAGGC ACGCGGTGGT CGCCCGATGT GATGGACAAC
19260

GTGAATCCCT TTAACCACCA CCGCAACTCG GCCTGCGTT ACCGCTCCCA GCTGCTGGGC
19320

AACGGCCGCT TCTGCGACTT TCACATTCAG GTGCCACAAA AGTTTTTGC TATTCGAAAC
19380

CTGCTTCTCC TGCCCGGCAC GTACACTTAC GAGTGGTCCT TTAGAAAGGA CGTAAACATG
19440

ATCCTTCAGA GCACTCTGGG CAATGATCTG CGGGTCGATG GGGCCACTGT TAATATTACC
19500

AGCGTCAACC TCTACGCCAG CTTCTTTCCC ATGTCACATA ACACCGCTTC CACTTTGGAA
19560

GCTATGCTCC GCAACGACAC TAATGACCAG TCTTTTAATG ACTATCTCTC GGCGGCTAAC
19620

ATGTTGTATC CCATTCCGCC CAATGCCACC CAACTGCCCA TCCCCTCACG CAACTGGGCA
19680

GCGTTCCGTG GCTGGAGTCT CACCCGGCTA AAACAGAGGG AGACACCGGC GCTGGGGTCC
19740

CCGTTCGATC CCTATTTCAC CTATTCGGGC ACCATCCCGT ACCTGGACGG CACTTTTTAC
19800

CTCAGCCACA CCTTTCGCAA GGTGGCCATC CAGTTTGACT CTTCTGTGAC CTGGCCCGGC
19860

AATGACAGGC TTTTAACCCC TAACGAGTTC GAAATAAAAA TAAGTGTGGA CGGTGAAGGC
19920

TACAACGTGG CTCAGAGCAA TATGACTAAG GACTGGTTCC TGGTGCAGAT GCTAGCGAAT
19980

TACAACATAG GCTACCAGGG ATATCACCTG CCCCCGGACT ACAAGGACAG GACATTTTCC
20040

TTCCTGCATA ACTTCATACC CATGTGCCGA CAGGTTCCCA ACCCAGCAAC CGAGGGCTAC
20100

TTTGGACTAG GCATAGTGAA CCATAGAACA ACTCCGGCTT ATTGGTTTCG ATTCTGCCGC
20160

*Fig. 20P*

```
GCTCCGCGCG AGGGCCACCC CTACCCCCAA CTGGCCTTAC CCCCTCATTG GGACCCACGC
20220

CATGCCCTCC GTGACCCAGA GAGAAAGTTT CTCTGCGACC GCACCCTCTG GCGAATCCCC
20280

TTCTCCTCGA ACTTCATGTC CATGGGGTCC CTCACAGATC TCGGACAGAA CCTACTGTAT
20340

GCCAATGCCG CGCATGCCCT AGACATGACT TTTGAGATGG ATCCCATCAA TGAGCCCACT
20400

CTGCTGTACG TTCTGTTTGA GGTGTTTGAC GTGGCCCGCG TTCACCAGCC CCACAGAGGC
20460

GTGATCGAAG TGGTGTACTT GAGAACGCCA TTCTCAGCCG GCAACGCTAC CACATAAGTG
20520

CCGGCTTCCC TCTCAGGCCC CGCGATGGGT TCTCGGGAAG AGGAGCTGAG ATTCATCCTT
20580

CACGATCTCG GTGTGGGGCC ATACTTCCTC GGCACTTTCG ATAAACACTT TCCGGGGTTC
20640

ATCTCCAAAG ACCGAATGAG CTGTGCCATA GTCAACACTG CCGGACGCGA AACCGGGGGC
20700

GTGCATTGGC TGGCCATGGC TTGGCACCCA GCCTCGCAGA CCTTTTACAT GTTTGACCCT
20760

TTCGGTTTCT CGGATCAAAA GCTAAAGCAA ATTTACAACT TGAGTATCA GGGCCTCCTA
20820

AAGCGCAGCG CCCTGACTTC CACTGCTGAC CGCTGCCTGA CCCTTATTCA AAGCACTCAA
20880

TCTGTCCAGG GACCCAACAG CGCCGCCTGC GGTCTGTTCT GCTGCATGTT CCTCCACGCC
20940

TTTGTCCGCT GGCCGCTTAG GGCCATGGAC AACAATCCCA CCATGAACCT CATCCACGGA
21000

GTTCCCAACA ACATGTTGGA GAGCCCCAGC TCCCAAAATG TGTTTTTGAG AAACCAGCAA
21060

AATCTGTACC GTTTCCTAAG ACGCCACTCC CCCCATTTTG TTAAGCATGC GGCTCAAATT
21120

GAGGCTGACA CCGCCTTTGA TAAAATGTTA ACAAATTAGA CCGTGAGCCA TGATTGCAGA
21180

AGCATGTCAT TTTTTTTTTA TTGTTTAAAA TAAAAACAAC ACATAACATC TGCCGCCTGT
21240

CCTCCCGTGA TTTCTTCTGC TTTATTTGCA AATGGGGGGC ACCTTAAAAC AAAGAGTCAT
21300

CTGCATCGTA CTGATCGATG GGCAGAATAA CATTCTGATG CTGGTACTGC GGGTCCCAGC
21360

GGAATTCGGG AATGGTAATG GGGGGGCTCT GTTTAACCAG CGCGGACCAC ATCTGCTTAA
21420
```

Fig. 20Q

```
CCAGCTGCAA GGCTGAAATC ATATCTGGAG CCGAAATCTT GAAATCGCAG TTTCGCTGGG
21480

CATTAGCCCG CGTCTGCCGG TACACAGGGT TACAGCACTG AAATACTAAC ACCGATGGGT
21540

GTTCTACGCT GGCCAGGAGT TTGGGATCTT CTACGAGGCT CTTATCTACC GCAGAGCCCG
21600

CGTTGATATT AAAGGGCGTT ATCTTGCATA CCTGACGGCC TAGGAGGGGC AATTGGGAGT
21660

GACCCCAGTT ACAATCACAC TTTAAAGGCA TAAGCAGATG AGTTCCGGCA CTTTGCATCC
21720

TGGGGTAACA GGCTTTCTGA AAGGTCATGA TCTGCCAGAA AGCCTGCAAA GCCTTGGGCC
21780

CCTCGCTGAA AAACATACCA CAAGACTTTG AGGTAAAGCT GCCGGCCGGC AAAGCGGCGT
21840

CAAAGTGACA GCAAGCCGCG TCTTCATTCT TTAGCTGCAC TACGTTCATA TTCCACCGGT
21900

TGGTGGTGAT CTTTGTCTTA TGCGGGGTCT CTTTTAAAGC CCGCTGCCCA TTTTCGCTGT
21960

TCACATCCAT CTCTATCACT TGGTCTTTGG TAAGCATAGG CAGGCCATGC AGGCAGTGAA
22020

GGGCCCCGTC TCCCCCCTCG GTACACTGGT GGCGCCAGAC CACACAGCCC GTGGGGCTCC
22080

ACGAGGTCGT CCCCAGGCCT GCGACTTTTA ACACAAAATC ATACAAGAAG CGGCCCATAA
22140

TAGTTAGCAC GGTTTTCTGA GTACTGAAAG TAAGAGGCAG GTACACTTTA GACTCATTAA
22200

GCCAAGCTTG TGCAACCTTC CTAAAACACT CGAGCGTGCC AGTGTCGGGC AGCAAGGTTA
22260

AGTTTTTAAT ATCCACTTTC AAAGGCACAC ACAGCCCCAC TGCTAATTCC ATGGCCCGCT
22320

GCCAAGCAAC TTCGTCGGCT TCCAGCAAGG CCCGGCTGGC CGCCGGCAGG GCGGGAGCGG
22380

CGGCCTCAGC GGCTGGGGCT GAAGGTTTGA AAATCTTGGC GCGCTTAACG GCTGTGACAT
22440

CTTCGGCGGG GGGCTCAGCG ATCGGCGCGC GCCGTTTGCG GCTGACTTTT TTCCGGGGCG
22500

TCTCATCTAT CACTAAGGGG TTCTCGTCCC CGCTGCTGTC AGCCGAACTC GTGGCTCGCG
22560

TTAAGTCACC GCTGCGATTC ATTATTCTCT CCTAGATAAC GACAACAAAT GGCAGAGAAA
22620

GGCAGTGAAA ATCAGCGGCC AGAGAACGAC ACTGAGCTAG CAGCGGTTTC AGAAGCCCTA
22680
```

Fig. 20R

```
GGCGCGGCCG CTTCGGCCCC CTCACGTAAC TCCCCGACTG ACACGGATTC AGGGGTGGAA
22740

ATGACGCCCA CCAGCAGCCC CGAGCCGCCC GCCGCTCCCC CAAGTTCGCC TGCCGCAGCA
22800

CCTGCCCCTC AGAAGAACCA GGAGGAGCTC TCTTCCCCCG AGCCCGCGGT AGCAGCAGCG
22860

GAGCCAGAAG CCGCTTCGCG GCCCAGACCA CCCACACCCA CCGTTCAGGT CCCGCGGGAG
22920

CCGAGCGAGG ATCAACCTGA CGGACCCGCG ACGAGGCCTT CGTACGTGAG CGAGGATTGC
22980

CTCATCCGCC ATATCTCTCG CCAGGCTAAC ATTGTTAGAG ACAGCCTGGC AGACCGCTGG
23040

GAGTTAGAGC CCACCGTGTC GGCTCTCTCC GAGGCTTACG AAAAGCTCCT CTTTTGTCCC
23100

AAGGTACCAC CCAAGAAGCA AGAGAATGGC ACTTGCGAAC CTGAACCTCG CGTTAATTTT
23160

TTCCCCACCT TTGTAGTGCC CGAAACTTTA GCCACGTACC ACATCTTTTT CCAAAACCAA
23220

AAAATCCCCC TGTCTTGTCG CGCCAACCGC ACCCACACAG ACACCATCAT GCACCTCTAC
23280

TCGGGGACT CCTTACCGTG CTTCCCCACG CTGCAGCTGG TCAACAAAAT CTTTGAAGGC
23340

TTGGGCTCAG AGGAGCGGCG CGCAGCCAAC TCGCTGAAAG ATCAAGAGGA TAACAGCGCG
23400

TTAGTTGAGC TCGAAGGGGA CAGTCCCCGA CTGGCTGTGG TTAAGCGCAC ACTGTCTTTG
23460

ACACATTTCG CCTACCCTGC CATAACACTA CCGCCTAAGG TGATGGCAGC TGTCACTGGC
23520

AGCCTCATTC ATGAATCAGC AGCGACCGCC GAACCGGAAG CTGAGGCGCT GCCAGAAGCC
23580

GAGGAGCCCG TGGTTAGTGA CCCTGAACTT GCTCGCTGGT TGGGGCTCAA CTTACAACAG
23640

GAGCCCGAGG CCACGGCCCA GGCTTTGGAA GAAAGACGCA AGATTATGTT GGCAGTATGC
23700

TTAGTCACAC TTCAGCTCGA GTGCCTGCAC AAGTTTTTTT CTTCAGAGGA TGTCATCAAA
23760

AAGCTGGGAG AGAGCCTCCA CTACGCCTTT CGCCACGGCT ACGTGCGCCA AGCCTGCTCC
23820

ATTTCTAACG TGGAACTAAC GAACATCGTC TCATACCTGG GTATCTTGCA CGAAAACCGC
23880

TTGGGACAGA GTACCCTACA CGCCACCCTT AAAGACGAGA ACCGCAGAGA CTACATCAGA
23940
```

Fig. 20S

```
GACACAGTCT TTCTCTTTCT GGTTTATACT TGGCAGACTG CCATGGGCAT TTGGCAGCAG
24000

TGCCTCGAGA CTGAGAACGT AAAAGAACTT GAAAAGCTCT TGCAAAAAAG CAAGAGGGCT
24060

CTCTGGACGG GCTTCGACGA GCTCACCATA GCTCAAGACC TAGCTGACAT AGTGTTCCCC
24120

CCCAAATTCT TGCACACCTT GCAAGCCGGC CTGCCAGACC TTACATCCCA GAGTCTCCTT
24180

CACAACTTTC GCTCCTTCAT TTTCGAACGC TCGGGCATTC TACCCGCCAT GTGCAATGCA
24240

CTGCCCACCG ACTTCATCCC TATCAGCTAC CGGGAGTGCC CTCCAACTTT CTGGGCCTAC
24300

ACCTACCTCT TTAAACTGGC CAATTACCTC ATGTTTCACT CCGACATCGC TTACGATCGG
24360

AGCGGCCCCG GTCTCATGGA ATGCTACTGT CGCTGCAACC TGTGCAGTCC TCACCGCTGC
24420

TTGGCGACCA ACCCCGCCCT GCTCAGCGAG ACCCAAGTTA TCGGTACCTT CGAGATTCAG
24480

GGCCCTCCTG CTCAAGACGG ACAGCCGACC AAACCGCCCC TCAGGCTGAC TGCAGGTCTC
24540

TGGACTTCCG CCTACCTGCG CAAATTTGTA CCGCAAGACT TCAACGCCCA CAAAATAGCC
24600

TTCTACGAAG ACCAATCCAA AAAGCCGAAA GTGACCCCCA GCGCTTGTGT CATCACTGAA
24660

GAAAAAGTTT TAGCCCAATT GCATGAAATT AAAAAAGCGC GGGAAGACTT TCCTCTTAAA
24720

AAGGGGCACG GAGTGTATCT GGACCCTCAG ACCGGCGAGG AGCTGAACGG ACCCGCACCC
24780

TCCGCAGCTA GGAATGAAAC CCCGCAGCAT GTCGGCAGCC GGGCCTTCCG CGGCTCAGGC
24840

TTCGGAGGGC CAACAGCTGC CGCCACAGAC AGCGGGGCTG CAGCCGAGCA AGAGGGCTGT
24900

GAGGAAGGTA GTAGCTTCTC TGAATCCCAC CGCCGCCCTG GAAGACATAT CCGAGGGGGA
24960

GGAAGGCTTC CCCCTGACGG ACGAGGAAGA CGGGGACACC CTGGAGAGCG ATTTCAGCGA
25020

CTTCACGGAC GAAGACGTCG AGGAGGAGGA TATGATTTCG ATACCCCGCG ACCAGGGGCA
25080

CTCCGGCGAG CTCGAGGAGG GCGAAATTCC CGCAACGGTA GCGGCGACGG CGGTCAAGAA
25140

GGGCCAGGGC AAGAAGAGTA GGTGGGACCA GCAGGTCCGC TCCACAGCGC CTCTAAAGGG
25200
```

Fig. 20T

CGCTAGAGGT AAGAGGAGCT ACAGCTCCTG GAAACCCCTC AAGCCCACTA TCCTTTCATG
25260

CTTACTGCAG AGCTCCGGCA GCACTGCCTT CACTCGCCGC TATCTGCTTT TTCGCCATGG
25320

CGTGTCCGTT CCCTCCAGGG TAATTCATTA CTATAATTCT TACTGCAGAC CCGAAGCTGA
25380

CCAAAACCGC CACTCAGAGC AAAAGAGCC GCCGGAGTGC CAGCGCGGCG CGCCCTCGCC
25440

CTCCTCCTCT TCCTCCCAAG CGTGCTCGGG CGCCCCGCCG CCCCAAAGGC CAGCGCCATC
25500

AGGCCGACGA CGCAAGCACC GAGGGCCGCG ACAAGCTTCG GGAGCTGATC TTTCCCACTC
25560

TCTATGCCAT ATTCCAACAA AGTCGCGCTC AGCGGTGTCA CCTCAAAGTG AAAAATAGAT
25620

CCTTACGTTC ACTGACGCGC AGCTGCCTCT ACCACAACAA GGAGGAACAG CTCCAGCGAA
25680

CCCTAGCAGA CTCCGAGGCG CTTCTCAGTA AATACTGCTC TGCAGCTCCG ACACGATTCT
25740

CGCCGCCCTC TTATACCGAG TCTCCCGCCA AGGACGAATC CGGACCCGCC TAAACTCTCA
25800

GCATGAGCAA AGAAATTCCC ACACCTTATG TTTGGACCTT TCAACCTCAG ATGGGAGCGG
25860

CCGCAGGTGC CAGTCAAGAT TACTCGACCC GCATGAATTG GTTCAGCGCG GGACCTGATA
25920

TGATCCACGA CGTTAACAAC ATTCGTGACG CCCAAAACCG CATCCTTATG ACTCAGTCGG
25980

CCATTACCGC CACTCCCAGG AATCTGATTG ATCCCAGACA GTGGGCCGCC CACCTCATCA
26040

AACAACCCGT GGTGGGCACC ACCCACGTGG AAATGCCTCG CAACGAAGTC CTAGAACAAC
26100

ATCTGACCTC ACATGGCGCT CAAATCGCGG GCGGAGGCGC TGCGGGCGAT TACTTTAAAA
26160

GCCCCACTTC AGCTCGAACC CTTATCCCGC TCACCGCCTC CTGCTTAAGA CCAGATGGAG
26220

TCTTTCAACT AGGAGGAGGC TCGCGTTCAT CTTTCAACCC CCTGCAAACA GATTTTGCCT
26280

TCCACGCCCT GCCCTCCAGA CCGCGCCACG GGGCATAGG ATCCAGGCAG TTTGTAGAGG
26340

AATTTGTGCC CGCCGTCTAC CTCAACCCCT ACTCGGGACC GCCGGACTCT TATCCGGACC
26400

AGTTTATACG CCACTACAAC GTGTACAGCA ACTCTGTGAG CGGTTATAGC TGAGATTGTA
26460

*Fig. 20U*

```
AGACTCTCCT ATCTGTCTCT GTGCTGCTTT TCCGCTTCAA GCCCCACAAG CATGAAGGGG
26520

TTTCTGCTCA TCTTCAGCCT GCTTGTGCAT TGTCCCCTAA TTCATGTTGG GACCATTAGC
26580

TTCTATGCTG CAAGGCCCGG GTCTGAGCCT AACGCGACTT ATGTTTGTGA CTATGGAAGC
26640

GAGTCAGATT ACAACCCCAC CACGGTTCTG TGGTTGGCTC GAGAGACCGA TGGCTCCTGG
26700

ATCTCTGTTC TTTTCCGTCA CAACGGCTCC TCAACTGCAG CCCCCGGGGT CGTCGCGCAC
26760

TTTACTGACC ACAACAGCAG CATTGTGGTG CCCCAGTATT ACCTCCTCAA CAACTCACTC
26820

TCTAAGCTCT GCTGCTCATA CCGGCACAAC GAGCGTTCTC AGTTTACCTG CAAACAAGCT
26880

GACGTCCCTA CCTGTCACGA GCCCGGCAAG CCGCTCACCC TCCGCGTCTC CCCCGCGCTG
26940

GGAACTGCCC ACCAAGCAGT CACTTGGTTT TTTCAAAATG TACCCATAGC TACTGTTTAC
27000

CGACCTTGGG GCAATGTAAC TTGGTTTTGT CCTCCCTTCA TGTGTACCTT TAATGTCAGC
27060

CTGAACTCCC TACTTATTTA CAACTTTTCT GACAAAACCG GGGGCAATA CACAGCTCTC
27120

ATGCACTCCG GACCTGCTTC CCTCTTTCAG CTCTTTAAGC CAACGACTTG TGTCACCAAG
27180

GTGGAGGACC CGCCGTATGC CAACGACCCG GCCTCGCCTG TGTGGCGCCC ACTGCTTTTT
27240

GCCTTCGTCC TCTGCACCGG CTGCGCGGTG TTGTTAACCG CCTTCGGTCC ATCGATTCTA
27300

TCCGGTACCC GAAAGCTTAT CTCAGCCCGC TTTTGGAGTC CCGAGCCCTA TACCACCCTC
27360

CACTAACAGT CCCCCCATGG AGCCAGACGG AGTTCATGCC GAGCAGCAGT TTATCCTCAA
27420

TCAGATTTCC TGCGCCAACA CTGCCCTCCA GCGTCAAAGG GAGGAACTAG CTTCCCTTGT
27480

CATGTTGCAT GCCTGTAAGC GTGGCCTCTT TGTCCAGTC AAAACTTACA AGCTCAGCCT
27540

CAACGCCTCG GCCAGCGAGC ACAGCCTGCA CTTTGAAAAA AGTCCCTCCC GATTCACCCT
27600

GGTCAACACT CACGCCGGAG CTTCTGTGCG AGTGGCCCTA CACCACCAGG GAGCTTCCGG
27660

CAGCATCCGC TGTTCCTGTT CCCACGCCGA GTGCCTCCCC GTCCTCCTCA AGACCCTCTG
27720
```

Fig. 20V

```
TGCCTTTAAC TTTTTAGATT AGCTGAAAGC AAATATAAAA TGGTGTGCTT ACCGTAATTC
27780

TGTTTTGACT TGTGTGCTTG ATTTCTCCCC CTGCGCCGTA ATCCAGTGCC CCTCTTCAAA
27840

ACTCTCGTAC CCTATGCGAT TCGCATAGGC ATATTTTCTA AAAGCTCTGA AGTCAACATC
27900

ACTCTCAAAC ACTTCTCCGT TGTAGGTTAC TTTCATCTAC AGATAAAGTC ATCCACCGGT
27960

TAACATCATG AAGAGAAGTG TGCCCCAGGA CTTTAATCTT GTGTATCCGT ACAAGGCTAA
28020

GAGGCCCAAC ATCATGCCGC CCTTTTTTGA CCGCAATGGC TTTGTTGAAA ACCAAGAAGC
28080

CACGCTAGCC ATGCTTGTGG AAAAGCCGCT CACGTTCGAC AAGGAAGGTG CGCTGACCCT
28140

GGGCGTCGGA CGCGGCATCC GCATTAACCC CGCGGGGCTT CTGGAGACAA ACGACCTCGC
28200

GTCCGCTGTC TTCCCACCGC TGGCCTCCGA TGAGGCCGGC AACGTCACGC TCAACATGTC
28260

TGACGGGCTA TATACTAAGG ACAACAAGCT AGCTGTCAAA GTAGGTCCCG GCTGTCCCT
28320

CGACTCCAAT AATGCTCTCC AGGTCCACAC AGGCGACGGG CTCACGGTAA CCGATGACAA
28380

GGTGTCTCTA AATACCCAAG CTCCCCTCTC GACCACCAGC GCGGGCCTCT CCCTACTTCT
28440

GGGTCCCAGC CTCCACTTAG GTGAGGAGGA ACGACTAACA GTAAACACCG GAGCGGGCCT
28500

CCAAATTAGC AATAACGCTC TGGCCGTAAA AGTAGGTTCA GGTATCACCG TAGATGCTCA
28560

AAACCAGCTC GCTGCATCCC TGGGGGACGG TCTAGAAAGC AGAGATAATA AAACTGTCGT
28620

TAAGGCTGGG CCCGGACTTA CAATAACTAA TCAAGCTCTT ACTGTTGCTA CCGGGAACGG
28680

CCTTCAGGTC AACCCGGAAG GCAACTGCA GCTAAACATT ACTGCCGGTC AGGGCCTCAA
28740

CTTTGCAAAC AACAGCCTCG CCGTGGAGCT GGGCTCGGGC CTGCATTTTC CCCTGGCCA
28800

AAACCAAGTA AGCCTTTATC CCGGAGATGG AATAGACATC CGAGATAATA GGGTGACTGT
28860

GCCCGCTGGG CCAGGCCTGA GAATGCTCAA CCACCAACTT GCCGTAGCTT CCGGAGACGG
28920

TTTAGAAGTC CACAGCGACA CCCTCCGGTT AAAGCTCTCC CACGGCCTGA CATTTGAAAA
28980
```

*Fig. 20W*

```
TGGCGCCGTA CGAGCAAAAC TAGGACCAGG ACTTGGCACA GACGACTCTG GTCGGTCCGT
29040

GGTTCGCACA GGTCGAGGAC TTAGAGTTGC AAACGGCCAA GTCCAGATCT TCAGCGGAAG
29100

AGGCACCGCC ATCGGCACTG ATAGCAGCCT CACTCTCAAC ATCCGGGCGC CCCTACAATT
29160

TTCTGGACCC GCCTTGACTG CTAGTTTGCA AGGCAGTGGT CCGATTACTT ACAACAGCAA
29220

CAATGGCACT TTCGGTCTCT CTATAGGCCC CGGAATGTGG GTAGACCAAA ACAGACTTCA
29280

GGTAAACCCA GGCGCTGGTT TAGTCTTCCA AGGAAACAAC CTTGTCCCAA ACCTTGCGGA
29340

TCCGCTGGCT ATTTCCGACA GCAAAATTAG TCTCAGTCTC GGTCCCGGCC TGACCCAAGC
29400

TTCCAACGCC CTGACTTTAA GTTTAGGAAA CGGGCTTGAA TTCTCCAATC AAGCCGTTGC
29460

TATAAAAGCG GGCCGGGGCT TACGCTTTGA GTCTTCCTCA CAAGCTTTAG AGAGCAGCCT
29520

CACAGTCGGA AATGGCTTAA CGCTTACCGA TACTGTGATC CGCCCAACC TAGGGGACGG
29580

CCTAGAGGTC AGAGACAATA AAATCATTGT TAAGCTGGGC GCGAATCTTC GTTTTGAAAA
29640

CGGAGCCGTA ACCGCCGGCA CCGTTAACCC TTCTGCGCCC GAGGCACCAC CAACTCTCAC
29700

TGCAGAACCA CCCCTCCGAG CCTCCAACTC CCATCTTCAA CTGTCCCTAT CGGAGGGCTT
29760

GGTTGTGCAT AACAACGCCC TTGCTCTCCA ACTGGGAGAC GGCATGGAAG TAAATCAGCA
29820

CGGACTTACT TTAAGAGTAG GCTCGGGTTT GCAAATGCGT GACGGCATTT TAACAGTTAC
29880

ACCCAGCGGC ACTCCTATTG AGCCCAGACT GACTGCCCCA CTGACTCAGA CAGAGAATGG
29940

AATCGGGCTC GCTCTCGGCG CCGGCTTGGA ATTAGACGAG AGCGCGCTCC AAGTAAAAGT
30000

TGGGCCCGGC ATGCGCCTGA ACCCTGTAGA AAAGTATGTA ACCCTGCTCC TGGGTCCTGG
30060

CCTTAGTTTT GGGCAGCCGG CCAACAGGAC AAATTATGAT GTGCGCGTTT CTGTGGAGCC
30120

CCCCATGGTT TTCGGACAGC GTGGTCAGCT CACATTTTTA GTGGGTCACG GACTACACAT
30180

TCAAAATTCC AAACTTCAGC TCAATTTGGG ACAAGGCCTC AGAACTGACC CCGTCACCAA
30240
```

Fig. 20X

CCAGCTGGAA GTGCCCCTCG GTCAAGGTTT GGAAATTGCA GACGAATCCC AGGTTAGGGT
30300

TAAATTGGGC GATGGCCTGC AGTTTGATTC ACAAGCTCGC ATCACTACCG CTCCTAACAT
30360

GGTCACTGAA ACTCTGTGGA CCGGAACAGG CAGTAATGCT AATGTTACAT GGCGGGGCTA
30420

CACTGCCCCC GGCAGCAAAC TCTTTTTGAG TCTCACTCGG TTCAGCACTG GTCTAGTTTT
30480

AGGAAACATG ACTATTGACA GCAATGCATC CTTTGGGCAA TACATTAACG CGGGACACGA
30540

ACAGATCGAA TGCTTTATAT TGTTGGACAA TCAGGGTAAC CTAAAAGAAG GATCTAACTT
30600

GCAAGGCACT TGGGAAGTGA AGAACAACCC CTCTGCTTCC AAAGCTGCTT TTTTGCCTTC
30660

CACCGCCCTA TACCCCATCC TCAACGAAAG CCGAGGGAGT CTTCCTGGAA AAAATCTTGT
30720

GGGCATGCAA GCCATACTGG GAGGCGGGGG CACTTGCACT GTGATAGCCA CCCTCAATGG
30780

CAGACGCAGC AACAACTATC CCGCGGGCCA GTCCATAATT TTCGTGTGGC AAGAATTCAA
30840

CACCATAGCC CGCCAACCTC TGAACCACTC TACACTTACT TTTTCTTACT GGACTTAAAT
30900

AAGTTGGAAA TAAAGAGTTA AACTGAATGT TTAAGTGCAA CAGACTTTTA TTGGTTTTGG
30960

CTCACAACAA ATTACAACAG CATAGACAAG TCATACCGGT CAAACAACAC AGGCTCTCGA
31020

AAACGGGCTA ACCGCTCCAA GAATCTGTCA CGCAGACGAG CAAGTCCTAA ATGTTTTTC
31080

ACTCTCTTCG GGGCCAAGTT CAGCATGTAT CGGATTTTCT GCTTACACCT TTTTAGACAG
31140

CAGTTTACAC TCATTTCCGT TAAAGGATTA CAACTGCGGC ATATGAGAAT TAAGTATATA
31200

CAACTATTGC CCTTTACCCA CAAACACTCC CCCCACGGGG TGCACCTGAT GTAGCTGCCC
31260

TCCTCAATCA TGAAAGTGCT ATTAAAGTAA ATTAAATGAA CATTATTCAC ATACACGCTT
31320

CCCACATAGG CCAAAAAAAC AGAGGACAAC TTTGACAGCT CCCGCCTGAA ATACCAATAC
31380

ACTCTATCAA ACTGCGCACC GTGCACGCAC TGCTTTACCA GGCCTTGAAA GTAAACAGCG
31440

GCGGACCGAC ACTGCAAGCT TCTAGGCTTT GGGCAGTGGC AGTGAATATA TAGCCACTCC
31500

*Fig. 20Y*

```
TCCCCATGCA CGTAGTAGGA ACGCCGCTTC CCGGGAATCA CAAATGACAA GCAGTAGTCA
31560

CAGAGGCAAC TAGTCAAGTG AGCGTCCTCC TGAGGCATGA TTACCTTCCA TGGAATGGGC
31620

CAGTGAATCA TAGTGGCAAA GCCAGCTGCA TCTGGAGCGC TGCGAACCTT GGCTACATGT
31680

GGTGATTGGC GACGCAGATG GAGACAGGAC CTTGCATTCT GAAGACCACT GCAACAGCTT
31740

CTGCGTACGC TTGTATTTAC AGTACATAAA AAAGCACTTT GCCACAGAG CGGTCTTACT
31800

CAACCGACAG CTTTTTTCTT TCTGACGCTG CCTTCTGCTA CTCAGGTAGT ACAAGTCCAA
31860

AAGAGCCAAA CGGACACTCA AATCCGGGTT ATCTCGATGC TGAAGCCAGA GTCCAAAAGT
31920

AACCACGCTA AAAGCCTGCA TCCATATTTT GTAACTGCTG TAACTCCATC CCAGAGCCGG
31980

GCACCGCACT TGGTCCACCA TAGCTGCAAA CAAACGGGAC AATTAAGGAA AGTAAAATGA
32040

GCGCTGGGGG CGGACTCTTC TCCCGTTCGT AGGAAACAGC CACGTATCAA ACACCCTTTT
32100

CAACACTGGC TCTCCAGCCG CTACTCGTTG AATTAATTTG TCCCTGTGCT CAAACAACCC
32160

ACACTGGTAA CGGTGGTCGC TAGGCAAACA TGTCAAATAG CACATAATCA TTTCCTTCAC
32220

TTTAAGCAAA CATCGACTAG CAGACACTTC ACTTAATTCA GCACAGTCAT AGCAAGGAAT
32280

GATTATACAC TTGTCATCTA ATCCACTGCC CATGTACACA TTGCCCCAGG CAAAAGTGGG
32340

CAGGGACTTT AAGAGCTGAT TGCTCGCCCC GACATAGTTG GTAAAATACA GCAAATGCAC
32400

CTTGTTAACA TACACACTCC CCACATAGTA AATATACCGA GTAGACAGCT TAGAAAGCTC
32460

CCTCCGAAAA AATGGGAACA TGGTATCAAA GGCAGTGCCC GCAACACACA TCTTGAACAG
32520

ATCCATCAGG ATAGTAGCTC GACACAGCCC CTGCAGACTT TGGTCAGCTT GCTTGCTGCA
32580

GCAGTACACT CTCCACGTAG CATCTCCGCT GATGAAGTAT TCGCTATCGC AGCGACCAAA
32640

AATACAGCAA TCACAAGGCA GACGCAACAG TCTTTCATCC AGACTGTTCA TGAGAGGCTT
32700

TAGAGGTATG GGAAAAAATC CAAAGTGCTC AAAATAAGCA GCGCTGGGCT CATTCTGACA
32760
```

Fig. 20Z

```
TTCCCCCAAC ATGCTGAGTC GAACCATAGC ACAGTCATAC AAACTCAGCT GTCGGAATTG
32820

ATCTTCCATG ATTGAGTTTC TACTGAGATA TTATCTCAAA CTTAAAACTG TTGCTCACCA
32880

ACTCTATGCG AACTTGCTCA AGAAGCTCTT GGTTTAGGGC GACCTCTTCT GGTCGTCGGA
32940

AGTTACTGAT GGAACAACAA GCGCCGCCCA ACTTCAAATT TCCAGCCGAC CCAATCCAGT
33000

GGTCTCTCAA CTCACGCGCA CAAGCTACTA TGCAGTCCTC ACTTTCGTCA AAGTCAGCAG
33060

CGCCTATAGA AATCAACACA CTGAGTCCAC CATCTTCAGC TTTTAAGGGA TAACAGCTGA
33120

TAGCAAACTG GTTCTGAGAC CACGGCAAAG CACGTAGGAA TTGCTGTTAA GTTAATTTCC
33180

AAACACCGCT GAAGCAGCTC TATGGTTGCT GGACATATGT CCTCTGCATA GAAGCTTTGA
33240

ACATAACTTA AGACAGGGCC GGGCACATGA AACACAAACA GAGAACTATA CACAATCTGG
33300

GCCATGATCA CTCACATTTA AATAGCAGCT GAAAAGTGGC TTTCTTCACT TGGGAGCAAA
33360

ATTAGCGAAG ACTGTGCCAG AATGCTCACG TCGAAAGGCG GTGGGTCTCG CAGAGGCAGG
33420

TTCGGAGCTC TAATTAAACA CAGGTGGGTA ATCCAGTCAA CGATGAGGAC CAGCTGAAAA
33480

GTGGCTTTCT TCACTTGGGA GCAAAATTAG CGAAGACTGT GCCAGAATGC TCACGTCGAA
33540

AGGCGGTGGG TCTCGCAGAG GCAGGTTCGG AGCTCTAATT AAACACAGGT GGGTAATCCA
33600

GTCAACGATG AGGACTTTTA AAAACTGTC TAAAACTGAA GCAGTTAAGT TAGAGGCAGA
33660

CACAGAAAAA ACTACAGTTA AACTATCAGT TGCTGAAATT GAAAAGCACC CAATAATTAT
33720

GCGCGAGGGC ACAGGCAATA AAGTGTTAG CCCCTCGGCT AACGCGTCAG CTAAAAAATC
33780

TTTAGCTAAA GTATCTACTG GCCGCGTGGT AAAAGTTTGA ATATAATTTA CGACAGGAGC
33840

TGGCAAGTGA AACTCCACAA AAAAGTAAA TGGCTGCACA CACGCCATTA TTTTGAAAAT
33900

AAGAAGTACT CACAAAATCA GCTGGAGCTG CCGCAAGTGA AAAAGACCAG CTGAAGTCTT
33960

ATTTTAAACT GTAAAATATA AAAAAAAAA TAGGGCGTGA ACAAAAATGA GAAATAATA
34020
```

*Fig. 20AA*

```
CCGGATATGA CTATTAAGGG CGTACACTGA AACTGGGTAA TATTTGAGAA AAAGATTAAG
34080

ATAATAGCTG AACAAATGTT GTGTGCAGAA CACGGAACAA TGGTGGCGAA AAAAAAAAAC
34140

AGTGTAAGCA CATGGCGCGC ACGTACTTCC GTGAGAAAAA TTAAAAAAAT TTACCCAGTA
34200

TAAGGTGCGT CATTAGACCC GCCTTGTGGC GCGGTTGTAG CCCTGCCCTT TGCCCCGCCC
34260

CGCGCGCCGC CCCGCGCGCC GCCCCCGCCG CCCTCAGCCC CGCCCAGCGC CGCCGCCTCC
34320

GCGACGCGCT CCGCCCCACA GTTACGTCAG CACGCCACGC TCGCCGTCGT TGCGTCATAA
34380

ATGACGTGGC AAAAATGATT GGCAGTTGGA CCGCTGCCAT CAGTGTACTG TAGATTATTG
34440

ATGATG
34446
```

*Fig. 20BB*

BOVINE ADENOVIRUS TYPE 3 GENOME AND VECTOR SYSTEMS DERIVED THEREFROM

CROSS-REFERENCE TO RELATED APPLICATIONS

This application is a continuation-in-part of U.S. patent application Ser. No. 08/880,234, filed Jun. 23, 1997, now abandoned, the disclosure of which is hereby incorporated herein by reference.

TECHNICAL FIELD

The present invention relates to novel bovine adenovirus (BAV) expression vector systems in which one or both of the early region 1 (E1) and the early region 3 (E3) gene deletions are replaced by a foreign gene and novel recombinant mammalian cell lines stably transformed with BAV E1 sequences, and therefore, expresses E1 gene products, to allow a bovine adenovirus with an E1 gene deletion replaced by a foreign gene to replicate therein. These materials are used in production of recombinant BAV expressing heterologous (antigenic) polypeptides or fragments for the purpose of live recombinant virus or subunit vaccines or for other therapies.

The present invention also relates to novel bovine adenovirus (BAV) expression vector systems comprising BAV genome sequences disclosed herein. The BAV genome sequences can be replaced by one or more foreign genes to generate recombinant BAV expressing heterologous (antigenic) polypeptides or fragments for the purpose of producing live recombinant virus or subunit vaccines or for other therapies. Further, various BAV transcriptional and translational regulatory signals can be used to modulate the expression of foreign genes that have been inserted into the vector systems of the invention. Additionally, the novel sequences of the present invention can be used for diagnostic purposes, to determine the presence of BAV in a subject or biological sample.

BACKGROUND OF THE INVENTION

The adenoviruses cause enteric or respiratory infection in humans as well as in domestic and laboratory animals.

The bovine adenoviruses (BAVs) comprise at least nine serotypes divided into two subgroups. These subgroups have been characterized based on enzyme-linked immunoassays (ELISA), serologic studies with immunofluorescence assays, virus-neutralization tests, immunoelectron microscopy, by their host specificity and clinical syndromes. Subgroup 1 viruses include BAV 1, 2, 3 and 9 and grow relatively well in established bovine cells compared to subgroup 2 which includes BAV 4,5,6,7 and 8.

BAV3 was first isolated in 1965 and is the best characterized of the BAV genotypes, containing a genome of approximately 35 kb (Kurokawa et al (1978) *J. Virol.* 28:212–218). BAV3, a representative of subgroup 1 of BAVs (Bartha (1969) *Acta Vet. Acad. Sci. Hung.* 19:319–321), is a common pathogen of cattle usually resulting in subclinical infection (Darbyshire et al. (1965). *J. Comp. Pathol.* 75:327–330), though occasionally associated with a more serious respiratory tract infection (Darbyshire et al., 1966 *Res. Vet Sci* 7:81–93; Mattson et al., 1988 *J. Vet Res* 49:67–69). Like other adenoviruses, BAV3 is a non-enveloped icosahedral particle of 75 nm in diameter (Niiyama et al. (1975) *J. Virol.* 16:621–633) containing a linear double-stranded DNA molecule. BAV3 can produce tumors when injected into hamsters (Darbyshire, 1966 *Nature* 211:102) and viral DNA can efficiently effect morphological transformation of mouse, hamster or rat cells in culture (Tsukamoto and Sugino, 1972 *J. Virol.* 9:465–473; Motoi et al., 1972 *Gann* 63:415–418; M. Hitt, personal communication). Cross hybridization was observed between BAV3 and human adenovirus type 2 (HAd2) (Hu et al., 1984 *J. Virol.* 49:604–608) in most regions of the genome including some regions near but not at the left end of the genome.

In the human adenovirus (HAd) genome there are two important regions: E1 and E3 in which foreign genes can be inserted to generate recombinant adenoviruses (Berkner and Sharp (1984) *Nuc. Acid Res.,* 12:1925–1941 and Haj-Ahmad and Graham (1986) *J. Virol.,* 57:267–274). E1 proteins are essential for virus replication in tissue culture, however, conditional-helper adenovirus recombinants containing foreign DNA in the E1 region, can be generated in a cell line which constitutively expresses E1 (Graham et al., (1977) *J. Gen. Virol.,* 36:59–72). In contrast, E3 gene products of HAd 2 and HAd 5 are not required for in vitro or in vivo infectious virion production, but have an important role in host immune responses to virus infection (Andersson et al (1985) *Cell* 43:215–222; Burgert et al (1987) *EMBO J.* 6:2019–2026; Carlin et al (1989) *Cell* 57:135–144; Ginsberg et al (1989) *PNAS, USA* 86:3823–3827; Gooding et al (1988) *Cell* 53:341–346; Tollefson et al (1991) *J. Virol.* 65:3095–3105; Wold and Gooding (1989) *Mol. Biol. Med.* 6:433–452 and Wold and Gooding (1991) *Virology* 184:1–8). The E3-19 kiloDalton (kDa) glycoprotein (gp19) of human adenovirus type 2 (HAd2) binds to the heavy chain of a number of class 1 major histocompatibility complex (MHC) antigens in the endoplasmic reticulum thus inhibiting their transport to the plasma membrane (Andersson et al. (1985) *Cell* 43:215–222; Burgert and Kvist, (1985) *Cell* 41:987–997; Burgert and Kvist, (1987) *EMBO J.* 6:2019–2026). The E3-14.7 kDa protein of HAd2 or HAd5 prevents lysis of virus-infected mouse cells by tumor necrosis factor (TNF) (Gooding et al. (1988) *Cell* 53:341–346). In addition, the E3-10.4 kDa and E3-14.5 kDa proteins form a complex to induce endosomal-mediated internalization and degradation of the epidermal growth factor receptor (EGF-R) in virus-infected cells (Carlin et al. *Cell* 57:135–144; Tollefson et al. (1991) *J. Virol.* 65:3095–3105). The helper-independent recombinant adenoviruses having foreign genes in the E3 region replicate and express very well in every permissive cell line (Chanda et al (1990) *Virology* 175:535–547; Dewar et al (1989) *J. Virol.* 63:129–136; Johnson et al (1988) *Virology* 164:1–14; Lubeck et al (1989) *PNAS, USA* 86:6763–6767; McDermott et al (1989) *Virology* 169:244–247; Mittal et al (1993) *Virus Res.* 28:67–90; Morin et al (1987) *PNAS, USA* 84:4626–4630; Prevec et al (1990) *J. Inf. Dis.* 161:27–30; Prevec et al (1989) *J. Gen. Virol.* 70:429–434; Schneider et al (1989) *J. Gen. Virol.* 70:417–427 and Yuasa et al (1991) *J. Gen. Virol.* 72:1927–1934). Based on the above studies and the suggestion that adenoviruses can package approximately 105% of the wild-type (wt) adenovirus genome (Bett et al (1993) *J. Virol.* 67:5911–5921 and Ghosh-Choudhury et al (1987) *EMBO. J.* 6:1733–1739), an insertion of up to 1.8 kb foreign DNA can be packaged into adenovirus particles for use as an expression vector for foreign proteins without any compensating deletion.

The E1A gene products of the group C human adenoviruses have been very extensively studied and shown to mediate transactivation of both viral and cellular genes (Berk et al., 1979 *Cell* 17:935–944; Jones and Shenk, 1979 *Cell* 16:683–689; Nevins, 1981 *Cell* 26:213–220; Nevins, 1982 *Cell* 29:913–919; reviewed in Berk, 1986 *Ann. Res. Genet* 20:45–79), to effect transformation of cells in culture (reviewed in Graham, F. L. (1984) "Transformation by and oncogenicity of human adenoviruses. In: The Adenoviruses." H. S. Ginsberg, Editor. Plenum Press, New York; Branton et al., 1985 *Biochim. Biophys. Acta* 780:67–94) and induce cell DNA synthesis and mitosis (Zerler et al., 1987 *Mol. Cell Biol.* 7:821–929; Bellet et al., 1989 *J. Virol.* 63:303–310; Howe et al., 1990 *PNAS, USA* 87:5883–5887; Howe and Bayley, 1992 *Virology* 186:15–24). The E1A transcription unit comprises two coding sequences separated by an intron region which is deleted from all processed E1A transcripts. In the two largest mRNA species produced from the E1A transcription unit, the first coding region is further subdivided into exon 1, a sequence found in both the 12s and 13s mRNA species, and the unique region, which is found only in the 13s mRNA species. By comparisons between E1A proteins of human and simian adenoviruses three regions of somewhat conserved protein sequence (CR) have been defined (Kimelman et al., 1985 *J. Virol.* 53:399–409). CR1 and CR2 are encoded in exon 1, while CR3 is encoded in the unique sequence and a small portion of exon 2. Binding sites for a number of cellular proteins including the retinoblastoma protein Rb, cyclin A and an associated protein kinase p33$^{cdk2}$, and other, as yet unassigned, proteins have been defined in exon 1-encoded regions of E1A proteins (Yee and Branton, 1985 *Virology* 147:142–153; Harlow et al., 1986 *Mol. Cell Biol.* 6:1579–1589; Barbeau et al., 1992 *Biochem. Cell Biol.* 70:1123–1134). Interaction of E1A with these cellular proteins has been implicated as the mechanism through which E1A participates in immortalization and oncogenic transformation (Egan et al, 1989 *Oncogene* 4:383–388; Whyte et al., 1988 *Nature* 334:124–129; Whyte et al, 1988 *J. Virol.* 62:257–265). While E1A alone may transform or immortalize cells in culture, the coexpression of both E1A and either the E1B-19 k protein or the E1B-55 k protein separately or together is usually required for high frequency transformation of rodent cells in culture (reviewed in Graham, 1984 supra; Branton et al., 1985 supra; McLorie et al., 1991 *J. Gen Virol.* 72:1467–1471).

Transactivation of other viral early genes in permissive infection of human cells is principally mediated by the amino acid sequence encoded in the CR3 region of E1A (Lillie et al., 1986 *Cell* 46:1043–1051). Conserved cysteine residues in a $CysX_2CysX_{13}CysX_2Cys$ sequence motif (SEQ ID NO: 30) in the unique region are associated with metal ion binding activity (Berg, 1986 supra) and are essential for transactivation activity (Jelsma et al., 1988 *Virology* 163:494–502; Culp et al., 1988 *PNAS, USA* 85:6450–6454). As well, the amino acids in CR3 which are immediately amino (N)-terminal to the metal binding domain have been shown to be important in transcription activation, while those immediately carboxy (C)-terminal to the metal binding domain are important in forming associations with the promoter region (Lillie and Green, 1989 *Nature* 338:39–44; see FIG. 3).

The application of genetic engineering has resulted in several attempts to prepare adenovirus expression systems for obtaining vaccines. Examples of such research include the disclosures in U.S. Pat. No. 4,510,245 on an adenovirus major late promoter for expression in a yeast host; U.S. Pat. No. 4,920,209 on a live recombinant adenovirus type 7 with a gene coding for hepatitis-B surface antigen located at a deleted early region 3; European Patent 389 286 on a non-defective human adenovirus 5 recombinant expression system in human cells for HCMV major envelope glycoprotein; WO 91/11525 on live non-pathogenic immunogenic viable canine adenovirus in a cell expressing E1A proteins; and French Patent 2 642 767 on vectors containing a leader and/or promoter from the E3 region of adenovirus 2.

It is assumed that an indigenous adenovirus vector would be better suited for use as a live recombinant virus vaccine in non-human animal species, as compared to an adenovirus of human origin. This requires that regions suitable for insertion of heterologous sequences be identified in the indigenous adenoviral vector, and that compositions and methods for insertion of heterologous sequence, isolation of recombinants and propagation of recombinants be devised. Regions suitable for insertion could include non-essential regions of a viral genome or essential regions, if an appropriate helper function is provided. For example, if, by analogy to HAds, the E3 regions in other adenoviruses are not essential for virus replication in cultured cells, adenovirus recombinants containing foreign gene inserts in the E3 region could be generated.

The selection of a suitable virus to act as a vector for foreign gene expression, the identification of suitable regions as sites for gene insertion, and the construction, isolation and propagation of recombinant virus pose significant challenges to the development of recombinant viral vaccine vectors. In particular, preferred insertion sites will be non-essential for the viable replication of the virus and its effective operation in tissue culture and also in vivo. Moreover, the insertion sites must be capable of accepting new genetic material, whilst ensuring that the virus continues to replicate. An essential region of a virus genome can also be utilized for foreign gene insertion if the recombinant virus is grown in a cell line which complements the function of that particular essential region in trans.

An efficient method for determining suitable insertion sites in a viral genome is to obtain the complete nucleotide sequence of that genome. This allows the various coding regions to be defined, facilitating their possible use as insertion sites. Definition of nonessential noncoding regions would also be revealed by sequence analysis, and these could also be used as potential insertion sites. The nucleotide sequence of certain regions of the BAV-3 genome has been determined. The sequence of the extreme left end of the genome, including the inverted terminal repeat (ITR), packaging signals, E1 and pIX, has been determined by several groups: nucleotides 1–195 (ITR) by Shinagawa et al., 1987, *Gene* 55:85–93; nucleotides 1–4060 (ITR, packaging signals, E1 and pIX) by Zheng et al., 1994, *Virus Research* 31:163–186; nucleotides 1–4091 (ITR, packaging signals, E1 and pIX) by Elgadi et al., 1993, *Intervirology* 36:113–120. (Nucleotide 1 designates the left-most nucleotide of the linear, 34.4 kb BAV-3 genome.) Additional sequences of the BAV-3 genome that have been determined include: nucleotides 5,235–5,891 (major late promoter, Song et al., 1996, *Virology* 220:390–401); nucleotides 17,736–20,584 (hexon gene, Hu et al., 1984, *J. Virology* 49:604–608); nucleotides 20,408–21,197 (proteinase gene, Cai et al., 1990, *Nucleic Acids Res.* 18:5568; and nucleotides 26,034–31,132 (E3 region, pVIII and fibre genes, Mittal et al., 1992, *J. Gen. Virol.* 73:3295–3300).

One of the many uses to which recombinant viruses and viral genomes could be applied, if they were available, is in the development of recombinant subunit vaccines. Vaccination has proven to be the most effective means for controlling respiratory and enteric viral diseases, especially when live attenuated viral vaccines have been employed. These vaccines, when administered orally or intranasally, induce strong mucosal immunity, which is required to block the initial infection and to reduce the development of disease caused by these viruses. This approach has been extended by using genetically engineered virus genomes (virulence gene-deleted) as vectors to deliver and express genes of other pathogens in vivo. Ertl et al. (1996) *J. Immunol* 156:3579–3582.

A recombinant viral vector system based on human adenoviruses (HAVs) has recently been developed. Graham et al. (1992) in "Vaccines: New approaches to immunological problems" (R. W. Ellis ed.), Butterworth-Heineman, Stoneham, pp. 363–390. Both replication-defective and replication-competent HAV vectors have been engineered to express various foreign antigens. For review see Grunhaus et al. (1992) *Seminar in Virol.* 3:237–252; Imler (1995) *Vaccine* 13:1143–1151. In addition to providing stable foreign gene expression, engineered adenoviruses have been shown to induce humoral, cellular and mucosal immune responses. Buge et al. (1997) *J. Virol.* 71:8531–8541.

The use of human adenoviruses as vectors for gene therapy has been hampered because of the presence, in the host, of preexisting neutralizing antibodies against HAVs, which may interfere with entry and replication of recombinant virus, and because of the possibility of recombination and/or complementation between recombinant virus and preexisting wild-type HAV in the host. Therefore, animal adenoviruses other than HAV, which are highly species-specific, are being considered as vectors for gene therapy and recombinant vaccines.

Molecular characterization of bovine adenovirus-3 (BAV3) would aid in the development of bovine adenoviruses as live viral vectors for vaccines and gene therapy, in humans and other mammalian species. Recently, the complete DNA sequence and transcriptional map of the BAV3 genome has been reported. This sequence has been disclosed in the parent U.S. patent application Ser. No. 08/880,234, filed Jun. 23, 1997, and in several publications. Baxi et al. (1998) *Virus Genes* 16:1–4; Lee et al. (1998). *Virus Genes* 17:99–100; and Reddy et al. (1998) *J. Virol.* 72:1394–1402.

DISCLOSURE OF THE INVENTION

The present inventors have now completed the sequence of the entire BAV-3 genome comprising 34,446 nucleotides, thereby identifying regions suitable both for insertion of foreign genes and for use as diagnostic probes. The present inventors have also inserted foreign genes into these regions to generate BAV recombinants, and propagated the recombinants. Such recombinants will be useful, for example, as recombinant subunit vaccines for a variety of pathogens, for overexpression of recombinant polypeptides, and for gene therapy purposes.

In one embodiment, the present invention relates to novel bovine adenovirus expression vector systems in which part or all of one or both of the E1 and E3 gene regions are deleted. It also relates to recombinant mammalian cell lines of bovine origin transformed with E1 sequences, preferably those of BAV, which constitutively express one or more E1 gene products to allow bovine adenovirus, having a deletion of part or all of the E1 gene region replaced by a heterologous nucleotide sequence encoding a foreign gene or fragment thereof, to replicate therein. It further relates to use of these materials in production of heterologous (antigenic) polypeptides or fragments thereof.

In another embodiment, the present invention relates to novel bovine adenovirus expression vector systems that utilize the following regions of the bovine adenovirus genome or fragments thereof: nucleotides 4,092–5,234; nucleotides 5,892–17,735; nucleotides 21,198–26,032 and nucleotides 31,132–34,446. These regions (and fragments thereof) can be used, among other things, for insertion of foreign sequences, for provision of DNA control sequences including transcriptional and translational regulatory sequences, or for diagnostic purposes to detect the presence of viral nucleic acids or proteins encoded by these regions, in a subject or biological sample.

The invention also relates to a method of preparing live recombinant viruses, or subunit vaccines, for producing antibodies, cell-mediated and/or mucosal immunity to an infectious organism in a mammal, including bovines, humans and other mammals. The method comprises inserting into the bovine adenovirus genome a gene or gene fragment coding for the antigen which corresponds to said antibodies or which induces said cell-mediated and/or mucosal immunity, together with or without an effective promoter therefor, to produce BAV recombinants.

In another aspect, the invention includes the use of recombinant viruses and recombinant viral vectors for the expression of a DNA sequence or amino acid sequence of interest in a cell system.

Generally, the foreign gene construct is cloned into a nucleotide sequence which represents only a part of the entire viral genome having one or more appropriate deletions. This chimeric DNA sequence is usually present in a plasmid which allows successful cloning to produce many copies of the sequence. The cloned foreign gene construct can then be included in the complete viral genome, for example, by in vivo recombination following a DNA-mediated cotransfection technique. Incorporation of the cloned foreign gene construct into the viral genome places the foreign gene into a DNA molecule containing replication and packaging signals, allowing generation of multiple copies of the recombinant adenovirus genome that can be packaged into infectious viral particles. Multiple copies of a coding sequence or more than one coding sequence can be inserted so that the recombinant vector can express more than one foreign protein. The foreign gene can have additions, deletions or substitutions to enhance expression and/or immunological effects of the expressed protein.

The invention also includes an expression system comprising a bovine adenovirus expression vector wherein heterologous nucleotide sequences with or without any exogenous regulatory elements replace the E1 gene region and/or part or all of the E3 gene region. In another embodiment, the invention includes an expression system wherein one or more regions of the BAV genome are replaced by heterologous sequences, or wherein heterologous nucleotide sequences are introduced into the BAV genome without removal of any BAV sequences. Intergenic regions of the BAV genome comprising DNA regulatory sequences are useful for the expression of homologous and heterologous (i.e., foreign) genes in the practice of the invention.

The invention also includes (A) a recombinant vector system comprising the entire BAV DNA and a plasmid or two plasmids capable of generating a recombinant virus by in vivo homologous recombination following cotransfection of a suitable cell line, comprising BAV DNA representing the entire wild-type BAV genome and a plasmid comprising bovine adenovirus left or right end sequences containing the E1 or E3 gene regions or bovine adenovirus E2, E4, L1, L2, L3, L4, L5, L6 or L7 sequences, with a heterologous nucleotide sequence encoding a foreign gene or fragment thereof substituted for part or all of the E1, E2, E3, E4, L1, L2, L3, L4, L5, L6 or L7 gene regions (i.e., an insertion cassette); (B) a live recombinant bovine adenovirus vector (BAV) system selected from the group consisting of: (a) a system wherein part or all of the E1 gene region is replaced by a heterologous nucleotide sequence encoding a foreign gene or fragment thereof; (b) a system wherein a part or all of the E3 gene region is replaced by a heterologous nucleotide sequence encoding a foreign gene or fragment thereof; and c) a system wherein part or all of the E1 gene region and part or all of the E3 gene region are deleted and a heterologous nucleotide sequence encoding a foreign gene or fragment thereof is inserted into at least one of the deletions; C) a recombinant bovine adenovirus (BAV) comprising a deletion of part or all of E1 gene region, a deletion of part or all of E3 gene region or deletion of both, and inserted into at least one deletion a heterologous nucleotide sequence coding for an antigenic determinant of a disease causing organism; (D) a recombinant bovine adenovirus expression system comprising a deletion of part or all of E1, a deletion of part or all of E3, or both deletions, and inserted into at least one deletion a heterologous nucleotide sequence coding for a foreign gene or fragment thereof under control of an expression promoter: or (E) a recombinant bovine adenovirus (BAV) for producing an immune response in a mammalian host comprising: (1) BAV recombinant containing a heterologous nucleotide sequence coding for an antigenic determinant needed to obtain the desired immune response in association with or without (2) an effective promoter to provide expression of said antigenic determinant in immunogenic quantities for use as a live recombinant virus or recombinant protein or subunit vaccine; (F) a mutant bovine adenovirus (BAV) comprising a deletion of part or all of E1 and/or a deletion of part or all of E3 and/or a deletion of part or all of at least one of the following regions of the BAV genome: E2, E4, L1, L2, L3, L4, L5, L6 or L7.

In addition to the E1 and E3 regions, other sites within the BAV genome are also useful for insertion of foreign nucleotide sequences. These include, but are not limited to, the E2 region, the E4 region, the region between the E4 promoter and the right end of the genome, the late regions (L1–L7), the 33 kD, 52 kD, 100 kD, DBP, pol, pTP and penton genes, and genes IIIA, pV, pVI, pVII, pVIII and pX.

The invention also provides methods and compositions for obtaining, at high efficienecy, viruses whose genomes contain deletions in the E3 region, as well as viruses whose genomes contain insertions of heterologous sequences into a deleted E3 region. In one embodiment, E3-deleted viral genomes (with or without insertion of heterologous sequences) are transfected into a suitable cell line, for example, MDBK cells expressing adenovirus E1 function or equivalent cells, and recombinant viruses are recovered from the transfected cells. In another embodiment, a segment of the BAV genome containing a deleted E3 region (with or without insertion of heterologous sequences) is allowed to undergo recombination, in a procaryotic cell, with a BAV genome to generate a recombinant BAV genome. For the purposes of the present invention, a BAV genome can be a full-length BAV genome, or it can contain one or more deletions, provided that it comprises one or more BAV replication and/or packaging sequences. The BAV genome segment containing a deleted E3 region can also contain one or more BAV replication and/or packaging sequences. A recombinant BAV genome includes an otherwise full-length BAV genome with one or more deletions in particular genomic region(s), as well as BAV genomes, either deleted or undeleted, in which heterologous sequences have been inserted. The recombinant BAV genome is then transfected into a suitable cell line such as, for example, primary fetal bovine retina (PFBR) cells, and recombinant virus is recovered from the transfected cells.

In another aspect, the invention provides recombinant mammalian cell lines stably transformed with BAV E1 gene region sequences, said recombinant cell lines thereby capable of allowing replication therein of a bovine adenovirus comprising a deletion of part or all of the E1 or E3 gene regions replaced by a heterologous or homologous nucleotide sequence encoding a foreign gene or fragment thereof. The invention also includes production, isolation and purification of polypeptides or fragments thereof, such as growth factors, receptors and other cellular proteins from recombinant bovine cell lines expressing BAV E1 gene products.

The invention also includes a method for providing gene therapy to a mammal in need thereof. Gene therapy can be used, for example, to control a gene deficiency, to introduce a therapeutic gene into a host cell, to change the sequence of a mutant gene to restore wild-type function, to change the sequence of a gene to inactivate its function, to provide exogenous gene function, etc. Gene therapy will be used, for example, in the treatment of cancer, AIDS, other virally-induced pathologies, infectious diseases, hereditary diseases, etc. The process of gene therapy comprises administering to said mammal a live recombinant bovine adenovirus containing a heterologous nucleotide sequence under conditions wherein the recombinant virus vector genome is incorporated into said mammalian genome or is maintained independently and extrachromosomally, to provide expression of the heterologous sequence in a target organ or tissue.

Another aspect of the invention provides a pharmaceutical composition which comprises a therapeutically effective amount of a recombinant virus, recombinant viral vector or recombinant protein in association with or without a pharmaceutically acceptable carrier. One example of such a pharmaceutical composition is a recombinant virus vaccine. The recombinant virus vaccine can be formulated for administration by an oral dosage (e.g. as an enteric coated tablet), by injection or otherwise. More specifically, these include a vaccine for protecting a mammalian host against infection comprising a live recombinant adenovirus or recombinant protein produced by the recombinant adenovirus of the invention wherein the foreign gene or fragment encodes an antigen and formulated with or without a pharmaceutically acceptable carrier. These compositions are capable of expressing antigenic polypeptides or protective antigens, thereby eliciting an immune response to a polypeptide or antigen of interest and providing protection from infection. Pharmaceutical compositions useful in the practice of the invention may also comprise cells harboring a recombinant BAV vector expressing a polypeptide or antigen of interest, or cells harboring a vector expressing BAV polypeptides or antigens.

The invention also includes methods of producing antibodies, cell-mediated and/or mucosal immunity in a mammal including (1) a method for eliciting an immune response in a mammalian host against an infection comprising: administering a vaccine comprising a live BAV recombinant of the invention wherein the foreign gene or fragment encodes an antigen with or without a pharmaceutically acceptable carrier, and (2) a method for eliciting an immune response in a mammalian host against an infection comprising: administering a vaccine comprising a recombinant antigen prepared by culturing a BAV recombinant wherein the foreign gene or fragment encodes the desired antigen with or without a pharmaceutically acceptable carrier.

The invention additionally provides compositions and methods useful in the practice of diagnostic procedures to detect the presence of BAV DNA and/or BAV-encoded proteins and antigens in a biological sample such as an infected cell or a mammalian subject, or a nucleic acid preparation from these sources. These include but are not limited to BAV genes and coding sequences and fragments thereof, as well as amino acid sequences encoded by the BAV genome and fragments thereof.

The following disclosure will render these and other embodiments of the present invention readily apparent to those of skill in the art. While the disclosure often refers to bovine adenovirus type 3 (BAV3), it should be understood that this is for the purpose of illustration and that the same features apply to bovine adenovirus of other types, e.g, 1, 2, 4, 5, 6, 7 8, and 9; and that the invention described and claimed herein is intended to cover all of these bovine adenovirus types.

BRIEF DESCRIPTION OF THE DRAWINGS

FIGS. 1-1 to 1-5. Sequence and major open reading frames of the left 11% of the BAV3 genome (SEQ ID NO: 1 through SEQ ID NO: 8). The region comprises the E1 and protein IX transcription region. The 195 nucleotide inverted terminal repeat sequence identified by Shinagawa et al., 1987 Gene 55:85–93 is shown in italics. The amino acid sequence for the largest E1A protein, two E1B proteins and protein IX are presented. The probable splice donor ([), splice acceptor (]) and intron sequence (underlined italics) within the E1A region are marked. A 35 base pair repeat sequence between E1A and E1B is indicated in bold underline. Possible transcription promoter TATA sequences and possible poly A addition sequences AATAA are also indicated.

FIG. 2. Regions of homology in the E1A proteins of BAV3 and human adenovirus type 5 (HAd5). The amino acid residue of each serotype is indicated. A. Conserved region 3 (CR3) of HAd5 (SEQ ID NO: 9) subdivided into three functional regions as defined by Lillie et al (1989) Nature 338:39–44 and described in the Background of the Invention. The intron sequence of BAV3 E1A occurs within the serine amino acid codon at position 204 (nucleotide positions 1216–1322 of SEQ ID NO: 1). B. A portion of conserved region 2 (CR2) of HAd5 (SEQ ID NO: 10) showing the residues thought to be important in the binding of retinoblastoma protein Rb (Dyson et al., 1990 J. Virol. 64:1353–1356), and the comparable sequence from BAV3 (SEQ ID NO: 34).

FIG. 3. Homology regions between the HAd5 E1B 19 k (176R) protein (SEQ ID NO: 11 and SEQ ID NO: 12) and the corresponding BAV3 (157R) protein (amino acid positions 83–97 and 136–182 of SEQ ID NO: 4). The amino acid residue number for each of the viruses is indicated.

FIG. 4. The C-terminal 346R of HAd5 E1B 56 k (496R) (SEQ ID NO: 13) and the corresponding BAV3 protein (420R) (amino acid positions 74–420 of SEQ ID NO: 6). The HAd5 protein comparison begins at residue 150 and the BAV3 (in italics) at residue 74. The amino terminal regions of these proteins which are not presented show no significant homology.

FIG. 5. Homology comparison of the amino acid sequence of HAd5 protein IX (SEQ ID NO: 14) and the corresponding protein of BAV3 (SEQ ID NO: 8) (in italics).

FIGS. 7-1 to 7-8. Nucleotide sequence of BAV3 between 77 and 92 m.u. (SEQ ID NO: 15 through SEQ ID NO: 26) showing ORFs that have the potential to encode polypeptides of at least 50 amino acids after the initiating methionine. The nucleotide sequence was analyzed using the program DISPCOD (PC/GENE). Potential N-glycosylation sites (N-X-T/S) and polyadenylation signals are underlined and the first methionine of each ORF is shown in bold.

FIGS. 8(a)–8(c)-2. Comparison between the predicted amino acid sequences for the ORFs of BAV3 and known proteins of HAd2 or -5 using the computer program PALIGN (PC/GENE), with comparison matrix structural-genetic matrix; open gap cost 6; unit gap cost 2. Identical residues are indicated by a colon and similar residues by a dot. (a) Comparison between the predicted amino acid sequence encoded by the 3' end of BAV3 ORF 1 (SEQ ID NO: 16) and the HAd2 hexon-associated pVIII precursor (SEQ ID NO: 27). (b) Comparison between the ORF 4 (amino acid positions 34–154 of SEQ ID NO: 22) and the HAd514.7K E3 protein (SEQ ID NO: 28). (c) Comparison between the predicted amino acid sequence encoded by BAV3 ORF 6 (amino acid positions 8–983 of SEQ ID NO: 26) and the HAd2 fibre protein (SEQ ID NO: 28).

FIGS. 20:1–20:19. Complete nucleotide sequence of the bovine adenovirus type-3 (BAV-3) genome (SEQ ID NO: 35).

a: 5'-ACGCGTCGACTCCTCCTCA (SEQ ID NO: 36);
b: 5'-TTGACAGCTAGCTTGTTC (SEQ ID NO: 37);
c: 5'-CCAAGCTTGCATGCCTG (SEQ ID NO: 38); and
d: 5'-GGCGATATCTCAGCTATAACCGCTC (SEQ ID NO: 39).

Figure 23:
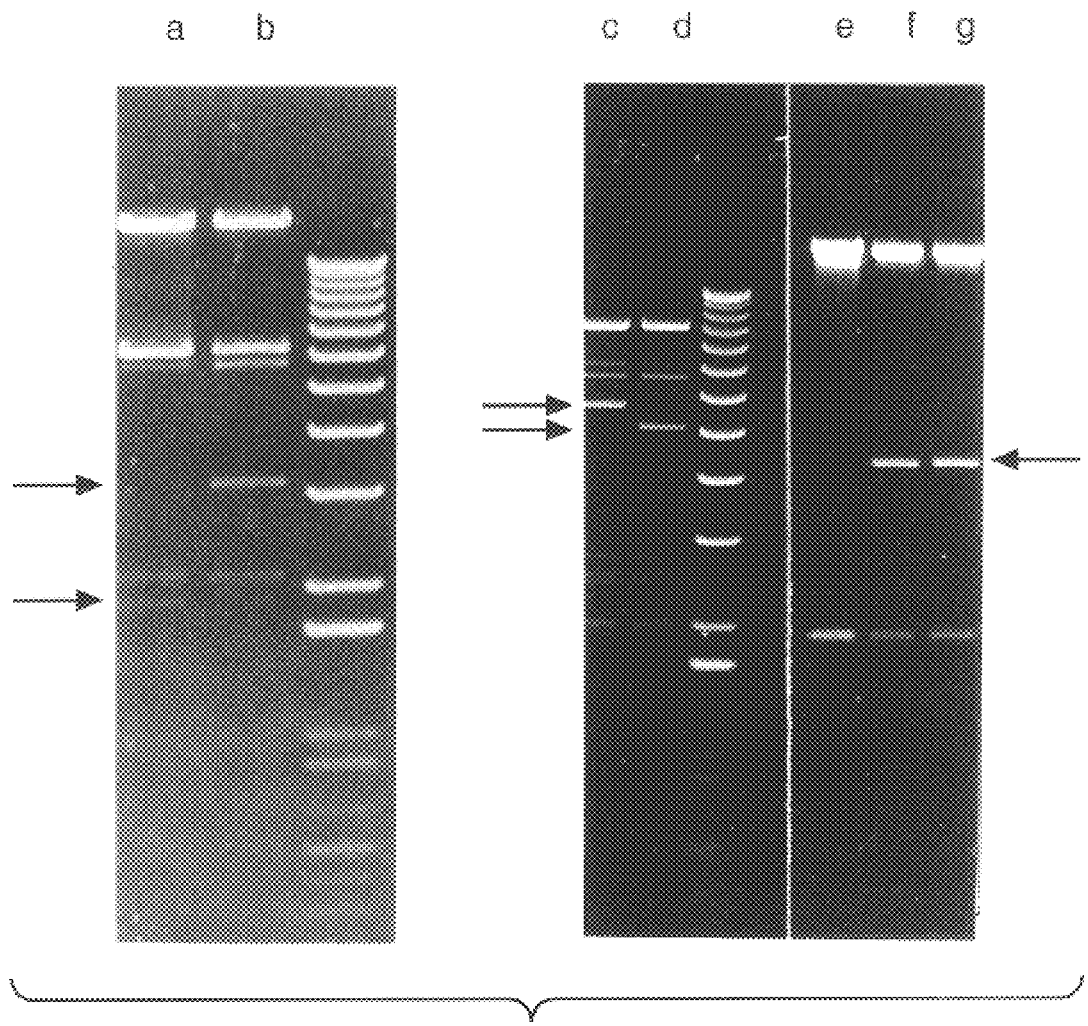

FIG. 23. Restriction enzyme analysis of recombinant BAV3 genomes. The DNAs were obtained from MDBK cells infected with BAV3 (lane b), BAV3.E3d (lanes a and e), BAV3.E3gD (lanes c and f) or BAV3.gDt (lanes d and g). DNA was extracted by Hirt's method (Hirt (1967) *J. Mol. Biol.* 26:365–369), and digested with BamHI (lanes a and b), NheI (lanes c and d) or NdeI (lanes e, f and g). The 1 kb plus DNA ladder (Gibco/BRL) was used for sizing the viral DNA fragments.

Figure 24A:
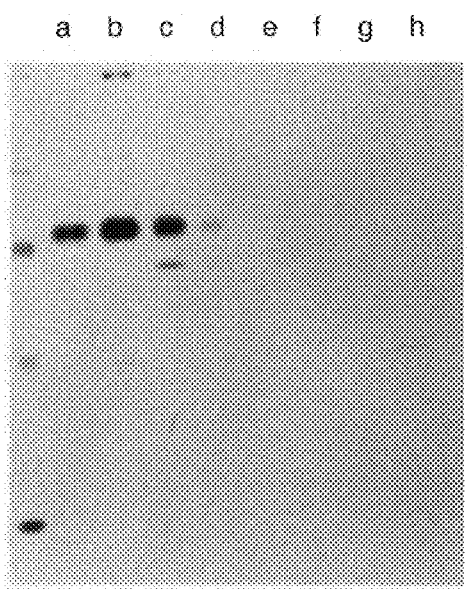
Figure 24B:
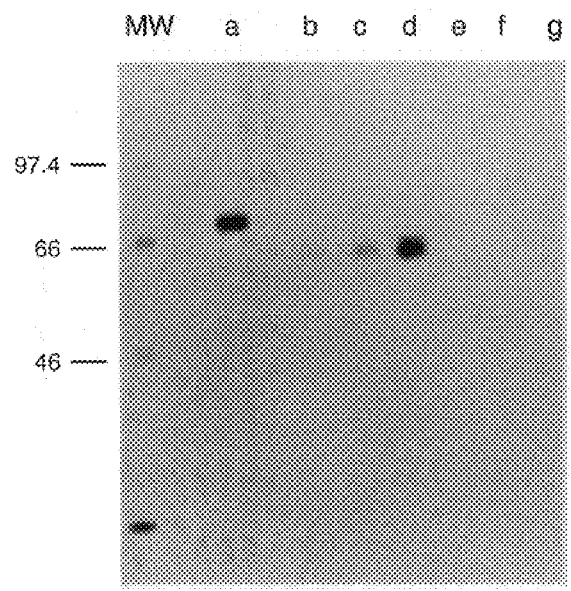

FIGS. 24A–24B. Expression of gD proteins in MDBK cells infected with recombinant BAV3 viruses. (A) Proteins from lysates of radiolabelled MDBK cells uninfected (lane h) or infected with BHV-1 (lane a), BAV3.E3d (lanes e, f and g), or BAV3.E3gD (lanes b, c and d) were immunoprecipitated with a pool of gD-specific MAbs and analyzed by SDS-PAGE under reducing conditions. Proteins were labelled from 6 to 16 h (lanes a and h), 36 to 48 h (lanes b and e), 48 to 50 h (lanes c and f), or 60 to 62 h (lanes d and g) post-infection. (B) Proteins from culture medium of radiolabelled MDBK cells infected with BHV-1 (lane a), BAV3.E3d (lanes e, f and g), or BAV3.E3gDt (lanes b, c and d) were immunoprecipitated with a pool of gD-specific MAbs and analyzed by SDS-PAGE under reducing conditions. Proteins were labelled from 6 to 16 h (lane a), 12 to 14 h (lanes b and e), 16 to 18 h (lanes c and f), or 22 to 26 h (lanes d and g), post-infection. Molecular size markers (MW) in kDa.

Figure 25:
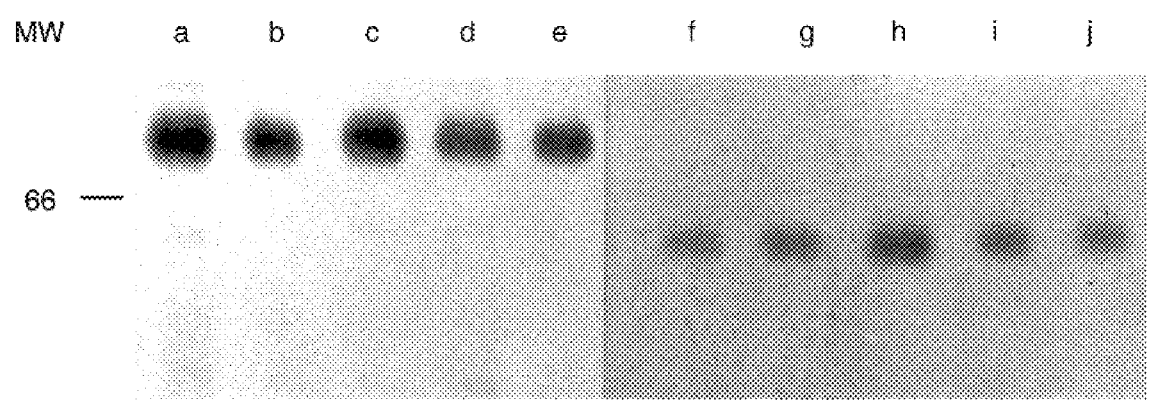

FIG. 25. Antigenic analysis of recombinant gD and gDt proteins. Proteins from lysates (lanes a–e) and culture medium (lanes f–j) of radiolabelled MDBK cells infected with BAV3.E3gD (lane a–e) or BAV3.E3gDt (lanes f–j) recombinant viruses were immunoprecipitated with MAb 136 (lanes a and f), MAb 3E7 (lanes b and g), MAb 4C1 (lanes c and h), MAb 2C8 (lanes d and i), or MAb 3C1 (lanes e and j), and analyzed by SDS-PAGE under reducing conditions. Molecular size marker (MW) in kDa.

Figure 26:
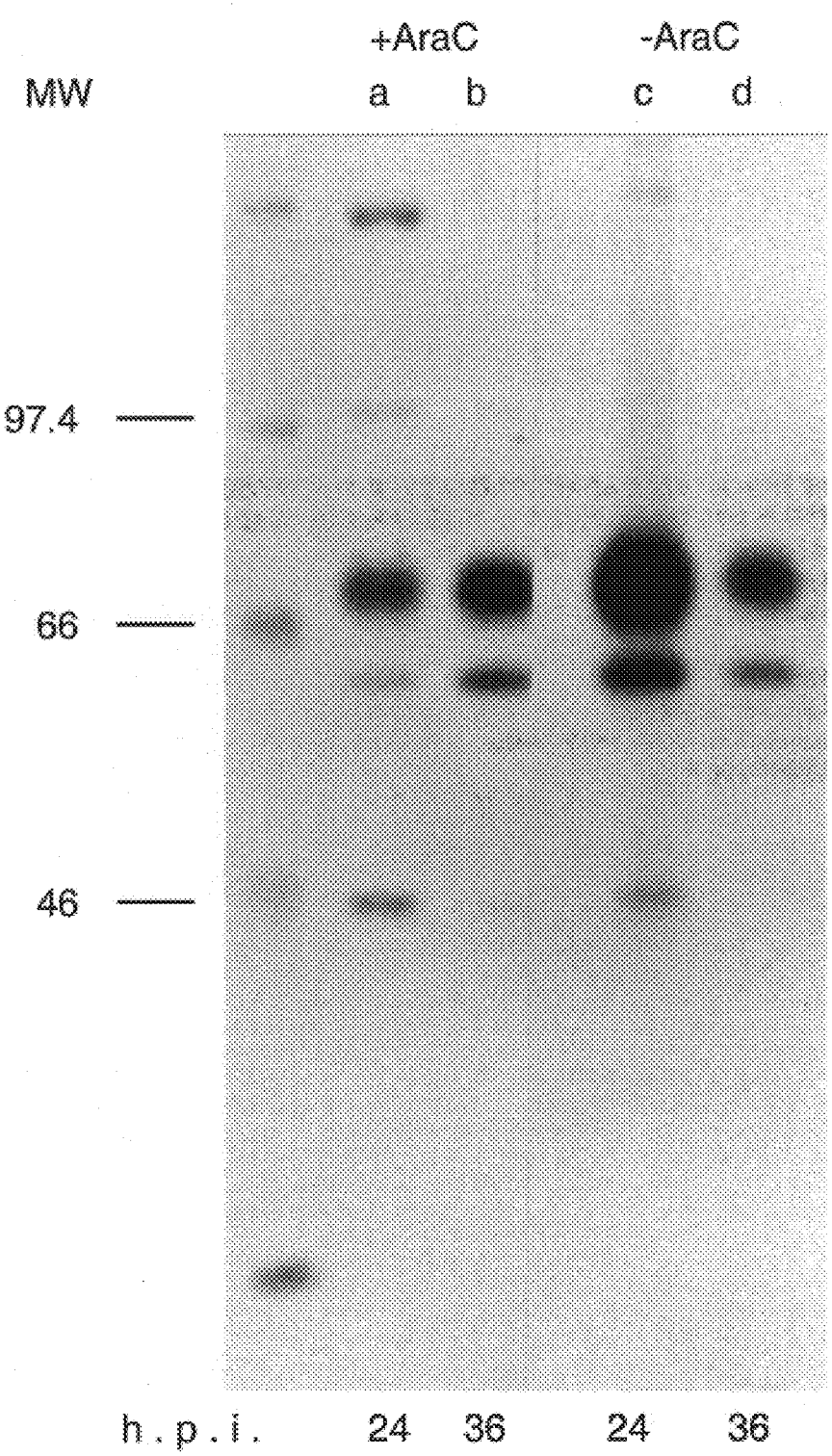

FIG. 26. Effect of AraC on gD expression in MDBK cells. Proteins from lysates of MDBK cells infected with BAV3.E3gD (lanes a–d) in the presence (lanes a, b) or absence (lanes c, d) of 100 µg/ml AraC and radiolabelled for 2 h at 22 h (lanes a and c) or 34 h (lanes b and d) post-infection were immunoprecipitated with a pool of gD-specific MAbs and analyzed by SDS-PAGE. Molecular size markers (MW) in kDa.

FIGS. 27A–27D. Antibody responses in cotton rats. Glycoprotein gD (A, B) or BAV3 specific (C, D) IgA (A, C) or IgG (B, D) ELISA titers in sera, lung washes (l.w) and nasal washes (n.w.) 12 days after secondary immunization with recombinant BAV's. Open bars represent BAV3.E3gD, filled bars represent BAV3.E3gDt, and stippled bars represent BAV3.E3d. Error bars represent the standard error of the mean of four animals per group.

Figure 28:
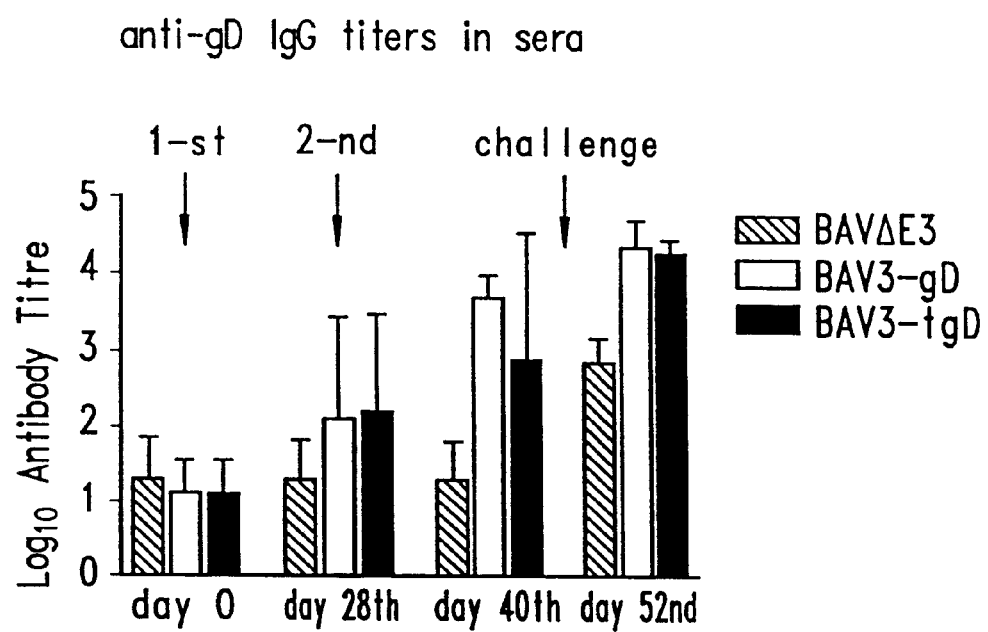

FIG. 28: Anti-gD IgG titers in calf sera (measured by gD-specific ELISA) at different time points post-immunization with different BAV recombinants. Stippled bars: animals immunized with BAV3.E3d; open bars: animals immunized with BAV3.E3gD; solid bars: animals vaccinated with BAV3.E3gDt.

Figure 29:
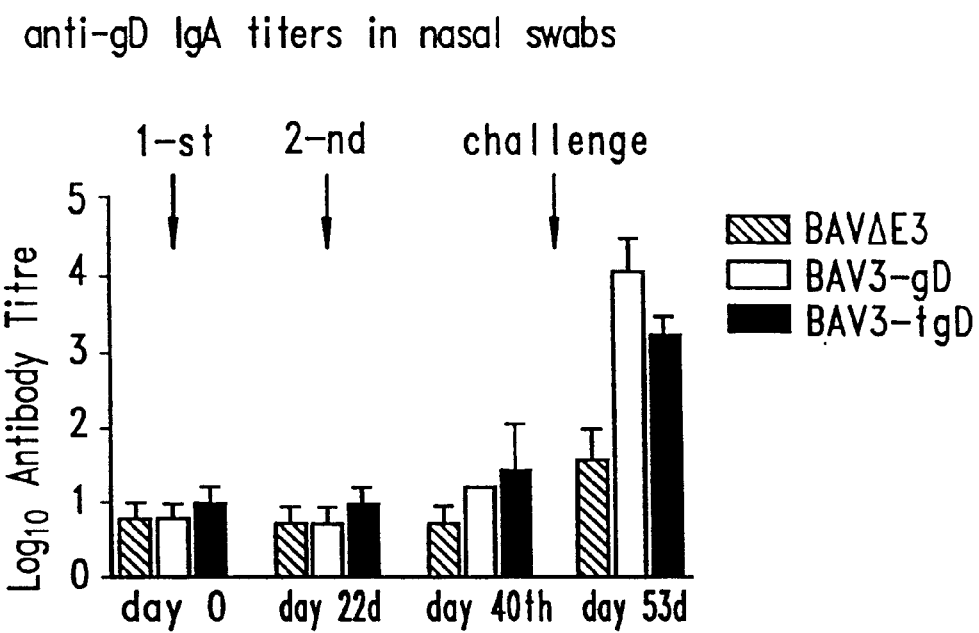

FIG. 29: Anti-gD IgA titers in calf nasal swabs (measured by gD specific ELISA) at different time points post immunization with different BAV recombinants. Stippled bars: animals immunized with BAV3.E3d; open bars: animals immunized with BAV3.E3gD; solid bars: animals vaccinated with BAV3.E3gDt.

Figure 30:
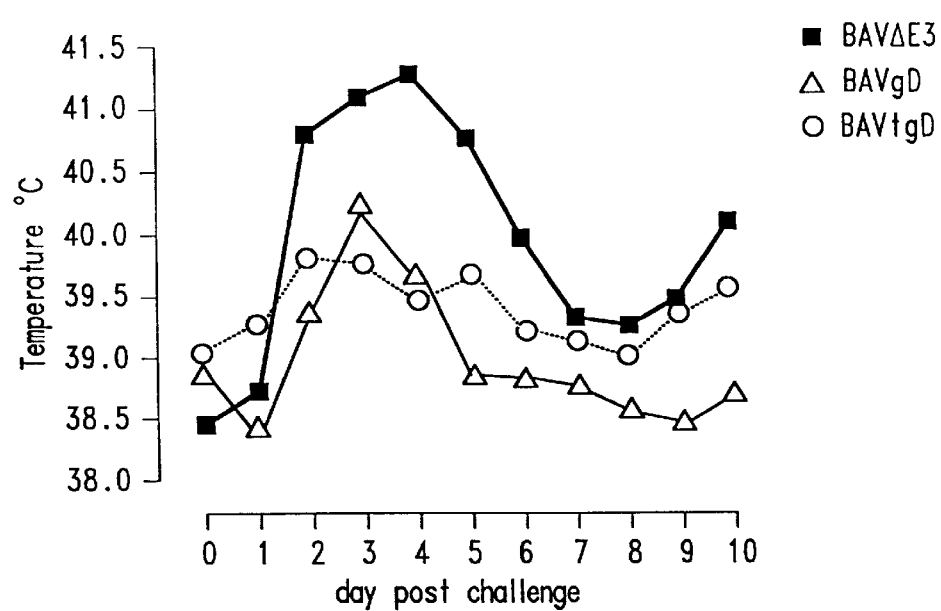

FIG. 30: Temperatures of vaccinated calves observed after BHV-1 challenge. Filled squares: animals immunized with BAV3.E3d; open triangles: animals immunized with BAV3.E3gD; open circles: animals vaccinated with BAV3.E3gDt.

Figure 31:
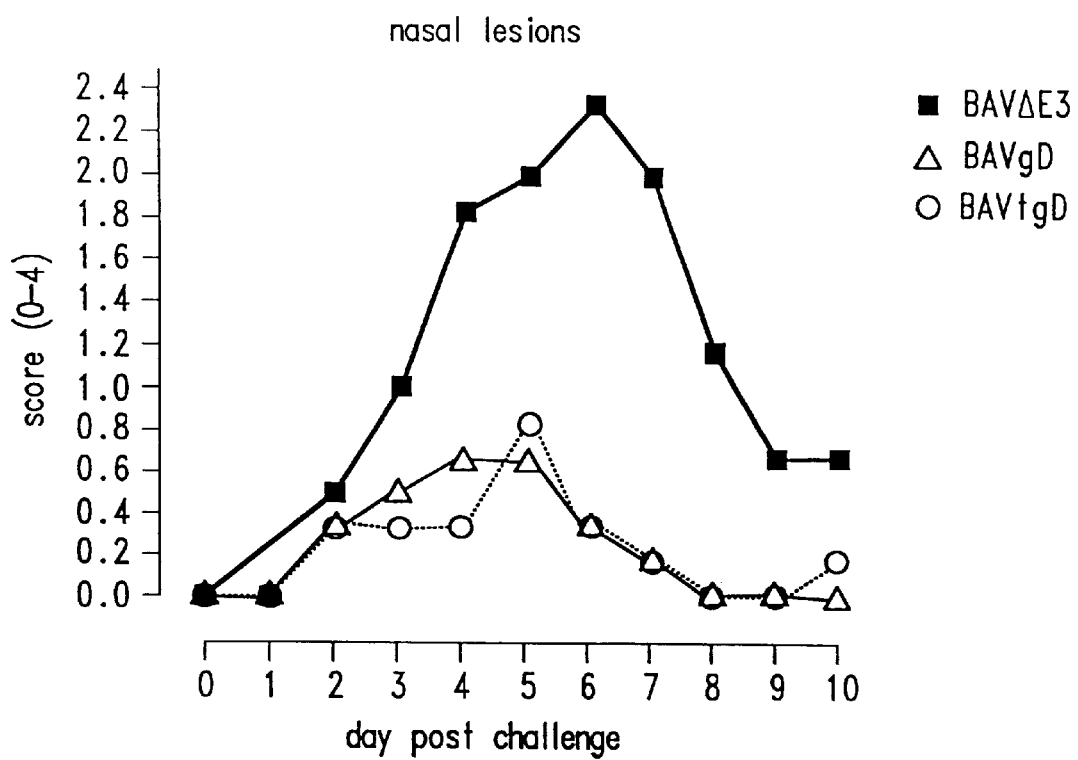

FIG. 31: Observations on the appearance and extent of nasal lesions after BHV-pb 1challenge in vaccinated calves. Filled squares: animals immunized with BAV3.E3d; open triangles: animals immunized with BAV3.E3gD; open circles: animals vaccinated with BAV3.E3gDt.

Figure 32:
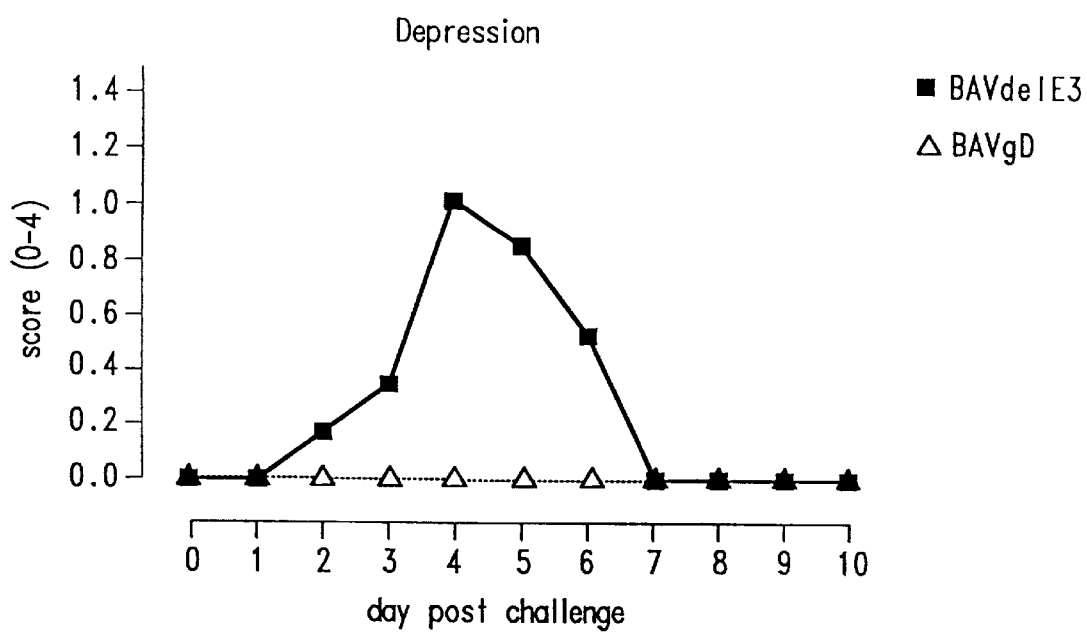

FIG. 32: Extent of depression observed in the test and control groups of vaccinated calves. Filled squares: animals immunized with BAV3.E3d; open triangles: animals immunized with BAV3.E3gD.

Figure 33:
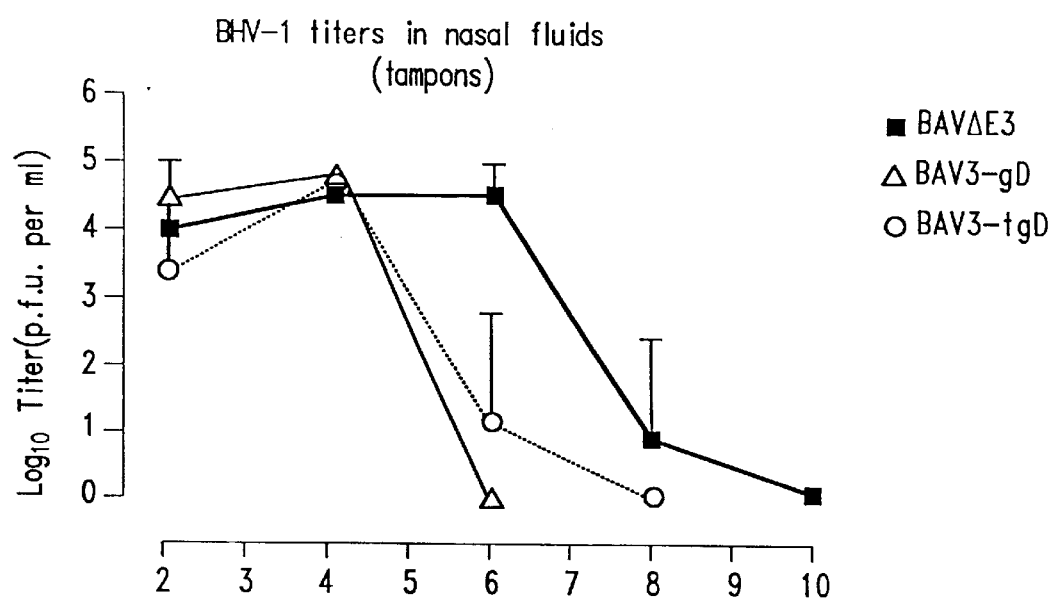

FIG. 33: Isolation of BHV-1 after BHV-1 challenge of test and control groups of vaccinated calves. Filled squares: animals immunized with BAV3.E3d; open triangles: animals immunized with BAV3.E3gD; open circles: animals vaccinated with BAV3.E3gDt.

MODES OF CARRYING OUT THE INVENTION

The practice of the present invention will employ, unless otherwise indicated, conventional microbiology, immunology, virology, molecular biology, and recombinant DNA techniques which are within the skill of the art. These techniques are fully explained in the literature. See, eg., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984). Sambrook et al., Molecular Cloning: A Laboratory Manual ($2^{nd}$ Edition); vols. I, II & III (1989).

A. Definitions

In describing the present invention, the following terminology, as defined below, will be used.

A "replicon" is any genetic element (e.g., plasmid, chromosome, virus) that functions as an autonomous unit of DNA replication in vivo; i.e., is capable of replication under its own control.

A "ivector" is a replicon, such as a plasmid, phage, cosmid or virus, to which another DNA segment may be attached so as to bring about the replication of the attached segment.

By "live virus" is meant, in contradistinction to "killed" virus, a virus which is capable of producing identical progeny in tissue culture and inoculated animals.

A "helper-free virus vector" is a vector that does not require a second virus or a cell line to supply something defective in the vector.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments of DNA from viruses, plasmids, and chromosomes). In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, viral DNA, and even synthetic DNA sequences. A polyadenylation signal and transcription termination sequence will usually be located 3' to the coding sequence.

A "transcriptional promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAAT" boxes. Procaryotic promoters contain Shine-Dalgarno sequences in addition to the −10 and −35 consensus sequences.

DNA "control sequences" refer collectively to promoter sequences, ribosome binding sites, splicing signals, polyadenylation signals, transcription termination sequences, upstream regulatory domains, enhancers, translational termination sequences and the like, which collectively provide for the transcription and translation of a coding sequence in a host cell.

A coding sequence or sequence encoding is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cell containing the exogenous DNA.

A "clone" is a population of daughter cells derived from a single cell or common ancestor. A "cell line" is a clone of a primary cell that is capable of stable growth in vitro for many generations.

Two polypeptide sequences are "substantially homologous" when at least about 80% (preferably at least about 90%, and most preferably at least about 95%) of the amino acids match over a defined length of the molecule.

Two DNA sequences are "substantially homologous" when they are identical to or not differing in more that 40% of the nucleotides, preferably not more than about 30% of the nucleotides (i.e. at least about 70% homologous) more preferably about 20% of the nucleotides, and most preferably about 10% of the nucleotides.

DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, vols. I & II, supra; *Nucleic Acid Hybridization*, supra.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

"Bovine host" refers to cattle of any breed, adult or infant.

The term "protein" is used herein to designate a polypeptide or glycosylated polypeptide, respectively, unless otherwise noted. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Fusion protein" is usually defined as the expression product of a gene comprising a first region encoding a leader sequence or a stabilizing polypeptide, and a second region encoding a heterologous protein. It involves a polypeptide comprising an antigenic protein fragment or a full length BAV protein sequence as well as (a) heterologous sequence (s), typically a leader sequence functional for secretion in a recombinant host for intracellularly expressed polypeptide, or an N-terminal sequence that protects the protein from host cell proteases, such as SOD. An antigenic protein fragment is usually about 5–7 amino acids in length.

"Native" proteins or polypeptides refer to proteins or polypeptides recovered from BAV or BAV-infected cells. Thus, the term "native BAV polypeptide" would include naturally occurring BAV proteins and fragments thereof. "Non-native" polypeptides refer to polypeptides that have been produced by recombinant DNA methods or by direct synthesis. "Recombinant" polypeptides refers to polypeptides produced by recombinant DNA techniques; i.e., produced from cells transformed by an exogenous DNA construct encoding the desired polypeptide.

A "substantially pure" protein will be free of other proteins, preferably at least 10% homogeneous, more preferably 60% homogeneous, and most preferably 95% homogeneous.

An "antigen" refers to a molecule containing one or more epitopes that will stimulate a host's immune system to make a humoral and/or cellular antigen-specific response. The term is also used interchangeably with "immunogen."

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds or is recognized by T cells. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody-dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody-dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the antigens. The term "treatment" as used herein refers to treatment of a mammal, such as bovine or human or other mammal, either (i) the prevention of infection or reinfection (prophylaxis), or (ii) the reduction or elimination of symptoms of an infection. The vaccine comprises the recombinant BAV itself or recombinant antigen produced by recombinant BAV.

By "infectious" is meant having the capacity to deliver the viral genome into cells.

B. General Method

Figure 21:
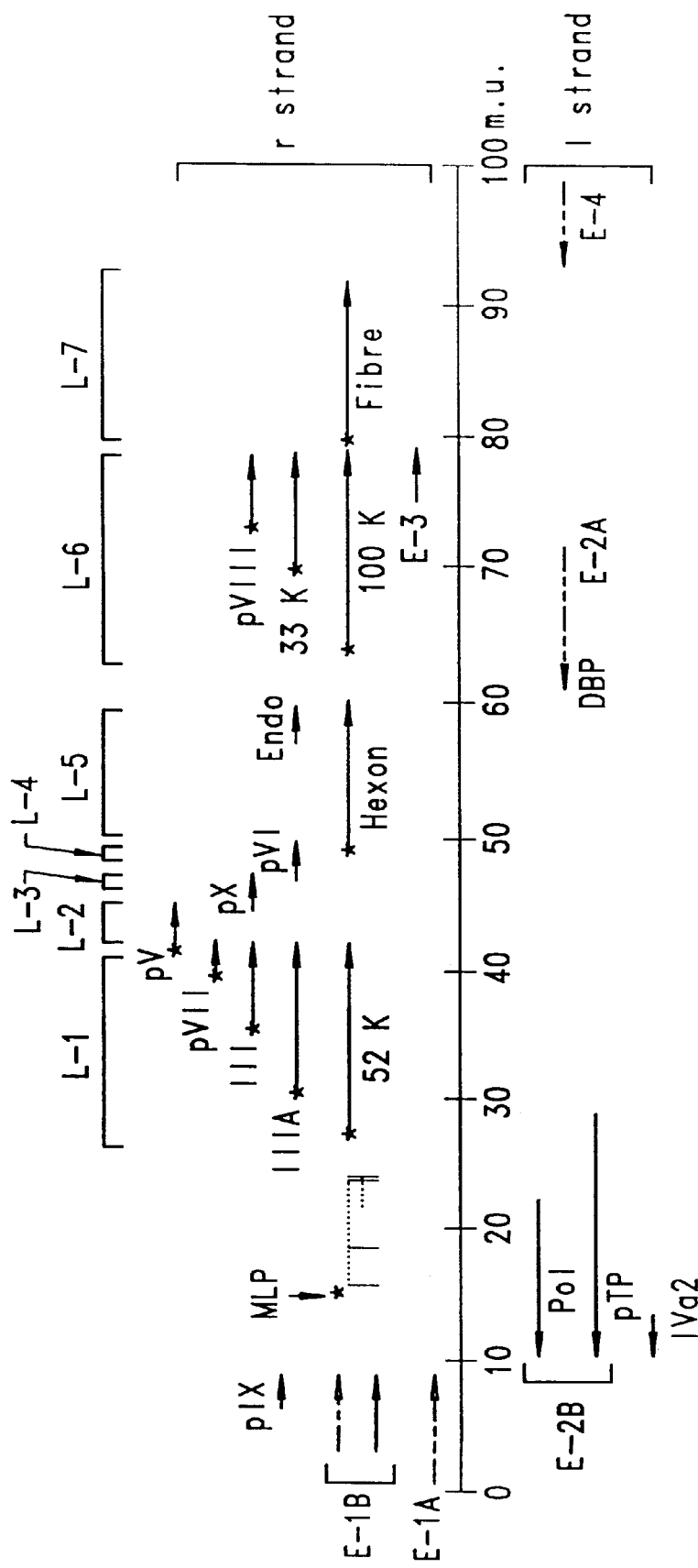
FIG. 21. Transcriptional map of BAV-3. The genome is represented by a solid line numbered from 0 to 100 (map units). Transcripts are represented, with respect to length and direction of transcription, by arrows. The locations of the E1A, E1B, E2A, E2B, E3, E4, L1, L2, L3, L4, L5, L6 and L7 regions are indicated. Packaging and replication sequences are located in the 195 bp ITR sequences and in a region between the left ITR and the E1 region.

The present invention discloses the complete nucleotide sequence of the BAV3 genome. See FIG. 20 and SEQ ID NO 35. A transcriptional map of the BAV3 genome, derived from transcriptional mapping of mRNAs and sequencing of cDNA clones, is presented in FIG. 21. Although the size (34,446 bp) and the overall organization of the BAV3 genome appear to be similar to that of HAVs, there are certain differences. Reddy et al. (1998) supra. One of the distinctive features of the BAV3 genome is the relatively small size of the E3 coding region (1517 bp). Mittal et al. (1992) *J. Gen. Virol.* 73:3295–3300; Mittal et al. (1993). *J. Gen. Virol.* 74:2825; and Reddy et al. (1998) supra. Analysis of the sequence of the BAV3 E3 region and its RNA transcripts suggests that BAV3 E3 may encode at least four proteins, one of which (121R) exhibits limited homology with the 14.7 kDa protein of HAV5. Idamakanti (1998) "Molecular characterization of E3 region of bovine adenovirus-3," M.Sc. thesis, University of Saskatchewan, Saskatoon, Saskatchewan.

In one embodiment, the present invention identifies and provides a means of deleting part or all of the nucleotide sequence of bovine adenovirus E1 and/or E3 regions to provide sites into which heterologous or homologous nucleotide sequences encoding foreign genes or fragments thereof can be inserted to generate bovine adenovirus recombinants. By "deleting part of" the nucleotide sequence is meant using conventional genetic engineering techniques for deleting the nucleotide sequence of part of the E1 and/or E3 region.

In another embodiment, the invention provides compositions and methods for constructing, isolating and propagating E3-deleted recombinant BAV3 (with or without insertion of heterologous sequences) at high efficiency. These include isolation of recombinant virus in suitable cell lines, such as MDBK cells expressing adenovirus E1 function or equivalent cell lines, and methods wherein recombinant BAV genomes are constructed via homologous recombination in procaryotic cells, the recombinant genomes obtained thereby are transfected into suitable cell lines such as, for example, primary fetal bovine retina cells or their equivalent, and recombinant virus is isolated from the transfected cells.

In addition, the construction of recombinant BAV3 expressing different forms of BHV-1 glycoprotein gD are provided, and it is shown that intranasal immunization of cotton rats with gD-expressing recombinant BAV viruses leads to the induction of gD-specific mucosal and systemic immune responses. See Example 9. Intranasal immunization of bovine hosts with BAV recombinants containing BHV-1 gD genes provides protection against BHV-1 challenge in calves, reducing the occurrence of clinical signs, facilitating more rapid clearance of virus, and providing increased titers of both IgG and IgA. See Example 10. In similar fashion, any genes encoding protective determinants of a mammalian pathogen can be inserted into E3-deleted BAV, and the resulting recombinant BAV can be used as a vaccine.

In one embodiment of the invention, a recombinant BAV expression cassette can be obtained by cleaving a wild-type BAV genome with one or more appropriate restriction enzyme(s) to produce a BAV restriction fragment comprising E1 or E3 region sequences, respectively. The BAV restriction fragment can be inserted into a cloning vehicle, such as a plasmid, and thereafter at least one heterologous sequence (which may or may not encode a foreign protein) can be inserted into the E1 or E3 region with or without an operatively-linked eukaryotic transcriptional regulatory sequence. The recombinant expression cassette is contacted with a BAV genome and, through homologous recombination or other conventional genetic engineering methods, the desired recombinant is obtained. In the case wherein the expression cassette comprises the E1 region or some other essential region, recombination between the expression cassette and a BAV genome can occur within an appropriate helper cell line such as, for example, an E1-transformed cell line. Restriction fragments of the BAV genome other than those comprising the E1 or E3 regions are also useful in the practice of the invention and can be inserted into a cloning vehicle such that heterologous sequences can be inserted into the BAV sequences. These DNA constructs can then undergo recombination in vitro or in vivo, with a BAV genome either before or after transformation or transfection of an appropriate host cell.

Suitable host cells include any cell that will support recombination between a BAV genome and a plasmid containing BAV sequences, or between two or more plasmids, each containing BAV sequences. Recombination is generally performed in procaryotic cells, such as *E. coli*, while transfection of a plasmid containing a viral genome, to generate virus particles, is conducted in eukaryotic cells, preferably mammalian cells, more preferably bovine cell cultures, most preferably MDBK or PFBR cells, and their equivalents. The growth of bacterial cell cultures, as well as culture and maintenance of eukaryotic cells and mammalian cell lines are procedures which are well-known to those of skill in the art.

One or more heterologous sequences can be inserted into one or more regions of the BAV genome to generate a recombinant BAV vector, limited only by the insertion capacity of the BAV genome and ability of the recombinant BAV vector to express the inserted heterologous sequences. In general, adenovirus genomes can accept inserts of approximately 5% of genome length and remain capable of being packaged into virus particles. The insertion capacity can be increased by deletion of non-essential regions and/or deletion of essential regions whose function is provided by a helper cell line.

In one embodiment of the invention, insertion can be achieved by constructing a plasmid containing the region of the BAV genome into which insertion is desired. The plasmid is then digested with a restriction enzyme having a recognition sequence in the BAV portion of the plasmid, and a heterologous sequence is inserted at the site of restriction digestion. The plasmid, containing a portion of the BAV genome with an inserted heterologous sequence, is co-transformed, along with a BAV genome or a linearized plasmid containing a BAV genome, into a bacterial cell (such as, for example, *E. coli*), wherein the BAV genome can be a full-length genome or can contain one or more deletions. Homologous recombination between the plasmids generates a recombinant BAV genome containing inserted heterologous sequences.

Deletion of BAV sequences, to provide a site for insertion of heterologous sequences or to provide additional capacity for insertion at a different site, can be accomplished by methods well-known to those of skill in the art. For example, for BAV sequences cloned in a plasmid, digestion with one or more restriction enzymes (with at least one recognition sequence in the BAV insert) followed by ligation will, in some cases, result in deletion of sequences between the restriction enzyme recognition sites. Alternatively, digestion at a single restriction enzyme recognition site within the BAV insert, followed by exonuclease treatment, followed by ligation will result in deletion of BAV sequences adjacent to the restriction site. A plasmid containing one or more portions of the BAV genome with one or more deletions, constructed as described above, can be co-transfected into a bacterial cell along with a BAV genome (full-length or deleted) or a plasmid containing either a full-length or a deleted BAV genome to generate, by homologous recombination, a plasmid containing a recombinant BAV genome with a deletion at one or more specific sites. BAV virions containing the deletion can then be obtained by transfection of mammalian cells (including, but not limited to, MDBK or PFBR cells and their equivalents) with the plasmid containing the recombinant BAV genome.

In one embodiment of the invention, insertion sites are adjacent to and downstream (in the transcriptional sense) of BAV promoters. Locations of BAV promoters, and restriction enzyme recognition sequences downstream of PAV promoters, for use as insertion sites, can be easily determined by one of skill in the art from the BAV nucleotide sequence provided herein. Alternatively, various in vitro techniques can be used for insertion of a restriction enzyme recognition sequence at a particular site, or for insertion of heterologous sequences at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) *Nucleic Acids Res.* 10:6487–6500; Brennan et al. (1990) *Roux's Arch. Dev. Biol.* 199:89–96; and Kunkel et al. (1987) *Meth. Enzymology* 154:367–382) and PCR-mediated methods for insertion of longer sequences. See, for example, Zheng et al. (1994) *Virus Research* 31:163–186.

It is also possible to obtain expression of a heterologous sequence inserted at a site that is not downstream from a BAV promoter, if the heterologous sequence additionally comprises transcriptional regulatory sequences that are active in eukaryotic cells. Such transcriptional regulatory sequences can include cellular promoters such as, for example, the bovine hsp70 promoter and viral promoters such as, for example, herpesvirus, adenovirus and papovavirus promoters and DNA copies of retroviral long terminal repeat (LTR) sequences.

In another embodiment, homologous recombination in a procaryotic cell can be used to generate a cloned BAV genome; and the cloned BAV genome can be propagated as a plasmid. Infectious virus can be obtained by transfection of mammalian cells with the cloned BAV genome rescued from plasmid-containing cells.

The invention also provides BAV regulatory sequences which can be used to regulate the expression of heterologous genes. A regulatory sequence can be, for example, a transcriptional regulatory sequence, a promoter, an enhancer, an upstream regulatory domain, a splicing signal, a polyadenylation signal, a transcriptional termination sequence, a translational regulatory sequence, a ribosome binding site and a translational termination sequence.

In another embodiment, the invention identifies and provides additional regions of the BAV genome (and fragments thereof) suitable for insertion of heterologous or homologous nucleotide sequences encoding foreign genes or fragments thereof to generate BAV recombinants. These regions include nucleotides 4,092–5,234; nucleotides 5,892–17,735; nucleotides 21,198–26,033 and the region extending from nucleotide 31,133 to the right end of the BAV genome and comprise the E2 region, the E4 region, the late region, the 33 kD, 52 kD, 100 kD, DBP, pol, pTP and penton genes, and genes IIIA, pV, pVI, pVII, pVIII and pX. These regions of the BAV genome can be used, among other things, for insertion of foreign sequences, for provision of DNA control sequences including transcriptional and translational regulatory sequences, or for diagnostic purposes to detect the presence of viral nucleic acids or proteins encoded by these regions, in a biological sample.

In another embodiment, the cloned BAV-3 genome can be propagated as a plasmid and infectious virus can be rescued from plasmid-containing cells.

The presence of viral nucleic acids can be detected by techniques known to one of skill in the art including, but not limited to, hybridization assays, polymerase chain reaction, and other types of amplification reactions. Similarly, methods for detection of proteins are well-known to those of skill in the art and include, but are not limited to, various types of immunoassay, ELISA, Western blotting, enzymatic assay, immunohistochemistry, etc. Diagnostic kits comprising the nucleotide sequences of the invention may also contain reagents for cell disruption and nucleic acid purification, as well as buffers and solvents for the formation, selection and detection of hybrids. Diagnostic kits comprising the polypeptides or amino acid sequences of the invention may also comprise reagents for protein isolation and for the formation, isolation, purification and/or detection of immune complexes.

Various foreign genes or nucleotide sequences or coding sequences (prokaryotic, and eukaryotic) can be inserted in the bovine adenovirus nucleotide sequence, e.g., DNA, in accordance with the present invention, particularly to provide protection against a wide range of diseases and many such genes are already known in the art. The problem heretofore has been to provide a safe, convenient and effective vaccine vector for the genes or sequences, as well as safe, effective means for gene transfer to be used in various gene therapy applications.

An exogenous (i.e., foreign) nucleotide sequence can consist of one or more gene(s) of interest, and preferably of therapeutic interest. In the context of the present invention, a gene of interest can code either for an antisense RNA, a ribozyme or for an mRNA which will then be translated into a protein of interest. A gene of interest can be of genomic type, of complementary DNA (cDNA) type or of mixed type (minigene, in which at least one intron is deleted). It can code for a mature protein, a precursor of a mature protein, in particular a precursor intended to he secreted and accordingly comprising a signal peptide, a chimeric protein originating from the fusion of sequences of diverse origins, or a mutant of a natural protein displaying improved or modified biological properties. Such a mutant may be obtained by, deletion, substitution and/or addition of one or more nucleotide(s) of the gene coding for the natural protein, or any other type of change in the sequence encoding the natural protein, such as, for example, transposition or inversion.

A gene of interest may be placed under the control of elements (DNA control sequences) suitable for its expression in a host cell. Suitable DNA control sequences are understood to mean the set of elements needed for transcription of a gene into RNA (antisense RNA or mRNA) and for the translation of an mRNA into protein. Among the elements needed for transcription, the promoter assumes special importance. It can be a constitutive promoter or a regulatable promoter, and can be isolated from any gene of eukaryotic, prokaryotic or viral origin, and even adenoviral origin. Alternatively, it can be the natural promoter of the gene of interest. Generally speaking, a promoter used in the present invention may be modified so as to contain regulatory sequences. As examples, a gene of interest in use in the present invention is placed under the control of the promoter of the immunoglobulin genes when it is desired to target its transfer to lymphocytic host cells. There may also be mentioned the HSV-1 TK (herpesvirus type 1 thymidine kinase) gene promoter, the adenoviral MLP (major late promoter), in particular of human adenovirus type 2, the RSV (Rous Sarcoma Virus) LTR (long terminal repeat), the CMV (Cytomegalovirus) early promoter, and the PGK (phosphoglycerate kinase) gene promoter, for example, permitting expression in a large number of cell types.

Alternatively, targeting of a recombinant BAV vector to a particular cell type can be achieved by constructing recombinant hexon and/or fiber genes. The protein products of these genes are involved in host cell recognition; therefore, the genes can be modified to contain peptide sequences that will allow the virus to recognize alternative host cells.

Among genes of interest which are useable in the context of the present invention, there may be mentioned:

genes coding for cytokines such as interferons and interleukins;

genes encoding lymphokines;

genes coding for membrane receptors such as the receptors recognized by pathogenic organisms (viruses, bacteria or parasites), preferably by the HIV virus (human immunodeficiency virus);

genes coding for coagulation factors such as factor VIII and factor IX;

genes coding for dystrophins;

genes coding for insulin;

genes coding for proteins participating directly or indirectly in cellular ion channels, such as the CFTR (cystic fibrosis transmembrane conductance regulator) protein;

genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene;

genes coding for a protein inhibiting an enzyme activity, such as $\alpha_1$-antitrypsin or a viral protease inhibitor, for example;

genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV;

genes coding for antigenic epitopes in order to increase the host cell's immunity;

genes coding for major histocompatibility complex classes I and II proteins, as well as the genes coding for the proteins which are inducers of these genes;

genes coding for antibodies;

genes coding for immunotoxins;

genes encoding toxins;

genes encoding growth factors or growth hormones;

genes encoding cell receptors and their ligands;

genes encoding tumor suppressors;

genes involved in cardiovascular disease including, but not limited to, oncogenes; genes encoding growth factors including, but not limited to, fibroblast growth factor (FGF), vascular endothelial growth factor (VEGF), and nerve growth factor (NGF); e-nos, tumor suppressor genes including, but not limited to, the Rb (retinoblastoma) gene; lipoprotein lipase; superoxide dismutase (SOD); catalase; oxygen and free radical scavengers; apolipoproteins; and pai-1 (plasminogen activator inhibitor-1);

genes coding for cellular enzymes or those produced by pathogenic organisms; and suicide genes. The HSV-1 TK suicide gene may be mentioned as an example. This viral TK enzyme displays markedly greater affinity compared to the cellular TK enzyme for certain nucleoside analogues (such as acyclovir or gancyclovir). It converts them to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

This list is not restrictive, and other genes of interest may be used in the context of the present invention.

It is also possible that only fragments of nucleotide sequences of genes can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above.

In some cases the gene for a particular antigen can contain a large number of introns or can be from an RNA virus, in these cases a complementary DNA copy (cDNA) can be used.

In order for successful expression of the gene to occur, it can be inserted into an expression vector together with a suitable promoter including enhancer elements and polyadenylation sequences. A number of eucaryotic promoter and polyadenylation sequences which provide successful expression of foreign genes in mammalian cells and how to construct expression cassettes, are known in the art, for example in U.S. Pat. No. 5,151,267, the disclosures of which are incorporated herein by reference. The promoter is selected to give optimal expression of immunogenic protein which in turn satisfactorily leads to humoral, cell mediated and mucosal immune responses according to known criteria.

The foreign protein produced by expression in vivo in a recombinant virus-infected cell may be itself immunogenic. More than one foreign gene can be inserted into the viral genome to obtain successful production of more than one effective protein.

Thus with the recombinant viruses of the present invention, it is possible to provide protection against a wide variety of diseases affecting cattle, humans and other mammals. Any of the recombinant antigenic determinants or recombinant live viruses of the invention can be formulated and used in substantially the same manner as described for the antigenic determinant vaccines or live vaccine vectors.

The present invention also includes pharmaceutical compositions comprising a therapeutically effective amount of a recombinant vector, recombinant virus or recombinant protein, prepared according to the methods of the invention, in combination with a pharmaceutically acceptable vehicle and/or an adjuvant. Such a pharmaceutical composition can be prepared and dosages determined according to techniques that are well-known in the art. The pharmaceutical compositions of the invention can be administered by any known administration route including, but not limited to, systemically (for example, intravenously, intratracheally, intravascularly, intrapulmonarilly, intraperitoneally, intranasally, parenterally, enterically, intramuscularly, subcutaneously, intratumorally or intracranially) or by aerosolization or intrapulmonary instillation. Administration can take place in a single dose or in doses repeated one or more times after certain time intervals. The appropriate administration route and dosage will vary in accordance with the situation (for example, the individual being treated, the disorder to be treated or the gene or polypeptide of interest), but can be determined by one of skill in the art.

The invention also encompasses a method of treatment, according to which a therapeutically effective amount of a BAV vector, recombinant BAV, or host cell of the invention is administered to a mammalian subject requiring treatment.

The antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host a "protective immune response;" i.e., an antibody- and/or a cell-mediated immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly bovine pathogens such as bovine rotavirus, bovine coronavirus, bovine herpes virus type 1, bovine respiratory syncytial virus, bovine parainfluenza virus type 3 (BPI-3), bovine diarrhea virus, *Pasteurella haemolytica, Haemophilus somnus* and the like. Genes encoding antigens of human pathogens also useful in the practice of the invention. The vaccines of the invention carrying foreign genes or fragments can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. Oral and/or intranasal vaccination may be preferable to raise mucosal immunity (which plays an important role in protection against pathogens infecting the respiratory and gastrointestinal tracts) in combination with systemic immunity.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit an antibody and/or T-cell mediated immune response to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1–10 cc. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between $10^3$ pfu and $10^{15}$ pfu, preferably between $10^5$ and $10^{13}$ pfu, more preferably between $10^6$ to $10^{11}$ pfu and the like can be used. As with in vitro subunit vaccines, additional dosages can be given as determined by the clinical factors involved.

In one embodiment of the invention, a number of recombinant cell lines are produced according to the present invention by constructing an expression cassette comprising the BAV E1 region and transforming host cells therewith to provide complementing cell lines or cultures expressing the E1 proteins. These recombinant complementing cell lines are capable of allowing a defective recombinant BAV with deleted E1 sequences to replicate and express a desired foreign gene or fragment thereof which is optionally encoded within the recombinant BAV. These cell lines are also extremely useful in generating recombinant BAV, having an E3 gene deletion replaced by heterologous nucleotide sequence encoding for a foreign gene or fragment, by in vivo recombination following DNA-mediated cotransfection. More generally, defective recombinant BAV vectors, lacking one or more essential functions encoded by the BAV genome, can be propagated in appropriate complementing cell lines, wherein a particular complementing cell line provides a function or functions that is (are) lacking in a particular defective recombinant BAV vector. Complementing cell lines can provide viral functions through, for example, co-infection with a helper virus, or by integrating or otherwise maintaining in stable form a fragment of a viral genome encoding a particular viral function.

In one embodiment of the invention, the recombinant expression cassette can be obtained by cleaving a BAV genome with an appropriate restriction enzyme to produce a DNA fragment representing the left end or the right end of the genome comprising E1 or E3 gene region sequences, respectively and inserting the left or right end fragment into a cloning vehicle, such as a plasmid, and thereafter inserting at least one heterologous DNA sequence into the E1 or E3 deletion with or without the control of an exogenous promoter. The recombinant expression cassette is contacted with a BAV genome within an appropriate cell and, through homologous recombination or other conventional genetic engineering method, a recombinant BAV genome is obtained. Appropriate cells include both prokaryotic cells, such as, for example, E. coli, and eukaryotic cells. Examples of suitable eukaryotic cells include, but are not limited to, MDBK cells, MDBK cells expressing adenovirus E1 function, primary fetal bovine retina cells, and cells expressing functions that are equivalent to those of the previously-recited cells. Restriction fragments of the BAV genome other than those comprising the E1 or E3 regions are also useful in the practice of the invention and can be inserted into a cloning vehicle such that heterologous sequences may be inserted into non-E1 and E3 BAV sequences. These DNA constructs can then undergo recombination in vitro or in vivo, with a BAV genome, either before or after transformation or transfection of a suitable host cell as described above. For the purposes of the present invention, a BAV genome can be either a full-length genome or a genome containing a deletion in a region other than that deleted in the fragment with which it recombines, as long as the resulting recombinant BAV genome contains BAV sequences required for replication and packaging. Methods for transfection, cell culture and recombination in procaryotic and eukaryotic cells such as those described above are well-known to those of skill in the art.

In another embodiment of the invention, E1 function (or the function of any other viral region which may be mutated or deleted in any particular viral vector) can be supplied (to provide a complementing cell line) by co-infection of cells with a virus which expresses the function that the vector lacks.

The invention also includes an expression system comprising a bovine adenovirus expression vector wherein a heterologous nucleotide sequence, e.g. DNA, replaces part or all of the E3 region, part or all of the E1 region, part or all of the E2 region, part or all of the E4 region, part or all of the region between E4 and the right end of the genome, part or all of the late regions (L1–L7) and/or part or all of the regions occupied by the 33 kD, 52 kD, 100 kD, DBP, pol, pTP and penton genes, and genes IIIA, pV, pVI, pVII, pVIII and pX. The expression system can be used wherein the foreign nucleotide sequences, e.g. DNA, is with or without the control of any other heterologous promoter. BAV expression vectors can also comprise inverted terminal repeat (ITR) sequences and packaging sequences.

The BAV 33 kD, 52 kD, 100 kD, DBP, pTP, penton (III), pIIIA, pIVa2, pV, pVI, pVII, pVIII and pX genes are essential for viral replication. Therefore, BAV vectors comprising deletions in any of these genes, or which lack functions encoded by any of these genes, must be grown in an appropriate complementing cell line (i.e., a helper cell line). In human adenoviruses, certain open reading frames in the E4 region (ORF 3 and ORF 6/7) are essential for viral replication. Deletions in analogous open reading frames in the E4 region of BAV-3 could necessitate the use of a helper cell line for growth of the viral vector.

The BAV E1 gene products of the adenovirus of the invention transactivate most of the cellular genes, and therefore, cell lines which constitutively express E1 proteins can express cellular polypeptides at a higher level than normal cell lines. The recombinant mammalian, particularly bovine, cell lines of the invention can be used to prepare and isolate polypeptides, including those such as (a) proteins associated with adenovirus E1A proteins: e.g. p300, retinoblastoma (Rb) protein, cyclins, kinases and the like; (b) proteins associated with adenovirus E1B protein: e.g. p53 and the like; growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IGF-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity) and the like; (f) other cellular proteins such as actins, collagens, fibronectins, integrins, phosphoproteins, proteoglycans, histones and the like, and (g) proteins involved in regulation of transcription such as TATA-box-binding protein (TBP), TBP-associated factors (TAFs), Sp1 binding protein and the like.

The invention also includes a method for providing gene therapy to a mammal, such as a bovine or a human or other mammal in need thereof, to control a gene deficiency, to provide a therapeutic gene or nucleotide sequence and/or to induce or correct a gene mutation. The method can be used, for example, in the treatment of conditions including, but not limited to hereditary disease, infectious disease, cardiovascular disease, and viral infection. The method comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in the target organ or tissue. These kinds of techniques are currently being used by those of skill in the art for the treatment of a variety of disease conditions, non-limiting examples of which are provided above. Examples of foreign genes, nucleotide sequences or portions thereof that can be incorporated for use in a conventional gene therapy include, cystic fibrosis transmembrane conductance regulator gene, human minidystrophin gene, alpha-1-antitrypsin gene, genes involved in cardiovascular disease, and the like.

In particular, the practice of the present invention in regard to gene therapy in humans is intended for the prevention or treatment of diseases including, but not limited to, genetic diseases (for example, hemophilia, thalassemias, emphysema, Gaucher's disease, cystic fibrosis, Duchenne muscular dystrophy, Duchenne's or Becker's myopathy, etc.), cancers, viral diseases (for example, AIDS, herpesvirus infection, cytomegalovirus infection and papillomavirus infection), cardiovascular diseases, and the like. For the purposes of the present invention, the vectors, cells and viral particles prepared by the methods of the invention may be introduced into a subject either ex vivo, (i.e., in a cell or cells removed from the patient) or directly in vivo into the body to be treated. Preferably, the host cell is a human cell and, more preferably, is a lung, fibroblast, muscle, liver or lymphocytic cell or a cell of the hematopoietic lineage.

EXAMPLES

Described below are examples of the present invention. These examples are provided only for illustrative purposes and are not intended to limit the scope of the present invention in any way. In light of the present disclosure, numerous embodiments within the scope of the claims will be apparent to those of ordinary skill in the art. The contents of the references cited in the specification are incorporated by reference herein.

Cells and Viruses

Cell culture media and reagents were obtained from GIBCO/BRL Canada (Burlington, Ontario, Canada). Media were supplemented with 25 mM HEPES and 50 μg/ml gentamicin. MDBK cells or MDBK cells transformed with a plasmid containing BAV3 E1 sequences were grown in MEM supplemented with 10% Fetal bovine serum. The wild-type BAV3 (strain WBR-1) (Darbyshire et al, 1965 *J. Comparative Pathology* 75:327), kindly provided by Dr. B. Darbyshire, University of Guelph, Guelph, Canada, and BAV3-luciferase recombinants working stocks and virus titrations were done in MDBK cells.

Enzymes, Bacteria and Plasmids

Restriction endonucleases, polymerase chain reaction (PCR) and other enzymes required for DNA manipulations were purchased from Pharmacia LKB Biotechnology (Canada) Ltd. (Dorval, Quebec, Canada), Boehringer-Mannheim, Inc. (Laval or Montreal, Quebec, Canada), New England BioLabs (Beverly, Mass.), or GIBCO/BRL Canada (Burlington, Ontario, Canada) and used as per manufacturer's instructions. Restriction enzyme fragments of BAV3 DNA were inserted into pUC18 or pUC19 (Yanich-Peron et al (1985) *Gene* 33:103–109) following standard procedures (Sambrook et al (1989) *Molecular Cloning: A Laboratory Manual*, $2^{nd}$ ed. Cold Spring Harbor Laboratory, New York). *E. coli* strain DH5 (supE44 hsdR17 recA1 endA1 gyrA96 thi-1 relA1) was transformed with recombinant plasmids by electroporation (Dower et al. (1988) *Nuc. Acids Res.*, 16:6127–6145). Plasmid DNA was prepared using the alkaline lysis procedure (Birnboim and Doly (1978) *Nuc. Acids Res.*, 7:1513–1523). The plasmid, pSVOA/L containing the entire cDNA encoding firefly luciferase (de Wet et al (1987) *Mol. Cell. Biol.* 7:725–737), was a gift from D. R. Helinski, University of California, San Diego, La Jolla, Calif.

Construction of Recombinant BAV3

MDBK cells transformed with a plasmid containing BAV3 E1 sequences were cotransfected with the wt BAV3 DNA digested with PvuI and the plasmid, pSM51-Luc (FIGS. 9 and 10) using the lipofection-mediated cotransfection protocol (GIBCO/BRL, Life Technologies, Inc., Grand Island, N.Y.). The virus plaques produced following cotransfection were isolated, plaque purified and the presence of the luciferase gene in the BAV3 genome was detected by agarose gel electrophoresis of recombinant virus DNA digested with appropriate restriction enzymes.

Southern blot and hybridization

Mock or virus-infected MDBK cells were harvested in lysis buffer (500 μg/ml pronase in 0.01 M Tris, pH 7.4, 0.01 M EDTA, 0.5% SDS) and DNA was extracted (Graham et al (1991) Manipulation of adenovirus vectors In: Methods and Molecular Biology, 7: Gene Transfer and Expression Techniques (Eds. Murray and Walker) Humana Press, Clifton, N.J. pp. 109–128). 100 ng DNA was digested either with BamHI, EcoRI or XbaI and resolved on a 1% agarose gel by electrophoresis. DNA bands from the agarose gel were transferred to a GeneScreenPlus™ membrane (Du Pont Canada Inc. (NEN Products), Lachine, Quebec, Canada) by the capillary blot procedure (Southern, E. M. (1975) *J. Mol. Biol.* 98:503–517). Probes were labeled with $^{32}P$ using an Oligolabeling Kit (Pharmacia LKB Biotechnology (Canada) Ltd., Dorval, Quebec, Canada) and the unincorporated label was removed by passing the labeled probe through a Sephadex G-50 column (Sambrook et al (1989) supra). Probes were kept in a boiling water bath for 2 min and used in hybridization experiments following GeneScreenPlus™ hybridization protocol. The DNA bands which hybridized with the probe were visualized by autoradiography.

Luciferase Assays

The protocol was essentially the same as described (Mittal et al (1993) *Virus Res.* 28:67–90). Briefly, MDBK cell monolayers in 25 mm multi-well dishes (Corning Glass Works, Corning, N.Y.) were infected in duplicate either with BAV3-Luc (3.1) or BAV3-Luc (3.2) at a m.o.i. of 50 p.fu. per cell. At indicated time points post-infection, recombinant virus-infected cell monolayers were washed once with PBS (0.137 M NaCl, 2.7 mM KCl, 8 mM $Na_2HPO_4$, 1.5 mM $KH_2PO_4$) and harvested in 1 ml luciferase extraction buffer (100 mM potassium phosphate, pH 7.8, 1 mM dithiothreitol). The cell pellets were resuspended in 200 μl of luciferase extraction buffer and lysed by three cycles of freezing and thawing. The supernatants were assayed for luciferase activity. For the luciferase assay, 20 μl of undiluted or serially diluted cell extract was mixed with 350 μl of luciferase assay buffer (25 mM glycylglycine, pH 7.8, 15 mM $MgCl_2$, 5 mM ATP) in a 3.5 ml tube (Sarstedt Inc., St-Laurent, Quebec, Canada). Up to 48 tubes can be kept in the luminometer rack and the equipment was programmed to inject 100 μl of luciferin solution (1 mM luciferin in 100 mM potassium phosphate buffer, pH 7.8) in the tube present in the luminometer chamber to start the enzyme reaction. The Luminometer (Packard Picolite Luminometer, Packard Instrument Canada, Ltd., Mississauga, Ontario, Canada) used in the present study produced 300 to 450 light units of background count in a 10 sec reaction time. Known amounts of the purified firefly luciferase were used in luciferase assays to calculate the amount of active luciferase present in each sample.

Western Blotting

Mock or virus-infected MDBK cells were lysed in 1:2 diluted 2× loading buffer (80 mM Tris-HCl, pH 6.8, 0.67 M urea, 25% glycerol, 2.5% SDS, 1 M mercaptoethanol, 0.001% bromophenol blue), boiled for 3 min and then centrifuged to pellet cell debris. Proteins were separated by SDS-polyacrylamide gel electrophoresis (SDS-PAGE) on 0.1% SDS-10% polyacrylamide gels (Laemmli, et al (1970) *Nature* 227:680–685). After the end of the run, polypeptide bands in the gel were electrophoretically transferred to a nitrocellulose membrane (Bio-Rad Laboratories, Richmond, Calif.). The membrane was incubated at room temperature for 2 h with 1:4000 diluted rabbit anti-luciferase antibody (Mittal et al (1993) supra). The binding of anti-luciferase antibody to the specific protein band/s on the membrane was detected with 1:5000 diluted horseradish peroxidase conjugated-goat anti-rabbit IgG (Bio-Rad Laboratories, Richmond, Calif.) and with an ECL Western blotting detection system (Amersham Canada Ltd., Oakville, Ontario).

Example 1

Cloning of BAV3 E1 Region DNA for sequencing

To complement the restriction site map (Kurokawa et al, 1978 *J. Virol.*, 28:212–218; Hu et al, 1984 *J. Virol.* 49:604–608) other restriction enzyme sites in the BAV3 genome were defined. The 8.4 kilobase pair (kb) SalI B fragment which extends from the left end of the genome to approximately 24% was cloned into the SmaI-SalI sites of pUC18 essentially as described previously (Graham et al, 1989 *EMBO Journal* 8:2077–2085). Beginning at the left end of the BAV3 genome, the relevant restriction sites used for subsequent subcloning and their approximate positions are: SacI (2%), EcoRI (3.5%), HindIII (5%), SacI (5.5%), SmaI (5.6%) and HindIII (11%). Through the use of appropriate restriction enzymes, the original plasmid was collapsed to contain smaller inserts which could be sequenced using the pUC universal primers. Some fragments were also subcloned in both pUC18 and pUC19 to allow confirmational sequencing in both directions. These procedures, together with the use of twelve different oligonucleotide primers hybridizing with BAV3 sequences, allowed the sequencing of the BAV3 genome from its left end to the HindIII site at 11%.

To ensure that some features of the sequence obtained were not unique to the initial clone selected for sequencing, two more pUC19 clones were prepared containing the SalI fragment from a completely independent DNA preparation. These clones were used to confirm the original sequence for the region from approximately 3% to 5.5% of the BAV3 genome.

DNA sequencing reactions were based on the chain-termination method (Sanger et al. 1977 *PNAS, USA* 74:5463–5467) and manual sequencing followed the DNA sequencing protocol described in the Sequenase™ kit produced by US Biochemical. [α-$^{35}$S]dATP was obtained from Amersham Canada Ltd. All oligonucleotides used as primers were synthesized by the Central Facility of the Molecular Biology and Biotechnology Institute (MOBIX) at McMaster University, Hamilton, Ontario. The entire region (0 to 11%) of the BAV3 genome was sequenced by at least two independent determinations for each position by automated sequencing on a 373A DNA Sequencer (Applied Biosystems) using Taq-Dye terminators. Over half of the region was further sequenced by manual procedures to confirm overlaps and other regions of interest.

DNA sequence analysis and protein comparisons were carried out on a MICROGENIE program.

Example 2

Coding Sequences of the BAV3 E1 Region

BAV3 genomic DNA, from the left end of the genome to the HindIII site at approximately 11%, was cloned into plasmids and sequenced by a combination of manual and automated sequencing. An examination of the resultant BAV3 E1 genomic sequence (FIG. 1) revealed a number of interesting features relevant both to transactivation and to other functions associated with adenovirus E1 proteins. On the basis of open reading frames (ORFs) it was possible to assign potential coding regions analogous to those defined in human Ad5 (HAd5). As shown in FIG. 1, ORFs corresponding roughly to the first exon and unique region of HAd5 E1A as well as ORFs corresponding to the 19 k and 58 k proteins of E1B and the ORF corresponding to protein IX were all defined in this sequence. The open reading frame defining the probable E1A coding region begins at the ATG at nucleotide 606 and continues to a probable splice donor site at position 1215. The first consensus splice acceptor site after this is located after nucleotide 1322 and defines an intron of 107 base pairs with an internal consensus splice branching site at position 1292. The putative BAV3 E1A polypeptide encoded by a message corresponding to these splice sites would have 211 amino acids and a unmodified molecular weight of 23,323. The major homology of the protein encoded by this ORF and HAd5 E1A is in the residues corresponding to CR3 (shown in FIG. 2). The homology of amino acid sequences on both sides of the putative intron strengthens the assignment of probable splice donor and acceptor sites. The CR3 has been shown to be of prime importance in the transactivation activity of HAd5

Figure 2A:
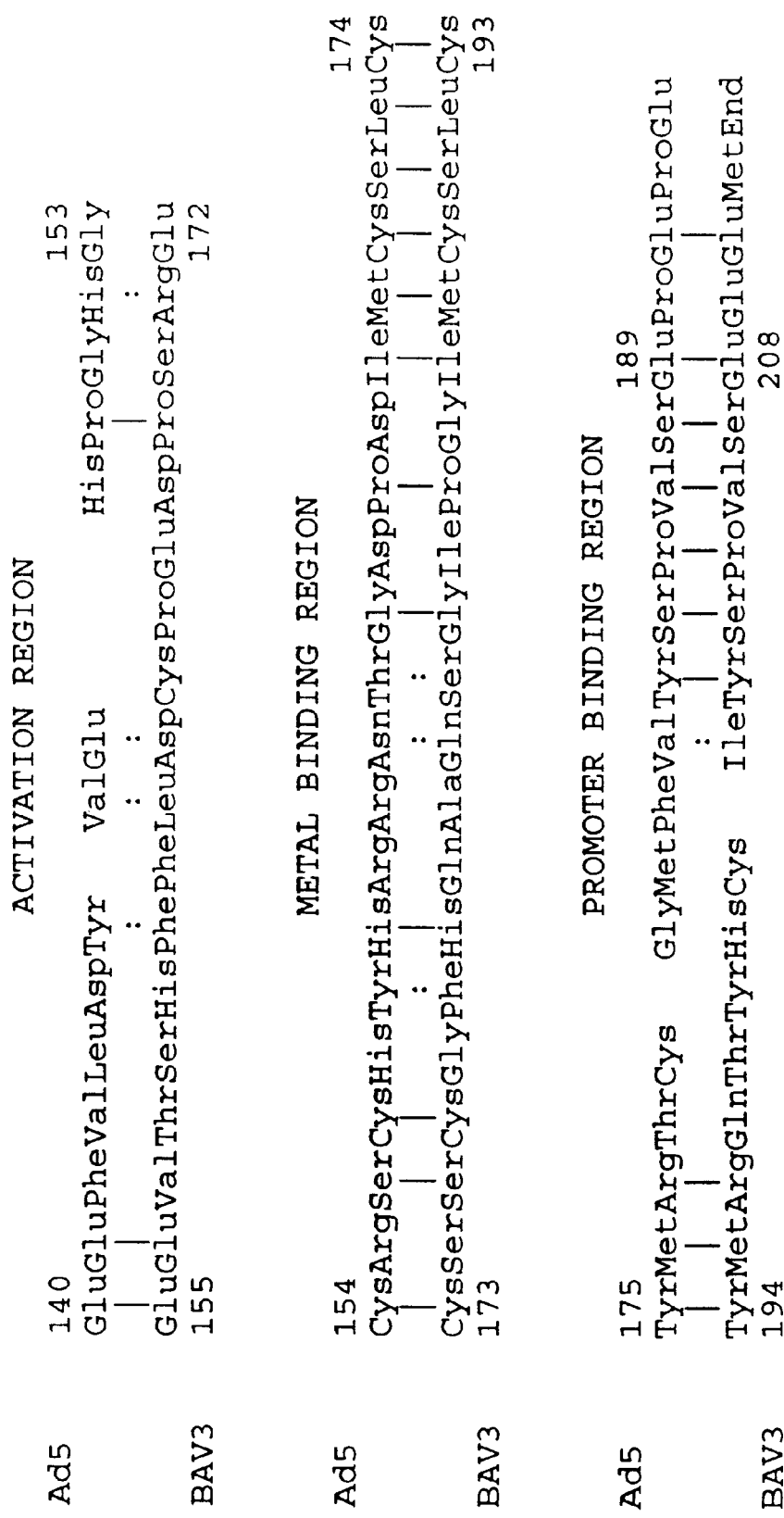

E1A gene products. As seen in FIG. 2A the homology of this sequence in the BAV3 protein to the corresponding region of the 289R E1A protein of HAd5 includes complete conservation of the $CysX_2CysX_{13}CysX_2Cys$ (SEQ ID NO: 30) sequence motif which defines the metal binding site of this protein (Berg, 1986 *Science* 232:485–487) as well as conservation of a number of amino acids within this region and within the promoter binding region as defined by Lillie and Green 1989 *Nature* 338:39–44.

The only other region of significant homology between the BAV3 E1A protein and that of HAd5 was a stretch of amino acids known to be important in binding of the cellular Rb protein to the HAd5 E1A protein (Dyson et al, 1990 *J. Virol.* 64:1353–1356). As shown in FIG. 2B, this sequence, which is located between amino acids 120 and 132 in the CR2 region of HAd5 E1A, is found near the amino (N-) terminus of the BAV3 protein between amino acids 26 and 37.

An open reading frame from the ATG at nucleotide 1476 to the termination signal at 1947 defines a protein of 157 amino acids with two regions of major homology to the HAd5 E1B 19 k protein. As shown in FIG. 3 both the BAV3 and the HAd5 proteins have a centrally located hydrophobic amino acid sequence. The sequence in BAV3, with substitutions of valine for alanine and leucine for valine, should result in a somewhat more hydrophobic pocket than the corresponding HAd5 region. The other portion of HAd5 19 k that may be conserved in the BAV3 protein is the serine rich sequence found near the N-terminus (residues 20 to 26) in HAd5 19 k and near the C-terminus (residues 136 to 142) in the BAV3 protein (also shown in FIG. 3).

An ORF beginning at the ATG at nucleotide 1850 and terminating at nucleotide 3110 overlaps the preceding BAV3 protein reading frame and thus has the same relationship to it as does the HAd5 E1B 56 k protein to E1B 19 k protein. As shown in FIG. 4 this BAV3 protein of 420R and the corresponding HAd5 E1B 56 k protein of 496R show considerable sequence homology over their C-terminal 346 residues. The N-terminal regions of these proteins (not depicted in the figure) show no significant homology and differ in overall length.

Following the E1B ORFs, the open reading frame beginning at nucleotide 3200 and ending at the translation terminator TAA at nucleotide 3575 defines a protein of 125R with an unmodified molecular weight of 13,706. As seen in FIG. 5 this protein shares some homology with the structural protein IX of HAd5 particularly in N-terminal sequences.

Possible Transcription Control Regions in BAV3 E1

The inverted terminal repeats (ITR) at the ends of the BAV3 genome have been shown to extend to 195 nucleotides (Shinagawa et al, 1987 *Gene* 55:85–93). The GC-rich 3' portion of the ITR contains a number of consensus binding sites for the transcription stimulating protein SP1 (Dynan and Tijan (1983) *Cell* 35:79–87) and possible consensus sites for the adenovirus transcription factor (ATF) (Lee et al. (1987) *Nature* 325:368–372) occur at nucleotides (nts) 60 and 220. While there are no exact consensus sites for the factors EF-1A (Bruder and Healing (1989) *Mol. Cell Biol.* 9:5143–5153) or E2F (Kovesdi et al, 1987 *PNAS, USA* 84:2180–2184) upstream of the ATG at nucleotide 606, there are numerous degenerate sequences which may define the enhancer region comparable to that seen in HAd5 (Hearing and Shenk, 1986 *Cell* 45:229–236).

The proposed BAV3 E1A coding sequence terminates at a TGA residue at nucleotide 1346 which is located within a 35 base pair sequence which is immediately directly repeated (see FIG. 1). Two repeats of this sequence were detected in three independently derived clones for a plaque purified stock of BAV3. The number of direct repeats can vary in any BAV3 population though plaque purification allows for isolation of a relatively homogeneous population of viruses. That direct repeats in the sequences can function as promoter or enhancer elements for E1B transcription is being tested. There are no strong polyA addition consensus sites between the E1A and the E1B coding sequences and in fact no AATAA sequence is found until after the protein IX coding sequences following E1B. The TATAAA sequence beginning at nucleotide 1453 could function as the proximal promoter for E1B but it is located closer to the ATG at 1476 than is considered usual (McKnight et al, 1982 *Science* 217:316–322). The TATA sequence located further upstream immediately before the proposed E1A intron sequence also seems inappropriately positioned to serve as a transcription box for the E1B proteins. There are clearly some unique features in this region of the BAV3 genome.

The transcriptional control elements for the protein IX transcription unit are conventional and well defined. Almost immediately following the open reading frame for the larger E1B protein there is, at nucleotide 3117, a SP1 binding sequence. This is followed at 3135 by a TATAAAT sequence which could promote a transcript for the protein IX open reading frame beginning at the ATG at 3200 and ending with the TAA at 3575. One polyA addition sequence begins within the translation termination codon and four other AATAA sequences are located at nucleotides 3612, 3664, 3796 and 3932.

In keeping with the general organization of the E1A region of other adenoviruses, the BAV3 E1A region contains an intron sequence with translation termination codons in all three reading frames and which is therefore probably deleted by splicing from all E1A mRNA transcripts. The largest possible protein produced from the BAV3 E1A region will have 211 amino acid residues and is the equivalent of the 289 amino acid protein translated from the 13 s mRNA of HAd5. Two striking features in a comparison of these proteins are the high degree of homology in a region corresponding to CR3 and the absence in BAV3 of most of amino acids corresponding to the second exon of HAd5. In fact the only amino acids encoded in the second exon of BAV3 are those which are considered to constitute part of CR3. A great deal of work carried out with HAd5 has identified the importance of the CR3 sequences in transactivation of other HAd5 genes. While a detailed analysis of the corresponding BAV3 region and its possible role in transactivation of BAV3 genes needs to be carried out, it is none-the-less interesting to note a couple of possibly pertinent features. The HAd5 CR3 region has been operationally subdivided into three regions (Lillie et al, 1989 *Nature* 338:39–44; see FIG. 8); an N-terminal region from 139 to 153 which has four acidic residues and is thought to be important in transcription activation, a central, metal-binding, region defined by the $Cys-X_2-Cys-X_{13}-CysX_2-Cys$ (SEQ ID NO: 30) sequence which is essential for both promoter binding and activation, and a C-terminal region (residues 175–189) which is essential for promoter binding. Since, in most instances, E1A protein is thought not to interact directly with DNA (Ferguson et al 1985), the promoter binding regions may be involved in forming associations with proteins which then allow association with DNA. In FIG. 2a the BAV3 E1A protein contains the central, metal binding domain and has considerable homology in the carboxy portion of this region. The BAV3 E1A protein also shows identity of sequence with HAd5 in the carboxy 6 amino acids of the promoter binding domain. These features may allow the BAV3 E1A protein to interact with the same transcription activating factors required for HAd5 E1A function. In contrast, except for a Glu-Glu pair there is little homology between the bovine and human viruses in the activation domain. The fact that this domain can be functionally substituted by a heterologous acidic activation sequence (Lillie et al, 1989 supra) suggests that protein specificity is not required in this region and this may allow the BAV3 E1A protein to function in the activation of BAV3 genes. The BAV3 E1A activation region contains six acidic residues in the 18 residues amino to the metal binding domain.

The other interesting feature of BAV3 E1A, which is undoubtedly relevant to the oncogenic potential of this virus, is the presence of the sequence Asp27-Leu-Glu-Cys-His-Glu which conforms to a core sequence known to be important in the binding of cellular Rb and related proteins by the transforming proteins of a number of DNA tumor viruses (Dyson et al, 1990 supra). From deletion mutant analysis there is a clear association between the potential of HAd5 E1A proteins to bind Rb and the ability of the protein to induce morphological transformation in appropriate cells (see references in Dyson et al, 1990 supra). The BAV3 E1A protein is distinct from its HAd5 counterpart in the relative position of this Rb binding sequence which is in the CR2 of HAd5 E1A and near the N-terminus of the BAV3 E1A protein.

Through the use of alternative splice sites HAd5 E1A transcripts can give rise to at least 5 distinct mRNA species (Berk et al, 1978 *Cell* 14:695–711; Stephens et al, 1987 *EMBO Journal* 6:2027–2035). Whether BAV3, like HAd5, can generate a number of different mRNA species through the use of alternative splice sites in the E1A transcripts remains to be determined. For example a potential splice donor site which could delete the sequence equivalent to the unique sequence of HAd5 is present immediately after nucleotide 1080 but it is not known if this site is actually used.

HAd5 E1B encodes two proteins (19 k and 56 k) either of which can cooperate with E1A, by pathways which are additive and therefore presumably independent (McLorie et al, 1991 *J. Gen. Virol.* 72:1467–1471), to produce morphological transformation of cells in culture (see for example: Branton et al, 1985 supra; Graham, 1984 supra). The significance of the conservation of the hydrophobic stretch of amino acids in the central portion of the shorter E1B proteins of HAd5 and BAV3 is not clear as yet. A second short region of homology Gln-Ser-Ser-X-Ser-Thr-Ser (SEQ ID NO: 31) at residue 136 near the C-terminus of the BAV3 protein is located near the N-terminus at residue 20 in the HAd5 19 k protein. The major difference in both length and sequence of the larger (420R) E1B protein of BAV3 from the corresponding HAd5 protein (496R) is confined to the N-terminus of these proteins. The two proteins show considerable evolutionary homology in the 345 amino acids that extend to their C-termini. A similar degree of homology extends into the N-terminal halves of protein IX of BAV3 and HAd5. Taken together these analyses suggest that while BAV3 and the human adenoviruses have diverged by simple point mutational events in some regions, more dramatic genetic events such as deletion and recombination may have been operating in other regions particularly those defining the junction between E1A and E1B.

Example 3

Cloning and sequencing of the BAV3 E3 and fibre genes

Figure 6:
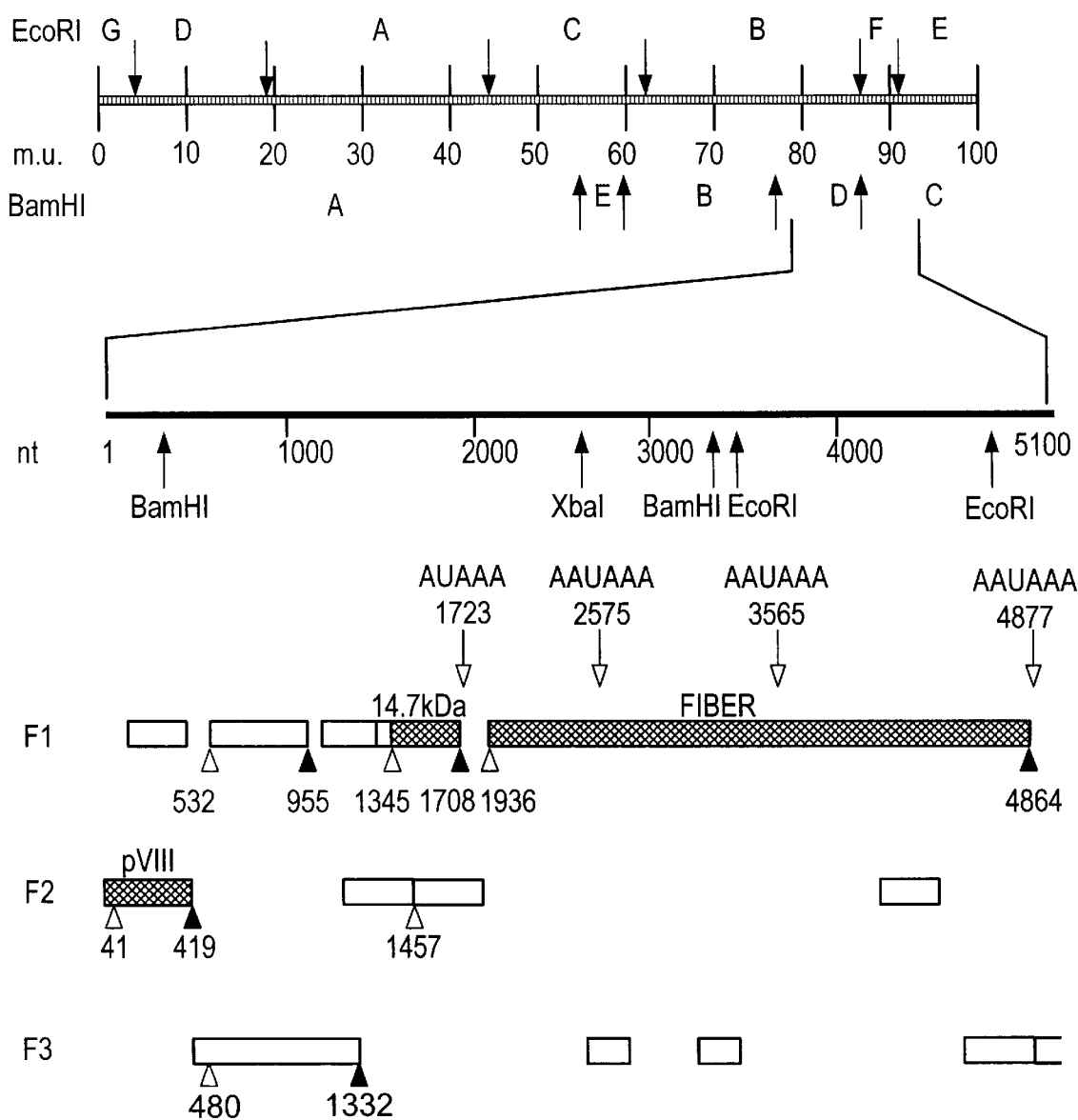
FIG. 6. The genome of BAV3 showing the location of EcoRI, XbaI and BamHI sites and the structure of the 5100 bp segment from 77 to 92 m.u. ORFs for the upper strand which can encode 60 amino acids or more are represented by bars. Shaded portions indicate regions of similarity to pVIII, 14.7K E3 and fibre proteins of HAd2 or -5. The first methionine followed by a stretch of amino acids of at least 50 is shown by an open triangle. Termination codons for ORFs likely to code for viral proteins are shown by closed triangles.

The general organization of adenovirus genomes seems to be relatively well conserved so it was possible to predict, from the locations of a number of HAd E3 regions, that BAV E3 should lie between map units (m.u.) 77 to 86. To prepare DNA for cloning and sequencing, BAV3 (strain WBR-1) was grown in Madin-Darby bovine kidney (MDBK) cells, virions were purified and DNA was extracted (Graham, F. L. & Prevec, L. (1991) Methods in Molecular Biology, vol. 7, *Gene Transfer and Expression Protocols*, pp. 109–146. Edited by E. J. Murray, Clifton, N.J.; Humana Press.). Previously published restriction maps for EcoRI and BamHI (Kurokawa et al., 1978) were confirmed (FIG. 6). The BamHI D and EcoRI F fragments of BAV3 DNA were isolated and inserted into pUC18 and pUC19 vectors, and nested sets of deletions were made using exonuclease III and S1 nuclease (Henikoff, S. (1984) *Gene*, 28:351–359). The resulting clones were sequenced by the dideoxynucleotide chain termination technique (Sanger, F., Nicklen, S. & Coulson, A. R. (1977) *Proceedings of the National Academy of Sciences, U.S.A.*, 74:5463–5467). The nucleotide sequence from positions 1 to 287 was obtained from the right end of the BamHI B fragment (FIG. 6). The sequence of the regions spanning (i) the BamHI site at nucleotide 3306 and the EcoRI site at nucleotide 3406, and (ii) the EcoRI site at nucleotide 4801 and the site at nucleotide 5100 was obtained from a plasmid containing the XbaI C fragment (m.u. 83 to 100; not shown) using primers hybridizing to BAV3 sequences. Analysis of the sequence was performed with the aid of the PC/GENE sequence analysis package developed by Amos Bairoch, Department of Medical Biochemistry, University of Geneva, Switzerland.

The 5100 nucleotide sequence which extends between 77 and 92 m.u. of the BAV3 genome is shown in FIG. 7. The upper strand contains 14 open reading frames (ORFs) which could encode polypeptides of 60 amino acid residues or more (FIGS. 6 and 7). The lower strand contains no ORF encoding a protein of longer than 50 amino acids after an initiation codon. The predicted amino acid sequence for each ORF on the upper strand was analyzed for homology with predicted amino acid sequences from several sequenced Ads: HAd-2 (Hérissé, J., Courtois, G. & Galibert, F. (1980) *Nucleic Acids Research*, 8:2173–2192; Hérissé, J., Courtois, G. & Galibert, F. (1981) *Nucleic Acids Research*, 9:1229–1249), HAd-3 (Signas, C., Akusjarvi, G. & Pettersson, U. (1985) *Journal of Virology*, 53:672–678.), Had-5 (Cladaras, C. & Wold, W. S. M. (1985) *Virology*, 140:28–43), HAd-7 (Hong, J. S., Mullis, K. G. & Engler, J. A. (1988) *Virology*, 167:545–553), HAd-35 (Flomenberg, P. R., Chen, M. & Horwitz, M. S. (1988) *Journal of Virology*, 62:4431–4437), murine Ad1 (MAd1) (Raviprakash, K. S., Grunhaus, A., El Kholy, M. A. & Horwitz, M. S. (1989) *Journal of Virology*, 63:5455–5458) and canine Ad1 (CAd1) (Dragulev, B. P., Sira, S., Abouhaidar, M. G. & Campbell, J. B. (1991) *Virology*, 183:298–305). Three of the BAV3 ORFs exhibited homology with characterized HAd proteins: pVIII, fibre and the 14.7K E3 protein. The amino acid sequence predicted from BAV3 ORF 1 shows overall identity of approximately 55% when compared to the C-terminal 75% of HAd2 pVIII (Cladaras & Wold, 1985, supra) (FIG. 8a), indicating that ORF 1 encodes the right end of BAd3 pVIII. Near the C-terminal end of BAd3 pVIII there is a 67 amino acid stretch (residues 59 to 125; FIG. 8a) which has 75% identity with HAd2 pVIII. This region has previously been shown to be highly conserved among different Ads (Cladaras & Wold, 1985, supra; Signas, C., Akusjarvi, G. & Pettersson, U. (1986) *Gene*, 50:173–184,; Raviprakash et al., 1989, supra; Dragulev et al., 1991, supra).

The fibre protein is present on the surface of the virion as long projections from each vertex of the icosahedral capsid and is involved in a number of Ad functions including attachment of the virus to the cell surface during infection, assembly of virions and antigenicity (Philipson, L. (1983) *Current Topics in Microbiology and Immunology*, 109:1–52). On the basis of the primary structure of HAd2 fibre protein, it has been proposed that the shaft region (between amino acid residues 40 and 400) is composed of a number of repeating structural motifs containing about 15 hydrophobic residues organized in two short β-sheets and two β-bends (Green, N. M., Wrigley, N. G., Russell, W. C., Martin, S. R. & McLachlan, A. D. (1983) *EMBO Journal*, 2:1357–1365). The amino acid sequences at the N-terminus of the BAV3 ORF 6-encoded protein share about 60% identity with the HAd2 fibre protein tail, but there is little or no similarity in the knob region, and about 45% identity overall (FIG. 8c). The BAd3 fibre gene would encode a protein of 976 residues if no splicing occurs, i.e. 394 amino acid residues longer than the HAd2 fibre protein. The number of repeating motifs in the shaft region of the fibre protein from different Ads varies between 28 and 23 (Signas et al., 1985, supra; Chroboczek, J. & Jacrot, B. (1987) *Virology*, 161:549–554; Hong et al., 1988, supra; Raviprakash et al., 1989, supra; Dragulev et al., 1991, supra). The BAV3 fibre protein can be organized into 52 such repeats in this region (not shown), which would account for most of the difference in size compared to those of HAd2, HAd3, HAd5, HAd7, CAd1 and MAd1 (Signas et al., 1985, supra; Hérissé et al., 1980, supra; Hérissé & Galibert, 1981, supra; Hong et al., 1988, supra; Raviprakash et al., 1989, supra; Dragulev et al., 1991, supra).

HAd2 and HAd5 E3 lies between the pVIII and the fibre genes an encodes at least 10 polypeptides (Cladaras & Wold, 1985, supra). The promoter for E3 of these two serotypes lies within the sequences encoding pVIII, about 320 bp 5' of the termination codon. No consensus TATA box is found in the corresponding region of the BAV3 sequences. A non-canonical polyadenylation signal (ATAAA) for E3 transcripts is located at position 1723, between the end of the putative E3 region and the beginning of ORF 6, encoding the fibre protein, and two consensus signals are located within ORF 6 at positions 2575 and 3565. The polyadenylation signal for the fibre protein is located at nucleotide 4877. Six ORFs were identified in the BAV3 genome between the pVIII and the fibre genes, but only four (ORFs 2, 3, 4 and 5) have the potential to encode polypeptides of at least 50 amino acids after an initiation codon (FIG. 7). The amino acid sequence predicted to be encoded by ORF 2 is 307 residues long and contains eight potential N-glycosylation sites (FIG. 7) as well as a hydrophobic sequence which may be a potential transmembrane domain (PLLFAFVLCTGCAVLLTAFGPSILSGT) (SEQ ID NO: 32) between residues 262 and 289. This domain may be a part of the protein homologous to the HAd2 and HAd5 19K E3 glycoprotein (Cladaras & Wold, 1985, supra), and the proposed CAd1 22.2K protein (Dragulev et al., 1991, supra), but ORF 2 does not show appreciable homology with these proteins. The ORF 4 shows approximately 44% identity with the 14.7K E3 protein of HAd5 (FIGS. 6 and 8b), which has been shown to prevent lysis of virus-infected mouse cells by tumor necrosis factor (Gooding, L. R., Elmore, L. W., Tollefson, A. E., Brody, H. A. & Wold, W. S. M. (1988) *Cell*, 53:341–346; Wold, W. S. M. & Gooding, L. R. (1989) *Molecular Biology and Medicine*, 6:433–452). Analysis of the 14.7K protein sequence from HAd2, -3, -5 and -7 has revealed a highly conserved domain, which in HAd5 lies between amino acid residues 41 and 56 (Horton, T. M., Tollefson, A. E., Wold, W. S. M. & Gooding, L. R. (1990) *Journal of Virology*, 64:1250–1255). The corresponding region in the BAV3 ORF 4-encoded protein, between amino acids 70 and 85, contains 11 amino acids identical to those of the HAd5 14.7K protein conserved domain (FIG. 8b).

The BAV3 E3 region appears to be approximately 1.5 kbp long, about half the size of those of HAd2 and -5 (Cladaras & Wold, 1985, supra), and novel splicing events in BAV3 E3 would be required to generate more homologues to the HAd3 E3 proteins. A similarly short E3 region has been reported for MAd1 (Raviprakash et al., 1989, supra) and CAd1 (Dragulev et al., 1991, supra).

Example 4

Construction of BAV3-luciferase recombinants

Adenovirus-based mammalian cell expression vectors have gained tremendous importance in the last few years as a vehicle for recombinant vaccine delivery, and also in gene therapy. BAV3-based expression vectors have a greater potential for developing novel recombinant vaccines for veterinary use. To show that BAV3 E3 gene products are not essential for virus growth in cultured cells and this locus could be used to insert foreign DNA sequences, a 1.7 kb fragment containing the firefly luciferase gene was introduced in the 696 bp deletion of the E3 region of the BAV3 genome in the E3 parallel orientation to generate a BAV3 recombinant.

The rationale of using the luciferase gene is that it acted as a highly sensitive reporter gene when introduced in the E3 region of the HAd5 genome to generate HAd5-Luc recombinants (Mittal et al (1993) *Virus Res.* 28:67–90).

Figure 9:
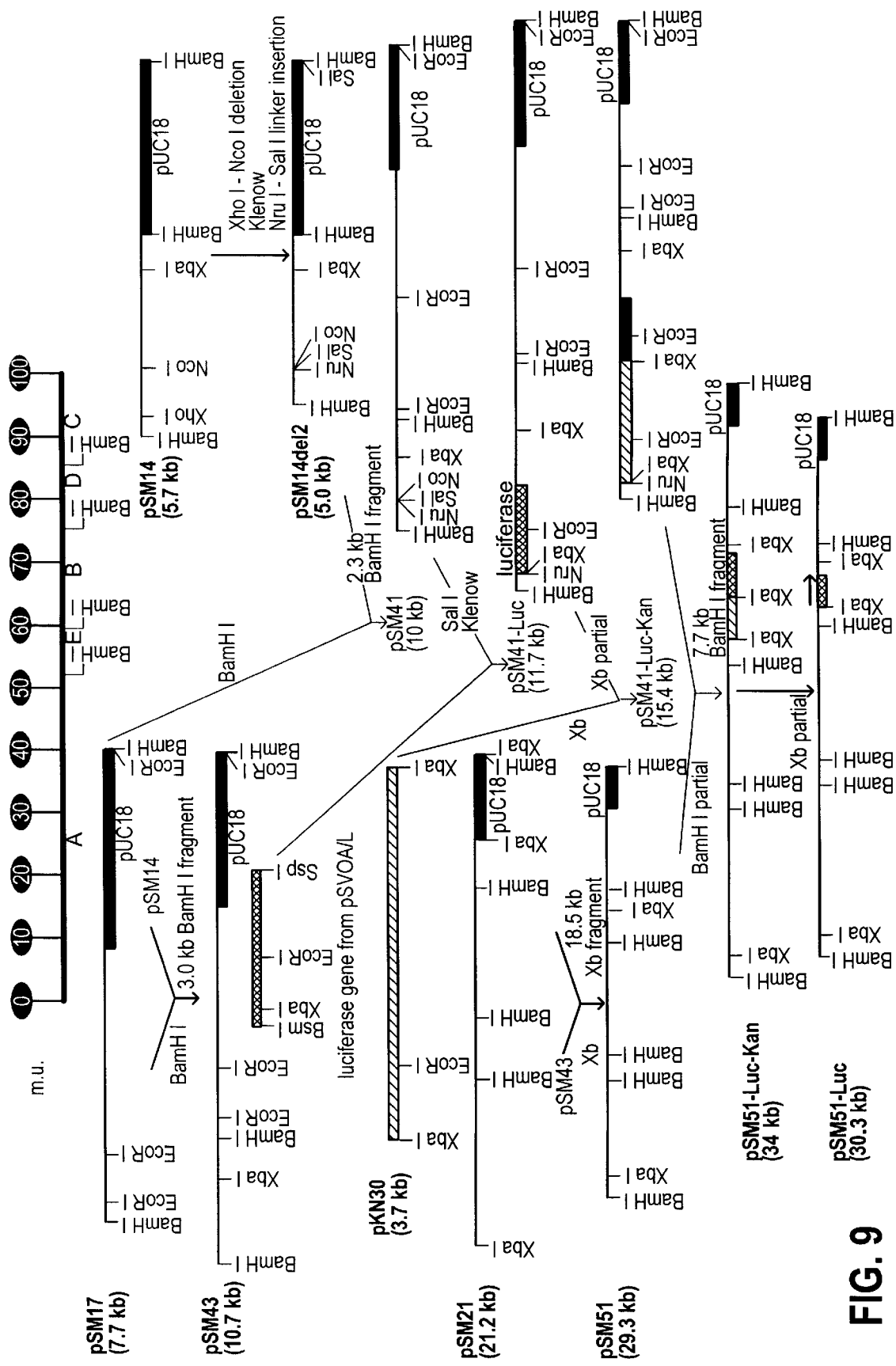
FIG. 9. Construction of BAV3 E3 transfer vector containing the firefly luciferase gene. The 3.0 kb BamHI 'D' fragment of the BAV3 genome which falls between m.u. 77.8 and 86.4, contains almost the entire E3 region (Mittal et al (1992) J. Gen. Virol. 73:3295–3000). This 3.0 kb fragment was isolated by digesting BAV3 DNA with BamHI and cloned into pUC18 at the BamHI site to obtain pSM14. Similarly, the 4.8 kb BamHI 'C' fragment of BAV3 DNA which extends between m.u. 86.4 and 100 was isolated and inserted into pUC18 to produce pSM17. To delete a 696 bp XhoI-NcoI fragment, pSM14 was cleaved with XhoI and NcoI, the larger fragment was purified and the ends were made blunt with Klenow fragment of DNA polymerase I and a NruI-SalI linker was inserted to generate pSM14de12. A 2.3 kb BamHI fragment containing BAV3 sequences, an E3 deletion and NruI and SalI cloning sites, was inserted into pSM17 at the BamHI site to obtain pSM41, however, this step was not required for construction of a BAV3 E3 transfer vector. A 1716 bp fragment containing the firefly luciferase gene (de Wet et al (1987) Mol. Cell. Biol. 7:725–737) was isolated by digesting pSVOA/L (provided by D. R. Helinski, University of California at San Diego, Calif.) with BsmI and SspI as described (Mittal et al (1993) Virus Res. 28:67–90), and the ends were made blunt with Klenow. The luciferase gene was inserted into pSM41 at the SalI site by blunt end ligation. The resultant plasmid was named pSM41-Luc which contained the luciferase gene in the same orientation as the E3 transcription unit. The plasmid pKN30 was digested with XbaI and inserted into pSM41-Luc (partially cleaved with XbaI) at a XbaI site present within the luciferase gene to obtain pSM41-Luc-Kan. The plasmid pSM14 was digested with BamHI and a 3.0 kb fragment was isolated and inserted into pSM17 at the BamHI site to generate pSM43. The 18.5 kb XbaI 'A' fragment of the BAV3 genome which falls between m.u. 31.5 and 84.3 was cloned into pUC18 at the XbaI site to generate pSM21. A 18.5 kb XbaI fragment was purified from pSM21 after cleavage with XbaI and inserted into pSM43 at the XbaI site and the resultant plasmid was named pSM51. A 7.7 kb BamHI fragment containing the luciferase gene and kan$^r$ gene was isolated after digesting pSM41-Luc-Kan with BamHI and ligated to pSM51, partially digested with BamHI, to isolate pSM51-Luc-Kan in the presence of ampicillin and kanamycin. Finally the kan$^r$ gene was deleted from pSM51-Luc-Kan by partial cleavage with XbaI and religation to obtain pSM51-Luc.

To facilitate the insertion of the firefly luciferase gene into the E3 region of the BAV3 genome, a BAV3 E3 transfer vector containing the luciferase gene was constructed (FIG. 9). The BAV3 E3 region falls approximately between m.u. 77 and 82. In our first series of vectors we replaced a 696 bp XhoI-NcoI E3 deletion (between m.u. 78.8 and 80.8) with NruI-SalI cloning sites for insertion of foreign genes to obtain pSM14de12. A 1716 bp BsmI-SspI fragment containing the luciferase gene was isolated and first inserted into an intermediate plasmid, pSM41, in the E3 locus at the SalI site by blunt end ligation to generate pSM41-Luc. The luciferase gene, without any exogenous regulatory sequences, was inserted into the E3 locus in the same orientation as the E3 transcription unit. The kan$^r$ gene was inserted into pSM41-Luc at the XbaI site present within the luciferase gene to generate an amp$^r$/kan$^r$ plasmid, pSM41-Luc-Kan. A 7.7 kb fragment containing the BAV3 sequences along with the luciferase gene and the kan$^r$ gene was obtained from pSM41-Luc-Kan by digestion with BamHI and inserted into an amp$^r$ plasmid, pSM51, partially digested with BamHI, to replace a 3.0 kb BamHI fragment (lies between m.u. 77.8 and 86.4) to generate a doubly resistant (kan$^r$ & amp$^r$) plasmid, pSM51-Luc-Kan. The kan$^r$ gene was deleted from pSM51-Luc-Kan by partial cleavage with XbaI to generate pSM51-Luc containing the luciferase gene in the E3-parallel orientation.

Figure 10:
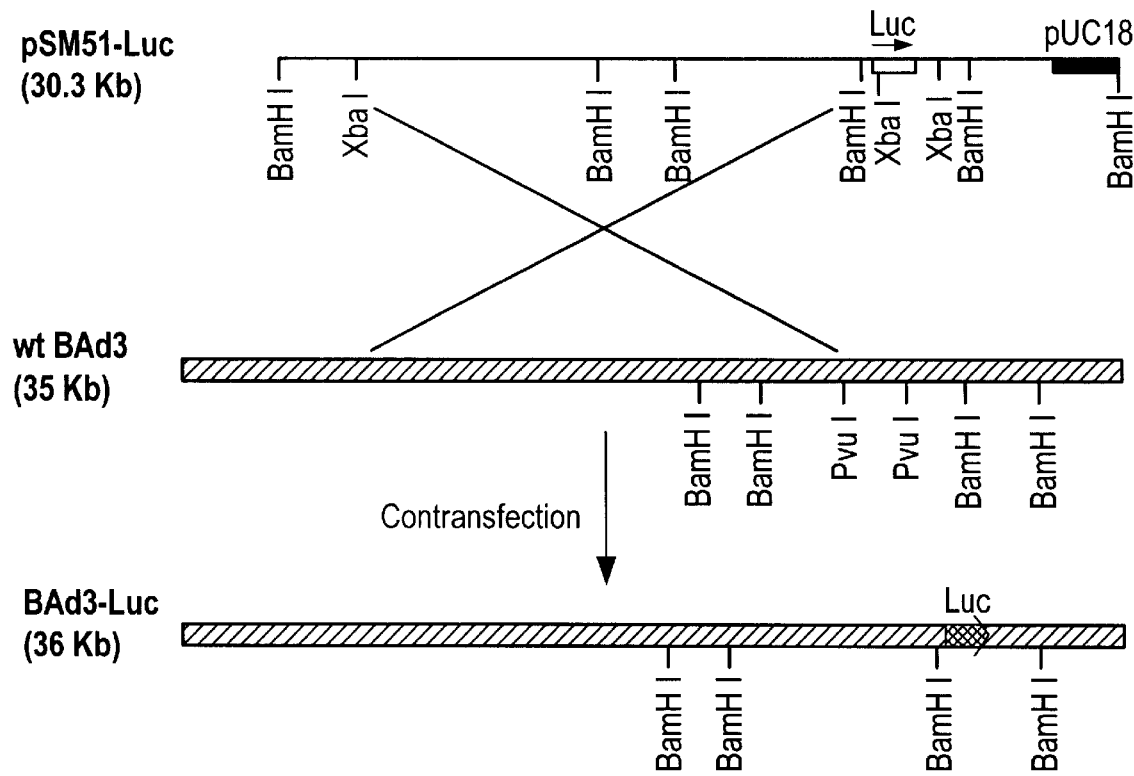
FIG. 10. Generation of BAV3 recombinants containing the firefly luciferase gene in the E3 region. The plasmid pSM51-Luc contains the BAV3 genome between m.u. 77.8–84.3 and 31.5–100, a 696 bp deletion in E3 and the luciferase gene in E3 in the E3 parallel orientation. The BAV3 genome digested with PvuI and uncut pSM51-Luc were used for cotransfection of MDBK cells transformed with a plasmid containing BAV3 E1 sequences to rescue the luciferase gene in E3 of the BAV3 genome by in vivo recombination. The resulting BAV3-luciferase recombinants (BAV3-Luc) isolated from two independent experiments were named BAV3-Luc (3.1) and BAV3-Luc (3.2). The BamHI restriction map of the BAV3-Luc genome is shown. The position and orientation of the firefly luciferase gene is shown as a hatched arrow.

MDBK cells transformed with a plasmid containing the BAV3 E1 sequences was cotransfected with wt BAV3 DNA digested with PvuI, which makes two cuts within the BAV3 genome at m.u 65.7 and 71.1, and the plasmid pSM51-Luc, to rescue the luciferase gene in E3 of the BAV3 genome by in vivo recombination (FIG. 10). The digestion of the wt BAV3 DNA with PvuI was helpful in minimizing the generation of wt virus plaques following cotransfection. The left end of the wt BAV3 genome, represented by the PvuI 'A' fragment, falls between m.u. 0 and 65.7, and pSM51-Luc which extends between m.u. 31.5 and 100 (except for the E3 deletion replaced with the luciferase gene) have sufficient overlapping BAV3 DNA sequences to generate recombinant viruses.

Two virus plaques were obtained in two independent cotransfection experiments which were grown in MDBK cells. The viral DNA from both plaques was extracted and analyzed by agarose gel electrophoresis after digesting either with BamHI, EcoRI or XbaI to identify the presence and orientation of the luciferase gene in the viral genome (data not shown). In the genomes of both recombinants, the luciferase gene was present in the E3 region in the E3 parallel orientation. The BAV3-luciferase recombinants were plaque purified and named BAV3-Luc (3.1) and BAV3-Luc (3.2) to represent plaques obtained from two independent experiments. Since both recombinant virus isolates were identical they will be referred to as BAV3-Luc. The presence of the luciferase gene in BAV3-Luc isolates are further confirmed by Southern blot analyses and luciferase assays using extracts from recombinant virus-infected cells.

Characterization of BAV3-recombinants

Figure 11A:
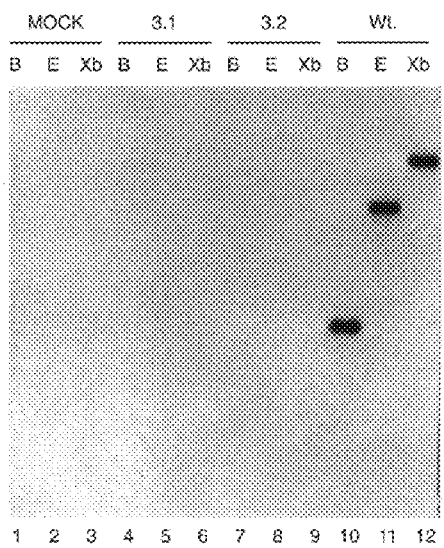
FIGS. 11A–11B. Southern blot analyses of restriction enzyme-digested DNA fragments of the wt BAV3 or recombinant genomes by using a 696 bp XhoI-NcoI fragment from pSM14 (FIG. 9) and a DNA fragment containing the luciferase gene as probes. 100 ng DNA isolated from the mock (lanes 1, 2, 3), BAV3-Luc (3.1) (lanes 4, 5, 6), BAV3-Luc (3.2) (lanes 7, 8, 9) or wt BAV3 (lanes 10, 11 12)-infected MDBK cells were digested with BamHI (lanes 1, 4, 7, 10), EcoRI (lanes 2, 5, 8, 11) or XbaI (lanes 3, 6, 9, 12) and analyzed by agarose gel electrophoresis. The DNA fragments from the gel were transferred onto a GeneScreen-Plus™ membrane and hybridized with a 696 bp XhoI-NcoI fragment from pSM14 (FIG. 9) labeled with $^{32}$P using Pharmacia Oligolabeling Kit (panel A). Panel B blot represents duplicate samples as in panel A but was probed with a 1716 bp BsmI-SspI fragment containing the luciferase gene (FIG. 9). The sizes of bands visualized following hybridization are shown in kb on the right in panel A and on the left in panel B.
B: BamHI, E: EcoRI, Xb: XbaI, 3.1: BAV3-Luc (3.1), 3.2: BAV3-Luc (3.2) and wt: wild-type BAV3.
Figure 11B:
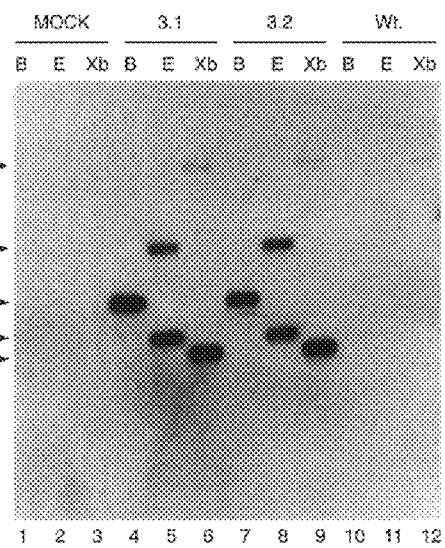

Southern blot analyses of the wt BAV3 and recombinants genomic DNA digested either with BamHI, EcoRI or XbaI, were carried out to confirm the presence and orientation of the luciferase gene in the E3 locus and the deletion of the 696 bp XhoI-NcoI fragment from E3 of the BAV3-Luc genome (FIG. 11). When the blot was probed with a 696 bp XhoI-NcoI fragment of E3 of the BAV3 genome (panel A, lanes 4 to 9) no hybridization signal was detected with the DNA fragments from the recombinant viruses, however, the expected bands (3.0 kb BamHI, 8.1 kb EcoRI, and 18.5 kb XbaI) of the wt BAV3 DNA fragments (panel A, lanes 10 to 12) showed hybridization, confirming that the 696 bp XhoI-NcoI fragment of the E3 region was indeed deleted in the BAV3-Luc genomic DNA. In panel B, when an identical blot was probed with the luciferase gene, there were strong hybridization signals with the DNA fragments from the recombinant viruses (4.0 kb BamHI (lane 4 & 7), 6.0 kb and 3.2 kb EcoRI (lanes 5 & 8), 16.7 kb and 2.9 kb XbaI (lanes 6 & 9)). These results confirmed that the BAV3-Luc contains the luciferase gene in the E3 parallel orientation within a 696 bp XhoI-NcoI E3 deletion.

Figure 12:
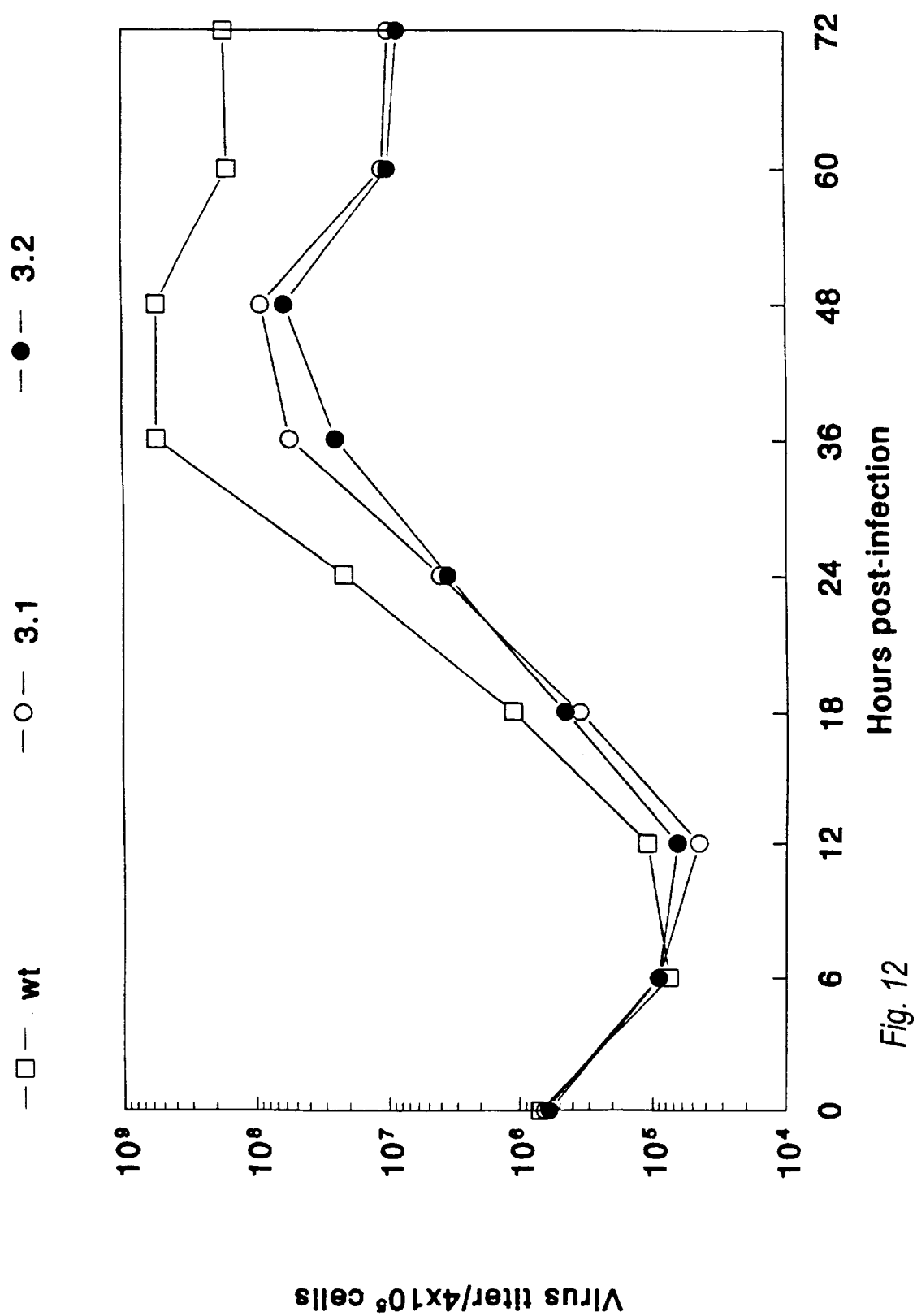
FIG. 12. Single step growth curve for wt BAV3 and BAV3-Luc. Confluent monolayers of MDBK cells in 25 mm multi-well culture plates were inoculated with the wt BAV3, BAV3-Luc (3.1) or BAV3-Luc (3.2) at a m.o.i. of 10 p.f.u. per cell. The virus was allowed to adsorb for 1 h at 37° C., cell monolayers were washed 3 times with PBS$^{++}$ (0.137 M NaCl, 2.7 mM KCl, 8 mM Na$_2$HPO$_4$, 1.5 mM KH$_2$PO$_4$, containing 0.01% CaCl$_2$.2H$_2$O and 0.01% MgCl$_2$.6H$_2$O) and incubated at 37° C. in 1 ml maintenance medium containing 2% horse serum. At various times post-infection, cells were harvested along with the supernatant, frozen and thawed three times and titrated on MDBK cells by plaque assay. Results are the means of duplicate samples.

The growth characteristics of the recombinant viruses were compared with the wt BAV3 in a single step growth curve (FIG. 12). Virus titers in MDBK cells infected with the wt BAV3 started increasing at 12 h post-infection reaching a maximum at 36–48 h post-infection and then declined thereafter. Virus titers of the recombinant viruses also started increasing at 12 h postinfection reaching a maximum at 48 h post-infection and then declined, however, the titers of recombinant viruses remained approximately one log lower than the wt virus. The plaque size of the recombinant viruses was also comparatively smaller than the wt virus (data not shown).

Kinetics of Luciferase Expression By BAV3-Luc

Figure 13:
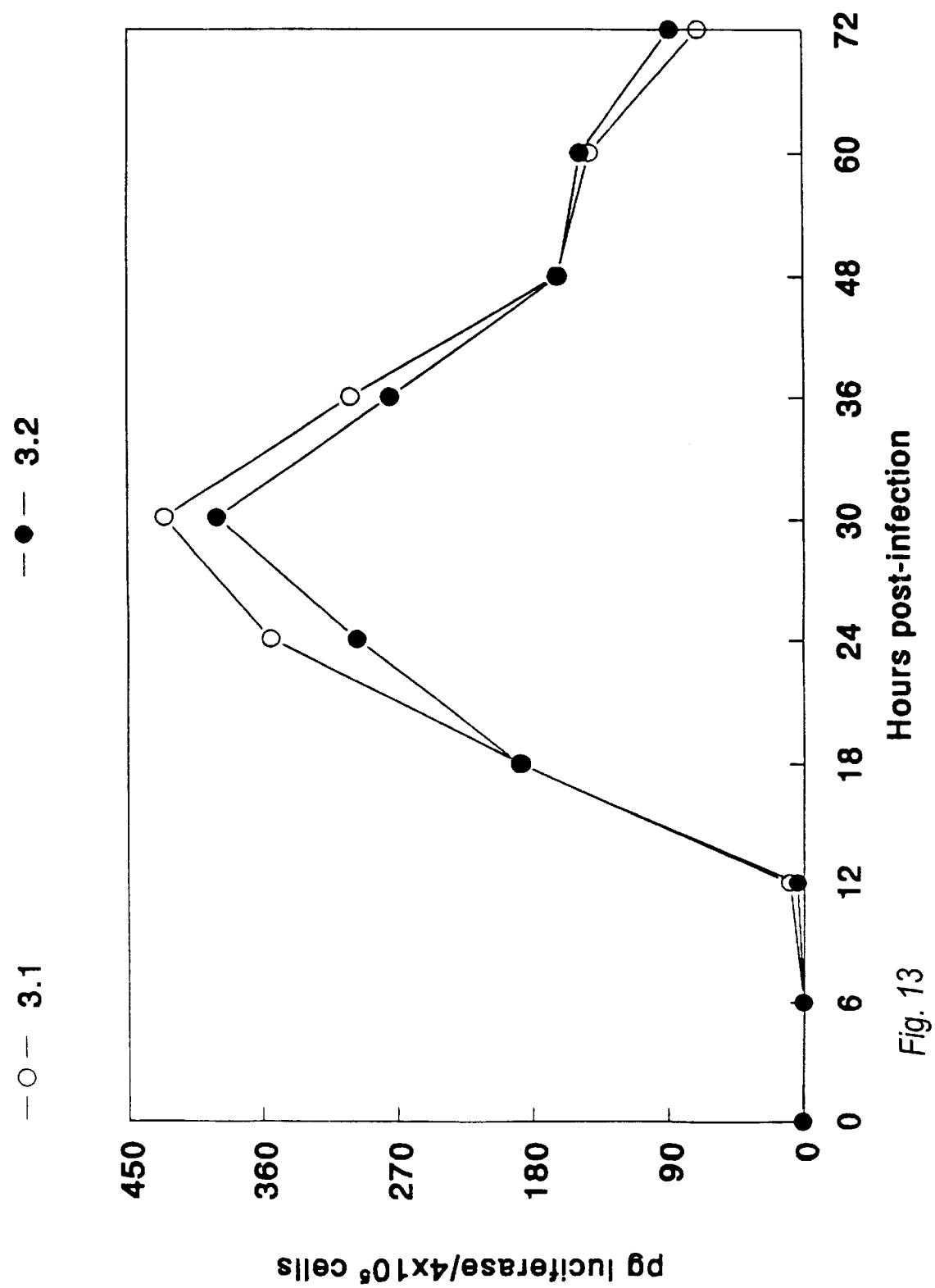
FIG. 13. Kinetics of luciferase expression in MDBK cells infected with BAV3-Luc. Confluent MDBK cell monolayers in 25 mm multi-well culture plates were infected with BAV3-Luc (3.1) or BAV3-Luc (3.2) at a m.o.i. of 50 p.f.u. per cell. At indicated time points post-infection, virus-infected cells were harvested and assayed in duplicate for luciferase activity.
Figure 14A:
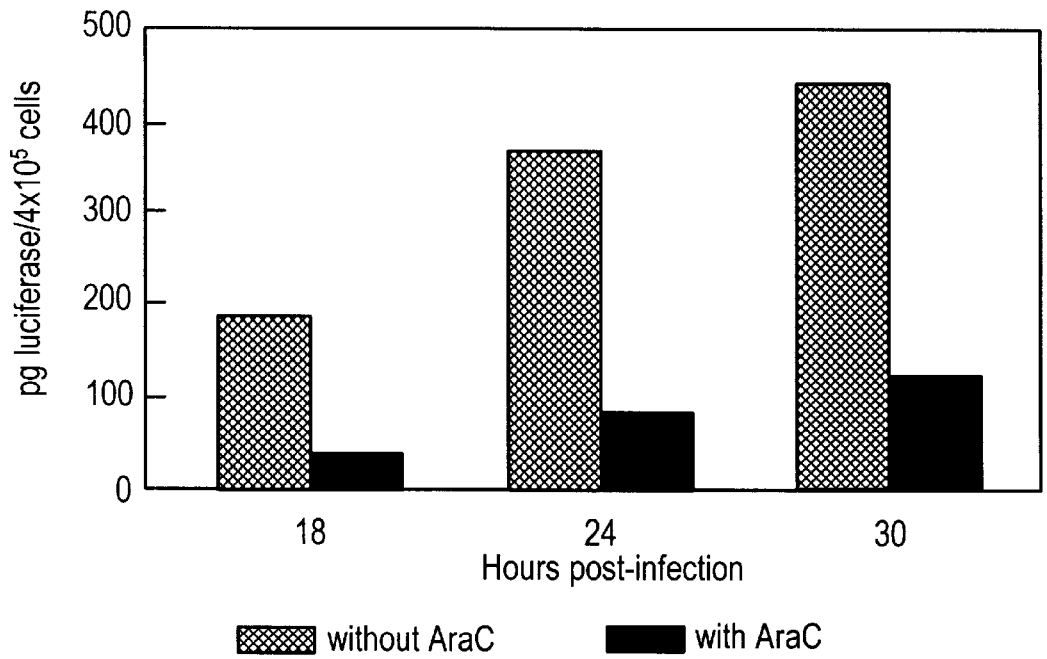
FIGS. 14A–14B. Luciferase expression in the presence of 1-β-D-arabinofuranosyl cytosine (AraC) in MDBK cells infected with BAV3-Luc. Confluent MDBK cell monolayers in 25 mm multi-well culture plates were infected with A) BAV3-Luc (3.1) or B) BAV3-Luc (3.2) at a m.o.i. of 50 p.f.u. per cell and incubated in the absence or presence of 50 μg AraC per ml of maintenance medium. At indicated time points post-infection, virus-infected cells were harvested and assayed in duplicate for luciferase activity.
Figure 14B:
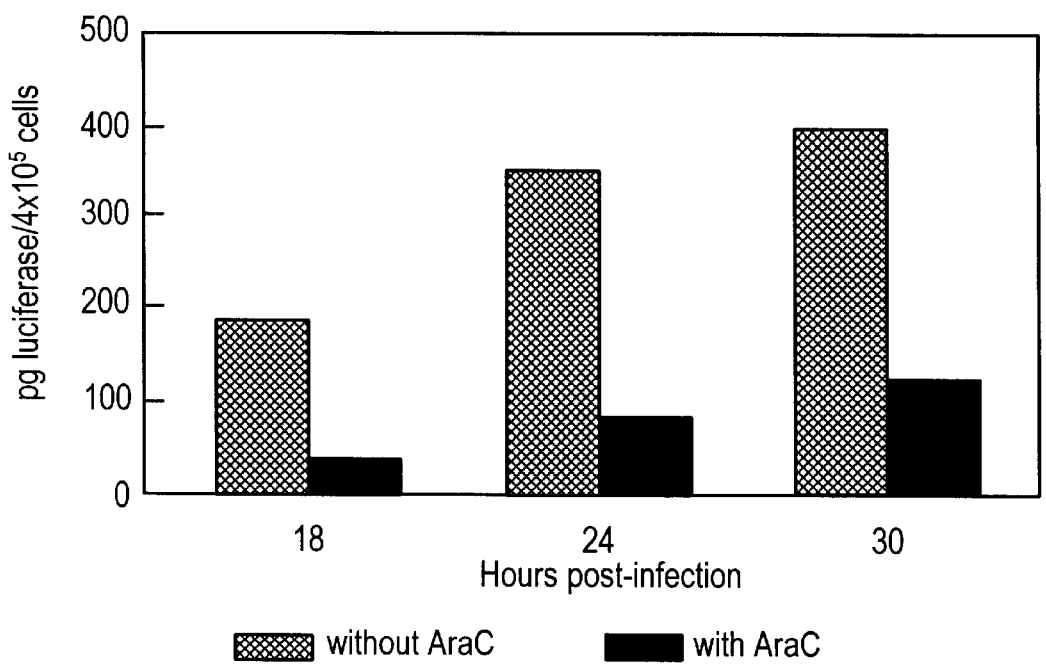

Luciferase activity in BAV3-Luc-infected MDBK cells was monitored at different times post-infection by luciferase assays (FIG. 13). A low level of luciferase activity was first observed at 12 h post-infection reaching a peak at 30 h post-infection and then dropped subsequently. At 30 h post-infection, approximately 425 pg luciferase was detected in $4\times10^5$ BAV3-Luc (3.1)-infected MDBK cells. In MDBK cells-infected with the wt BAV3, luciferase expression was not detected (data not shown). The kinetics of luciferase expression by BAV3-Luc (3.1) and BAV3-Luc (3.2) appears very similar. The kinetics of luciferase expression also showed that the majority of enzyme expression in virus-infected cells seemed to occur late in infection. To determine luciferase expression in the absence of viral DNA replication, BAV3-Luc-infected MDBK cells were incubated in the presence of an inhibitor of DNA synthesis, 1-β-D-arabinofuranosyl cytosine (AraC) and luciferase activity was measured in virus-infected cell extracts at various times post-infection and compared to luciferase expression obtained in the absence of AraC (FIG. 14). When the recombinant virus-infected cells were incubated in the presence of AraC, luciferase expression at 18, 24 and 30 h post-infection was approximately 20–30% of the value obtained in the absence of AraC. These results indicated that the majority of luciferase expression in MDBK cells infected with BAV3-Luc took place after the onset of viral DNA synthesis. To confirm this, MDBK cells-infected with BAV3-Luc were grown in the absence or presence of AraC, harvested at 18 h, 24 h, and 30 h post-infection, viral DNA extracted and analyzed by dot blot analysis using pSM51-Luc (see FIG. 9) as a probe (data not shown). In the presence of AraC, viral DNA synthesis was severely reduced compared to viral DNA synthesis in the absence of AraC.

Western Blot Analysis of BAV3-Luc-infected Cells

Figure 15A:
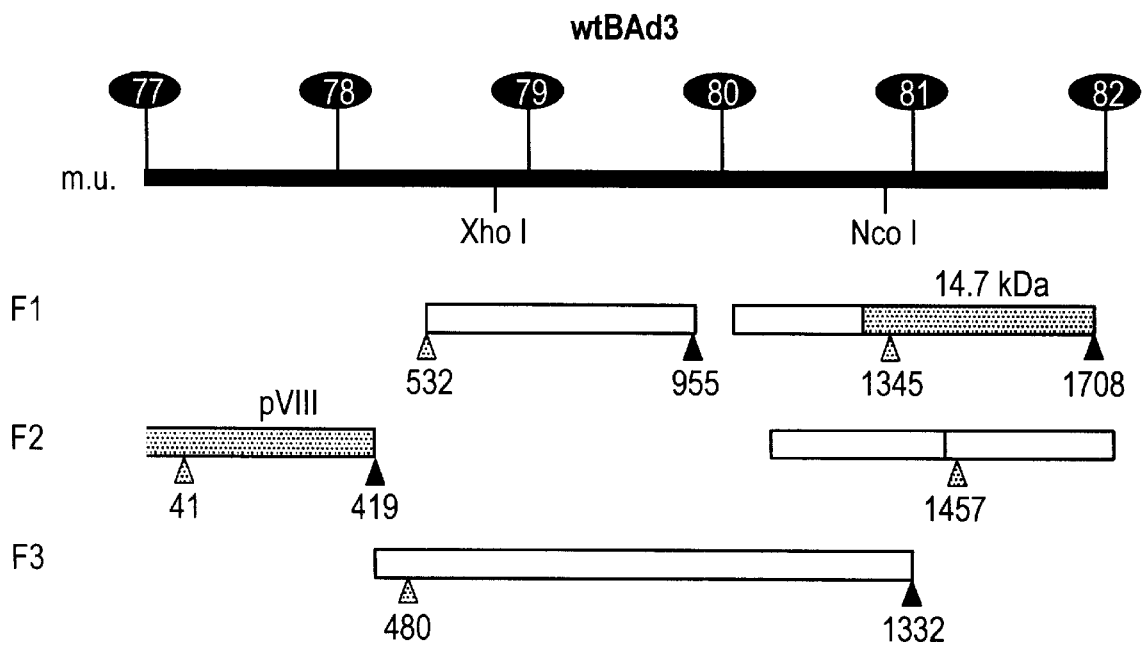
FIGS. 15A–15B. Transcription maps of the wt BAV3 and BAV3-Luc genomes in the E3 region. The genome of wt BAV3 between m.u. 77 and 82 is shown which represents the E3 region. The location of XhoI and NcoI sites which were used to make an E3 deletion are shown. (a) The three frames (F1, F2 and F3) representing the open reading frames (ORFs) in the upper strand of the wt BAV3 genome in the E3 region are represented by bars. The shaded portions indicate regions of similarities to pVIII and E3-14.7 kDa proteins of HAd5. The positions of the initiation and termination codons for ORFs likely to code for viral proteins are shown by open and closed triangles, respectively. (b) The predicted ORFs for the upper strand in E3 of the BAV3-Luc genome are shown after a 696 bp XhoI-NcoI E3 deletion replaced by the luciferase gene. The ORFs for pVIII and E3-14.7 kDa proteins are intact. The transcription map of the wt BAV3 E3 was adapted from the DNA sequence submitted to the GenBank database under accession number D16839.
Figure 15B:
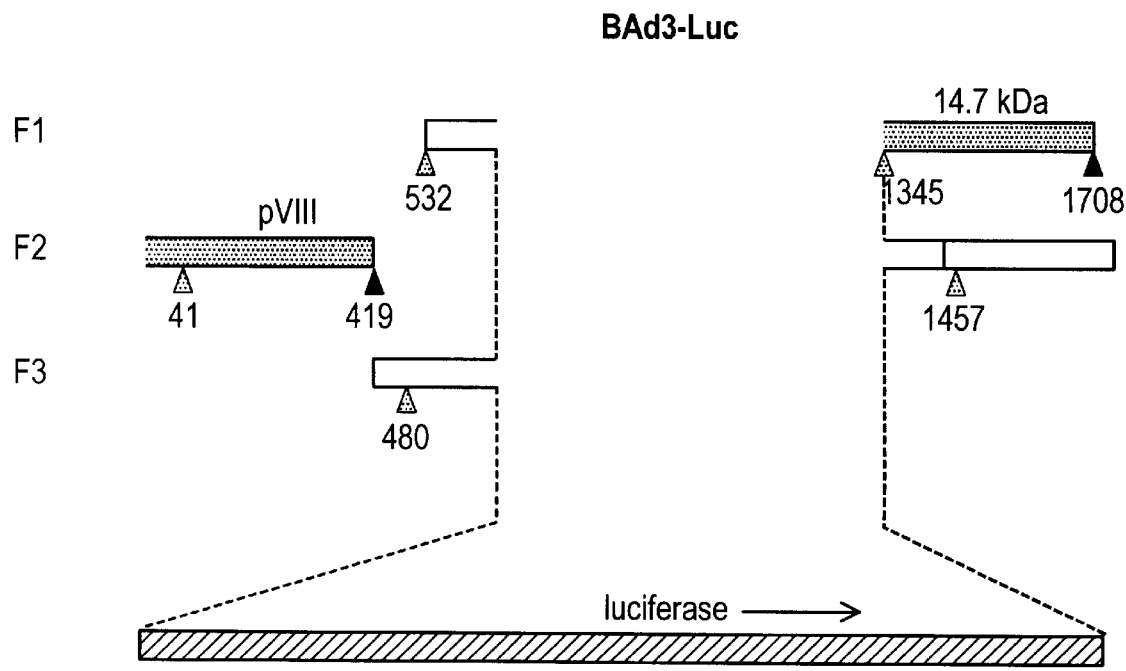
Figure 16:
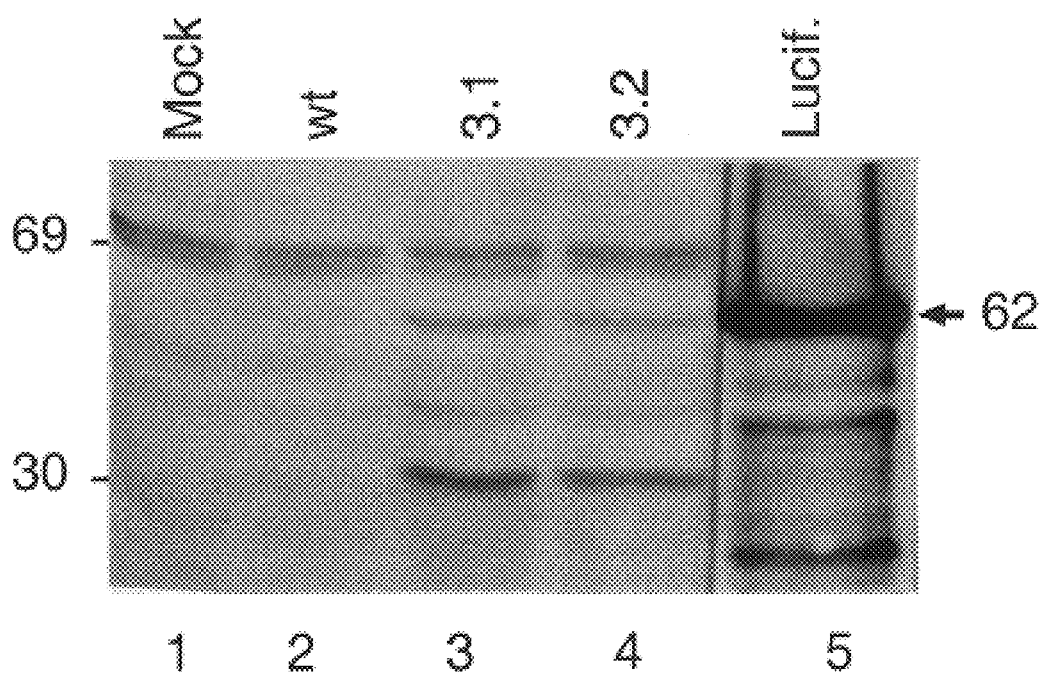
FIG. 16. Western blot analysis of virus-infected MDBK cells using an anti-luciferase antibody. Confluent monolayers of MDBK cells were mock-infected (lane 1) or infected with the wt BAV3 (lane 2), BAV3-Luc (3.1) (lane 3) and BAV3-Luc (3.2) (lane 4) at a m.o.i. of 50 p.f.u. per cell, harvested at 18 h post-infection, cell extracts prepared and analyzed by SDS-PAGE and Western blotting using a rabbit anti-luciferase antibody. Purified firefly luciferase was used as a positive control (lane 5). The lane 5 was excised to obtain a shorter exposure. The protein molecular weight markers in kDa are shown on the left. The arrow indicates the 62 kDa luciferase bands reacted with the anti-luciferase antibody.
wt: wild-type BAV3, 3.1: BAV3-Luc (3.1) and 3.2: BAV3-Luc (3.2).
Figure 17:
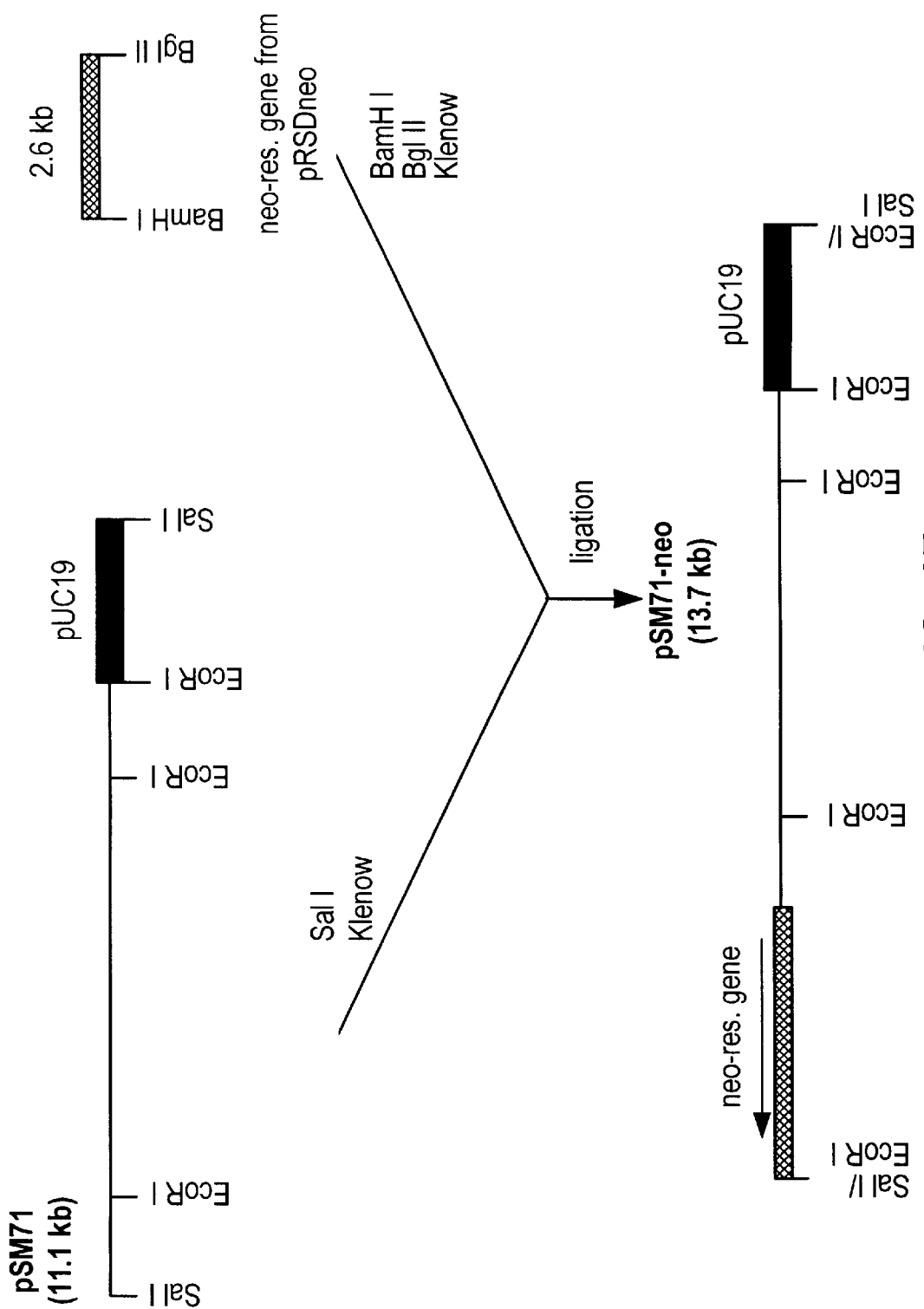
FIG. 17. Construction of pSM71-neo. A 8.4 kb SalI fragment of the BAV3 genome which falls between m.u. 0 and 24 was isolated and inserted into pUC19 at the SalI-SmaI site to generate pSM71. The plasmid, pRSDneo (Fitzpatrick et al (1990) *Virology* 176:145–157) contains the neomycin-resistant (neo$^r$) gene flanked with the simian virus 40 (SV40) regulatory sequences originally from the plasmid, pSV2neo (Southern et al (1982) *J. Mol. Appl. Genet* 1:327–341) after deleting a portion of the SV40 sequences upstream of the neo$^r$ gene to remove several false initiation codons. A 2.6 kb fragment containing the neo$^r$ gene under the control of the SV40 regulatory sequences, was obtained from the plasmid, pRSDneo after digestion with BamHI and BglII, and cloned into pSM71 at the SalI site by blunt end ligation to obtain pSM71-neo containing the neo$^r$ gene in the E1 parallel orientation.
Figure 18:
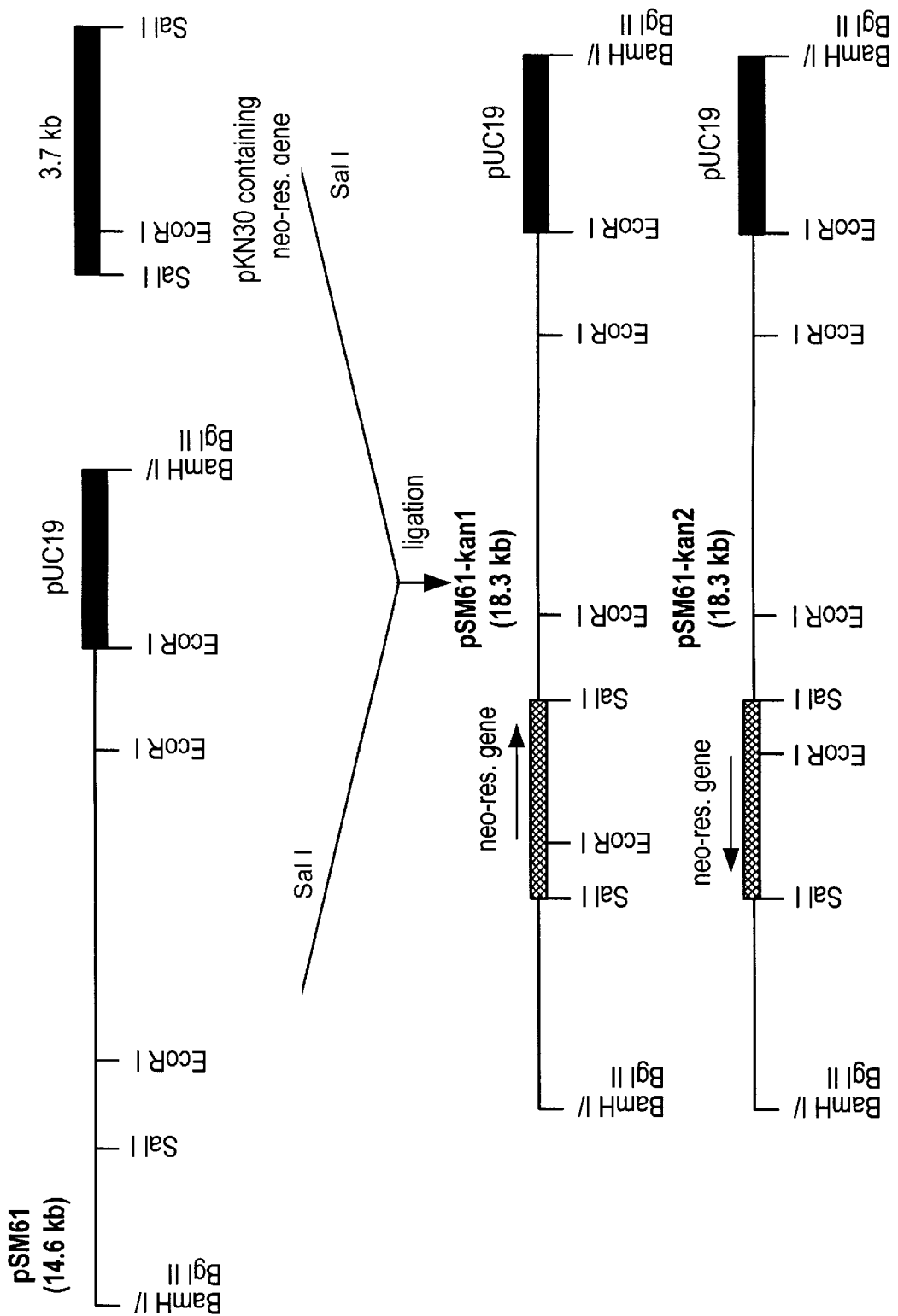
FIG. 18. Construction of pSM61-kan 1 and pSM61-kan2. A 11.9 kb BglII fragment of the BAV3 genome which extends between m.u. 0 and 34 was purified and introduced into pUC19 at the BamHI-HincII site to obtain pSM61. The plasmid, pKN30 contains the neo$^r$ gene along with SV40 promoter and polyadenylation sequences from the plasmid pSV2neo without any modification. The entire pKN30 plasmid was inserted into pSM61 at the SalI site to generate pSM61-kan1 having the neo$^r$ gene in the E1 anti-parallel orientation and pSM61-kan2 when the neo$^r$ gene is in the E1 parallel orientation.
Figure 19:
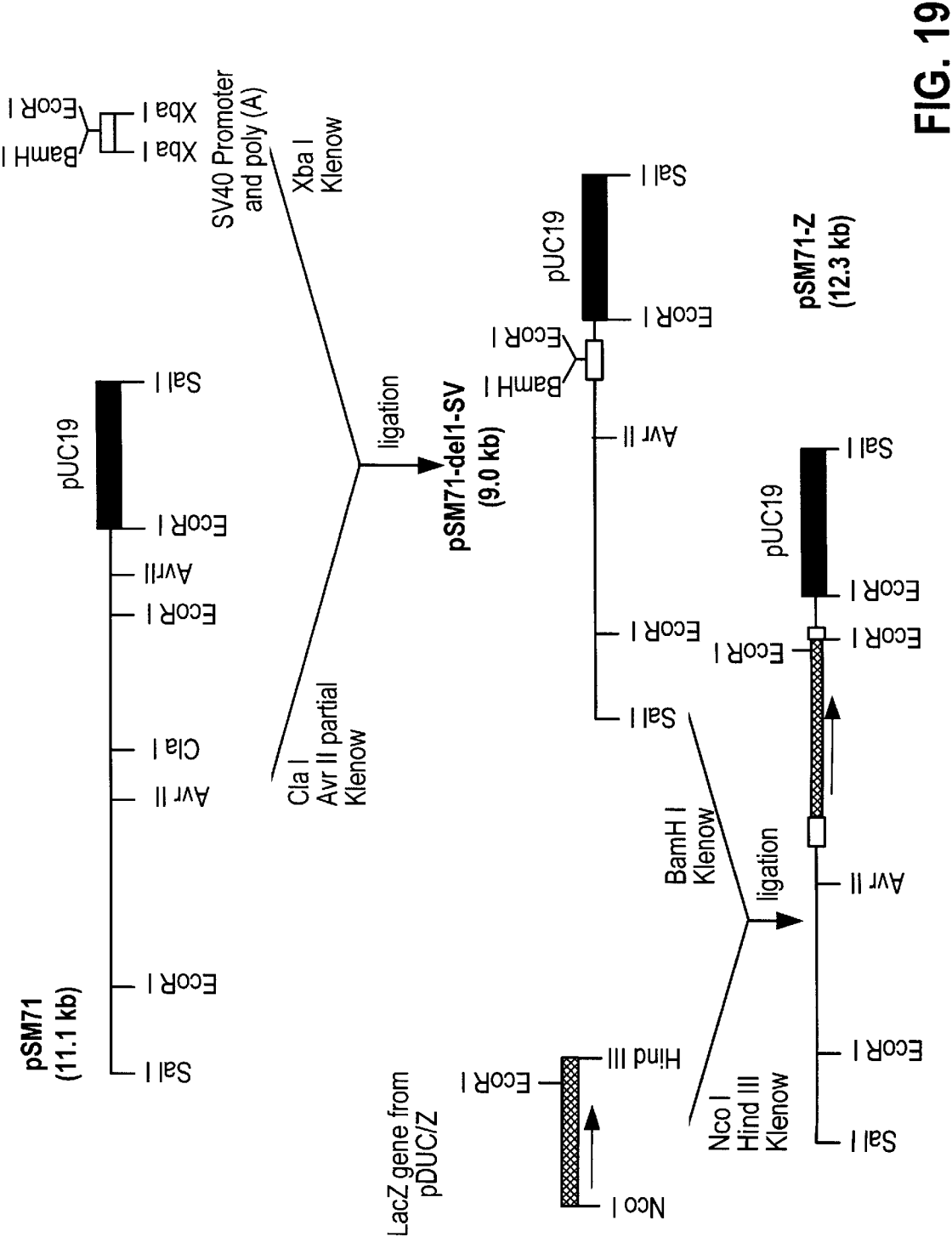
FIG. 19. Construction of an E1 transfer plasmid containing the beta-galactosidase gene. The plasmid, pSM71 which contains the BAV3 genome between m.u. 0 and 24, was cleaved with ClaI and partially with AvrII to delete a 2.6 kb AvrII-ClaI fragment (between m.u. 1.3 and 8.7) which falls within the E1 region. A 0.5 kb fragment containing the SV40 promoter and polyadenylation sequences was obtained from pFG144K5-SV by digesting with XbaI and inserted into pSM71 to replace the 2.6 kb deletion to generate pSM71-de11-SV. A 3.26 kb fragment containing the bacterial beta-galactosidase gene was isolated from pDUC/Z (Liang et al (1993) *Virology* 195:42–50) after cleavage with NcoI and HindIII and cloned into pSM71-de11-SV at the BamHI site to put the beta-galactosidase gene under the control of the SV40 regulatory sequences to obtain pSM71-Z.

Luciferase was expressed as an active enzyme as determined by luciferase assays using extracts from MDBK cells-infected with BAV3-Luc (see FIG. 13). The luciferase gene without any exogenous regulatory sequences was inserted into E3 of the BAV3 genome, therefore, there was a possibility of luciferase expression as a fusion protein with part of an E3 protein if the luciferase gene was in the same frame (such as F1 and F3 which represent open reading frames (ORFs) for E3 proteins, FIG. 15) or the fusion protein may arise due to recognition of an upstream initiation codon in the luciferase ORF. To explore this possibility we sequenced the DNA at the junction of the luciferase gene and the BAV3 sequences with the help of a plasmid, pSM51-Luc and a synthetic primer designed to bind luciferase coding sequences near the initiation codon (data not shown). The luciferase coding region fell in frame F2. The luciferase initiation codon was the first start codon in this frame, however, the ORF started 84 nucleotides upstream of the luciferase start codon. To further confirm that luciferase protein is of the same molecular weight as purified firefly luciferase, unlabeled mock-infected, wt BAV3-infected or BAV3-Luc-infected MDBK cell extracts were reacted with an anti-luciferase antibody in a Western blot (FIG. 16). A 62 kDa polypeptide band was visible in the BAV3-Luc (lanes 3 and 4)-infected cell extracts which was of the same molecular weight as pure firefly luciferase (lane 5). A band of approximately 30 kDa also reacted with the anti-luciferase antibody (lanes 3 and 4) and may represent a degraded luciferase protein.

The majority of luciferase expression is probably driven from the major late promoter (MLP) to provide expression paralleling viral late gene expression, while the enzyme expression seen in the presence of AraC may be taking place from the E3 promoter. In HAd5 vectors, foreign genes without any exogenous regulatory sequences when inserted in E3 also displayed late kinetics and were inhibited by AraC. The BAV3 recombinant virus replicated relatively well in cultured cells but not as well as the wt BAV3. This is not surprising as infectious virus titers of a number of HAd5 recombinants were slightly lower than the wt HAd5 (Bett et al (1993) *J. Virol.* 67:5911–5921). This may be because of reduced expression of fiber protein in recombinant adenoviruses having inserts in the E3 region compared to the wt virus (Bett et al, supra and Mittal et al (1993) *Virus Res.* 28:67–90).

The E3 of BAV3 is approximately half the size of the E3 region of HAd2 or HAd5 and thus has the coding potential for only half the number of proteins compared to E3 of HAd2 or HAd5 (Cladaras et al (1985) *Virology* 140:28–43:

Herisse et al (1980) *Nuc. Acids Res.* 8:2173–2192; Herisse et al (1981) *Nuc. Acids Res.* 9:1229–1249 and Mittal et al (1993 *J. Gen. Virol.* 73:3295–3000). BAV3 E3 gene products have been shown to be non-essential for virus growth in tissue culture. However, presently it is known that BAV3 E3 gene products also evade immune surveillance in vivo like HAds E3 proteins. One of the BAV3 E3 open reading frames (ORFs) has been shown to have amino acid homology with the 14.7 kDa E3 protein of HAds (Mittal et al (1993) supra). The 14.7 kDa E3 protein of HAds prevents lysis of virus-infected mouse cells by tumor necrosis factor (Gooding et al (1988) *Cell* 53:341–346 and Horton et al (1990) *J. Virol.* 64:1250–1255). The study of pathogenesis and immune responses of a series of BAV3 E3 deletion mutants in cattle provides very useful information regarding the role of E3 gene products in modulating immune responses in their natural host.

The BAV3-based vector has a 0.7 kb E3 deletion which can accommodate an insert up to 2.5 kb in size. The BAV3 E3 deletion can extend probably up to 1.4 kb which in turn would also increase the insertion capacity of this system. The role of the MLP and the E3 promoter is examined to determine their ability to drive expression of a foreign gene inserted into E3 when a proper polyadenylation signal is provided. Exogenous promoters, such as the simian virus 40 (SV40) promoter (Subramant et al (1983) *Anal. Biochem.* 135:1–15), the human cytomegalovirus immediate early promoter (Boshart et al (1985) *Cell* 43:215–222), and the human beta-actin promoter (Gunning et al (1987) *PNAS, USA* 84:4831–4835) are tested to evaluate their ability to facilitate expression of foreign genes when introduced into E3 of the BAV3 genome.

Recently HAd-based expression vectors are under close scrutiny for their potential use in human gene therapy (Ragot et al (1993) *Nature* 361:647–650; Rosenfeld et al (1991) *Science* 252:431–434; Rosenfeld et al (1992) *Cell* 68:141–155 and Stratford-Perricaudet et al (1990) *Hum. Gene. Ther.* 1:241–256). A preferable adenovirus vector for gene therapy would be one which maintains expression of the required gene for indefinite or long periods in the target organ or tissue. It may be obtained if the recombinant virus vector genome is incorporated into the host genome or maintained its independent existence extrachromosomally without active virus replication. HAds replicate very well in human, being their natural host. HAds can be made defective in replication by deleting the E1 region, however, how such vectors would maintain the expression of the target gene in a required fashion is not very clear. Moreover, the presence of anti-HAds antibodies in almost every human being may create some problems with the HAd-based delivery system. The adenovirus genomes have a tendency to form circles in non-permissive cells. BAV-based vectors could provide a possible alternative to HAd-based vectors for human gene therapy. As BAV3 does not replicate in human, the recombinant BAV3 genomes may be maintained as independent circles in human cells providing expression of the essential protein for a long period of time.

The foreign gene insertion in animal adenoviruses is much more difficult than HAds because it is hard to develop a cell line which is also good for adenovirus DNA-mediated transfection. This may be one of the major reasons that the development of an animal adenovirus-based expression system has not been reported so far. It took us more than a year to isolate a cell line suitable for BAV3 DNA-mediated transfection. Suitable cell lines for use in the practice of the invention may be derived from any primary or established mammalian cell line, preferably of bovine origin. However, the rapid implementation of BAV-based expression vectors for the production of live virus recombinant vaccines for farm animals, is very promising. BAVs grow in the respiratory and gastrointestinal tracts of cattle, therefore, recombinant BAV-based vaccines have use to provide a protective mucosal immune response, in addition to humoral and cellular immune responses, against pathogens where mucosal immunity plays a major role in protection.

Example 5

Generation of Cell Lines Transformed With the BAV3 E1 Sequences

MDBK cells in monolayer cultures were transfected with pSM71-neo, pSM61-kan1 or pSM61-kan2 by a lipofection-mediated transfection technique (GIBCO/BRL, Life Technologies, Inc., Grand Island, N.Y.). At 48 h after transfection, cells were maintained in the MEM supplemented with 5% fetal bovine serum and 700 μg/ml G418. The medium was changed every $3^{rd}$ day. In the presence of G418, only those cells would grow which have stably incorporated the plasmid DNA used in transfection experiments into their genomes and are expressing the $neo^r$ gene. The cells which have incorporated the $neo^r$ gene might also have taken up the BAV3 E1 sequences and thus may be expressing BAV3 E1 protein/s. A number of $neo^r$ (i.e., G418-resistant) colonies were isolated, expanded and tested for the presence of BAV3 E1 message/s by Northern blot analyses using a DNA probe containing only the BAV3 E1 sequences. Expression of BAV3 E1 protein/s were confirmed by a complementation assay using a HAd5 deletion mutant defective in E1 function due to an E1 deletion.

Fetal bovine kidney cells in monolayers were also transfected with pSM71-neo, pSM61kan-1 or pSM61-kan2 by the lipofection-mediated transfection technique, electroporation (Chu et al (1987) *Nucl. Acids Res.* 15:1311–1326), or calcium phosphate precipitation technique (Graham et al (1973) *Virology* 52:456–467). Similarly, a number of G418-resistant colonies were isolated, expanded and tested for the presence of BAV3 E1 gene products as mentioned above.

Example 6

Generation of a BAV3 Recombinant Containing the Beta-galactosidase Gene as an E1 Insert As E1 gene products are essential for virus replication, adenovirus recombinants containing E1 inserts will grow only in a cell line which is transformed with the adenovirus E1 sequences and expresses E1. A number of cell lines which are transformed with the BAV3 E1 sequences were isolated as described earlier. The technique of foreign gene insertions into the E1 regions is similar to the gene insertion into the E3 region of the BAV3 genome, however, for insertion into E1 there is a need for an E1 transfer plasmid which contains DNA sequences from the left end of the BAV3 genome, an appropriate deletion and a cloning site for the insertion of foreign DNA sequences. G418-resistant MDBK cell monolayers were cotransfected with the wild-type (wt) BAV3 DNA and pSM71-Z following the lipofection-mediated transfection procedure (GIBCO/BRL, Life Technologies, Inc., Grand Island, N.Y.). The monolayers were incubated at 37° C. under an agarose overlay. After a week post-incubation another layer of overlay containing 300 μg/ml Blu-gal™ (GIBCO/BRL Canada, Burlington, Ontario, Canada) was put onto each monolayer. The blue plaques were isolated, plaque purified and the presence of the beta-galactosidase gene in the BAV3 genome was identified by agarose gel electrophoresis of recombinant virus DNA digested with suitable restriction enzymes and confirmed by beta-galactosidase assays using extracts from recombinant virus infected cells.

Example 7
Determination of the Nucleotide Sequence of Nucleotides 4,092–5,234; Nucleotides 5,892–17,735; Nucleotides 21,198–26,033 and Nucleotides 31,133–34,445.

To complete the nucleotide sequence of the bovine adenovirus type 3 genome, the following BAV-3 restriction fragments were cloned into bacterial plasmids and their nucleotide sequences were determined by methods known to those of skill in the art.

| | |
|---|---|
| Hind III B | 11.7–26.3 m.u. |
| Hind III K | 26.3–30.8 m.u. |
| Hind III A | 30.8–53.2 m.u. |
| Eco RI-Hind III | 62.5–64.5 m.u. |
| Hind III D | 64.3–73.7 m.u. |
| Hind III-Bam HI | 73.7–76.6 m.u. |
| Bam HI-C | 84.9–100 m.u. |

Example 8
Insertions in the Regions of the BAV-3 Genome Defined By Nucleotides 4,092–5,234; Nucleotides 5,892–17,735; Nucleotides 21,198–26,033 and Nucleotides 31,133–34,445.

Insertions are made by art-recognized techniques including, but not limited to, restriction digestion, nuclease digestion, ligation, kinase and phosphatase treatment, DNA polymerase treatment, reverse transcriptase treatment, and chemical oligonucleotide synthesis. Foreign nucleic acid sequences of interest are cloned into plasmid vectors such that the foreign sequences are flanked by sequences having substantial homology to a region of the BAV genome into which insertion is to be directed. These constructs are then introduced into host cells that are coinfected with BAV-3. During infection, homologous recombination between these constructs and BAV genomes will occur to generate recombinant BAV vectors. If the insertion occurs in an essential region of the BAV genome, the recombinant BAV vector is propagated in a helper cell line which supplies the viral function that was lost due to the insertion. For insertions in the E4 region, which is non-essential for viral replication, propagation of BAV vectors in a helper cell line is not necessary.

Example 9
Construction and Characterization of E3-deleted BAV3 Expressing Full Length and Truncated Forms of Bovine Herpesvirus 1 Glycoprotein gD This example demonstrates the construction of a 1.245 kb deletion in the E3 region of BAV3, using the homologous recombination machinery of *E. coli*. First, a 1.245 kb deletion was introduced in the E3 region of bovine adenovirus-3 (BAV3) genomic DNA cloned in a plasmid. Transfection of linear, restriction enzyme-excised, E3-deleted BAV3 genomic DNA into primary fetal bovine retina cells produced infectious virus (BAV3.E3d) suggesting that all BAV E3-specific open reading frames are non-essential for virus replication in vitro. Using a similar approach, replication-competent BAV3 recombinants expressing full length (BAV3.E3gD) or truncated (BAV3.E3gDt) glycoprotein D of bovine herpesvirus-1 (BHV-1) were constructed. Recombinant gD and gDt proteins expressed by BAV3.E3gD and BAV3.E3gDt were recognized by gD-specific monoclonal antibodies directed against conformational epitopes, suggesting that antigenicity of recombinant gD and gDt was similar to that of the native gD expressed in BHV-1-infected cells. Intranasal immunization of cotton rats induced strong gD- and BAV3-specific IgA and IgG immune responses. These results exemplify the use of replication-competent bovine adenovirus-3-based vectors for the delivery of vaccine antigens to the mucosal surfaces of animals.

MATERIALS AND METHODS

Cells and Viruses. #

Madin Darby bovine kidney (MDBK) cells and primary fetal bovine retina (PFBR) cells were grown in Eagle's minimal essential medium (MEM) supplemented with 5% fetal bovine serum (FBS). The wild type (WBR-1 strain) and recombinant BAV3 viruses were propagated in MDBK cells as described previously. Mittal et al (1995) *J. Gen. Virol.* 76:93–102. The P8-2 strain of BHV-1 was propagated and quantitated as described. Rouse et al. (1974) *J. Immunol.* 113:1391–1398.

Animals. #

An inbred colony of cotton rats (*Sigmodon hispidus*) maintained at the Veterinary Infectious Disease Organization (Saskatoon) was the source of animals for this study.

Construction of Recombinant Plasmids.

a) Construction of plasmid pBAV302. #

Figure 22:
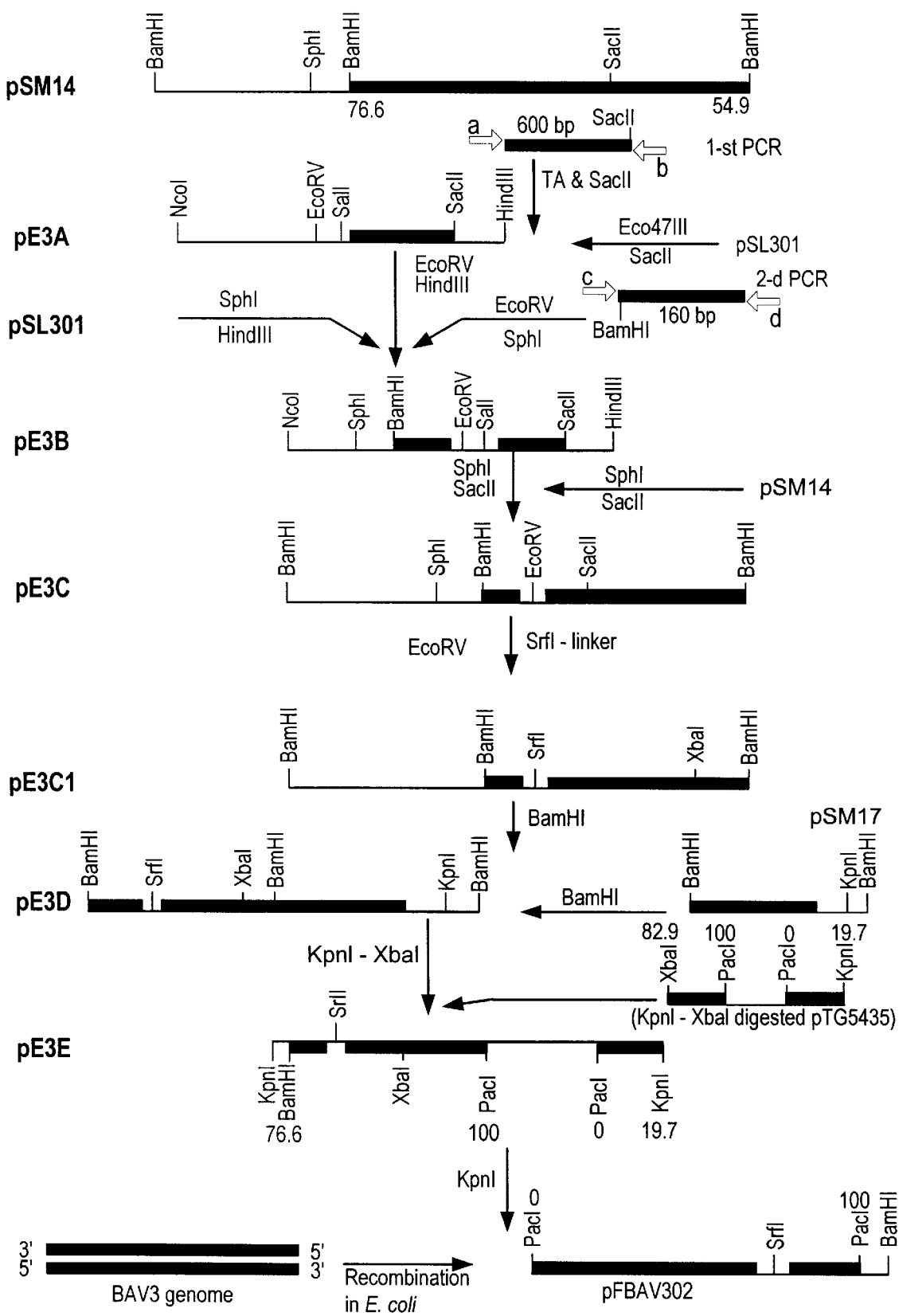
FIG. 22. Construction of a plasmid containing E3-deleted BAV3 genomic DNA. The plasmid pBAV302 was constructed from different genomic clones as described in Example 9, supra. The origin of the DNA sequences is as follows: plasmid DNA, thin line; BAV3 genomic DNA sequences, thick line. Hollow arrows represent the PCR primers, as follows.

See FIG. 22. A T4 polymerase-treated 587 bp fragment isolated by PCR amplification, using oligonucleotides E3C5' ACGCGTCGACTCCTCCTCA (SEQ ID NO. 36) and E3C3' TTGACAGCTAGCTTGTTG (SEQ ID NO. 37) and plasmid pSM14 (Mittal et al. (1995) supra) as a template, was digested with SacII and ligated to Eco47III-SacII-digested plasmid pSL301, creating plasmid pE3A. A 164 bp fragment isolated by PCR amplification, using oligonucleotides E3N5' CCAAGCTTGCATGCCTG (SEQ ID NO. 38) and E3N3' GGCGATATCTCAGCTATAACCGCTC (SEQ ID NO. 39) and plasmid pSM14 (Mittal et al. (1995) supra), was digested with SphI and EcoRV, then ligated to a 531 bp EcoRV-HindIII fragment of pE3A and to SphI-HindIII-digested plasmid pSL301, creating plasmid pE3B. The 614 bp SphI-SacII fragment was isolated from plasmid pE3B and ligated to SphI-SacII-digested pSM14, to create plasmid pE3C. The plasmid pE3C was digested with EcoRV and ligated to a SrfI linker (TTGCCCGGGCTT, SEQ ID NO: 40), creating plasmid pE3CI. A 1.755 kb BamHI fragment of pE3CI was isolated and ligated to BamHI-digested pSM17 (Mittal et al. (1995) supra), creating plasmid pE3D. Finally, an 8783 bp KpnI-XbaI fragment of plasmid pE3D was isolated and ligated to KpnI/XbaI-digested plasmid pTG5435 (which contains full-length BAV3 genomic DNA) to create plasmid pE3E. The plasmid pE3E contained end fragments of the BAV3 genome (0–19.7 m.u. and 76.6–100 m.u.), with a 1.245 kb deletion in the E3 region and a unique KpnI site located within the vector sequences.

A plasmid (pBAV302) containing a BAV3 genome with a 1.245 kb deletion in the E3 region was generated by homologous DNA recombination, in *E. coli* BJ5183, between KpnI-digested pE3E and deproteinized BAV3 genomic DNA.

b) Construction of Plasmids pBAV302gD and pBAV302gDt. #

The transfer plasmid for generation of recombinant BAV3 expressing foreign genes in the E3 region was constructed by ligating an 8783 bp KpnI-XbaI fragment of pBAV302 to KpnI/XbaI-digested plasmid pGEM3zf(−), creating plasmid pBAV300. A 1.3 kb Bgl II fragment of plasmid pRSV1.3 (Tikoo et al. (1993) *J. Virol.* 67:2103–2109), containing a full-length BHV-1 gD gene, was treated with T4 DNA polymerase and ligated to SrfI-digested pBAV300, creating plasmid pBAV300.gD. Similarly, a 1.3 kb Bgl II fragment of plasmid pRSV1.3XN (Tikoo et al. (1993) supra), containing a truncated BHV-1 gD gene, was treated with T4 DNA polymerase and ligated to SrfI-digested pBAV300, creating plasmid pBAV300.gDt.

Recombinant BAV3 genomes, containing a gene encoding either a full-length or a truncated gD protein, were generated by homologous DNA recombination in E. coli BJ5183 between SrfI-linearized pBAV302 and a 10 kb KpnI/XbaI fragment of pBAV300.gD (creating plasmid pBAV302.gD), or between SrfI-linearized pBAV302 and a 10 kb KpnI/XbaI fragment of pBAV300.gDt (creating plasmid pBAV302.gDt).

Construction of recombinant BAV3.

PFBR cell monolayers in 60 mm dishes were transfected with 10 μg of PacI-digested pBAV302, pBAV302.gD or pBAV302.gDt recombinant plasmid DNAs using the calcium phosphate method. Graham et al (1973) Virology 52:456–467. After 15–20 days of incubation at 37° C., the transfected cells showing 50% cytopathic effects were collected, freeze-thawed two times and the recombinant virus was plaque-purified on MDBK cells. Mittal et al. (1995) supra.

Radiolabelling and Immunoprecipitation of Proteins.

About 70–80% confluent MDBK cell monolayers in 28 cm$^2$ wells were infected with 10 PFU of recombinant or wild-type BAV3 per cell. After virus adsorption for 60 min, the cells were incubated in MEM containing 5% FBS. At different times post-infection, the cells were incubated in methionine- and cysteine-free Dulbecco's MEM for 60 min, before labelling with [$^{35}$S] methionine-cysteine (100 μCi per well). After 2 or 12 h of labelling, cells or medium were harvested. Proteins were immunoprecipitated from the medium, and cells were lysed with modified RIPA buffer, prior to analysis of proteins by SDS-PAGE as described. Tikoo et al. (1993) supra.

Animal Inoculations.

A total of twenty-five 4–6 week old cotton rats of either sex were divided into three groups. Following anesthesia with halothane, animals were inoculated twice, at day 1 and day 21, by the intranasal route with 100 μl of inoculum containing 10$^7$ PFU of individual recombinant virus. Blood samples were collected 0, 21 and 28 days after primary inoculation, to examine the development of antibody responses to BHV-1 gD and BAV3, by enzyme linked immunosorbent assay (ELISA) and virus neutralization (VN) assay. Four animals in each group were euthanized, by an overdose of halothane, at 21 and 28 days after primary inoculation. Lung and nasal secretions were collected separately to monitor the development of BHV-1 gD-specific and BAV3-specific mucosal IgG and IgA antibody responses by ELISA. Papp et al (1997) J. Gen. Virol. 78:2933–2943. In addition, lungs were collected and the frequency of BHV-1 gD-specific, and BAV3-specific, IgA antibody-secreting cells was determined by enzyme linked immunospot (ELISPOT). Papp et al., supra.

Preparation of Lung Lymphocytes.

Aseptically removed lung tissue was cut into small pieces and incubated for one hour in complete medium: MEM supplemented with 10% FBS, 2 mM L-arginine, 1 mM sodium pyruvate, 100 μM non-essential amino acids, 10 mM HEPES buffer, 50 μM 2-mercaptoethanol, 100 U/ml penicillin G, 100 μg/ml streptomycin solution, 150 U/ml collagenase A and 50 U/ml DNaseI. The tissue was then pushed through a plastic mesh. The lung cell suspension was centrifuged through a discontinuous Percoll gradient and washed with MEM. The cells were resuspended in complete medium and incubated for 1 hour in a flask, to allow adherent cells to attach. The non-adherent cell population was then resuspended and used in the antigen-specific ELISPOT assay as described earlier. Papp et al., supra.

ELISA.

Antibodies specific for BHV-1 and BAV3 in sera, lung secretions, and nasal secretions were determined by ELISA as described earlier. Papp et al., supra. Briefly, 96-well Immunol-2 microtiter plates were coated with either purified truncated gD (0.01 μg/well) or BAV3 (0.5 μg/well) and incubated with different dilutions of each sample. Antigen-specific IgG was detected using biotinylated rabbit anti-rat IgG. Antigen-specific IgA was measured using rabbit anti-rat IgA and horseradish peroxidase-conjugated goat anti-rabbit IgG.

Virus Neutralization.

Two-fold serial dilutions of heat-inactivated serum samples were incubated with 100 PFU of BHV-1 for 1 hour at 37° C. The virus-sample mixture was then plated on confluent MDBK cells in 12-well tissue culture plates and incubated for 2 days. Titers were expressed as reciprocals of the highest antibody dilution that caused 50% reduction in the number of plaques relative to the control.

RESULTS

Construction of E3-deleted Recombinant BAV3.

Initially, it was assumed that the role of BAV3 E3 in virus replication would be similar to that of the E3 region of HAV. Wold et al. (1991) Virology 184:1–8. Accordingly, BAV E3-based vectors were constructed by making deletions of the E3 sequences. However, attempts to isolate an E3-deleted BAV3 recombinant in different bovine cell lines, including MDBK, were unsuccessful. A partially deleted BAV3 recombinant (BAV3-Luc), expressing a luciferase gene, could only be isolated when BAV3 E1-transformed MDBK cells were used for transfection. Mittal et al. (1995) supra. However, once isolated, BAV3-Luc could be propagated on normal bovine cells, suggesting that the E3 region of BAV3 is not essential for virus replication in vitro. Mittal et al. (1995) supra. In order to increase the efficiency of isolating a BAV3 recombinant, PBFR cells were used, along with a novel procedure for generating BAV3 recombinants. Degryse (1996) Gene 170:45–50. Using this method, targeted modifications were introduced into plasmid-borne viral sequences, using the highly efficient homologous recombination machinery of E. coli, and infectious virions were isolated after transfection of the modified genome, excised from the plasmid vector, into appropriate host cells. Chartier et al. (1996) J. Virol. 70:4805–4610.

Taking advantage of the homologous recombination machinery of E. coli, a plasmid (pBAV302) was constructed, which contained a 1.245 kb deletion (from nt 26456 to 27701) and a SrfI restriction enzyme site (FIG. 22). PacI-digested pBAV302 DNA, when transfected into PFBR cells, produced cytopathic effects in 14 days. Virus was plaque-purified and expanded in MDBK cells, and named BAV3.E3d. Viral DNA was extracted and analyzed by agarose gel electrophoresis after digestion with BamHI restriction enzyme. As compared to wild-type (FIG. 23, lane b), the 3.019 kb BamHI "D" fragment of the recombinant BAV3.E3d genome was 1.245 kb smaller (FIG. 23, lane a), confirming that an E3-deleted recombinant BAV3 had been isolated. Comparison of the growth characteristics of this recombinant virus with those of wild-type BAV3 revealed no significant differences in the plaque size or replication, as the E3-deleted recombinant replicated with similar kinetics to wild-type BAV3.

Construction of Recombinant BAV3 Expressing BHV-1 Glycoprotein D.

In order to determine the usefulness of E3-deleted, replication competent BAV3 recombinants as delivery vehicles for live recombinant vaccine antigens, recombinant BAV3 viruses expressing different forms of BHV-1 glycoprotein gD (Tikoo et al. (1993) supra) were constructed. Full-length and truncated forms of gD genes (devoid of any exogenous promoter) were inserted individually into the E3 region of the BAV3.E3d genome in a parallel orientation, using the homologous recombination machinery of E. coli. Degryse, (1996) supra. PacI-digested pBAV302.gD or pBAV302.gDt plasmid DNA, when transfected into primary bovine retina cells, produced cytopathic effects in 14 days. Infected cell monolayers showing 50% cytopathic effects were collected, freeze thawed, and recombinant viruses were plaque-purified and propagated in MDBK cells. The recombinant BAV3s were named BAV3.E3gD (insertion of full-length gD gene in E3 region) and BAV3.E3gDt (insertion of truncated gD gene in E3 region). Viral DNA was extracted and analyzed by agarose gel electrophoresis after digestion with different restriction enzymes. Since the gD gene contains a unique NdeI site, the recombinant viral DNA was cut with NdeI. As seen in FIG. 23, compared to the BAV3.E3d (FIG. 23, lane e), the BAV3.E3gD (FIG. 23, lane f) and BAV3.E3gDt (FIG. 23, lane g) genomes contain an additional expected band of 4.6 kb, suggesting that recombinant BAV3.E3gD and BAV3.gDt contained gD or gDt genes in the E3 region. To differentiate between the gD and gDt gene, the recombinant viral DNAs were digested with NheI, as the gDt but not the gD gene contains a unique NheI restriction enzyme site. Tikoo et al. (1993) supra. As expected, the 5.4 kb BAV3.E3gD DNA fragment (FIG. 23, lane c) was replaced with a 5.0 kb fragment in BAV3.E3gDt (FIG. 23, lane d). This suggested that recombinant BAV3.E3gD and BAV3.E3gDt contained gD and gDt genes, respectively. A comparison of the growth characteristics of these recombinants with wild type or E3-deleted BAV3 showed no significant differences in either the kinetics of replication or the titer of virus produced.

Analysis of Expression of gD By BAV3.E3gD and BAV3.E3gDt.

To examine the product(s) expressed by recombinant BAV3 viruses containing the BHV-1 gD or gDt gene, MDBK cells were infected with recombinant BAV3.E3gD, BAV3.E3gDt or BAV3.E3d and metabolically labelled with [$^{35}$S] methionine-cysteine for different time periods. For comparison with authentic gD, MDBK cells were infected with BHV-1 and labelled similarly with [$^{35}$S] methionine-cysteine. The radiolabelled proteins were immunoprecipitated with a pool of gD-specific monoclonal antibodies (MAbs; Hughes et al. (1988) Arch. Virol. 103:47–60), and analyzed by SDS-PAGE under reducing conditions. The immunoprecipitation of recombinant BAV3.E3gD-infected cells revealed a major band of approximately 71 kDa (FIG. 24A, lanes b–d), which comigrated with the gD protein produced in BHV-1-infected cells (FIG. 24A, lane a), suggesting that the recombinant gD contained post-translational modifications similar to authentic gD. No similar band was observed in uninfected cells (FIG. 24A, lane h), or in cells infected with recombinant BAV3.E3d (FIG. 24A, lanes e–g). Radioimmunoprecipitation of recombinant BAV3.E3gDt-infected cell supernatants revealed a major band of 61 kDa (FIG. 24B, lanes b–d). Both recombinant proteins were expressed throughout the infection of MDBK cells (FIG. 24).

In order to test the antigenicity of recombinant gD proteins, radiolabelled proteins were immunoprecipitated from recombinant BAV3-infected cell lysate (BAV3.E3gD) or supernatant (BAV3.E3gDt) with gD-specific MAbs (Hughes et al. (1988) supra), and analyzed by SDS-PAGE under reducing conditions. As shown in FIG. 25, both gD and gDt proteins were recognized by MAbs directed against discontinuous epitopes Ib (MAb 136; lanes a and f), II (MAb 3E7; lanes b and g), IIIb (MAb 4C1; lanes c and h) IIIC (MAb 2C8; lanes d and i) and IIId (MAb 3C1; lanes e and j). These results suggest that the antigenic structure of recombinant proteins gD and gDt is similar to that of authentic gD produced in MDBK cells. Tikoo et al. (1993) supra.

To determine whether gD expression occurred in the absence of DNA synthesis, the amount of gD produced in BAV3.E3gD-infected MDBK cells was compared in the presence (FIG. 26, lanes a and b) and absence (FIG. 26, lanes c and d) of an inhibitor of DNA synthesis, I-β-D-arabinofuranosylcytosine (AraC). The results suggest that gD expression was reduced in the presence of AraC.

Antibody Responses in Animals:

To determine the ability of BAV3 recombinants to induce gD-specific immune responses, cotton rats were inoculated twice intranasally, three weeks apart, with $10^7$ PFU of BAV3.E3gD, BAV3.E3gDt or BAV3.E3d recombinants. Serum, lung washes and nasal washes were collected for the analysis of IgG and IgA antibodies, while lungs were collected for analyzing the number of IgA antibody-secreting cells (ASC). Both BAV3.E3gD and BAV3.E3gDt induced gD-specific IgG antibody response (FIG. 27B) in the serum and lung washes, which was significantly higher (P<0.05) than the response induced in BAV3.E3d-immunized animals (control). However, gD-specific IgG response induced by BAV3.E3gDt was higher than the response induced by BAV3.E3gD (P<0.05).

Figure 27A:
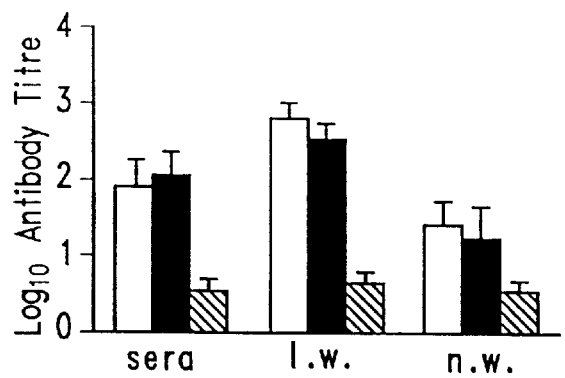
Figure 27B:
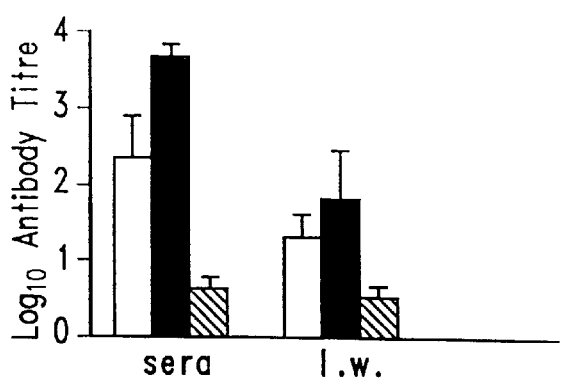

Immunization with BAV3.E3gD and BAV3.E3gDt induced significantly higher (p<0.05) IgA antibody responses to gD in the serum and lung washes than immunization with BAV3.E3d (FIG. 27A). However, there was no significant difference in the IgA antibody response between the BAV3.E3gD- and the BAV3.E3gDt-immunized groups. These recombinants also induced a BAV3-specific IgG antibody response (FIG. 27D) in the serum and lung washes and IgA antibody response (FIG. 27C) in serum, lung washes, and nasal washes, which was not significantly different among the groups.

Figure 27C:
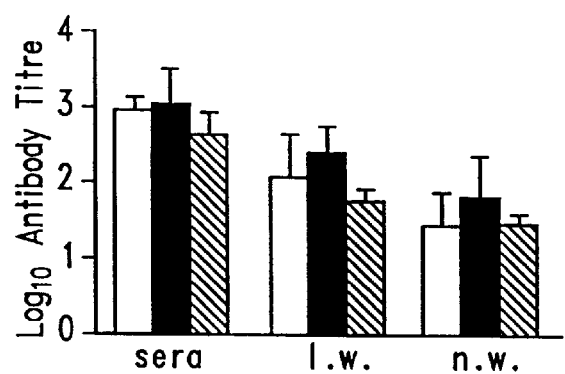
Figure 27D:
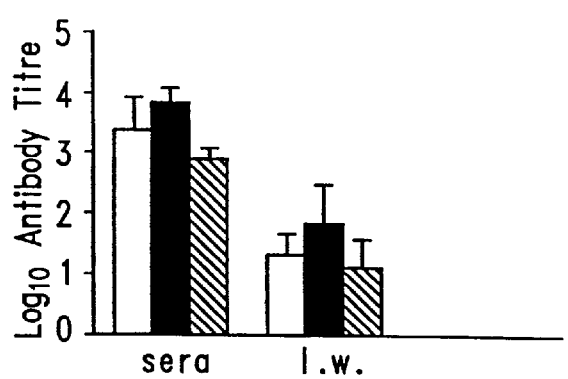

Interestingly, nasal washes contained only IgA antibodies specific for gD (FIGS. 27A and 27B) or BAV3 (FIGS. 27C and 27D). In addition, IgA antibody-secreting cells specific for both gD and BAV3 could be detected in the lungs of immunized animals, the number of which increased significantly after booster immunization.

To measure the biological activity of the gD-specific serum antibody, anti-BHV-1 titers were determined. Immunization with BAV3.E3gDt induced a BHV-1 $\log_2$ titer of 4.3±0.5, which was significantly higher (P<0.05) than the titers of 3.0±0.6 and 0.8±0.3 induced by BAV3.E3gD and BAV3.E3d respectively.

DISCUSSION

The use of human adenoviruses as a vaccine delivery system in domestic animals is limited. Since non-human adenoviruses are species-specific, development of animal-specific adenovirus as vaccine delivery systems would be a logical choice. Herein is described the development of a replication-competent (E3-deleted) recombinant BAV3 for use in the delivery of vaccine antigens to the mucosal surfaces of animals. In addition, replication-competent BAV3 expressing BHV-1 gD or gDt glycoprotein were constructed and tested for their ability to induce mucosal and systemic immune responses in cotton rats.

Initial attempts to isolate an E3-deleted BAV3 recombinant in different bovine cell lines, which support the formation of infectious progeny following BAV3 DNA-mediated transfection were unsuccessful. However, a partially E3-deleted BAV3 recombinant expressing a luciferase gene was isolated when a BAV3 E1-transformed MDBK cell line was used for transfection. Mittal et al. (1995) supra. This suggested that some function related to the presence of E1 sequences may be required for the isolation of E3-deleted BAV3. However, subsequent to their isolation, recombinant BAV3 viruses expressing a luciferase gene in their E3 region replicated efficiently in normal MDBK cells. Mittal et al. (1995) supra. Thus, an alternative possibility is that normal MDBK cells may have efficiencies of transfection and/or growth rates that are too low to allow isolation of BAV recombinants.

In order to develop a reliable and efficient method for isolating replication-competent BAV3 recombinants without using BAV3 E1-transformed MDBK cells, the homologous recombination machinery of *E. coli* (Chartier et al. (1996) supra; and Degryse (1996) supra) was first used to introduce a 1.245 kb deletion into the E3 region of a full-length BAV3 genome cloned in a plasmid. Secondly, for isolating the recombinant virus, PFBR cells, instead of MDBK cells, were used for transfection of the modified BAV3 genome, excised from the plasmid.

It has been reported that up to 105% of the wild-type genome can be packaged into the HAV5 virion without causing any rearrangements or deletion of the foreign genes in subsequent rounds of replication. Bett et al. (1993) *J. Virol.* 67:5911–5921. Recently, it was reported that the insertion capacity of the ovine adenovirus (OAV) vector is 114% of the wild type genome. Xu et al. (1997) *Virology* 230:62–71. Since the size of the BAV3 genome is similar to that of the HAV5 genome, the insertion capacity of the BAV3 genome may be similar to that of HAV5. Therefore, as the BAV3.E3d vector described herein has a 1.245 kb E3 deletion, its insertion capacity is at least 3.0 kb.

Earlier, it was reported that recombinant BAV3.luc, containing a 0.696 kb deletion in the E3 region, replicated less efficiently than the wild-type BAV3 in cell culture. Mittal et al. (1995) supra. In contrast, the recombinant BAV3.E3d containing a 1.245 kb deletion in the E3 region replicated as efficiently as the wild-type BAV3 in cell culture. This difference may be due to the insertion of the luciferase gene in recombinant BAV3.luc, which may affect the expression of genes downstream of the E3 region. Mittal et al. (1995) supra. However, the recombinant BAV3.E3gD or BAV3.E3gDt also replicated as efficiently as wild-type BAV3, suggesting that different foreign gene products may differentially affect the replication of recombinant BAV3 viruses in cell culture.

To confirm the utility of the BAV3 vector system for the expression of potential vaccine antigens, recombinant BAV3.E3gD and BAV3.E3gDt were constructed, which express BHV-1 gD or gDt glycoprotein, respectively. As expected, gD expressed by BAV3.E3gD had the expected molecular weight and comigrated with the authentic gD expressed in BHV-1-infected cells. Similarly, the gDt expressed by BAV3.E3gDt had the expected molecular weight. Tikoo et al. (1993) supra. In addition, gD and gDt expressed by BAV3 recombinants were recognized by MAbs directed particularly against conformational epitopes. Hughes et al. (1988) supra. These results suggest that recombinant gD and gDt had post-translational modifications and antigenic profiles that were indistinguishable from that of the authentic gD synthesized after viral infection. Hughes et al. (1988) supra.

Foreign genes without any flanking regulatory sequences, inserted in the left-to-right orientation in the E3 region of human adenoviruses are expressed efficiently, either from the upstream MLP or from the E3 promoter of the viral genome. Dronin et al. (1993) *Gene* 126:247–250.; Morin et al. (1987) *Proc. Natl. Acad. Sci. USA* 84:4626–4630; and Xu et al. (1995) *J. Gen. Virol.* 76:1971–1980. In the present experiments, glycoprotein gD expression was partially reduced in the presence of AraC, a replication inhibitor, suggesting that foreign gene expression was driven by both the MLP (a replication-dependent promoter) and the E3 promoter (an early, replication-independent promoter). Similar results have been reported earlier. Mittal et al. (1995) supra.

Intranasal immunization of cotton rats with BAV3.E3gD or BAV3.E3gDt induced gD-specific mucosal and systemic immune responses. gDt induced a stronger IgG antibody response than gD. In contrast, intradermal immunization of cotton rats with recombinant HAV5 induced lower immune response to gDt than to gD. Mittal et al. (1996) *Virology* 222:299–309. In addition, a purified preparation of recombinant gDt incorporated with an adjuvant, when injected into mice, produced a secondary immune response similar to that of authentic gD. Baca-Estrada et al. (1996) *Viral Immunol.* 9:11–22. These results strongly suggest that the route of immunization and vaccine formulation may affect the ability of an immunogen to induce an effective immune response to a greater extent than whether the immunogen is anchored in the membrane (gD) or secreted as a soluble protein (gDt).

Surprisingly, gD and gDt elicited similar IgA but significantly different IgG responses in the nasal passage and in the serum. Mucosal and systemic immune responses have been shown to be elicited and regulated with a considerable degree of independence. Alley et al. (1988) The mucosal immune system. In "B lymphocytes in human disease" (G. Bird and J. E. Calvert, Eds.), Oxford University Press, Oxford, pp. 222–254; and Conley et al. (1987) *Ann. Intern. Med.* 106:892–899. Induction of an immune response in one of these systems does not necessarily lead to a response in the other. Thus, it is possible that the two different forms of gD (full-length and truncated) are recognized differently in the mucosal and systemic compartments.

Induction of mucosal immunity is thought to be crucial in protecting the host from a respiratory or enteric infection. Moreover, the presence of secretory IgA has usually been found to correlate with resistance to such infections. Murphy (1994) Mucosal immunity to viruses. In "Handbook of mucosal immunity" (P. L. Ogra, J. Mestecky, M. E. Lamm, W. Strober, J. R. McGhee and J. Bienenstock ed.), Academic Press, San Diego, pp. 333–339. Interestingly, intranasal immunization induced a gD-specific IgA antibody response, not only in the serum and lung but also in nasal washes of cotton rats. High levels of IgA and the presence of ASC in the lung suggests that the antibody was produced locally.

In conclusion, the present invention describes an efficient and reliable system for the production of BAV3 recombinants. In addition, intranasal immunization of cotton rats with replication-competent recombinant BAV3 induces vaccine antigen-specific mucosal and systemic immune responses.

Example 10
Immunization of Cattle With Recombinant BAV3 Expressing BHV-1 Glycoprotein D In this example, replication-competent recombinant BAV3 viruses expressing BHV-1 gD (full-length and truncated) were assessed for their ability to provide protection against BHV-1 challenge. Groups of three 3–4 month old calves were immunized intranasally according to the following protocol. Group 1 was immunized with BAV3.E3gD, a virus expressing full-length BHV-1 gD. See Example 9. Group 2 was immunized with BAV3.E3gDt, a virus expressing a truncated BHV-1 gD. See Example 9 and Tikoo et al. (1993) supra. Group 3 was immunized with BAV3.E3d, a virus with a deleted E3 region, but no inserted heterologous sequences. See Example 9.

Animals were vaccinated on days 1 and 28, and challenged with aerosolized BHV-1 on day 42. On days 1, 28, 40 and 52, blood was taken for serology, and lymphocyte proliferation was measured in the day 28 blood sample. Clinical signs, including temperature, nasal lesions and depression, were assessed daily for ten days after challenge (days 42 through 52). Between days 1 and 15, nasal swabs for virus isolation were taken every third day. After challenge, viral titers were measured every two days, for ten days, by nasal swab and nasal tampon. On days 22 and 40, and from days 42–52, antibody titers were determined, using nasal tampons.

The results indicate that, in animals immunized with gD- or gDt-expressing BAV recombinants, IgG titers increased after both initial and booster vaccinations, and were increased further after challenge (FIG. 28). By comparison, animals vaccinated with E3-deleted BAV3 lacking an inserted gD gene showed increased IgG titers only after challenge, and the titers were at least one log lower than those obtained in vaccinated animals. IgA titers were measured and the results are shown in FIG. 29. As seen, there was no detectable increase in the IgA titers after first immunization. However, gD-specific IgA titers increased after second immunization and after BHV-1 challenge. Once again, control animals vaccinated with E3-deleted BAV3 lacking an inserted gD gene exhibited increased IgA titers only after challenge, and to a lower extent than animals vaccinated with gD- or gDt-expressing BAV.

Clinical symptoms were reduced in animals vaccinated with gD- and gDt-expressing BAV, compared to animals that had been vaccinated with E3-deleted BAV. These included fever (FIG. 30), appearance and extent of nasal lesions (FIG. 31) and depression (FIG. 32). Finally, viral titers in nasal fluids were reduced more rapidly after challenge in the BAV.E3gD- and BAV.E3gDt-vaccinated animals, compared to controls (FIG. 33).

These results indicate that recombinant BAV viruses expressing a BHV-1 glycoprotein provide protection against BHV-1 challenge in calves, reducing the occurrence of clinical signs, facilitating more rapid clearance of virus, and providing increased titers of both IgG and IgA, indicating induction of both humoral and mucosal immunity in a bovine host.

Deposit of Biological Materials

The following materials were deposited and are maintained with the Veterinary Infectious Disease Organization (VIDO), Saskatoon, Saskatchewan, Canada.

The nucleotide sequences of the deposited materials are incorporated by reference herein, as well as the sequences of the polypeptides encoded thereby. In the event of any discrepancy between a sequence expressly disclosed herein and a deposited sequence, the deposited sequence is controlling.

| Material | Internal Accession No. | Deposit Date |
|---|---|---|
| Recombinant plasmids | | |
| pSM51 | pSM51 | Dec 6, 1993 |
| pSM71 | pSM71 | Dec 6, 1993 |
| Recombinant cell lines | | |
| MDBK cells transformed with BAV3 E1 sequences (MDBK-BAVE1) | | Dec 6, 1993 |
| Fetal bovine kidney cells transformed with BAV3 E1 sequences (FBK-BAV-E1) | | Dec 6, 1993 |

While the present invention has been illustrated above by certain specific embodiments, the specific examples are not intended to limit the scope of the invention as described in the appended claims.

What is claimed is:

1. A method for constructing a recombinant BAV3 vector containing a heterologous sequence inserted into an insertion site, the method comprising:
   (a) linking the heterologous sequence to sequences which are substantially homologous to BAV3 sequences surrounding the insertion site, to form an insertion cassette; wherein said insertion site is located in a region of the BAV3 genome consisting of nucleotides 4092 through 5234; nucleotides 5892 through 17,735; nucleotides 21,198 through 26,033; or nucleotides 31,133 through 34,445 of FIGS. 20:1–20:19 (SEQ ID NO: 35);
   (b) introducing the insertion cassette into a cell, along with a polynucleotide comprising a sequence that is substantially homologous to a BAV3 genome; and
   (c) allowing homologous recombination to occur between the insertion cassette and the polynucleotide to generate the recombinant BAV3 vector.

2. The method according to claim 1 wherein the cell is a procaryotic cell.

3. The method according to claim 2 wherein the cell is *E. coli*.

4. The method according to claim 2 wherein the sequences which are substantially homologous to BAV3 sequences surrounding the insertion site are present in a plasmid and said linking is achieved by inserting a restriction fragment comprising said heterologous sequence into said plasmid.

5. A method for obtaining a recombinant BAV3 virus, the method comprising:
   (a) introducing the recombinant BAV3 vector constructed according to claim 1 into a eucaryotic cell;
   (b) culturing the cell under conditions conducive to BAV3 replication; and
   (c) collecting the recombinant BAV3 virus from the cell or the culture medium.

6. The method according to claim 5 wherein the cell is a mammalian cell.

7. The method according to claim 5, further comprising the step of digesting the recombinant BAV3 vector with a restriction enzyme prior to step (a), wherein the restriction enzyme digestion separates BAV3 sequences from other sequences present in the vector.

8. The method of claim 1 wherein said insertion site is located in a region of the BAV3 genome selected from the group consisting of the E2 region; the E4 region; the L1 region; the L2 region; the L3 region; the L4 region; the L6 region; and the region between E4 and the right end of the genome.

9. The method of claim 1 wherein said insertion site is located in a region of the BAV3 genome selected from the group consisting of the 33 kD gene; the 52 kD gene; the 100 kD gene; the DBP; pol; pTP; penton gene; IIIA gene; pV gene; pVI gene; pVII gene; pVIII gene; and pX gene.

10. The method of claim 1 wherein said insertion site is in an essential region of the BAV3 genome.

11. The method of claim 1 wherein said insertion site is in a non-essential region of the BAV3 genome.

12. The method of claim 1 wherein said recombinant BAV3 vector further comprises a deletion of part or all of the E1 region.

13. The method of claim 1 wherein said recombinant BAV3 vector further comprises a deletion of part or all of the E3 region.

14. The method of claim 1 wherein said recombinant BAV3 vector further comprises a deletion in part or all of the E1 region and part or all of the E3 region.

15. The method of claim 1 wherein said heterologous sequence is an antigen.

16. The method of claim 15 wherein said antigen is under the control of an expression promoter.

17. The method of claim 1 wherein said recombinant BAV3 vector further comprises inverted terminal repeat (ITR) sequences.

18. The method of claim 1 wherein said recombinant BAV3 vector further comprises packaging sequences.

19. The method of claim 1 wherein said insertion site is located in a region of the BAV3 genome consisting of nucleotides 4092 through 5234.

20. The method of claim 1 wherein said insertion site is located in a region of the BAV3 genome consisting of nucleotides 5892 through 17,735.

21. The method of claim 1 wherein said insertion site is located in a region of the BAV3 genome consisting of nucleotides 21,198 through 26,033.

22. The method of claim 1 wherein said insertion site is located in a region of the BAV3 genome consisting of nucleotides 31,133 through 34,445.

23. A method for constructing a recombinant BAV3 vector containing a heterologous sequence inserted into an insertion site, the method comprising:

(a) linking the heterologous sequence to sequences which are substantially homologous to BAV3 sequences surrounding the insertion site, to form an insertion cassette; wherein said insertion site is located in a region of the BAV3 genome consisting of nucleotides 4092 through 5234; nucleotides 5892 through 17,735; or nucleotides 21,198 through 26,033;

(b) introducing the insertion cassette into a cell, along with a polynucleotide comprising a sequence that is substantially homologous to a BAV3 genome; and (c) allowing homologous recombination to occur between the insertion cassette and the polynucleotide to generate the recombinant BAV3 vector.

24. The method of claim 23 wherein said insertion site is located in a region of the BAV3 genome selected from the group consisting of the E2 region; the E4 region; the L1 region; the L2 region; the L3 region; the L4 region; and the L6 region.

25. The method of claim 23 wherein said insertion site is located in a region of the BAV3 genome selected from the group consisting of the 33 kD gene; the 52 kD gene; the 100 kD gene; the DBP; pol; pTP; penton gene; IIIA gene; pV gene pVI gene; pVII gene; pVIII gene; and pX gene.

26. The method of claim 23 wherein said insertion site is in an essential region of the BAV3 genome.

27. The method of claim 23 wherein said insertion site is in a non-essential region of the BAV3 genome.

28. The method of claim 23 wherein said insertion site is located in a region of the BAV3 genome consisting of nucleotides 4092 through 5234.

29. The method of claim 23 wherein said insertion site is located in a region of the BAV3 genome consisting of nucleotides 5892 through 17,735.

30. The method of claim 23 wherein said insertion site is located in a region of the BAV3 genome consisting of nucleotides 21,198 through 26,033.

31. The method of claim 23 wherein said heterologous sequence is an antigen.

32. The method of claim 31 wherein said antigen is under the control of an expression promoter.

33. A method for obtaining a recombinant BAV3 virus, the method comprising:

(a) introducing the recombinant BAV3 vector constructed according to claim 23 into a eucaryotic cell;

(b) culturing the cell under conditions conducive to BAV3 replication; and (c) collecting the recombinant BAV3 virus from the cell or the culture medium.

34. The method according to claim 33 wherein the cell is a mammalian cell.

35. The method according to claim 33, further comprising the step of digesting the recombinant BAV3 vector with a restriction enzyme prior to step (a), wherein the restriction enzyme digestion separates BAV3 sequences from other sequences present in the vector.

* * * * *

UNITED STATES PATENT AND TRADEMARK OFFICE
CERTIFICATE OF CORRECTION

PATENT NO. : 6,319,716 B1　　　　　　　　　　　　　　　　　　Page 1 of 1
DATED : November 20, 2001
INVENTOR(S) : Suresh Kumar Tikoo et al.

It is certified that error appears in the above-identified patent and that said Letters Patent is hereby corrected as shown below:

Column 163,
Line 23, before "pVI gene", please insert -- ; --.

Signed and Sealed this

Twenty-first Day of May, 2002

Attest:

Attesting Officer

JAMES E. ROGAN
Director of the United States Patent and Trademark Office

SEQUENCE LISTING

<160> NUMBER OF SEQ ID NOS: 40

<210> SEQ ID NO 1
<211> LENGTH: 4060
<212> TYPE: DNA
<213> ORGANISM: Bovine adenovirus type 3
<220> FEATURE:
<221> NAME/KEY: CDS
<222> LOCATION: join (606..1215, 1323..1345)

<400> SEQUENCE: 1

```
catcatcaat aatctacagt acactgatgg cagcggtcca actgccaatc attttttgcca      60 cgtcatttat gacgcaacga cggcgagcgt ggcgtgctga cgtaactgtg gggcggagcg     120
cgtcgcggag gcggcggcgc tgggcggggc tgagggcggc ggggcggcg cgcggggcgg     180 cgcgcggggc ggggcgaggg gcggagttcc gcaccgcta cgtcattttc agacattttt     240
```

-continued

```
tagcaaattt gcgccttttg caagcatttt tctcacattt caggtattta gagggcggat    300
ttttggtgtt cgtacttccg tgtcacatag ttcactgtca atcttcatta cggcttagac    360 aaatttcgg cgtcttttcc gggtttatgt ccccggtcac ctttatgact gtgtgaaaca     420
cacctgccca ttgtttaccc ttggtcagtt ttttcgtctc ctagggtggg aacatcaaga    480
acaaatttgc cgagtaattg tgcacctttt tccgcgttag gactgcgttt cacacgtaga    540
cagacttttt ctcattttct cacactccgt cgtccgcttc agagctctgc gtcttcgctg    600 ccacc atg aag tac ctg gtc ctc gtt ctc aac gac ggc atg agt cga att    650
      Met Lys Tyr Leu Val Leu Val Leu Asn Asp Gly Met Ser Arg Ile
       1               5                  10                  15 gaa aaa gct ctc ctg tgc agc gat ggt gag gta gat tta gag tgt cat    698
Glu Lys Ala Leu Leu Cys Ser Asp Gly Glu Val Asp Leu Glu Cys His
             20                  25                  30 gag gta ctt ccc cct tct ccc gcg cct gtc ccc gct tct gtg tca ccc    746
Glu Val Leu Pro Pro Ser Pro Ala Pro Val Pro Ala Ser Val Ser Pro
         35                  40                  45 gtg agg agt cct cct cct ctg tct ccg gtg ttt cct ccg tct ccg cca    794
Val Arg Ser Pro Pro Pro Leu Ser Pro Val Phe Pro Pro Ser Pro Pro
     50                  55                  60 gcc ccg ctt gtg aat cca gag gcg agt tcg ctg ctg cag cag tat cgg    842
Ala Pro Leu Val Asn Pro Glu Ala Ser Ser Leu Leu Gln Gln Tyr Arg
 65                  70                  75 aga gag ctg tta gag agg agc ctg ctc cga acg gcc gaa ggt cag cag    890
Arg Glu Leu Leu Glu Arg Ser Leu Leu Arg Thr Ala Glu Gly Gln Gln
 80                  85                  90                  95 cgt gca gtg tgt cca tgt gag cgg ttg ccc gtg gaa gag gat gag tgt    938
Arg Ala Val Cys Pro Cys Glu Arg Leu Pro Val Glu Glu Asp Glu Cys
                 100                 105                 110 ctg aat gcc gta aat ttg ctg ttt cct gat ccc tgg cta aat gca gct    986
Leu Asn Ala Val Asn Leu Leu Phe Pro Asp Pro Trp Leu Asn Ala Ala
             115                 120                 125 gaa aat ggg ggt gat att ttt aag tct ccg gct atg tct cca gaa ccg   1034
Glu Asn Gly Gly Asp Ile Phe Lys Ser Pro Ala Met Ser Pro Glu Pro
         130                 135                 140 tgg ata gat ttg tct agc tac gat agc gat gta gaa gag gtg act agt   1082
Trp Ile Asp Leu Ser Ser Tyr Asp Ser Asp Val Glu Glu Val Thr Ser
     145                 150                 155 cac ttt ttt ctg gat tgc cct gaa gac ccc agt cgg gag tgt tca tct   1130
His Phe Phe Leu Asp Cys Pro Glu Asp Pro Ser Arg Glu Cys Ser Ser
 160                 165                 170                 175 tgt ggg ttt cat cag gct caa agc gga att cca ggc att atg tgc agt   1178
Cys Gly Phe His Gln Ala Gln Ser Gly Ile Pro Gly Ile Met Cys Ser
                 180                 185                 190 ttg tgc tac atg cgc caa acc tac cat tgc atc tat agtaagtaca         1224
Leu Cys Tyr Met Arg Gln Thr Tyr His Cys Ile Tyr
             195                 200 ttctgtaaaa gaacatcttg gtgatttcta ggtattgttt agggattaac tgggtggagt   1284
gatcttaatc cggcataacc aaatacatgt tttcacag gt cca gtt tct gaa gag    1339
                                            Ser Pro Val Ser Glu Glu gaa atg tgagtcatgt tgactttggc gcgcaagagg aaatgtgagt catgttgact     1395
Glu Met
210 ttggcgcgcc ctacggtgac tttaaagcaa tttgaggatc acttttttgt tagtcgctat   1455 aaagtagtca cggagtcttc atggatcact taagcgttct tttggatttg aagctgcttc   1515
```

-continued

```
gctctatcgt agcgggggct tcaaatcgca ctggagtgtg aagaggcgg ctgtggctgg     1575 gacgcctgac tcaactggtc catgatacct gcgtagagaa cgagagcata tttctcaatt    1635
ctctgccagg gaatgaagct tttttaaggt tgcttcggag cggctatttt gaagtgtttg    1695
acgtgtttgt ggtgcctgag ctgcatctgg acactccggg tcgagtggtc gccgctcttg    1755
ctctgctggt gttcatcctc aacgatttag acgctaattc tgcttcttca ggctttgatt    1815
caggttttct cgtggaccgt ctctgcgtgc cgctatggct gaaggccagg gcgttcaaga    1875
tcacccagag ctccaggagc acttcgcagc cttcctcgtc gcccgacaag acgacccaga    1935
ctaccagcca gtagacgggg acagcccacc ccgggctagc ctggaggagg ctgaacagag    1995
cagcactcgt ttcgagcaca tcagttaccg agacgtggtg gatgacttca atagatgcca    2055
tgatgttttt tatgagaggt acagttttga ggacataaag agctacgagg ctttgcctga    2115
ggacaatttg gagcagctca tagctatgca tgctaaaatc aagctgctgc ccggtcggga    2175
gtatgagttg actcaaccct tgaacataac atcttgcgcc tatgtgctcg gaaatggggc    2235
tactattagg gtaacagggg aagcctcccc ggctattaga gtgggggcca tggccgtggg    2295
tccgtgtgta acaggaatga ctgggtgac ttttgtgaat tgtaggtttg agagagagtc     2355
aacaattagg gggtccctga tacgagcttc aactcacgtg ctgtttcatg gctgttattt    2415
tatgggaatt atgggcactt gtattgaggt gggggcggga gcttacattc ggggttgtga    2475
gtttgtgggc tgttaccggg gaatctgttc tacttctaac agagatatta aggtgaggca    2535
gtgcaacttt gacaaatgct tactgggtat tacttgtaag ggggactatc gtctttcggg    2595
aaatgtgtgt tctgagactt tctgctttgc tcatttagag ggagagggtt tggttaaaaa    2655
caacacagtc aagtcccta gtcgctggac cagcgagtct ggcttttcca tgataacttg     2715
tgcagacggc agggttacgc ctttggttc cctccacatt gtgggcaacc gttgtaggcg     2775
ttggccaacc atgcagggga atgtgtttat catgtctaaa ctgtatctgg gcaacagaat    2835
agggactgta gccctgcccc agtgtgcttt ctacaagtcc agcatttgtt tggaggagag    2895
ggcgacaaac aagctggtct tggcttgtgc ttttgagaat aatgtactgg tgtacaaagt    2955
gctgagacgg gagagtccct caaccgtgaa aatgtgtgtt tgtgggactt ctcattatgc    3015 aaagccttg acactggcaa ttatttcttc agatattcgg gctaatcgat acatgtacac     3075
tgtggactca acagagttca cttctgacga ggattaaaag tgggcggggc aagaggggt     3135 ataaataggt ggggaggttg aggggagccg tagtttctgt ttttcccaga ctgggggga     3195 caacatggcc gaggaagggc gcatttatgt gccttatgta actgcccgcc tgcccaagtg    3255
gtcgggttcg gtgcaggata agacgggctc gaacatgttg ggggtgtgg tactccctcc     3315 taattcacag gcgcaccgga cggagaccgt gggcactgag gccaccagag acaacctgca    3375
cgccgaggga gcgcgtcgtc ctgaggatca gacgccctac atgatcttgg tggaggactc    3435
tctgggaggt ttgaagaggc gaatggactt gctggaagaa tctaatcagc agctgctggc    3495
aactctcaac cgtctccgta caggactcgc tgcctatgtg caggctaacc ttgtgggcgg    3555
ccaagttaac ccctttgttt aaataaaaat acactcatac agtttattat gctgtcaata    3615
aaattcttta ttttcctgt gataataccg tgtccagcgt gctctgtcaa taagggtcct     3675
atgcatcctg agaagggcct catatacca tggcatgaat attaagatac atgggcataa     3735
ggccctcaga agggttgagg tagagccact gcagactttc gtggggaggt aaggtgttgt    3795
aaataatcca gtcatactga ctgtgctggg cgtggaagga aaagatgtct tttagaagaa    3855
gggtgattgg caaagggagg ctcttagtgt aggtattgat aaatctgttc agttgggagg    3915
```

```
gatgcattcg ggggctaata aggtggagtt tagcctgaat cttaaggttg gcaatgttgc      3975
cccctaggtc tttgcgagga ttcatgttgt gcagtaccac aaaaacagag tagcctgtgc      4035
atttggggaa tttatcatga agctt                                            4060

<210> SEQ ID NO 2
<211> LENGTH: 211
<212> TYPE: PRT
<213> ORGANISM: Bovine adenovirus type 3

<400> SEQUENCE: 2

Met Lys Tyr Leu Val Leu Val Leu Asn Asp Gly Met Ser Arg Ile Glu
  1               5                  10                  15

Lys Ala Leu Leu Cys Ser Asp Gly Glu Val Asp Leu Glu Cys His Glu
             20                  25                  30

Val Leu Pro Pro Ser Pro Ala Pro Val Pro Ala Ser Val Ser Pro Val
         35                  40                  45

Arg Ser Pro Pro Leu Ser Pro Val Phe Pro Pro Ser Pro Pro Ala
     50                  55                  60

Pro Leu Val Asn Pro Glu Ala Ser Ser Leu Leu Gln Gln Tyr Arg Arg
 65                  70                  75                  80

Glu Leu Leu Glu Arg Ser Leu Leu Arg Thr Ala Glu Gly Gln Gln Arg
                 85                  90                  95

Ala Val Cys Pro Cys Glu Arg Leu Pro Val Glu Glu Asp Glu Cys Leu
            100                 105                 110

Asn Ala Val Asn Leu Leu Phe Pro Asp Pro Trp Leu Asn Ala Ala Glu
        115                 120                 125

Asn Gly Gly Asp Ile Phe Lys Ser Pro Ala Met Ser Pro Glu Pro Trp
130                 135                 140

Ile Asp Leu Ser Ser Tyr Asp Ser Asp Val Glu Glu Val Thr Ser His
145                 150                 155                 160

Phe Phe Leu Asp Cys Pro Glu Asp Pro Ser Arg Glu Cys Ser Ser Cys
                165                 170                 175

Gly Phe His Gln Ala Gln Ser Gly Ile Pro Gly Ile Met Cys Ser Leu
            180                 185                 190

Cys Tyr Met Arg Gln Thr Tyr His Cys Ile Tyr Ser Pro Val Ser Glu
        195                 200                 205

Glu Glu Met
    210

<210> SEQ ID NO 3
<211> LENGTH: 4060
<212> TYPE: DNA
<213> ORGANISM: Bovine adenovirus type 3
<220> FEATURE:
<221> NAME/KEY: CDS
<222> LOCATION: (1476)..(1946)

<400> SEQUENCE: 3
catcatcaat aatctacagt acactgatgg cagcggtcca actgccaatc atttttgcca        60
cgtcatttat gacgcaacga cggcgagcgt ggcgtgctga cgtaactgtg gggcggagcg       120
cgtcgcggag gcggcggcgc tgggcggggc tgagggcggg ggggcggcg cgcggggcgg        180 cgcgcggggc gggcgaggg gcggagttcc gcacccgcta cgtcattttc agacattttt        240
tagcaaattt gcgccttttg caagcatttt tctcacattt caggtattta gagggcggat       300
ttttggtgtt cgtacttccg tgtcacatag ttcactgtca atcttcatta cggcttagac       360
```

```
aaattttcgg cgtctttttcc gggtttatgt ccccggtcac ctttatgact gtgtgaaaca    420
cacctgccca ttgtttaccc ttggtcagtt ttttcgtctc ctagggtggg aacatcaaga    480
acaaatttgc cgagtaattg tgcacctttt tccgcgttag gactgcgttt cacacgtaga    540
cagacttttt ctcattttct cacactccgt cgtccgcttc agagctctgc gtcttcgctg    600
ccaccatgaa gtacctggtc ctcgttctca acgacggcat gagtcgaatt gaaaaagctc    660
tcctgtgcag cgatggtgag gtggatttag agtgtcatga ggtacttccc ccttctcccg    720
cgcctgtccc cgcttctgtg tcacccgtga ggagtcctcc tcctctgtct ccggtgtttc    780
ctccgtctcc gccagccccg cttgtgaatc agaggcgag ttcgctgctg cagcagtatc    840
ggagagagct gttagagagg agcctgctcc gaacggccga aggtcagcag cgtgcagtgt    900
gtccatgtga gcggttgccc gtggaagagg atgagtgtct gaatgccgta aatttgctgt    960
ttcctgatcc ctggctaaat gcagctgaaa atgggggtga tattttaag tctccggcta   1020
tgtctccaga accgtggata gatttgtcta gctacgatag cgatgtagaa gaggtgacta   1080
gtcacttttt tctggattgc cctgaagacc ccagtcggga gtgttcatct tgtgggtttc   1140
atcaggctca aagcggaatt ccaggcatta tgtgcagttt gtgctacatg cgccaaacct   1200
accattgcat ctatagtaag tacattctgt aaaagaacat cttggtgatt tctaggtatt   1260
gtttagggat taactgggtg gagtgatctt aatccggcat aaccaaatac atgttttcac   1320
aggtccagtt tctgaagagg aaatgtgagt catgttgact ttggcgcgca agaggaaatg   1380
tgagtcatgt tgactttggc gcgccctacg gtgactttaa agcaatttga ggatcacttt   1440
tttgttagtc gctataaagt agtcacggag tcttc atg gat cac tta agc gtt       1493
                                     Met Asp His Leu Ser Val
                                      1               5
ctt ttg gat ttg aag ctg ctt cgc tct atc gta gcg ggg gct tca aat      1541
Leu Leu Asp Leu Lys Leu Leu Arg Ser Ile Val Ala Gly Ala Ser Asn
         10                  15                  20 cgc act gga gtg tgg aag agg cgg ctg tgg ctg gga cgc ctg act caa      1589
Arg Thr Gly Val Trp Lys Arg Arg Leu Trp Leu Gly Arg Leu Thr Gln
     25                  30                  35 ctg gtc cat gat acc tgc gta gag aac gag agc ata ttt ctc aat tct      1637
Leu Val His Asp Thr Cys Val Glu Asn Glu Ser Ile Phe Leu Asn Ser
 40                  45                  50 ctg cca ggg aat gaa gct ttt tta agg ttg ctt cgg agc ggc tat ttt      1685
Leu Pro Gly Asn Glu Ala Phe Leu Arg Leu Leu Arg Ser Gly Tyr Phe
 55                  60                  65                  70 gaa gtg ttt gac gtg ttt gtg gtg cct gag ctg cat ctg gac act ccg      1733
Glu Val Phe Asp Val Phe Val Val Pro Glu Leu His Leu Asp Thr Pro
             75                  80                  85 ggt cga gtg gtc gcc gct ctt gct ctg ctg gtg ttc atc ctc aac gat      1781
Gly Arg Val Val Ala Ala Leu Ala Leu Leu Val Phe Ile Leu Asn Asp
         90                  95                 100 tta gac gct aat tct gct tct tca ggc ttt gat tca ggt ttt ctc gtg      1829
Leu Asp Ala Asn Ser Ala Ser Ser Gly Phe Asp Ser Gly Phe Leu Val
    105                 110                 115 gac cgt ctc tgc gtg ccg cta tgg ctg aag gcc agg gcg ttc aag atc      1877
Asp Arg Leu Cys Val Pro Leu Trp Leu Lys Ala Arg Ala Phe Lys Ile
120                 125                 130 acc cag agc tcc agg agc act tcg cag cct tcc tcg tcg ccc gac aag      1925
Thr Gln Ser Ser Arg Ser Thr Ser Gln Pro Ser Ser Ser Pro Asp Lys
135                 140                 145                 150 acg acc cag act acc agc cag tagacgggga cagcccaccc cgggctagcc         1976
Thr Thr Gln Thr Thr Ser Gln
```

-continued

```
            155
tggaggaggc tgaacagagc agcactcgtt tcgagcacat cagttaccga gacgtggtgg     2036
atgacttcaa tagatgccat gatgtttttt atgagaggta cagttttgag gacataaaga     2096
gctacgaggc tttgcctgag acaatttgg agcagctcat agctatgcat gctaaaatca      2156
agctgctgcc cggtcgggag tatgagttga ctcaacctt gaacataaca tcttgcgcct      2216
atgtgctcgg aaatggggct actattaggg taacagggga agcctccccg gctattagag     2276
tgggggccat ggccgtgggt ccgtgtgtaa caggaatgac tggggtgact tttgtgaatt     2336
gtaggtttga gagagagtca acaattaggg ggtccctgat acgagcttca actcacgtgc     2396
tgtttcatgg ctgttatttt atgggaatta tgggcacttg tattgaggtg ggggcgggag     2456
cttacattcg gggttgtgag tttgtgggct gttaccgggg aatctgttct acttctaaca     2516
gagatattaa ggtgaggcag tgcaactttg acaaatgctt actgggtatt acttgtaagg     2576
gggactatcg tctttcggga aatgtgtgtt ctgagacttt ctgctttgct catttagagg     2636
gagagggttt ggttaaaaac aacacagtca agtcccctag tcgctggacc agcgagtctg     2696
gcttttccat gataacttgt gcagacggca gggttacgcc tttgggttcc ctccacattg     2756
tgggcaaccg ttgtaggcgt tggccaacca tgcaggggaa tgtgtttatc atgtctaaac     2816
tgtatctggg caacagaata gggactgtag ccctgcccca gtgtgctttc tacaagtcca     2876
gcatttgttt ggaggagagg gcgacaaaca agctggtctt ggcttgtgct tttgagaata     2936
atgtactggt gtacaaagtg ctgagacggg agagtccctc aaccgtgaaa atgtgtgttt     2996
gtgggacttc tcattatgca aagcctttga cactggcaat tatttcttca gatattcggg     3056
ctaatcgata catgtacact gtggactcaa cagagttcac ttctgacgag gattaaaagt     3116
gggcggggcc aagaggggta taaataggtg gggaggttga ggggagccgt agtttctgtt     3176
tttcccagac tggggggggac aacatggccg aggaagggcg catttatgtg ccttatgtaa     3236
ctgcccgcct gcccaagtgg tcgggttcgg tgcaggataa gacgggctcg aacatgttgg     3296
ggggtgtggt actccctcct aattcacagg cgcaccggac ggagaccgtg ggcactgagg     3356
ccaccagaga caacctgcac gccgagggag cgcgtcgtcc tgaggatcag acgccctaca     3416
tgatcttggt ggaggactct ctgggaggtt tgaagaggcg aatggacttg ctggaagaat     3476
ctaatcagca gctgctggca actctcaacc gtctccgtac aggactcgct gcctatgtgc     3536
aggctaacct tgtgggcggc caagttaacc cctttgttta ataaaaaata cactcataca     3596
gtttattatg ctgtcaataa aattctttat ttttcctgtg ataataccgt gtccagcgtg     3656
ctctgtcaat aagggtccta tgcatcctga gaagggcctc atatacccat ggcatgaata     3716
ttaagataca tgggcataag gccctcagaa gggttgaggt agagccactg cagactttcg     3776
tggggaggta aggtgttgta aataatccag tcatactgac tgtgctgggc gtggaaggaa     3836
aagatgtctt ttagaagaag ggtgattggc aaagggaggc tcttagtgta ggtattgata     3896
aatctgttca gttgggaggg atgcattcgg gggctaataa ggtggagttt agcctgaatc     3956
ttaaggttgg caatgttgcc ccctaggtct ttgcgaggat tcatgttgtg cagtaccaca     4016
aaaacagagt agcctgtgca tttggggaat ttatcatgaa gctt                      4060
```

<210> SEQ ID NO 4
<211> LENGTH: 157
<212> TYPE: PRT
<213> ORGANISM: Bovine adenovirus type 3

<400> SEQUENCE: 4

```
Met Asp His Leu Ser Val Leu Leu Asp Leu Lys Leu Leu Arg Ser Ile
 1               5                  10                  15

Val Ala Gly Ala Ser Asn Arg Thr Gly Val Trp Lys Arg Arg Leu Trp
            20                  25                  30

Leu Gly Arg Leu Thr Gln Leu Val His Asp Thr Cys Val Glu Asn Glu
        35                  40                  45

Ser Ile Phe Leu Asn Ser Leu Pro Gly Asn Glu Ala Phe Leu Arg Leu
    50                  55                  60

Leu Arg Ser Gly Tyr Phe Glu Val Phe Asp Val Phe Val Val Pro Glu
65                  70                  75                  80

Leu His Leu Asp Thr Pro Gly Arg Val Val Ala Leu Ala Leu Leu
                85                  90                  95

Val Phe Ile Leu Asn Asp Leu Asp Ala Asn Ser Ala Ser Ser Gly Phe
            100                 105                 110

Asp Ser Gly Phe Leu Val Asp Arg Leu Cys Val Pro Leu Trp Leu Lys
        115                 120                 125

Ala Arg Ala Phe Lys Ile Thr Gln Ser Ser Arg Ser Thr Ser Gln Pro
    130                 135                 140

Ser Ser Ser Pro Asp Lys Thr Thr Gln Thr Thr Ser Gln
145                 150                 155
```

<210> SEQ ID NO 5
<211> LENGTH: 4060
<212> TYPE: DNA
<213> ORGANISM: Bovine adenovirus type 3
<220> FEATURE:
<221> NAME/KEY: CDS
<222> LOCATION: (1850)..(3109)

<400> SEQUENCE: 5

| | | | | | |
|---|---|---|---|---|---|
| catcatcaat | aatctacagt | acactgatgg | cagcggtcca | actgccaatc | attttttgcca | 60 |
| cgtcatttat | gacgcaacga | cggcgagcgt | ggcgtgctga | cgtaactgtg | gggcggagcg | 120 |
| cgtcgcggag | gcggcggcgc | tgggcgggc | tgagggcggc | ggggcggcg | cgcggggcgg | 180 |
| cgcgcgggc | ggggcgaggg | gcggagttcc | gcacccgcta | cgtcattttc | agacattttt | 240 |
| tagcaaattt | gcgccttttg | caagcatttt | tctcacattt | caggtattta | gagggcggat | 300 |
| ttttggtgtt | cgtacttccg | tgtcacatag | ttcactgtca | atcttcatta | cggcttagac | 360 |
| aaattttcgg | cgtcttttcc | gggtttatgt | ccccggtcac | ctttatgact | gtgtgaaaca | 420 |
| cacctgccca | ttgtttaccc | ttggtcagtt | ttttcgtctc | ctagggtggg | aacatcaaga | 480 |
| acaaatttgc | cgagtaattg | tgcaccttt | tccgcgttag | gactgcgttt | cacacgtaga | 540 |
| cagactttt | ctcattttct | cacactccgt | cgtccgcttc | agagctctgc | gtcttcgctg | 600 |
| ccaccatgaa | gtacctggtc | ctcgttctca | acgacggcat | gagtcgaatt | gaaaaagctc | 660 |
| tcctgtgcag | cgatggtgag | gtggatttag | agtgtcatga | ggtacttccc | ccttctcccg | 720 |
| cgcctgtccc | cgcttctgtg | tcacccgtga | ggagtcctcc | tcctctgtct | ccggtgtttc | 780 |
| ctccgtctcc | gccagccccg | cttgtgaatc | cagaggcgag | ttcgctgctg | cagcagtatc | 840 |
| ggagagagct | gttagagagg | agcctgctcc | gaacggccga | aggtcagcag | cgtgcagtgt | 900 |
| gtccatgtga | gcggttgccc | gtggaagagg | atgagtgtct | gaatgccgta | aatttgctgt | 960 |
| ttcctgatcc | ctggctaaat | gcagctgaaa | atggggtga | tatttttaag | tctccggcta | 1020 |
| tgtctccaga | accgtgata | gattttgtcta | gctacgatag | cgatgtagaa | gaggtgacta | 1080 |
| gtcacttttt | tctggattgc | cctgaagacc | ccagtcggga | gtgttcatct | tgtgggtttc | 1140 |

-continued

```
atcaggctca aagcggaatt ccaggcatta tgtgcagttt gtgctacatg cgccaaacct    1200
accattgcat ctatagtaag tacattctgt aaaagaacat cttggtgatt tctaggtatt    1260
gtttagggat taactgggtg gagtgatctt aatccggcat aaccaaatac atgttttcac    1320
aggtccagtt tctgaagagg aaatgtgagt catgttgact ttggcgcgca agaggaaatg    1380
tgagtcatgt tgactttggc gcgccctacg gtgactttaa agcaatttga ggatcacttt    1440
tttgttagtc gctataaagt agtcacggag tcttcatgga tcacttaagc gttcttttgg    1500
atttgaagct gcttcgctct atcgtagcgg gggcttcaaa tcgcactgga gtgtggaaga    1560
ggcggctgtg gctgggacgc ctgactcaac tggtccatga tacctgcgta gagaacgaga    1620
gcatatttct caattctctg ccaggaatg aagcttttt aaggttgctt cggagcggct    1680
attttgaagt gtttgacgtg tttgtggtgc ctgagctgca tctggacact ccgggtcgag    1740
tggtcgccgc tcttgctctg ctggtgttca tcctcaacga tttagacgct aattctgctt    1800
cttcaggctt tgattcaggt tttctcgtgg accgtctctg cgtgccgct atg gct gaa    1858
                                                    Met Ala Glu
                                                      1
```

| ggc cag ggc gtt caa gat cac cca gag ctc cag gag cac ttc gca gcc | 1906 |
|---|---|
| Gly Gln Gly Val Gln Asp His Pro Glu Leu Gln Glu His Phe Ala Ala |  |
| 5              10              15 |  |

| ttc ctc gtc gcc cga caa gac gac cca gac tac cag cca gta gac ggg | 1954 |
|---|---|
| Phe Leu Val Ala Arg Gln Asp Asp Pro Asp Tyr Gln Pro Val Asp Gly |  |
| 20              25              30              35 |  |

| gac agc cca ccc cgg gct agc ctg gag gag gct gaa cag agc agc act | 2002 |
|---|---|
| Asp Ser Pro Pro Arg Ala Ser Leu Glu Glu Ala Glu Gln Ser Ser Thr |  |
| 40              45              50 |  |

| cgt ttc gag cac atc agt tac cga gac gtg gtg gat gac ttc aat aga | 2050 |
|---|---|
| Arg Phe Glu His Ile Ser Tyr Arg Asp Val Val Asp Asp Phe Asn Arg |  |
| 55              60              65 |  |

| tgc cat gat gtt ttt tat gag agg tac agt ttt gag gac ata aag agc | 2098 |
|---|---|
| Cys His Asp Val Phe Tyr Glu Arg Tyr Ser Phe Glu Asp Ile Lys Ser |  |
| 70              75              80 |  |

| tac gag gct ttg cct gag gac aat ttg gag cag ctc ata gct atg cat | 2146 |
|---|---|
| Tyr Glu Ala Leu Pro Glu Asp Asn Leu Glu Gln Leu Ile Ala Met His |  |
| 85              90              95 |  |

| gct aaa atc aag ctg ctg ccc ggt cgg gag tat gag ttg act caa cct | 2194 |
|---|---|
| Ala Lys Ile Lys Leu Leu Pro Gly Arg Glu Tyr Glu Leu Thr Gln Pro |  |
| 100              105              110              115 |  |

| ttg aac ata aca tct tgc gcc tat gtg ctc gga aat ggg gct act att | 2242 |
|---|---|
| Leu Asn Ile Thr Ser Cys Ala Tyr Val Leu Gly Asn Gly Ala Thr Ile |  |
| 120              125              130 |  |

| agg gta aca ggg gaa gcc tcc ccg gct att aga gtg ggg gcc atg gcc | 2290 |
|---|---|
| Arg Val Thr Gly Glu Ala Ser Pro Ala Ile Arg Val Gly Ala Met Ala |  |
| 135              140              145 |  |

| gtg ggt ccg tgt gta aca gga atg act ggg gtg act ttt gtg aat tgt | 2338 |
|---|---|
| Val Gly Pro Cys Val Thr Gly Met Thr Gly Val Thr Phe Val Asn Cys |  |
| 150              155              160 |  |

| agg ttt gag aga gag tca aca att agg ggg tcc ctg ata cga gct tca | 2386 |
|---|---|
| Arg Phe Glu Arg Glu Ser Thr Ile Arg Gly Ser Leu Ile Arg Ala Ser |  |
| 165              170              175 |  |

| act cac gtg ctg ttt cat ggc tgt tat ttt atg gga att atg ggc act | 2434 |
|---|---|
| Thr His Val Leu Phe His Gly Cys Tyr Phe Met Gly Ile Met Gly Thr |  |
| 180              185              190              195 |  |

| tgt att gag gtg ggg gcg gga gct tac att cgg ggt tgt gag ttt gtg | 2482 |
|---|---|
| Cys Ile Glu Val Gly Ala Gly Ala Tyr Ile Arg Gly Cys Glu Phe Val |  |
| 200              205              210 |  |

-continued

```
ggc tgt tac cgg gga atc tgt tct act tct aac aga gat att aag gtg    2530
Gly Cys Tyr Arg Gly Ile Cys Ser Thr Ser Asn Arg Asp Ile Lys Val
        215                 220                 225 agg cag tgc aac ttt gac aaa tgc tta ctg ggt att act tgt aag ggg    2578
Arg Gln Cys Asn Phe Asp Lys Cys Leu Leu Gly Ile Thr Cys Lys Gly
    230                 235                 240 gac tat cgt ctt tcg gga aat gtg tgt tct gag act ttc tgc ttt gct    2626
Asp Tyr Arg Leu Ser Gly Asn Val Cys Ser Glu Thr Phe Cys Phe Ala
    245                 250                 255 cat tta gag gga gag ggt ttg gtt aaa aac aac aca gtc aag tcc cct    2674
His Leu Glu Gly Glu Gly Leu Val Lys Asn Asn Thr Val Lys Ser Pro
260                 265                 270                 275 agt cgc tgg acc agc gag tct ggc ttt tcc atg ata act tgt gca gac    2722
Ser Arg Trp Thr Ser Glu Ser Gly Phe Ser Met Ile Thr Cys Ala Asp
            280                 285                 290 ggc agg gtt acg cct ttg ggt tcc ctc cac att gtg ggc aac cgt tgt    2770
Gly Arg Val Thr Pro Leu Gly Ser Leu His Ile Val Gly Asn Arg Cys
        295                 300                 305 agg cgt tgg cca acc atg cag ggg aat gtg ttt atc atg tct aaa ctg    2818
Arg Arg Trp Pro Thr Met Gln Gly Asn Val Phe Ile Met Ser Lys Leu
    310                 315                 320 tat ctg ggc aac aga ata ggg act gta gcc ctg ccc cag tgt gct ttc    2866
Tyr Leu Gly Asn Arg Ile Gly Thr Val Ala Leu Pro Gln Cys Ala Phe
    325                 330                 335 tac aag tcc agc att tgt ttg gag gag agg gcg aca aac aag ctg gtc    2914
Tyr Lys Ser Ser Ile Cys Leu Glu Glu Arg Ala Thr Asn Lys Leu Val
340                 345                 350                 355 ttg gct tgt gct ttt gag aat aat gta ctg gtg tac aaa gtg ctg aga    2962
Leu Ala Cys Ala Phe Glu Asn Asn Val Leu Val Tyr Lys Val Leu Arg
            360                 365                 370 cgg gag agt ccc tca acc gtg aaa atg tgt gtt tgt ggg act tct cat    3010
Arg Glu Ser Pro Ser Thr Val Lys Met Cys Val Cys Gly Thr Ser His
        375                 380                 385 tat gca aag cct ttg aca ctg gca att att tct tca gat att cgg gct    3058
Tyr Ala Lys Pro Leu Thr Leu Ala Ile Ile Ser Ser Asp Ile Arg Ala
    390                 395                 400 aat cga tac atg tac act gtg gac tca aca gag ttc act tct gac gag    3106
Asn Arg Tyr Met Tyr Thr Val Asp Ser Thr Glu Phe Thr Ser Asp Glu
    405                 410                 415 gat taaaagtggg cggggccaag agggggtataa ataggtgggg aggttgaggg        3159
Asp
420 gagccgtagt ttctgttttt cccagactgg ggggacaac atggccgagg aagggcgcat    3219 ttatgtgcct tatgtaactg cccgcctgcc caagtggtcg ggttcggtgc aggataagac    3279 gggctcgaac atgttggggg gtgtggtact ccctcctaat tcacaggcgc accggacgga    3339 gaccgtgggc actgaggcca ccagagacaa cctgcacgcc gagggagcgc gtcgtcctga    3399 ggatcagacg ccctacatga tcttggtgga ggactctctg ggaggtttga agaggcgaat    3459 ggacttgctg gaagaatcta atcagcagct gctggcaact ctcaaccgtc ccgtacagg     3519 actcgctgcc tatgtgcagg ctaaccttgt gggcggccaa gttaacccct tgtttaaat     3579 aaaaatacac tcatacagtt tattatgctg tcaataaaat tctttatttt tcctgtgata    3639 ataccgtgtc cagcgtgctc tgtcaataag ggtcctatgc atcctgagaa gggcctcata    3699 tacccatggc atgaatatta agatacatgg gcataaggcc ctcagaaggg ttgaggtaga    3759 gccactgcag actttcgtgg ggaggtaagg tgttgtaaat aatccagtca tactgactgt    3819 gctgggcgtg gaaggaaaag atgtctttta gaagaagggt gattggcaaa gggaggctct    3879
```

-continued

```
tagtgtaggt attgataaat ctgttcagtt gggagggatg cattcggggg ctaataaggt    3939
ggagtttagc ctgaatctta aggttggcaa tgttgccccc taggtctttg cgaggattca    3999
tgttgtgcag taccacaaaa acagagtagc ctgtgcattt ggggaattta tcatgaagct    4059
t                                                                    4060
```

<210> SEQ ID NO 6
<211> LENGTH: 420
<212> TYPE: PRT
<213> ORGANISM: Bovine adenovirus type 3

<400> SEQUENCE: 6

```
Met Ala Glu Gly Gln Gly Val Gln Asp His Pro Glu Leu Gln Glu His
  1               5                  10                  15

Phe Ala Ala Phe Leu Val Ala Arg Gln Asp Asp Pro Asp Tyr Gln Pro
                 20                  25                  30

Val Asp Gly Asp Ser Pro Pro Arg Ala Ser Leu Glu Glu Ala Glu Gln
             35                  40                  45

Ser Ser Thr Arg Phe Glu His Ile Ser Tyr Arg Asp Val Val Asp Asp
         50                  55                  60

Phe Asn Arg Cys His Asp Val Phe Tyr Glu Arg Tyr Ser Phe Glu Asp
 65                  70                  75                  80

Ile Lys Ser Tyr Glu Ala Leu Pro Glu Asp Asn Leu Glu Gln Leu Ile
                 85                  90                  95

Ala Met His Ala Lys Ile Lys Leu Leu Pro Gly Arg Glu Tyr Glu Leu
            100                 105                 110

Thr Gln Pro Leu Asn Ile Thr Ser Cys Ala Tyr Val Leu Gly Asn Gly
        115                 120                 125

Ala Thr Ile Arg Val Thr Gly Glu Ala Ser Pro Ala Ile Arg Val Gly
    130                 135                 140

Ala Met Ala Val Gly Pro Cys Val Thr Gly Met Thr Gly Val Thr Phe
145                 150                 155                 160

Val Asn Cys Arg Phe Glu Arg Glu Ser Thr Ile Arg Gly Ser Leu Ile
                165                 170                 175

Arg Ala Ser Thr His Val Leu Phe His Gly Cys Tyr Phe Met Gly Ile
            180                 185                 190

Met Gly Thr Cys Ile Glu Val Gly Ala Gly Ala Tyr Ile Arg Gly Cys
        195                 200                 205

Glu Phe Val Gly Cys Tyr Arg Gly Ile Cys Ser Thr Ser Asn Arg Asp
    210                 215                 220

Ile Lys Val Arg Gln Cys Asn Phe Asp Lys Cys Leu Leu Gly Ile Thr
225                 230                 235                 240

Cys Lys Gly Asp Tyr Arg Leu Ser Gly Asn Val Cys Ser Glu Thr Phe
                245                 250                 255

Cys Phe Ala His Leu Glu Gly Glu Gly Leu Val Lys Asn Asn Thr Val
            260                 265                 270

Lys Ser Pro Ser Arg Trp Thr Ser Glu Ser Gly Phe Ser Met Ile Thr
        275                 280                 285

Cys Ala Asp Gly Arg Val Thr Pro Leu Gly Ser Leu His Ile Val Gly
    290                 295                 300

Asn Arg Cys Arg Arg Trp Pro Thr Met Gln Gly Asn Val Phe Ile Met
305                 310                 315                 320

Ser Lys Leu Tyr Leu Gly Asn Arg Ile Gly Thr Val Ala Leu Pro Gln
                325                 330                 335
```

-continued

```
Cys Ala Phe Tyr Lys Ser Ser Ile Cys Leu Glu Glu Arg Ala Thr Asn
            340                 345                 350
Lys Leu Val Leu Ala Cys Ala Phe Glu Asn Asn Val Leu Val Tyr Lys
            355                 360                 365
Val Leu Arg Arg Glu Ser Pro Ser Thr Val Lys Met Cys Val Cys Gly
        370                 375                 380
Thr Ser His Tyr Ala Lys Pro Leu Thr Leu Ala Ile Ile Ser Ser Asp
385                 390                 395                 400
Ile Arg Ala Asn Arg Tyr Met Tyr Thr Val Asp Ser Thr Glu Phe Thr
                405                 410                 415
Ser Asp Glu Asp
            420

<210> SEQ ID NO 7
<211> LENGTH: 4060
<212> TYPE: DNA
<213> ORGANISM: Bovine adenovirus type 3
<220> FEATURE:
<221> NAME/KEY: CDS
<222> LOCATION: (3200)..(3574)

<400> SEQUENCE: 7
```

| | | | | | |
|---|---|---|---|---|---|
| catcatcaat | aatctacagt | acactgatgg | cagcggtcca | actgccaatc | attttttgcca | 60 |
| cgtcattat | gacgcaacga | cggcgagcgt | ggcgtgctga | cgtaactgtg | gggcggagcg | 120 |
| cgtcgcggag | gcggcggcgc | tgggcggggc | tgagggcggc | ggggcggcg | cgcggggcgg | 180 |
| cgcgcgggc | ggggcgaggg | gcggagttcc | gcacccgcta | cgtcattttc | agacattttt | 240 |
| tagcaaattt | gcgccttttg | caagcatttt | tctcacattt | caggtattta | gagggcggat | 300 |
| ttttggtgtt | cgtacttccg | tgtcacatag | ttcactgtca | atcttcatta | cggcttagac | 360 |
| aaattttcgg | cgtctttttcc | gggtttatgt | ccccggtcac | ctttatgact | gtgtgaaaca | 420 |
| cacctgccca | ttgtttaccc | ttggtcagtt | ttttcgtctc | ctagggtggg | aacatcaaga | 480 |
| acaaatttgc | cgagtaattg | tgcacctttt | tccgcgttag | gactgcgttt | cacacgtaga | 540 |
| cagacttttt | ctcattttct | cacactccgt | cgtccgcttc | agagctctgc | gtcttcgctg | 600 |
| ccaccatgaa | gtacctggtc | ctcgttctca | acgacggcat | gagtcgaatt | gaaaaagctc | 660 |
| tcctgtgcag | cgatggtgag | gtggatttag | agtgtcatga | ggtacttccc | ccttctcccg | 720 |
| cgcctgtccc | cgcttctgtg | tcacccgtga | ggagtcctcc | tcctctgtct | ccggtgtttc | 780 |
| ctccgtctcc | gccagccccg | cttgtgaatc | cagaggcgag | ttcgctgctg | cagcagtatc | 840 |
| ggagagagct | gttagagagg | agcctgctcc | gaacggccga | aggtcagcag | cgtgcagtgt | 900 |
| gtccatgtga | gcggttgccc | gtggaagagg | atgagtgtct | gaatgccgta | aatttgctgt | 960 |
| tcctgatcc | ctggctaaat | gcagctgaaa | atggggggtga | tattttttaag | tctccggcta | 1020 |
| tgtctccaga | accgtggata | gatttgtcta | gctacgatag | cgatgtagaa | gaggtgacta | 1080 |
| gtcactttt | tctggattgc | cctgaagacc | ccagtcggga | gtgttcatct | tgtgggtttc | 1140 |
| atcaggctca | aagcggaatt | ccaggcatta | tgtgcagttt | gtgctacatg | cgccaaacct | 1200 |
| accattgcat | ctatagtaag | tacattctgt | aaaagaacat | cttggtgatt | tctaggtatt | 1260 |
| gtttagggat | taactgggtg | gagtgatctt | aatccggcat | aaccaaatac | atgttttcac | 1320 |
| aggtccagtt | tctgaagagg | aaatgtgagt | catgttgact | ttggcgcgca | agaggaaatg | 1380 |
| tgagtcatgt | tgactttggc | gcgccctacg | gtgacttttaa | agcaatttga | ggatcacttt | 1440 |
| tttgttagtc | gctataaagt | agtcacggag | tcttcatgga | tcacttaagc | gttcttttgg | 1500 |

-continued

```
atttgaagct gcttcgctct atcgtagcgg gggcttcaaa tcgcactgga gtgtggaaga    1560
ggcggctgtg gctgggacgc ctgactcaac tggtccatga tacctgcgta gagaacgaga    1620
gcatatttct caattctctg ccagggaatg aagcttttt aaggttgctt cggagcggct    1680
attttgaagt gtttgacgtg tttgtggtgc ctgagctgca tctggacact ccgggtcgag    1740
tggtcgccgc tcttgctctg ctggtgttca tcctcaacga tttagacgct aattctgctt    1800
cttcaggctt tgattcaggt tttctcgtgg accgtctctg cgtgccgcta tggctgaagg    1860
ccagggcgtt caagatcacc cagagctcca ggagcacttc gcagccttcc tcgtcgcccg    1920
acaagacgac ccagactacc agccagtaga cggggacagc ccaccccggg ctagcctgga    1980
ggaggctgaa cagagcagca ctcgtttcga gcacatcagt taccgagacg tggtggatga    2040
cttcaataga tgccatgatg ttttttatga gaggtacagt tttgaggaca taaagagcta    2100
cgaggctttg cctgaggaca atttggagca gctcatagct atgcatgcta aaatcaagct    2160
gctgcccggt cgggagtatg agttgactca acctttgaac ataacatctt gcgcctatgt    2220
gctcggaaat gggctacta ttagggtaac aggggaagcc tccccggcta ttagagtggg    2280
ggccatggcc gtgggtccgt gtgtaacagg aatgactggg gtgacttttg tgaattgtag    2340
gtttgagaga gagtcaacaa ttagggggtc cctgatacga gcttcaactc acgtgctgtt    2400
tcatggctgt tattttatgg gaattatggg cacttgtatt gaggtggggg cgggagctta    2460
cattcgggggt tgtgagtttg tgggctgtta ccggggaatc tgttctactt ctaacagaga    2520
tattaaggtg aggcagtgca actttgacaa atgcttactg ggtattactt gtaagggga    2580
ctatcgtctt tcgggaaatg tgtgttctga gactttctgc tttgctcatt tagagggaga    2640
gggtttggtt aaaaacaaca cagtcaagtc ccctagtcgc tggaccagcg agtctggctt    2700
ttccatgata acttgtgcag acggcagggt tacgcctttg ggttccctcc acattgtggg    2760
caaccgttgt aggcgttggc caaccatgca ggggaatgtg tttatcatgt ctaaactgta    2820
tctgggcaac agaataggga ctgtagcct gccccagtgt gctttctaca agtccagcat    2880
ttgtttggag gagagggcga caaacaagct ggtcttggct tgtgcttttg agaataatgt    2940
actggtgtac aaagtgctga gacgggagag tccctcaacc gtgaaaatgt gtgtttgtgg    3000
gacttctcat tatgcaaagc ctttgacact ggcaattatt tcttcagata ttcgggctaa    3060
tcgatacatg tacactgtgg actcaacaga gttcacttct gacgaggatt aaaagtgggc    3120
ggggccaaga ggggtataaa taggtgggga ggttgagggg agccgtagtt tctgttttc    3180 ccagactggg ggggacaac atg gcc gag gaa ggg cgc att tat gtg cct tat    3232
                     Met Ala Glu Glu Gly Arg Ile Tyr Val Pro Tyr
                      1               5                  10 gta act gcc cgc ctg ccc aag tgg tcg ggt tcg gtg cag gat aag acg    3280
Val Thr Ala Arg Leu Pro Lys Trp Ser Gly Ser Val Gln Asp Lys Thr
         15                  20                  25 ggc tcg aac atg ttg ggg ggt gtg gta ctc cct cct aat tca cag gcg    3328
Gly Ser Asn Met Leu Gly Gly Val Val Leu Pro Pro Asn Ser Gln Ala
     30                  35                  40 cac cgg acg gag acc gtg ggc act gag gcc acc aga gac aac ctg cac    3376
His Arg Thr Glu Thr Val Gly Thr Glu Ala Thr Arg Asp Asn Leu His
 45                  50                  55 gcc gag gga gcg cgt cgt cct gag gat cag acg ccc tac atg atc ttg    3424
Ala Glu Gly Ala Arg Arg Pro Glu Asp Gln Thr Pro Tyr Met Ile Leu
 60                  65                  70                  75
```

```
gtg gag gac tct ctg gga ggt ttg aag agg cga atg gac ttg ctg gaa      3472
Val Glu Asp Ser Leu Gly Gly Leu Lys Arg Arg Met Asp Leu Leu Glu
                80                  85                  90 gaa tct aat cag cag ctg ctg gca act ctc aac cgt ctc cgt aca gga      3520
Glu Ser Asn Gln Gln Leu Leu Ala Thr Leu Asn Arg Leu Arg Thr Gly
            95                  100                 105 ctc gct gcc tat gtg cag gct aac ctt gtg ggc ggc caa gtt aac ccc      3568
Leu Ala Ala Tyr Val Gln Ala Asn Leu Val Gly Gly Gln Val Asn Pro
        110                 115                 120 ttt gtt taaataaaaa tacactcata cagtttatta tgctgtcaat aaaattcttt       3624
Phe Val
    125 attttcctg tgataatacc gtgtccagcg tgctctgtca ataagggtcc tatgcatcct     3684
gagaagggcc tcatataccc atggcatgaa tattaagata catgggcata aggccctcag    3744
aagggttgag gtagagccac tgcagacttt cgtgggagg taaggtgttg taaataatcc     3804
agtcatactg actgtgctgg gcgtggaagg aaaagatgtc ttttagaaga aggtgattg     3864 gcaaagggag gctcttagtg taggtattga taaatctgtt cagttgggag ggatgcattc    3924
gggggctaat aaggtggagt ttagcctgaa tcttaaggtt ggcaatgttg ccccctaggt    3984
ctttgcgagg attcatgttg tgcagtacca caaaaacaga gtagcctgtg catttgggga   4044
atttatcatg aagctt                                                   4060

<210> SEQ ID NO 8
<211> LENGTH: 125
<212> TYPE: PRT
<213> ORGANISM: Bovine adenovirus type 3

<400> SEQUENCE: 8

Met Ala Glu Glu Gly Arg Ile Tyr Val Pro Tyr Val Thr Ala Arg Leu
  1               5                  10                  15

Pro Lys Trp Ser Gly Ser Val Gln Asp Lys Thr Gly Ser Asn Met Leu
             20                  25                  30

Gly Gly Val Val Leu Pro Pro Asn Ser Gln Ala His Arg Thr Glu Thr
         35                  40                  45

Val Gly Thr Glu Ala Thr Arg Asp Asn Leu His Ala Glu Gly Ala Arg
     50                  55                  60

Arg Pro Glu Asp Gln Thr Pro Tyr Met Ile Leu Val Glu Asp Ser Leu
 65                  70                  75                  80

Gly Gly Leu Lys Arg Arg Met Asp Leu Leu Glu Glu Ser Asn Gln Gln
                 85                  90                  95

Leu Leu Ala Thr Leu Asn Arg Leu Arg Thr Gly Leu Ala Ala Tyr Val
            100                 105                 110

Gln Ala Asn Leu Val Gly Gly Gln Val Asn Pro Phe Val
        115                 120                 125

<210> SEQ ID NO 9
<211> LENGTH: 54
<212> TYPE: PRT
<213> ORGANISM: Human adenovirus type 5

<400> SEQUENCE: 9

Glu Glu Phe Val Leu Asp Tyr Val Glu His Pro Gly His Gly Cys Arg
  1               5                  10                  15

Ser Cys His Tyr His Arg Arg Asn Thr Gly Asp Pro Asp Ile Met Cys
             20                  25                  30
```

-continued

```
Ser Leu Cys Tyr Met Arg Thr Cys Gly Met Phe Val Tyr Ser Pro Val
        35                  40                  45

Ser Glu Pro Glu Pro Glu
    50

<210> SEQ ID NO 10
<211> LENGTH: 13
<212> TYPE: PRT
<213> ORGANISM: Human adenovirus type 5

<400> SEQUENCE: 10

Ile Asp Leu Thr Cys His Glu Ala Gly Phe Pro Pro Ser
 1               5                  10

<210> SEQ ID NO 11
<211> LENGTH: 19
<212> TYPE: PRT
<213> ORGANISM: Human adenovirus type 5

<400> SEQUENCE: 11

Leu Asp Phe Ser Thr Pro Gly Arg Ala Ala Ala Val Ala Phe Leu
 1               5                  10                  15

Ser Phe Ile

<210> SEQ ID NO 12
<211> LENGTH: 7
<212> TYPE: PRT
<213> ORGANISM: Human adenovirus type 5

<400> SEQUENCE: 12

Gln Ser Ser Asn Ser Thr Ser
 1               5

<210> SEQ ID NO 13
<211> LENGTH: 347
<212> TYPE: PRT
<213> ORGANISM: Human adenovirus type 5

<400> SEQUENCE: 13

Gln Lys Tyr Ser Ile Glu Gln Leu Thr Thr Tyr Trp Leu Gln Pro Gly
 1               5                  10                  15

Asp Asp Phe Glu Glu Ala Ile Arg Val Tyr Ala Lys Val Ala Leu Arg
                20                  25                  30

Pro Asp Cys Lys Tyr Lys Ile Ser Lys Leu Val Asn Ile Arg Asn Cys
            35                  40                  45

Cys Tyr Ile Ser Gly Asn Gly Ala Glu Val Glu Ile Asp Thr Glu Asp
        50                  55                  60

Arg Val Ala Phe Arg Cys Ser Met Ile Asn Met Trp Pro Gly Val Leu
 65                  70                  75                  80

Gly Met Asp Gly Val Val Ile Met Asn Val Arg Phe Thr Gly Pro Asn
                85                  90                  95

Phe Ser Gly Thr Val Phe Leu Ala Asn Thr Asn Leu Ile Leu His Gly
            100                 105                 110

Val Ser Phe Tyr Gly Phe Asn Asn Thr Cys Val Glu Ala Trp Thr Asp
        115                 120                 125

Val Arg Val Arg Gly Cys Ala Phe Tyr Cys Cys Trp Lys Gly Val Val
    130                 135                 140

Cys Arg Pro Lys Ser Arg Ala Ser Ile Lys Lys Cys Leu Phe Glu Arg
145                 150                 155                 160
```

```
Cys Thr Leu Gly Ile Leu Ser Glu Gly Asn Ser Arg Val Arg His Asn
                165                 170                 175

Val Ala Ser Asp Cys Gly Cys Phe Met Leu Val Lys Ser Val Ala Val
            180                 185                 190

Ile Lys His Asn Met Val Cys Gly Asn Cys Glu Asp Arg Ala Ser Gln
        195                 200                 205

Met Leu Thr Cys Ser Asp Gly Asn Cys His Leu Leu Lys Thr Ile His
    210                 215                 220

Val Ala Ser His Ser Arg Lys Ala Trp Pro Val Phe Glu His Asn Ile
225                 230                 235                 240

Leu His Arg Cys Ser Leu His Leu Gly Asn Arg Arg Gly Val Phe Leu
                245                 250                 255

Pro Tyr Gln Cys Asn Leu Ser His Thr Lys Ile Leu Leu Glu Pro Glu
            260                 265                 270

Ser Met Ser Lys Val Asn Leu Asn Gly Val Phe Asp Met Thr Met Lys
        275                 280                 285

Ile Trp Lys Val Leu Arg Tyr Asp Glu Thr Arg Thr Arg Cys Arg Pro
    290                 295                 300

Cys Glu Cys Gly Gly Lys His Ile Arg Asn Gln Pro Val Met Leu Asp
305                 310                 315                 320

Val Thr Glu Glu Leu Arg Pro Asp His Leu Val Leu Ala Cys His Arg
                325                 330                 335

Ala Glu Phe Gly Ser Ser Asp Glu Asp Thr Asp
            340                 345

<210> SEQ ID NO 14
<211> LENGTH: 140
<212> TYPE: PRT
<213> ORGANISM: Human adenovirus type 5

<400> SEQUENCE: 14

Met Ser Thr Asn Ser Phe Asp Gly Ser Ile Val Ser Ser Tyr Leu Thr
  1               5                  10                  15

Thr Arg Met Pro Pro Trp Ala Gly Val Arg Gln Asn Val Met Gly Ser
            20                  25                  30

Ser Ile Asp Gly Arg Pro Val Leu Pro Ala Asn Ser Thr Thr Leu Thr
        35                  40                  45

Tyr Glu Thr Val Ser Gly Thr Pro Leu Glu Thr Ala Ala Ser Ala Ala
    50                  55                  60

Ala Ser Ala Ala Ala Thr Ala Arg Gly Ile Val Thr Asp Phe Ala
65                  70                  75                  80

Phe Leu Ser Pro Leu Ala Ser Ser Ala Ala Ser Arg Ser Ser Ala Arg
                85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
        115                 120                 125

Ser Ala Leu Lys Ala Ser Ser Pro Pro Asn Ala Val
    130                 135                 140

<210> SEQ ID NO 15
<211> LENGTH: 5100
<212> TYPE: DNA
<213> ORGANISM: Bovine adenovirus type 3
<220> FEATURE:
<221> NAME/KEY: CDS
```

<222> LOCATION: (2)..(418)

<400> SEQUENCE: 15

```
c ctc atc aaa caa ccc gtg gtg ggc acc acc cac gtg aaa atg cct cgc         49
  Leu Ile Lys Gln Pro Val Val Gly Thr Thr His Val Glu Met Pro Arg
   1               5                  10                  15 aac gaa gtc cta gaa caa cat ctg acc tca cat ggc gct caa atc gcg           97
Asn Glu Val Leu Glu Gln His Leu Thr Ser His Gly Ala Gln Ile Ala
             20                  25                  30 ggc gga ggc gct gcg ggc gat tac ttt aaa agc ccc act tca gct cga          145
Gly Gly Gly Ala Ala Gly Asp Tyr Phe Lys Ser Pro Thr Ser Ala Arg
         35                  40                  45 acc ctt atc ccg ctc acc gcc tcc tgc tta aga cca gat gga gtc ttt          193
Thr Leu Ile Pro Leu Thr Ala Ser Cys Leu Arg Pro Asp Gly Val Phe
     50                  55                  60 caa cta gga gga ggc tcg cgt tca tct ttc aac ccc ctg caa aca gat          241
Gln Leu Gly Gly Gly Ser Arg Ser Ser Phe Asn Pro Leu Gln Thr Asp
 65                  70                  75                  80 ttt gcc ttc cac gcc ctg ccc tcc aga ccg cgc cac ggg ggc ata gga          289
Phe Ala Phe His Ala Leu Pro Ser Arg Pro Arg His Gly Gly Ile Gly
                 85                  90                  95 tcc agg cag ttt gta gag gaa ttt gtg ccc gcc gtc tac ctc aac ccc          337
Ser Arg Gln Phe Val Glu Glu Phe Val Pro Ala Val Tyr Leu Asn Pro
            100                 105                 110 tac tcg gga ccg ccg gac tct tat ccg gac cag ttt ata cgc cac tac          385
Tyr Ser Gly Pro Pro Asp Ser Tyr Pro Asp Gln Phe Ile Arg His Tyr
        115                 120                 125 aac gtg tac agc aac tct gtg agc ggt tat agc tgagattgta agactctcct        438
Asn Val Tyr Ser Asn Ser Val Ser Gly Tyr Ser
    130                 135 atctgtctct gtgctgcttt tccgcttcaa gccccacaag catgaagggg tttctgctca         498
tcttcagcct gcttgtgcat tgtcccctaa ttcatgttgg gaccattagc ttctatgctg         558
caaggcccgg gtctgagcct aacgcgactt atgtttgtga ctatggaagc gagtcagatt         618
acaaccccac cacggttctg tggttggctc gagagaccga tggctcctgg atctctgttc         678
ttttccgtca caacggctcc tcaactgcag cccccggggt cgtcgcgcac tttactgacc         738
acaacagcag cattgtggtg ccccagtatt acctcctcaa caactcactc tctaagctct         798
gctgctcata ccggcacaac gagcgttctc agtttacctg caaacaagct gacgtcccta         858
cctgtcacga gccggcaag ccgctcaccc tccgcgtctc cccgcgctg ggaactgccc           918 accaagcagt cacttggttt tttcaaaatg tacccatagc tactgtttac cgaccttggg         978
gcaatgtaac ttggttttgt cctcccttca tgtgtacctt taatgtcagc ctgaactccc        1038
tacttattta caacttttct gacaaaaccg gggggcaata cacagctctc atgcactccg        1098
gacctgcttc cctctttcag ctctttaagc caacgacttg tgtcaccaag gtggaggacc        1158
cgccgtatgc caacgacccg gcctcgcctg tgtggcgccc actgcttttt gccttcgtcc        1218
tctgcaccgg ctgcgcggtg ttgttaaccg ccttcggtcc atcgattcta ccggtaccc         1278 gaaagcttat ctcagcccgc ttttggagtc ccgagcccta taccaccctc cactaacagt        1338 cccccatga agccagacgg agttcatgcc gagcagcagt ttatcctcaa tcagatttcc        1398
tgcgccaaca ctgccctcca gcgtcaaagg gaggaactag cttcccttgt catgttgcat       1458
gcctgtaagc gtgccctctt ttgtccagtc aaaacttaca agctcagcct caacgcctcg       1518
gccagcgagc acagcctgca ctttgaaaaa gtccctccc gattcaccct ggtcaacact        1578
cacgccggag cttctgtgcg agtggcccta caccaccagg gagcttccgg cagcatccgc       1638
```

```
tgttcctgtt cccacgccga gtgcctcccc gtcctcctca agaccctctg tgcctttaac   1698
tttttagatt agctgaaagc aaatataaaa tggtgtgctt accgtaattc tgtttttgact  1758
tgtgtgcttg atttctcccc ctgcgccgta atccagtgcc cctcttcaaa actctcgtac   1818
cctatgcgat tcgcataggc atattttcta aaagctctga agtcaacatc actctcaaac   1878
acttctccgt tgtaggttac tttcatctac agataaagtc atccaccggt taacatcatg   1938
aagagaagtg tgcccagga ctttaatctt gtgtatccgt acaaggctaa gaggcccaac    1998
atcatgccgc cctttttga ccgcaatggc tttgttgaaa accaagaagc cacgctagcc    2058
atgcttgtgg aaaagccgct cacgttcgac aaggaaggtg cgctgaccct gggcgtcgga   2118
cgcggcatcc gcattaaccc cgcggggctt ctggagacaa acgacctcgc gtccgctgtc   2178
ttcccaccgc tggcctccga tgaggccggc aacgtcacgc tcaacatgtc tgacgggcta   2238
tatactaagg acaacaagct agctgtcaaa gtaggtcccg ggctgtccct cgactccaat   2298
aatgctctcc aggtccacac aggcgacggg ctcacggtaa ccgatgacaa ggtgtctcta   2358
aatacccaag ctcccctctc gaccaccagc gcgggcctct ccctacttct gggtcccagc   2418
ctccacttag gtgaggagga acgactaaca gtaaacaccg gagcgggcct ccaaattagc   2478
aataacgctc tggccgtaaa agtaggttca ggtatcaccg tagatgctca aaaccagctc   2538
gctgcatccc tgggggacgg tctagaaagc agagataata aaactgtcgt taaggctggg   2598
cccggactta caataactaa tcaagctctt actgttgcta ccgggaacgg ccttcaggtc   2658
aacccggaag ggcaactgca gctaaacatt actgccggtc agggcctcaa ctttgcaaac   2718
aacagcctcg ccgtggagct gggctcgggc ctgcattttc cccctggcca aaaccaagta   2778
agcctttatc ccggagatgg aatagacatc cgagataata gggtgactgt gcccgctggg   2838
ccaggcctga gaatgctcaa ccaccaactt gccgtagctt ccggagacgg tttagaagtc   2898
cacagcgaca ccctccggtt aaagctctcc cacggcctga catttgaaaa tggcgccgta   2958
cgagcaaaac taggaccagg acttggcaca gacgactctg gtcggtccgt ggttcgcaca   3018
ggtcgaggac ttagagttgc aaacggccaa gtccagatct tcagcggaag aggcaccgcc   3078
atcggcactg atagcagcct cactctcaac atccgggcgc cctacaatt ttctggaccc    3138
gccttgactg ctagtttgca aggcagtggt ccgattactt acaacagcaa caatggcact   3198
ttcggtctct ctataggccc cggaatgtgg gtagaccaaa acagacttca ggtaaaccca   3258
ggcgctggtt tagtcttcca aggaaacaac cttgtcccaa accttgcgga tccgctggct   3318
atttccgaca gcaaaattag tctcagtctc ggtcccggcc tgacccaagc ttccaacgcc   3378
ctgactttaa gtttaggaaa cgggcttgaa ttctccaatc aagccgttgc tataaaagcg   3438
ggccggggct tacgctttga gtcttcctca caagctttag agagcagcct cacagtcgga   3498
aatggcttaa cgcttaccga tactgtgatc cgccccaacc taggggacgg cctagaggtc   3558
agagacaata aaatcattgt taagctgggc gcgaatcttc gttttgaaaa cggagccgta   3618
accgccggca ccgttaaccc ttctgcgccc gaggcaccac caactctcac tgcagaacca   3678
cccctccgag cctccaactc ccatcttcaa ctgtccctat cggagggctt ggttgtgcat   3738
aacaacgccc ttgctctcca actgggagac ggcatggaag taaatcagca cggacttact   3798
ttaagagtag gctcgggttt gcaaatgcgt gacggcattt taacagttac acccagcggc   3858
actcctattg agcccagact gactgcccca ctgactcaga cagagaatgg aatcgggctc   3918
gctctcggcg ccggcttgga attagacgag agcgcgctcc aagtaaaagt tgggcccggc   3978
```

-continued

```
atgcgcctga accctgtaga aaagtatgta accctgctcc tgggtcctgg ccttagtttt      4038
gggcagccgg ccaacaggac aaattatgat gtgcgcgttt ctgtggagcc ccccatggtt      4098
ttcggacagc gtggtcagct cacatttttta gtgggtcacg gactacacat tcaaaattcc    4158
aaacttcagc tcaatttggg acaaggcctc agaactgacc ccgtcaccaa ccagctggaa      4218
gtgcccctcg gtcaaggttt ggaaattgca gacgaatccc aggttagggt taaattgggc      4278
gatggcctgc agtttgattc acaagctcgc atcactaccg ctcctaacat ggtcactgaa      4338
actctgtgga ccggaacagg cagtaatgct aatgttacat ggcggggcta cactgccccc      4398
ggcagcaaac tcttttttgag tctcactcgg ttcagcactg gtctagtttt aggaaacatg    4458
actattgaca gcaatgcatc ctttgggcaa tacattaacg cggacacga acagatcgaa      4518 tgctttatat tgttggacaa tcagggtaac ctaaaagaag gatctaactt gcaaggcact      4578
tgggaagtga agaacaaccc ctctgcttcc aaagctgctt ttttgccttc caccgcccta      4638 tacccccatcc tcaacgaaag ccgagggagt cttcctggaa aaaatcttgt gggcatgcaa    4698
gccatactgg gaggcggggg cacttgcact gtgatagcca ccctcaatgg cagacgcagc      4758
aacaactatc ccgcgggcca gtccataatt ttcgtgtggc aagaattcaa caccatagcc      4818
cgccaacctc tgaaccactc tacacttact ttttcttact ggacttaaat aagttggaaa      4878
taaagagtta aactgaatgt ttaagtgcaa cagacttta ttggttttgg ctcacaacaa       4938
attacaacag catagacaag tcataccggt caaacaacac aggctctcga aaacgggcta      4998
accgctccaa gaatctgtca cgcagacgag caagtcctaa atgttttttc actctcttcg     5058
gggccaagtt cagcatgtat cggattttct gcttacacct tt                        5100
```

<210> SEQ ID NO 16
<211> LENGTH: 139
<212> TYPE: PRT
<213> ORGANISM: Bovine adenovirus type 3

<400> SEQUENCE: 16

```
Leu Ile Lys Gln Pro Val Val Gly Thr Thr His Val Glu Met Pro Arg
  1               5                  10                  15

Asn Glu Val Leu Glu Gln His Leu Thr Ser His Gly Ala Gln Ile Ala
             20                  25                  30

Gly Gly Gly Ala Ala Gly Asp Tyr Phe Lys Ser Pro Thr Ser Ala Arg
         35                  40                  45

Thr Leu Ile Pro Leu Thr Ala Ser Cys Leu Arg Pro Asp Gly Val Phe
     50                  55                  60

Gln Leu Gly Gly Gly Ser Arg Ser Ser Phe Asn Pro Leu Gln Thr Asp
 65                  70                  75                  80

Phe Ala Phe His Ala Leu Pro Ser Arg Pro Arg His Gly Gly Ile Gly
                 85                  90                  95

Ser Arg Gln Phe Val Glu Glu Phe Val Pro Ala Val Tyr Leu Asn Pro
            100                 105                 110

Tyr Ser Gly Pro Pro Asp Ser Tyr Pro Asp Gln Phe Ile Arg His Tyr
        115                 120                 125

Asn Val Tyr Ser Asn Ser Val Ser Gly Tyr Ser
    130                 135
```

<210> SEQ ID NO 17
<211> LENGTH: 5100
<212> TYPE: DNA
<213> ORGANISM: Bovine adenovirus type 3
<220> FEATURE:

<221> NAME/KEY: CDS
<222> LOCATION: (408)..(1331)

<400> SEQUENCE: 17

```
cctcatcaaa caacccgtgg tgggcaccac ccacgtggaa atgcctcgca acgaagtcct      60
agaacaacat ctgacctcac atggcgctca atcgcgggc ggaggcgctg cgggcgatta     120
ctttaaaagc cccacttcag ctcgaaccct tatcccgctc accgcctcct gcttaagacc    180
agatggagtc tttcaactag gaggaggctc gcgttcatct ttcaaccccc tgcaaacaga    240
ttttgccttc cacgccctgc cctccagacc gcgccacggg gcataggat ccaggcagtt     300 tgtagaggaa tttgtgcccg ccgtctacct caaccctac tcgggaccgc cggactctta     360
tccggaccag tttatacgcc actacaacgt gtacagcaac tctgtga gcg gtt ata      416
                                                    Ala Val Ile
                                                      1
```

| | | | | | | | | | | | | | | | | |
|---|---|---|---|---|---|---|---|---|---|---|---|---|---|---|---|---|
| gct | gag | att | gta | aga | ctc | tcc | tat | ctg | tct | ctg | tgc | tgc | ttt | tcc | gct | 464 |
| Ala | Glu | Ile | Val | Arg | Leu | Ser | Tyr | Leu | Ser | Leu | Cys | Cys | Phe | Ser | Ala | |
| | 5 | | | | 10 | | | | | 15 | | | | | | |
| tca | agc | ccc | aca | agc | atg | aag | ggg | ttt | ctg | ctc | atc | ttc | agc | ctg | ctt | 512 |
| Ser | Ser | Pro | Thr | Ser | Met | Lys | Gly | Phe | Leu | Leu | Ile | Phe | Ser | Leu | Leu | |
| 20 | | | | | 25 | | | | | 30 | | | | | 35 | |
| gtg | cat | tgt | ccc | cta | att | cat | gtt | ggg | acc | att | agc | ttc | tat | gct | gca | 560 |
| Val | His | Cys | Pro | Leu | Ile | His | Val | Gly | Thr | Ile | Ser | Phe | Tyr | Ala | Ala | |
| | | | | 40 | | | | | 45 | | | | | 50 | | |
| agg | ccc | ggg | tct | gag | cct | aac | gcg | act | tat | gtt | tgt | gac | tat | gga | agc | 608 |
| Arg | Pro | Gly | Ser | Glu | Pro | Asn | Ala | Thr | Tyr | Val | Cys | Asp | Tyr | Gly | Ser | |
| | | | 55 | | | | | 60 | | | | | 65 | | | |
| gag | tca | gat | tac | aac | ccc | acc | acg | gtt | ctg | tgg | ttg | gct | cga | gag | acc | 656 |
| Glu | Ser | Asp | Tyr | Asn | Pro | Thr | Thr | Val | Leu | Trp | Leu | Ala | Arg | Glu | Thr | |
| | | 70 | | | | | 75 | | | | | 80 | | | | |
| gat | ggc | tcc | tgg | atc | tct | gtt | ctt | ttc | cgt | cac | aac | ggc | tcc | tca | act | 704 |
| Asp | Gly | Ser | Trp | Ile | Ser | Val | Leu | Phe | Arg | His | Asn | Gly | Ser | Ser | Thr | |
| | 85 | | | | | 90 | | | | | 95 | | | | | |
| gca | gcc | ccc | ggg | gtc | gtc | gcg | cac | ttt | act | gac | cac | aac | agc | agc | att | 752 |
| Ala | Ala | Pro | Gly | Val | Val | Ala | His | Phe | Thr | Asp | His | Asn | Ser | Ser | Ile | |
| 100 | | | | | 105 | | | | | 110 | | | | | 115 | |
| gtg | gtg | ccc | cag | tat | tac | ctc | ctc | aac | aac | tca | ctc | tct | aag | ctc | tgc | 800 |
| Val | Val | Pro | Gln | Tyr | Tyr | Leu | Leu | Asn | Asn | Ser | Leu | Ser | Lys | Leu | Cys | |
| | | | 120 | | | | | 125 | | | | | 130 | | | |
| tgc | tca | tac | cgg | cac | aac | gag | cgt | tct | cag | ttt | acc | tgc | aaa | caa | gct | 848 |
| Cys | Ser | Tyr | Arg | His | Asn | Glu | Arg | Ser | Gln | Phe | Thr | Cys | Lys | Gln | Ala | |
| | | | 135 | | | | | 140 | | | | | 145 | | | |
| gac | gtc | cct | acc | tgt | cac | gag | ccc | ggc | aag | ccg | ctc | acc | ctc | cgc | gtc | 896 |
| Asp | Val | Pro | Thr | Cys | His | Glu | Pro | Gly | Lys | Pro | Leu | Thr | Leu | Arg | Val | |
| | 150 | | | | | 155 | | | | | 160 | | | | | |
| tcc | ccc | gcg | ctg | gga | act | gcc | cac | caa | gca | gtc | act | tgg | ttt | ttt | caa | 944 |
| Ser | Pro | Ala | Leu | Gly | Thr | Ala | His | Gln | Ala | Val | Thr | Trp | Phe | Phe | Gln | |
| 165 | | | | | 170 | | | | | 175 | | | | | | |
| aat | gta | ccc | ata | gct | act | gtt | tac | cga | cct | tgg | ggc | aat | gta | act | tgg | 992 |
| Asn | Val | Pro | Ile | Ala | Thr | Val | Tyr | Arg | Pro | Trp | Gly | Asn | Val | Thr | Trp | |
| 180 | | | | | 185 | | | | | 190 | | | | | 195 | |
| ttt | tgt | cct | ccc | ttc | atg | tgt | acc | ttt | aat | gtc | agc | ctg | aac | tcc | cta | 1040 |
| Phe | Cys | Pro | Pro | Phe | Met | Cys | Thr | Phe | Asn | Val | Ser | Leu | Asn | Ser | Leu | |
| | | | | 200 | | | | | 205 | | | | | 210 | | |
| ctt | att | tac | aac | ttt | tct | gac | aaa | acc | ggg | ggg | caa | tac | aca | gct | ctc | 1088 |
| Leu | Ile | Tyr | Asn | Phe | Ser | Asp | Lys | Thr | Gly | Gly | Gln | Tyr | Thr | Ala | Leu | |
| | | | 215 | | | | | 220 | | | | | 225 | | | |
| atg | cac | tcc | gga | cct | gct | tcc | ctc | ttt | cag | ctc | ttt | aag | cca | acg | act | 1136 |
| Met | His | Ser | Gly | Pro | Ala | Ser | Leu | Phe | Gln | Leu | Phe | Lys | Pro | Thr | Thr | |

-continued

```
               230                 235                 240
tgt gtc acc aag gtg gag gac ccg ccg tat gcc aac gac ccg gcc tcg      1184
Cys Val Thr Lys Val Glu Asp Pro Pro Tyr Ala Asn Asp Pro Ala Ser
    245                 250                 255 cct gtg tgg cgc cca ctg ctt ttt gcc ttc gtc ctc tgc acc ggc tgc      1232
Pro Val Trp Arg Pro Leu Leu Phe Ala Phe Val Leu Cys Thr Gly Cys
260                 265                 270                 275 gcg gtg ttg tta acc gcc ttc ggt cca tcg att cta tcc ggt acc cga      1280
Ala Val Leu Leu Thr Ala Phe Gly Pro Ser Ile Leu Ser Gly Thr Arg
                280                 285                 290 aag ctt atc tca gcc cgc ttt tgg agt ccc gag ccc tat acc acc ctc      1328
Lys Leu Ile Ser Ala Arg Phe Trp Ser Pro Glu Pro Tyr Thr Thr Leu
                295                 300                 305 cac taacagtccc cccatggagc cagacggagt tcatgccgag cagcagttta           1381
His
```

```
tcctcaatca gatttcctgc gccaacactg ccctccagcg tcaaagggag gaactagctt    1441
cccttgtcat gttgcatgcc tgtaagcgtg gcctcttttg tccagtcaaa acttacaagc    1501
tcagcctcaa cgcctcggcc agcgagcaca gcctgcactt tgaaaaaagt ccctcccgat    1561
tcaccctggt caacactcac gccggagctt ctgtgcgagt ggccctacac caccagggag    1621
cttccggcag catccgctgt tcctgttccc acgccgagtg cctccccgtc tcctcaaga    1681
ccctctgtgc ctttaacttt ttagattagc tgaaagcaaa tataaaatgg tgtgcttacc    1741
gtaattctgt tttgacttgt gtgcttgatt ctcccctg cgccgtaatc cagtgcccct      1801
cttcaaaact ctcgtaccct atgcgattcg cataggcata ttttctaaaa gctctgaagt    1861
caacatcact ctcaaacact tctccgttgt aggttacttt catctacaga taaagtcatc    1921
caccggttaa catcatgaag agaagtgtgc cccaggactt taatcttgtg tatccgtaca    1981
aggctaagag gcccaacatc atgccgccct tttttgaccg caatggcttt gttgaaaacc    2041
aagaagccac gctagccatg cttgtggaaa agccgctcac gttcgacaag gaaggtgcgc    2101
tgaccctggg cgtcggacgc ggcatccgca ttaaccccgc ggggcttctg gagacaaacg    2161
acctcgcgtc cgctgtcttc ccaccgctgg cctccgatga ggccggcaac gtcacgctca    2221
acatgtctga cgggctatat actaaggaca caagctagc tgtcaaagta ggtccccgggc    2281
tgtccctcga ctccaataat gctctccagg tccacacagg cgacgggctc acggtaaccg    2341
atgacaaggt gtctctaaat acccaagctc ccctctcgac caccagcgcg ggcctctccc    2401
tacttctggg tcccagcctc cacttaggtg aggaggaacg actaacagta aacaccggag    2461
cgggcctcca aattagcaat aacgctctgg ccgtaaaagt aggttcaggt atcaccgtag    2521
atgctcaaaa ccagctcgct gcatccctgg gggacggtct agaaagcaga gataataaaa    2581
ctgtcgttaa ggctgggccc ggacttacaa taactaatca agctcttact gttgctaccg    2641
ggaacggcct tcaggtcaac ccggaagggc aactgcagct aaacattact gccggtcagg    2701
gcctcaactt tgcaaacaac agcctcgccg tggagctggg ctcgggcctg cattttcccc    2761
ctggccaaaa ccaagtaagc ctttatcccg gagatggaat agacatccga gataataggg    2821
tgactgtgcc cgctgggcca ggcctgagaa tgctcaacca ccaacttgcc gtagcttccg    2881
gagacggttt agaagtccac agcgacaccc tccggttaaa gctctcccac ggcctgacat    2941
ttgaaaatgg cgccgtacga gcaaaactag gaccaggact tggcacagac gactctggtc    3001
ggtccgtggt tcgcacaggt cgaggactta gagttgcaaa cggccaagtc cagatcttca    3061
gcggaagagg caccgccatc ggcactgata gcagcctcac tctcaacatc cgggcgcccc    3121
```

-continued

```
tacaattttc tggacccgcc ttgactgcta gtttgcaagg cagtggtccg attacttaca    3181
acagcaacaa tggcactttc ggtctctcta taggccccgg aatgtgggta gaccaaaaca    3241
gacttcaggt aaacccaggc gctggtttag tcttccaagg aaacaacctt gtcccaaacc    3301
ttgcggatcc gctggctatt tccgacagca aaattagtct cagtctcggt cccggcctga    3361
cccaagcttc caacgccctg actttaagtt taggaaacgg gcttgaattc tccaatcaag    3421
ccgttgctat aaaagcgggc cggggcttac gctttgagtc ttcctcacaa gctttagaga    3481
gcagcctcac agtcggaaat ggcttaacgc ttaccgatac tgtgatccgc cccaacctag    3541
gggacggcct agaggtcaga gacaataaaa tcattgttaa gctgggcgcg aatcttcgtt    3601
ttgaaaacgg agccgtaacc gccggcaccg ttaacccttc tgcgcccgag gcaccaccaa    3661
ctctcactgc agaaccaccc ctccgagcct ccaactccca tcttcaactg tccctatcgg    3721
agggcttggt tgtgcataac aacgcccttg ctctccaact gggagacggc atggaagtaa    3781
atcagcacgg acttacttta agagtaggct cgggtttgca aatgcgtgac ggcattttaa    3841
cagttacacc cagcggcact cctattgagc ccagactgac tgccccactg actcagacag    3901
agaatggaat cgggctcgct ctcggcgccg gcttggaatt agacgagagc gcgctccaag    3961
taaaagttgg gcccggcatg cgcctgaacc ctgtagaaaa gtatgtaacc ctgctcctgg    4021
gtcctggcct tagttttggg cagccggcca acaggacaaa ttatgatgtg cgcgtttctg    4081
tggagccccc catggttttc ggacagcgtg gtcagctcac attttttagtg ggtcacggac    4141
tacacattca aaattccaaa cttcagctca atttgggaca aggcctcaga actgaccccg    4201
tcaccaacca gctggaagtg cccctcggtc aaggtttgga aattgcagac gaatcccagg    4261
ttagggttaa attgggcgat ggcctgcagt ttgattcaca agctcgcatc actaccgctc    4321
ctaacatggt cactgaaact ctgtggaccg gaacaggcag taatgctaat gttacatggc    4381
ggggctacac tgcccccggc agcaaactct ttttgagtct cactcggttc agcactggtc    4441
tagttttagg aaacatgact attgacagca atgcatcctt tgggcaatac attaacgcgg    4501
gacacgaaca gatcgaatgc tttatattgt tggacaatca gggtaaccta aaagaaggat    4561
ctaacttgca aggcacttgg gaagtgaaga acaaccctc tgcttccaaa gctgcttttt    4621
tgccttccac cgcccctatac cccatcctca acgaaagccg agggagtctt cctggaaaaa    4681
atcttgtggg catgcaagcc atactgggag gcgggggcac ttgcactgtg atagccaccc    4741
tcaatggcag acgcagcaac aactatcccg cgggccagtc cataattttc gtgtggcaag    4801
aattcaacac catagcccgc caacctctga accactctac acttactttt tcttactgga    4861
cttaaataag ttggaaataa agagttaaac tgaatgttta agtgcaacag acttttattg    4921
gttttggctc acaacaaatt acaacagcat agacaagtca taccggtcaa acaacacagg    4981
ctctcgaaaa cgggctaacc gctccaagaa tctgtcacgc agacgagcaa gtcctaaatg    5041
ttttttcact ctcttcgggg ccaagttcag catgtatcgg attttctgct tacacctttt    5100
```

<210> SEQ ID NO 18
<211> LENGTH: 308
<212> TYPE: PRT
<213> ORGANISM: Bovine adenovirus type 3

<400> SEQUENCE: 18

Ala Val Ile Ala Glu Ile Val Arg Leu Ser Tyr Leu Ser Leu Cys Cys
 1               5                  10                  15

Phe Ser Ala Ser Ser Pro Thr Ser Met Lys Gly Phe Leu Leu Ile Phe
            20                  25                  30

Ser Leu Leu Val His Cys Pro Leu Ile His Val Gly Thr Ile Ser Phe
        35                  40                  45

Tyr Ala Ala Arg Pro Gly Ser Glu Pro Asn Ala Thr Tyr Val Cys Asp
    50                  55                  60

Tyr Gly Ser Glu Ser Asp Tyr Asn Pro Thr Thr Val Leu Trp Leu Ala
65                  70                  75                  80

Arg Glu Thr Asp Gly Ser Trp Ile Ser Val Leu Phe Arg His Asn Gly
                85                  90                  95

Ser Ser Thr Ala Ala Pro Gly Val Val Ala His Phe Thr Asp His Asn
            100                 105                 110

Ser Ser Ile Val Val Pro Gln Tyr Tyr Leu Leu Asn Asn Ser Leu Ser
        115                 120                 125

Lys Leu Cys Cys Ser Tyr Arg His Asn Glu Arg Ser Gln Phe Thr Cys
    130                 135                 140

Lys Gln Ala Asp Val Pro Thr Cys His Glu Pro Gly Lys Pro Leu Thr
145                 150                 155                 160

Leu Arg Val Ser Pro Ala Leu Gly Thr Ala His Gln Ala Val Thr Trp
                165                 170                 175

Phe Phe Gln Asn Val Pro Ile Ala Thr Val Tyr Arg Pro Trp Gly Asn
            180                 185                 190

Val Thr Trp Phe Cys Pro Pro Phe Met Cys Thr Phe Asn Val Ser Leu
        195                 200                 205

Asn Ser Leu Leu Ile Tyr Asn Phe Ser Asp Lys Thr Gly Gly Gln Tyr
    210                 215                 220

Thr Ala Leu Met His Ser Gly Pro Ala Ser Leu Phe Gln Leu Phe Lys
225                 230                 235                 240

Pro Thr Thr Cys Val Thr Lys Val Glu Asp Pro Tyr Ala Asn Asp
                245                 250                 255

Pro Ala Ser Pro Val Trp Arg Pro Leu Leu Phe Ala Phe Val Leu Cys
            260                 265                 270

Thr Gly Cys Ala Val Leu Leu Thr Ala Phe Gly Pro Ser Ile Leu Ser
        275                 280                 285

Gly Thr Arg Lys Leu Ile Ser Ala Arg Phe Trp Ser Pro Glu Pro Tyr
    290                 295                 300

Thr Thr Leu His
305

<210> SEQ ID NO 19
<211> LENGTH: 5100
<212> TYPE: DNA
<213> ORGANISM: Bovine adenovirus type 3
<220> FEATURE:
<221> NAME/KEY: CDS
<222> LOCATION: (529)..(954)

<400> SEQUENCE: 19
cctcatcaaa caacccgtgg tgggcaccac ccacgtggaa atgcctcgca acgaagtcct     60
agaacaacat ctgacctcac atggcgctca atcgcgggc ggaggcgctg cgggcgatta    120
ctttaaaagc cccacttcag ctcgaaccct tatcccgctc accgcctcct gcttaagacc    180
agatggagtc tttcaactag gaggaggctc gcgttcatct ttcaaccccc tgcaaacaga    240
ttttgccttc cacgccctgc cctccagacc gcgccacggg ggcataggat ccaggcagtt    300

-continued

```
tgtagaggaa tttgtgcccg ccgtctacct caacccctac tcgggaccgc cggactctta    360
tccggaccag tttatacgcc actacaacgt gtacagcaac tctgtgagcg gttatagctg    420
agattgtaag actctcctat ctgtctctgt gctgcttttc cgcttcaagc cccacaagca    480 tgaagggggtt tctgctcatc ttcagcctgc ttgtgcattg tcccctaa ttc atg ttg    537
                                                   Phe Met Leu
                                                     1 gga cca tta gct tct atg ctg caa ggc ccg ggt ctg agc cta acg cga     585
Gly Pro Leu Ala Ser Met Leu Gln Gly Pro Gly Leu Ser Leu Thr Arg
  5                  10                  15 ctt atg ttt gtg act atg gaa gcg agt cag att aca acc cca cca cgg     633
Leu Met Phe Val Thr Met Glu Ala Ser Gln Ile Thr Thr Pro Pro Arg
 20                  25                  30                  35 ttc tgt ggt tgg ctc gag aga ccg atg gct cct gga tct ctg ttc ttt     681
Phe Cys Gly Trp Leu Glu Arg Pro Met Ala Pro Gly Ser Leu Phe Phe
                 40                  45                  50 tcc gtc aca acg gct cct caa ctg cag ccc cgg ggg tcg tcg cgc act     729
Ser Val Thr Thr Ala Pro Gln Leu Gln Pro Pro Gly Ser Ser Arg Thr
             55                  60                  65 tta ctg acc aca aca gca gca ttg tgg tgc ccc agt att acc tcc tca     777
Leu Leu Thr Thr Thr Ala Ala Leu Trp Cys Pro Ser Ile Thr Ser Ser
         70                  75                  80 aca act cac tct cta agc tct gct gct cat acc ggc aca acg agc gtt     825
Thr Thr His Ser Leu Ser Ser Ala Ala His Thr Gly Thr Thr Ser Val
     85                  90                  95 ctc agt tta cct gca aac aag ctg acg tcc cta cct gtc acg agc ccg     873
Leu Ser Leu Pro Ala Asn Lys Leu Thr Ser Leu Pro Val Thr Ser Pro
100                 105                 110                 115 gca agc cgc tca ccc tcc gcg tct ccc ccg cgc tgg gaa ctg ccc acc     921
Ala Ser Arg Ser Pro Ser Ala Ser Pro Pro Arg Trp Glu Leu Pro Thr
                 120                 125                 130 aag cag tca ctt ggt ttt ttc aaa atg tac cca tagctactgt ttaccgacct   974
Lys Gln Ser Leu Gly Phe Phe Lys Met Tyr Pro
                 135                 140 tggggcaatg taacttggtt ttgtcctccc ttcatgtgta cctttaatgt cagcctgaac   1034
tccctactta tttacaactt ttctgacaaa accggggggc aatacacagc tctcatgcac   1094
tccggacctg cttccctctt tcagctcttt aagccaacga cttgtgtcac caaggtggag   1154
gacccgccgt atgccaacga cccggcctcg cctgtgtggc gcccactgct ttttgccttc   1214
gtcctctgca ccggctgcgc ggtgttgtta accgccttcg gtccatcgat tctatccggt   1274
acccgaaagc ttatctcagc ccgcttttgg agtcccgagc cctataccac cctccactaa   1334 cagtccccccc atggagccag acggagttca tgccgagcag cagtttatcc tcaatcagat   1394
ttcctgcgcc aacactgccc tccagcgtca aagggaggaa ctagcttccc ttgtcatgtt   1454
gcatgcctgt aagcgtggcc tcttttgtcc agtcaaaact acaagctca gcctcaacgc    1514 ctcggccagc gagcacagcc tgcactttga aaaagtccc tcccgattca ccctggtcaa    1574
cactcacgcc ggagcttctg tgcgagtggc cctacaccac cagggagctt ccggcagcat   1634
ccgctgttcc tgttcccacg ccgagtgcct ccccgtcctc ctcaagaccc tctgtgcctt   1694 taactttttta gattagctga aagcaaatat aaaatggtgt gcttaccgta attctgtttt   1754
gacttgtgtg cttgatttct cccctgcgc cgtaatccag tgccctctt caaaactctc     1814 gtaccctatg cgattcgcat aggcatattt tctaaaagct ctgaagtcaa catcactctc   1874
aaacacttct ccgttgtagg ttactttcat ctacagataa agtcatccac cggttaacat   1934
catgaagaga agtgtgcccc aggactttaa tcttgtgtat ccgtacaagg ctaagaggcc   1994
```

-continued

```
caacatcatg ccgccctttt ttgaccgcaa tggctttgtt gaaaaccaag aagccacgct      2054
agccatgctt gtggaaaagc cgctcacgtt cgacaaggaa ggtgcgctga ccctgggcgt      2114
cggacgcggc atccgcatta accccgcggg gcttctggag acaaacgacc tcgcgtccgc      2174
tgtcttccca ccgctggcct ccgatgaggc cggcaacgtc acgctcaaca tgtctgacgg      2234
gctatatact aaggacaaca agctagctgt caaagtaggt cccgggctgt ccctcgactc      2294
caataatgct ctccaggtcc acacaggcga cgggctcacg gtaaccgatg acaaggtgtc      2354
tctaaatacc caagctcccc tctcgaccac cagcgcgggc ctctccctac ttctgggtcc      2414
cagcctccac ttaggtgagg aggaacgact aacagtaaac accggagcgg gcctccaaat      2474
tagcaataac gctctggccg taaaagtagg ttcaggtatc accgtagatg ctcaaaacca      2534
gctcgctgca tccctggggg acggtctaga aagcagagat aataaaactg tcgttaaggc      2594
tgggcccgga cttacaataa ctaatcaagc tcttactgtt gctaccggga acggccttca      2654
ggtcaacccg gaagggcaac tgcagctaaa cattactgcc ggtcagggcc tcaactttgc      2714
aaacaacagc ctcgccgtgg agctgggctc gggcctgcat tttccccctg gccaaaacca      2774
agtaagcctt tatcccggag atggaataga catccgagat aatagggtga ctgtgcccgc      2834
tgggccaggc ctgagaatgc tcaaccacca acttgccgta gcttccggag acggtttaga      2894
agtccacagc gacaccctcc ggttaaagct ctcccacggc ctgacatttg aaaatggcgc      2954
cgtacgagca aaactaggac caggacttgg cacagacgac tctggtcggt ccgtggttcg      3014
cacaggtcga ggacttagag ttgcaaacgg ccaagtccag atcttcagcg gaagaggcac      3074
cgccatcggc actgatagca gcctcactct caacatccgg gcgcccctac aatttttctgg      3134 acccgccttg actgctagtt tgcaaggcag tggtccgatt acttacaaca gcaacaatgg      3194
cactttcggt ctctctatag gccccggaat gtgggtagac caaaacagac ttcaggtaaa      3254
cccaggcgct ggtttagtct tccaaggaaa caaccttgtc ccaaaccttg cggatccgct      3314
ggctatttcc gacagcaaaa ttagtctcag tctcggtccc ggcctgaccc aagcttccaa      3374
cgccctgact ttaagtttag gaaacgggct tgaattctcc aatcaagccg ttgctataaa      3434
agcgggccgg ggcttacgct ttgagtcttc ctcacaagct ttagagagca gcctcacagt      3494
cggaaatggc ttaacgctta ccgatactgt gatccgcccc aacctagggg acggcctaga      3554
ggtcagagac aataaaatca ttgttaagct gggcgcgaat cttcgttttg aaaacggagc      3614
cgtaaccgcc ggcaccgtta accttctgc gcccgaggca ccaccaactc tcactgcaga      3674
accacccctc cgagcctcca actcccatct tcaactgtcc ctatcggagg cttggttgt      3734 gcataacaac gcccttgctc tccaactggg agacggcatg gaagtaaatc agcacggact      3794
tactttaaga gtaggctcgg gtttgcaaat gcgtgacggc attttaacag ttacacccag      3854
cggcactcct attgagccca gactgactgc cccactgact cagacagaga atggaatcgg      3914
gctcgctctc ggcgccggct tggaattaga cgagagcgcg ctccaagtaa agttgggcc      3974 cggcatgcgc ctgaaccctg tagaaaagta tgtaaccctg ctcctgggtc ctggccttag      4034
ttttgggcag ccggccaaca ggacaaatta tgatgtgcgc gtttctgtgg agcccccat      4094 ggttttcgga cagcgtggtc agctcacatt tttagtgggt cacggactac acattcaaaa      4154
ttccaaactt cagctcaatt tgggacaagg cctcagaact gacccccgtca ccaaccagct      4214 ggaagtgccc ctcggtcaag gtttggaaat tgcagacgaa tccaggttta gggttaaatt      4274
gggcgatggc ctgcagtttg attcacaagc tcgcatcact accgctccta acatggtcac      4334
```

-continued

```
tgaaactctg tggaccggaa caggcagtaa tgctaatgtt acatggcggg gctacactgc      4394
ccccggcagc aaactctttt tgagtctcac tcggttcagc actggtctag ttttaggaaa      4454
catgactatt gacagcaatg catcctttgg gcaatacatt aacgcgggac acgaacagat      4514
cgaatgcttt atattgttgg acaatcaggg taacctaaaa gaaggatcta acttgcaagg      4574
cacttgggaa gtgaagaaca accccctgc ttccaaagct gctttttgc cttccaccgc       4634 cctataccc atcctcaacg aaagccgagg gagtcttcct ggaaaaaatc ttgtgggcat       4694
gcaagccata ctgggaggcg ggggcacttg cactgtgata gccaccctca atggcagacg      4754
cagcaacaac tatcccgcgg gccagtccat aattttcgtg tggcaagaat caacaccat       4814 agcccgccaa cctctgaacc actctacact tactttttct tactggactt aaataagttg      4874
gaaataaaga gttaaactga atgtttaagt gcaacagact tttattggtt ttggctcaca      4934
acaaattaca acagcataga caagtcatac cggtcaaaca acacaggctc tcgaaaacgg      4994
gctaaccgct ccaagaatct gtcacgcaga cgagcaagtc ctaaatgttt tttcactctc      5054
ttcggggcca agttcagcat gtatcggatt ttctgcttac acctttt                     5100
```

<210> SEQ ID NO 20
<211> LENGTH: 142
<212> TYPE: PRT
<213> ORGANISM: Bovine adenovirus type 3

<400> SEQUENCE: 20

```
Phe Met Leu Gly Pro Leu Ala Ser Met Leu Gln Gly Pro Gly Leu Ser
  1               5                  10                  15

Leu Thr Arg Leu Met Phe Val Thr Met Glu Ala Ser Gln Ile Thr Thr
             20                  25                  30

Pro Pro Arg Phe Cys Gly Trp Leu Glu Arg Pro Met Ala Pro Gly Ser
         35                  40                  45

Leu Phe Phe Ser Val Thr Thr Ala Pro Gln Leu Gln Pro Pro Gly Ser
     50                  55                  60

Ser Arg Thr Leu Leu Thr Thr Thr Ala Ala Leu Trp Cys Pro Ser Ile
 65                  70                  75                  80

Thr Ser Ser Thr Thr His Ser Leu Ser Ser Ala Ala His Thr Gly Thr
                 85                  90                  95

Thr Ser Val Leu Ser Leu Pro Ala Asn Lys Leu Thr Ser Leu Pro Val
            100                 105                 110

Thr Ser Pro Ala Ser Arg Ser Pro Ser Ala Ser Pro Arg Trp Glu
        115                 120                 125

Leu Pro Thr Lys Gln Ser Leu Gly Phe Phe Lys Met Tyr Pro
    130                 135                 140
```

<210> SEQ ID NO 21
<211> LENGTH: 5100
<212> TYPE: DNA
<213> ORGANISM: Bovine adenovirus type 3
<220> FEATURE:
<221> NAME/KEY: CDS
<222> LOCATION: (1246)..(1707)

<400> SEQUENCE: 21

```
cctcatcaaa caacccgtgg tgggcaccac ccacgtggaa atgcctcgca acgaagtcct       60
agaacaacat ctgacctcac atggcgctca aatcgcgggc ggaggcgctg cgggcgatta      120
ctttaaaagc cccacttcag ctcgaaccct tatcccgctc accgcctcct gcttaagacc      180
agatggagtc tttcaactag gaggaggctc gcgttcatct ttcaaccccc tgcaaacaga      240
```

-continued

```
ttttgccttc cacgccctgc cctccagacc gcgccacggg ggcataggat ccaggcagtt    300
tgtagaggaa tttgtgcccg ccgtctacct caaccccta  tcgggaccgc cggactctta    360
tccggaccag tttatacgcc actacaacgt gtacagcaac tctgtgagcg gttatagctg    420
agattgtaag actctcctat ctgtctctgt gctgcttttc cgcttcaagc cccacaagca    480 tgaagggggtt tctgctcatc ttcagcctgc ttgtgcattg tcccctaatt catgttggga   540
ccattagctt ctatgctgca aggcccgggt ctgagcctaa cgcgacttat gtttgtgact    600
atggaagcga gtcagattac aacccacca  cggttctgtg gttggctcga gagaccgatg    660
gctcctggat ctctgttctt ttccgtcaca acggctcctc aactgcagcc cccggggtcg    720
tcgcgcactt tactgaccac aacagcagca ttgtggtgcc ccagtattac ctcctcaaca    780
actcactctc taagctctgc tgctcatacc ggcacaacga gcgttctcag tttacctgca    840
aacaagctga cgtccctacc tgtcacgagc ccggcaagcc gctcaccctc cgcgtctccc    900
ccgcgctggg aactgcccac caagcagtca cttggttttt tcaaaatgta cccatagcta    960
ctgtttaccg accttggggc aatgtaactt ggttttgtcc tcccttcatg tgtacccttta  1020 atgtcagcct gaactcccta cttatttaca acttttctga caaaaccggg gggcaataca   1080
cagctctcat gcactccgga cctgcttccc tctttcagct ctttaagcca acgacttgtg   1140
tcaccaaggt ggaggacccg ccgtatgcca acgaccggc  ctcgcctgtg tggcgcccac   1200
tgctttttgc cttcgtcctc tgcaccggct gcgcggtgtt gttaa ccg cct tcg gtc   1257
                                                 Pro Pro Ser Val
                                                  1 cat cga ttc tat ccg gta ccc gaa agc tta tct cag ccc gct ttt gga    1305
His Arg Phe Tyr Pro Val Pro Glu Ser Leu Ser Gln Pro Ala Phe Gly
 5              10                  15                  20 gtc ccg agc cct ata cca ccc tcc act aac agt ccc ccc atg gag cca    1353
Val Pro Ser Pro Ile Pro Pro Ser Thr Asn Ser Pro Pro Met Glu Pro
             25                  30                  35 gac gga gtt cat gcc gag cag cag ttt atc ctc aat cag att tcc tgc    1401
Asp Gly Val His Ala Glu Gln Gln Phe Ile Leu Asn Gln Ile Ser Cys
         40                  45                  50 gcc aac act gcc ctc cag cgt caa agg gag gaa cta gct tcc ctt gtc    1449
Ala Asn Thr Ala Leu Gln Arg Gln Arg Glu Glu Leu Ala Ser Leu Val
     55                  60                  65 atg ttg cat gcc tgt aag cgt ggc ctc ttt tgt cca gtc aaa act tac    1497
Met Leu His Ala Cys Lys Arg Gly Leu Phe Cys Pro Val Lys Thr Tyr
 70                  75                  80 aag ctc agc ctc aac gcc tcg gcc agc gag cac agc ctg cac ttt gaa    1545
Lys Leu Ser Leu Asn Ala Ser Ala Ser Glu His Ser Leu His Phe Glu
 85                  90                  95                 100 aaa agt ccc tcc cga ttc acc ctg gtc aac act cac gcc gga gct tct    1593
Lys Ser Pro Ser Arg Phe Thr Leu Val Asn Thr His Ala Gly Ala Ser
             105                 110                 115 gtg cga gtg gcc cta cac cac cag gga gct tcc ggc agc atc cgc tgt    1641
Val Arg Val Ala Leu His His Gln Gly Ala Ser Gly Ser Ile Arg Cys
         120                 125                 130 tcc tgt tcc cac gcc gag tgc ctc ccc gtc ctc ctc aag acc ctc tgt    1689
Ser Cys Ser His Ala Glu Cys Leu Pro Val Leu Leu Lys Thr Leu Cys
     135                 140                 145 gcc ttt aac ttt tta gat tagctgaaag caaatataaa atggtgtgct            1737
Ala Phe Asn Phe Leu Asp
 150 taccgtaatt ctgttttgac ttgtgtgctt gatttctccc cctgcgccgt aatccagtgc  1797
```

-continued

```
ccctcttcaa aactctcgta ccctatgcga ttcgcatagg catattttct aaaagctctg    1857
aagtcaacat cactctcaaa cacttctccg ttgtaggtta ctttcatcta cagataaagt    1917
catccaccgg ttaacatcat gaagagaagt gtgccccagg actttaatct tgtgtatccg    1977
tacaaggcta agaggcccaa catcatgccg ccctttttg accgcaatgg ctttgttgaa     2037
aaccaagaag ccacgctagc catgcttgtg gaaaagccgc tcacgttcga caaggaaggt    2097
gcgctgaccc tgggcgtcgg acgcggcatc cgcattaacc ccgcggggct tctggagaca    2157
aacgacctcg cgtccgctgt cttcccaccg ctggcctccg atgaggccgg caacgtcacg    2217
ctcaacatgt ctgacgggct atatactaag acaacaagc tagctgtcaa agtaggtccc     2277
gggctgtccc tcgactccaa taatgctctc caggtccaca caggcgacgg gctcacggta    2337
accgatgaca aggtgtctct aaatacccaa gctcccctct cgaccaccag cgcgggcctc    2397
tccctacttc tgggtcccag cctccactta ggtgaggagg aacgactaac agtaaacacc    2457
ggagcgggcc tccaaattag caataacgct ctggccgtaa aagtaggttc aggtatcacc    2517
gtagatgctc aaaaccagct cgctgcatcc ctgggggacg gtctagaaag cagagataat    2577
aaaactgtcg ttaaggctgg gcccggactt acaataacta atcaagctct tactgttgct    2637
accgggaacg gccttcaggt caacccgaa gggcaactgc agctaaacat tactgccggt     2697
cagggcctca actttgcaaa caacagcctc gccgtggagc tgggctcggg cctgcatttt    2757 cccctggcc aaaaccaagt aagcctttat cccggagatg aatagacat ccgagataat      2817 agggtgactg tgccgctgg gccaggcctg agaatgctca accaccaact tgccgtagct     2877
tccggagacg gtttagaagt ccacagcgac accctccggt taaagctctc ccacggcctg    2937
acatttgaaa atgcgccgt acgagcaaaa ctaggaccag gacttggcac agacgactct     2997
ggtcggtccg tggttcgcac aggtcgagga cttagagttg caaacggcca agtccagatc    3057 ttcagcgaa gaggcaccgc catcggcact gatagcagcc tcactctcaa catccgggcg     3117
cccctacaat tttctggacc cgccttgact gctagtttgc aaggcagtgg tccgattact    3177
tacaacagca acaatggcac tttcggtctc tctataggcc ccggaatgtg ggtagaccaa    3237
aacagacttc aggtaaaccc aggcgctggt ttagtcttcc aaggaaacaa ccttgtccca    3297
aaccttgcgg atccgctggc tatttccgac agcaaaatta gtctcagtct cggtcccggc    3357
ctgacccaag cttccaacgc cctgactta agtttaggaa acgggcttga attctccaat     3417
caagccgttg ctataaaagc gggccggggc ttacgctttg agtcttcctc acaagcttta    3477
gagagcagcc tcacagtcgg aaatggctta acgcttaccg atactgtgat ccgccccaac    3537
ctaggggacg gcctagagt cagagacaat aaaatcattg ttaagctggg gcgaatctt     3597 cgttttgaaa acggagccgt aaccgccggc accgttaacc cttctgcgcc cgaggcacca    3657
ccaactctca ctgcagaacc accctccga gcctccaact cccatcttca actgtccct     3717 tcggagggct tggttgtgca taacaacgcc cttgctctcc aactgggaga cggcatggaa    3777
gtaaatcagc acgacttac tttaagagta ggctcgggtt tgcaaatgcg tgacggcatt     3837
ttaacagtta cacccagcgg cactcctatt gagcccagac tgactgcccc actgactcag    3897
acagagaatg gaatcgggct cgctctcggc gccggcttgg aattagacga gagcgcgctc    3957
caagtaaaag ttgggcccgg catgcgcctg aaccctgtag aaaagtatgt aaccctgctc    4017
ctgggtcctg gccttagttt tgggcagccg gccaacagga caaattatga tgtgcgcgtt    4077
tctgtggagc cccccatggt tttcggacag cgtggtcagc tcacattttt agtgggtcac    4137
ggactacaca ttcaaaattc caaacttcag ctcaatttgg gacaaggcct cagaactgac    4197
```

-continued

```
cccgtcacca accagctgga agtgcccctc ggtcaaggtt tggaaattgc agacgaatcc      4257
caggttaggg ttaaattggg cgatggcctg cagtttgatt cacaagctcg catcactacc      4317
gctcctaaca tggtcactga aactctgtgg accggaacag gcagtaatgc taatgttaca      4377
tggcggggct acactgcccc cggcagcaaa ctcttttga gtctcactcg gttcagcact       4437
ggtctagttt taggaaacat gactattgac agcaatgcat cctttgggca atacattaac      4497
gcgggacacg aacagatcga atgctttata ttgttggaca atcagggtaa cctaaaagaa      4557
ggatctaact tgcaaggcac ttgggaagtg aagaacaacc cctctgcttc caaagctgct      4617
tttttgcctt ccaccgccct ataccccatc ctcaacgaaa gccgagggag tcttcctgga      4677
aaaaatcttg tgggcatgca agccatactg ggaggcgggg gcacttgcac tgtgatagcc      4737
accctcaatg gcagacgcag caacaactat cccgcgggcc agtccataat tttcgtgtgg      4797
caagaattca acaccatagc ccgccaacct ctgaaccact ctacacttac tttttcttac      4857
tggacttaaa taagttggaa ataaagagtt aaactgaatg tttaagtgca acagactttt      4917
attggttttg gctcacaaca aattacaaca gcatagacaa gtcataccgg tcaaacaaca      4977
caggctctcg aaaacgggct aaccgctcca agaatctgtc acgcagacga gcaagtccta      5037
aatgtttttt cactctcttc ggggccaagt tcagcatgta tcggattttc tgcttacacc      5097
ttt                                                                    5100
```

<210> SEQ ID NO 22
<211> LENGTH: 154
<212> TYPE: PRT
<213> ORGANISM: Bovine adenovirus type 3

<400> SEQUENCE: 22

```
Pro Pro Ser Val His Arg Phe Tyr Pro Val Pro Glu Ser Leu Ser Gln
  1               5                  10                  15

Pro Ala Phe Gly Val Pro Ser Pro Ile Pro Pro Ser Thr Asn Ser Pro
             20                  25                  30

Pro Met Glu Pro Asp Gly Val His Ala Glu Gln Gln Phe Ile Leu Asn
         35                  40                  45

Gln Ile Ser Cys Ala Asn Thr Ala Leu Gln Arg Gln Arg Glu Glu Leu
     50                  55                  60

Ala Ser Leu Val Met Leu His Ala Cys Lys Arg Gly Leu Phe Cys Pro
 65                  70                  75                  80

Val Lys Thr Tyr Lys Leu Ser Leu Asn Ala Ser Ala Ser Glu His Ser
                 85                  90                  95

Leu His Phe Glu Lys Ser Pro Ser Arg Phe Thr Leu Val Asn Thr His
            100                 105                 110

Ala Gly Ala Ser Val Arg Val Ala Leu His His Gln Gly Ala Ser Gly
        115                 120                 125

Ser Ile Arg Cys Ser Cys Ser His Ala Glu Cys Leu Pro Val Leu Leu
    130                 135                 140

Lys Thr Leu Cys Ala Phe Asn Phe Leu Asp
145                 150
```

<210> SEQ ID NO 23
<211> LENGTH: 5100
<212> TYPE: DNA
<213> ORGANISM: Bovine adenovirus type 3
<220> FEATURE:
<221> NAME/KEY: CDS
<222> LOCATION: (1439)..(1702)

-continued

```
<400> SEQUENCE: 23
cctcatcaaa caacccgtgg tgggcaccac ccacgtggaa atgcctcgca acgaagtcct     60
agaacaacat ctgacctcac atggcgctca atcgcgggc ggaggcgctg cgggcgatta    120
ctttaaaagc cccacttcag ctcgacccct tatcccgctc accgcctcct gcttaagacc    180
agatggagtc tttcaactag gaggaggctc gcgttcatct ttcaacccc tgcaaacaga    240 ttttgccttc cacgccctgc cctccagacc gcgccacggg ggcataggat ccaggcagtt    300
tgtagaggaa tttgtgcccg ccgtctacct caaccccta tcgggaccgc cggactctta    360
tccggaccag tttatacgcc actacaacgt gtacagcaac tctgtgagcg ttatagctg     420 agattgtaag actctcctat ctgtctctgt gctgcttttc cgcttcaagc cccacaagca    480
tgaaggggtt tctgctcatc ttcagcctgc ttgtgcattg tcccctaatt catgttggga    540
ccattagctt ctatgctgca aggcccgggt ctgagcctaa cgcgacttat gtttgtgact    600
atggaagcga gtcagattac aaccccacca cggttctgtg gttggctcga gagaccgatg    660
gctcctggat ctctgttctt ttccgtcaca acggctcctc aactgcagcc cccggggtcg    720
tcgcgcactt tactgaccac aacagcagca ttgtggtgcc ccagtattac ctcctcaaca    780
actcactctc taagctctgc tgctcatacc ggcacaacga gcgttctcag tttacctgca    840
aacaagctga cgtccctacc tgtcacgagc ccggcaagcc gctcaccctc cgcgtctccc    900
ccgcgctggg aactgcccac caagcagtca cttggttttt tcaaaatgta cccatagcta    960
ctgtttaccg accttgggc aatgtaactt ggttttgtcc tcccttcatg tgtacctta    1020 atgtcagcct gaactccta cttatttaca acttttctga caaaccggg gggcaataca    1080 cagctctcat gcactccgga cctgcttccc tctttcagct ctttaagcca acgacttgtg    1140
tcaccaaggt ggaggacccg ccgtatgcca acgacccggc ctcgcctgtg tggcgcccac    1200 tgcttttgc cttcgtcctc tgcaccggct gcgcggtgtt gttaaccgcc ttcggtccat    1260
cgattctatc cggtacccga aagcttatct cagcccgctt ttggagtccc gagccctata    1320
ccaccctcca ctaacagtcc cccatggag ccagacggag ttcatgccga gcagcagttt    1380
atcctcaatc agatttcctg cgccaacact gccctccagc gtcaaaggga ggaactag    1438 ctt ccc ttg tca tgt tgc atg cct gta agc gtg gcc tct ttt gtc cag    1486
Leu Pro Leu Ser Cys Cys Met Pro Val Ser Val Ala Ser Phe Val Gln
 1               5                  10                  15 tca aaa ctt aca agc tca gcc tca acg cct cgg cca gcg agc aca gcc    1534
Ser Lys Leu Thr Ser Ser Ala Ser Thr Pro Arg Pro Ala Ser Thr Ala
            20                  25                  30 tgc act ttg aaa aaa gtc cct ccc gat tca ccc tgg tca aca ctc acg    1582
Cys Thr Leu Lys Lys Val Pro Pro Asp Ser Pro Trp Ser Thr Leu Thr
        35                  40                  45 ccg gag ctt ctg tgc gag tgg ccc tac acc acc agg gag ctt ccg gca    1630
Pro Glu Leu Leu Cys Glu Trp Pro Tyr Thr Thr Arg Glu Leu Pro Ala
    50                  55                  60 gca tcc gct gtt cct gtt ccc acg ccg agt gcc tcc ccg tcc tcc tca    1678
Ala Ser Ala Val Pro Val Pro Thr Pro Ser Ala Ser Pro Ser Ser Ser
65                  70                  75                  80 aga ccc tct gtg cct tta act ttt tagattagct gaaagcaaat ataaatggt    1732
Arg Pro Ser Val Pro Leu Thr Phe
                85 gtgcttaccg taattctgtt ttgacttgtg tgcttgattt ctcccctgc gccgtaatcc    1792 agtgcccctc ttcaaaactc tcgtacccta tgcgattcgc ataggcatat tttctaaaag    1852
```

```
ctctgaagtc aacatcactc tcaaacactt ctccgttgta ggttactttc atctacagat    1912
aaagtcatcc accggttaac atcatgaaga gaagtgtgcc ccaggacttt aatcttgtgt    1972
atccgtacaa ggctaagagg cccaacatca tgccgccctt ttttgaccgc aatggctttg    2032
ttgaaaacca agaagccacg ctagccatgc ttgtggaaaa gccgctcacg ttcgacaagg    2092
aaggtgcgct gaccctgggc gtcggacgcg gcatccgcat taacccgcg gggcttctgg     2152 agacaaacga cctcgcgtcc gctgtcttcc caccgctggc ctccgatgag gccggcaacg    2212
tcacgctcaa catgtctgac gggctatata ctaaggacaa caagctagct gtcaaagtag    2272
gtcccgggct gtccctcgac tccataatg ctctccaggt ccacacaggc gacgggctca     2332
cggtaaccga tgacaaggtg tctctaaata cccaagctcc cctctcgacc accagcgcgg    2392
gcctctccct acttctgggt cccagcctcc acttaggtga ggaggaacga ctaacagtaa    2452
acaccggagc gggcctccaa attagcaata acgctctggc cgtaaaagta ggttcaggta    2512
tcaccgtaga tgctcaaaac cagctcgctg catccctggg ggacggtcta gaaagcagag    2572
ataataaaac tgtcgttaag gctgggcccg gacttacaat aactaatcaa gctcttactg    2632
ttgctaccgg gaacggcctt caggtcaacc cggaagggca actgcagcta acattactg     2692 ccggtcaggg cctcaacttt gcaaacaaca gcctcgccgt ggagctgggc tcgggcctgc    2752
attttccccc tggccaaaac caagtaagcc tttatcccgg agatggaata gacatccgag    2812
ataatagggt gactgtgccc gctgggccag gcctgagaat gctcaaccac caacttgccg    2872
tagcttccgg agacggttta gaagtccaca gcgacacccct ccggttaaag ctctcccacg    2932
gcctgacatt tgaaaatggc gccgtacgag caaaactagg accaggactt ggcacagacg    2992
actctggtcg gtccgtggtt cgcacaggtc gaggacttag agttgcaaac ggccaagtcc    3052
agatcttcag cggaagaggc accgccatcg gcactgatag cagcctcact ctcaacatcc    3112
gggcgcccct acaattttct ggacccgcct tgactgctag tttgcaaggc agtggtccga    3172
ttacttacaa cagcaacaat ggcactttcg gtctctctat aggccccgga atgtgggtag    3232
accaaaacag acttcaggta aacccaggcg ctggtttagt cttccaagga aacaaccttg    3292
tcccaaacct tgcggatccg ctggctattt ccgacagcaa aattagtctc agtctcggtc    3352
ccggcctgac ccaagcttcc aacgccctga ctttaagttt aggaaacggg cttgaattct    3412
ccaatcaagc cgttgctata aaagcgggcc ggggcttacg ctttgagtct tcctcacaag    3472 cttttagagag cagcctcaca gtcggaaatg gcttaacgct taccgatact gtgatccgcc    3532
ccaacctagg ggacggccta gaggtcagag acaataaaat cattgttaag ctgggcgcga    3592
atcttcgttt tgaaaacgga gccgtaaccg ccggcaccgt taaccttct gcgcccgagg     3652 caccaccaac tctcactgca gaaccacccc tccgagcctc caactcccat cttcaactgt    3712
ccctatcgga gggcttggtt gtgcataaca acgcccttgc tctccaactg ggagacggca    3772
tggaagtaaa tcagcacgga cttactttaa gagtaggctc gggtttgcaa atgcgtgacg    3832
gcattttaac agttacaccc agcggcactc ctattgagcc cagactgact gccccactga    3892
ctcagacaga gaatggaatc gggctcgctc tcggcgccgg cttggaatta acgagagcg     3952 cgctccaagt aaaagttggg cccggcatgc gcctgaaccc tgtagaaaag tatgtaaccc    4012
tgctcctggg tcctggcctt agttttgggc agccggccaa caggacaaat tatgatgtgc    4072
gcgtttctgt ggagcccccc atggttttcg gacagcgtgg tcagctcaca ttttagtgg     4132 gtcacggact acacattcaa aattccaaac ttcagctcaa tttgggacaa ggcctcagaa    4192
ctgaccccgt caccaaccag ctggaagtgc ccctcggtca aggtttggaa attgcagacg    4252
```

```
aatcccagyt tagggttaaa ttgggcgatg gcctgcagtt tgattcacaa gctcgcatca    4312
ctaccgctcc taacatggtc actgaaactc tgtggaccgg aacaggcagt aatgctaatg    4372
ttacatggcg gggctacact gcccccggca gcaaactctt tttgagtctc actcggttca    4432
gcactggtct agttttagga aacatgacta ttgacagcaa tgcatccttt gggcaataca    4492
ttaacgcggg acacgaacag atcgaatgct ttatattgtt ggacaatcag ggtaacctaa    4552
aagaaggatc taacttgcaa ggcacttggg aagtgaagaa caaccctct gcttccaaag     4612
ctgctttttt gccttccacc gccctatacc ccatcctcaa cgaaagccga gggagtcttc    4672
ctggaaaaaa tcttgtgggc atgcaagcca tactgggagg cgggggcact tgcactgtga    4732
tagccaccct caatggcaga cgcagcaaca actatcccgc gggccagtcc ataattttcg    4792
tgtggcaaga attcaacacc atagcccgcc aacctctgaa ccactctaca cttactttt     4852
cttactggac ttaaataagt tggaaataaa gagttaaact gaatgtttaa gtgcaacaga    4912
cttttattgg ttttggctca caacaaatta caacagcata gacaagtcat accggtcaaa    4972
caacacaggc tctcgaaaac gggctaaccg ctccaagaat ctgtcacgca gacgagcaag    5032
tcctaaatgt ttttcactc tcttcggggc caagttcagc atgtatcgga ttttctgctt     5092
acaccttt                                                              5100
```

<210> SEQ ID NO 24
<211> LENGTH: 88
<212> TYPE: PRT
<213> ORGANISM: Bovine adenovirus type 3

<400> SEQUENCE: 24

Leu Pro Leu Ser Cys Cys Met Pro Val Ser Val Ala Ser Phe Val Gln
 1               5                  10                  15

Ser Lys Leu Thr Ser Ser Ala Ser Thr Pro Arg Pro Ala Ser Thr Ala
            20                  25                  30

Cys Thr Leu Lys Lys Val Pro Pro Asp Ser Pro Trp Ser Thr Leu Thr
        35                  40                  45

Pro Glu Leu Leu Cys Glu Trp Pro Tyr Thr Thr Arg Glu Leu Pro Ala
    50                  55                  60

Ala Ser Ala Val Pro Val Pro Thr Pro Ser Ala Ser Pro Ser Ser Ser
65                  70                  75                  80

Arg Pro Ser Val Pro Leu Thr Phe
                85

<210> SEQ ID NO 25
<211> LENGTH: 5100
<212> TYPE: DNA
<213> ORGANISM: Bovine adenovirus type 3
<220> FEATURE:
<221> NAME/KEY: CDS
<222> LOCATION: (1915)..(4863)

<400> SEQUENCE: 25

```
cctcatcaaa caacccgtgg tgggcaccac ccacgtggaa atgcctcgca acgaagtcct      60
agaacaacat ctgacctcac atggcgctca atcgcgggc ggaggcgctg cgggcgatta     120
ctttaaaagc cccacttcag ctcgaaccct tatcccgctc accgcctcct gcttaagacc    180
agatggagtc tttcaactag gaggaggctc gcgttcatct tcaacccccc tgcaaacaga    240
ttttgccttc cacgccctgc cctccagacc gcgccacggg ggcataggat ccaggcagtt    300
tgtagaggaa tttgtgcccg ccgtctacct caaccccctac tcgggaccgc cggactctta    360
```

-continued

```
tccggaccag tttatacgcc actacaacgt gtacagcaac tctgtgagcg gttatagctg    420
agattgtaag actctcctat ctgtctctgt gctgcttttc cgcttcaagc cccacaagca    480 tgaagggtt tctgctcatc ttcagcctgc ttgtgcattg tcccctaatt catgttggga    540
ccattagctt ctatgctgca aggcccgggt ctgagcctaa cgcgacttat gtttgtgact    600
atggaagcga gtcagattac aaccccacca cggttctgtg gttggctcga gagaccgatg    660
gctcctggat ctctgttctt ttccgtcaca acggctcctc aactgcagcc cccggggtcg    720
tcgcgcactt tactgaccac aacagcagca ttgtggtgcc ccagtattac ctcctcaaca    780
actcactctc taagctctgc tgctcatacc ggcacaacga gcgttctcag tttacctgca    840
aacaagctga cgtccctacc tgtcacgagc ccggcaagcc gctcaccctc cgcgtctccc    900
ccgcgctggg aactgcccac caagcagtca cttggttttt tcaaaatgta cccatagcta    960
ctgtttaccg accttgggc aatgtaactt ggttttgtcc tcccttcatg tgtaccttta   1020
atgtcagcct gaactcccta cttatttaca acttttctga caaaccgggg ggcaataca   1080 cagctctcat gcactccgga cctgcttccc tctttcagct ctttaagcca acgacttgtg   1140
tcaccaaggt ggaggacccg ccgtatgcca acgacccggc ctcgcctgtg tggcgcccac   1200 tgcttttttgc cttcgtcctc tgcaccggct gcgcggtgtt gttaaccgcc ttcggtccat   1260
cgattctatc cggtacccga aagcttatct cagcccgctt ttggagtccc gagccctata   1320
ccaccctcca ctaacagtcc ccccatggag ccagacggag ttcatgccga gcagcagttt   1380
atcctcaatc agatttcctg cgccaacact gccctccagc gtcaaaggga ggaactagct   1440
tcccttgtca tgttgcatgc ctgtaagcgt ggcctctttt gtccagtcaa aacttacaag   1500
ctcagcctca acgcctcggc cagcgagcac agcctgcact ttgaaaaaag tccctcccga   1560
ttcaccctgg tcaacactca cgccggagct tctgtgcgag tggccctaca ccaccaggga   1620
gcttccggca gcatccgctg ttcctgttcc cacgccgagt gcctccccgt cctcctcaag   1680
accctctgtg cctttaactt tttagattag ctgaaagcaa atataaaatg gtgtgcttac   1740
cgtaattctg ttttgacttg tgtgcttgat ttctcccct gcgccgtaat ccagtgcccc   1800
tcttcaaaac tctcgtaccc tatgcgattc gcataggcat atttttctaaa agctctgaag   1860 tcaacatcac tctcaaacac ttctccgttg taggttactt tcatctacag ataa agt     1917
                                                                Ser
                                                                  1 cat cca ccg gtt aac atc atg aag aga agt gtg ccc cag gac ttt aat     1965
His Pro Pro Val Asn Ile Met Lys Arg Ser Val Pro Gln Asp Phe Asn
         5                  10                  15 ctt gtg tat ccg tac aag gct aag agg ccc aac atc atg ccg ccc ttt     2013
Leu Val Tyr Pro Tyr Lys Ala Lys Arg Pro Asn Ile Met Pro Pro Phe
         20                  25                  30 ttt gac cgc aat ggc ttt gtt gaa aac caa gaa gcc acg cta gcc atg     2061
Phe Asp Arg Asn Gly Phe Val Glu Asn Gln Glu Ala Thr Leu Ala Met
         35                  40                  45 ctt gtg gaa aag ccg ctc acg ttc gac aag gaa ggt gcg ctg acc ctg     2109
Leu Val Glu Lys Pro Leu Thr Phe Asp Lys Glu Gly Ala Leu Thr Leu
 50                  55                  60                  65 ggc gtc gga cgc ggc atc cgc att aac ccc gcg ggg ctt ctg gag aca     2157
Gly Val Gly Arg Gly Ile Arg Ile Asn Pro Ala Gly Leu Leu Glu Thr
                     70                  75                  80 aac gac ctc gcg tcc gct gtc ttc cca ccg ctg gcc tcc gat gag gcc     2205
Asn Asp Leu Ala Ser Ala Val Phe Pro Pro Leu Ala Ser Asp Glu Ala
                 85                  90                  95
```

```
ggc aac gtc acg ctc aac atg tct gac ggg cta tat act aag gac aac    2253
Gly Asn Val Thr Leu Asn Met Ser Asp Gly Leu Tyr Thr Lys Asp Asn
        100                 105                 110 aag cta gct gtc aaa gta ggt ccc ggg ctg tcc ctc gac tcc aat aat    2301
Lys Leu Ala Val Lys Val Gly Pro Gly Leu Ser Leu Asp Ser Asn Asn
        115                 120                 125 gct ctc cag gtc cac aca ggc gac ggg ctc acg gta acc gat gac aag    2349
Ala Leu Gln Val His Thr Gly Asp Gly Leu Thr Val Thr Asp Asp Lys
130                 135                 140                 145 gtg tct cta aat acc caa gct ccc ctc tcg acc acc agc gcg ggc ctc    2397
Val Ser Leu Asn Thr Gln Ala Pro Leu Ser Thr Thr Ser Ala Gly Leu
                150                 155                 160 tcc cta ctt ctg ggt ccc agc ctc cac tta ggt gag gag gaa cga cta    2445
Ser Leu Leu Leu Gly Pro Ser Leu His Leu Gly Glu Glu Glu Arg Leu
            165                 170                 175 aca gta aac acc gga gcg ggc ctc caa att agc aat aac gct ctg gcc    2493
Thr Val Asn Thr Gly Ala Gly Leu Gln Ile Ser Asn Asn Ala Leu Ala
        180                 185                 190 gta aaa gta ggt tca ggt atc acc gta gat gct caa aac cag ctc gct    2541
Val Lys Val Gly Ser Gly Ile Thr Val Asp Ala Gln Asn Gln Leu Ala
    195                 200                 205 gca tcc ctg ggg gac ggt cta gaa agc aga gat aat aaa act gtc gtt    2589
Ala Ser Leu Gly Asp Gly Leu Glu Ser Arg Asp Asn Lys Thr Val Val
210                 215                 220                 225 aag gct ggg ccc gga ctt aca ata act aat caa gct ctt act gtt gct    2637
Lys Ala Gly Pro Gly Leu Thr Ile Thr Asn Gln Ala Leu Thr Val Ala
                230                 235                 240 acc ggg aac ggc ctt cag gtc aac ccg gaa ggg caa ctg cag cta aac    2685
Thr Gly Asn Gly Leu Gln Val Asn Pro Glu Gly Gln Leu Gln Leu Asn
            245                 250                 255 att act gcc ggt cag ggc ctc aac ttt gca aac aac agc ctc gcc gtg    2733
Ile Thr Ala Gly Gln Gly Leu Asn Phe Ala Asn Asn Ser Leu Ala Val
        260                 265                 270 gag ctg ggc tcg ggc ctg cat ttt ccc cct ggc caa aac caa gta agc    2781
Glu Leu Gly Ser Gly Leu His Phe Pro Pro Gly Gln Asn Gln Val Ser
    275                 280                 285 ctt tat ccc gga gat gga ata gac atc cga gat aat agg gtg act gtg    2829
Leu Tyr Pro Gly Asp Gly Ile Asp Ile Arg Asp Asn Arg Val Thr Val
290                 295                 300                 305 ccc gct ggg cca ggc ctg aga atg ctc aac cac caa ctt gcc gta gct    2877
Pro Ala Gly Pro Gly Leu Arg Met Leu Asn His Gln Leu Ala Val Ala
                310                 315                 320 tcc gga gac ggt tta gaa gtc cac agc gac acc ctc cgg tta aag ctc    2925
Ser Gly Asp Gly Leu Glu Val His Ser Asp Thr Leu Arg Leu Lys Leu
            325                 330                 335 tcc cac ggc ctg aca ttt gaa aat ggc gcc gta cga gca aaa cta gga    2973
Ser His Gly Leu Thr Phe Glu Asn Gly Ala Val Arg Ala Lys Leu Gly
        340                 345                 350 cca gga ctt ggc aca gac gac tct ggt cgg tcc gtg gtt cgc aca ggt    3021
Pro Gly Leu Gly Thr Asp Asp Ser Gly Arg Ser Val Val Arg Thr Gly
    355                 360                 365 cga gga ctt aga gtt gca aac ggc caa gtc cag atc ttc agc gga aga    3069
Arg Gly Leu Arg Val Ala Asn Gly Gln Val Gln Ile Phe Ser Gly Arg
370                 375                 380                 385 ggc acc gcc atc ggc act gat agc agc ctc act ctc aac atc cgg gcg    3117
Gly Thr Ala Ile Gly Thr Asp Ser Ser Leu Thr Leu Asn Ile Arg Ala
                390                 395                 400 ccc cta caa ttt tct gga ccc gcc ttg act gct agt ttg caa ggc agt    3165
Pro Leu Gln Phe Ser Gly Pro Ala Leu Thr Ala Ser Leu Gln Gly Ser
            405                 410                 415
```

-continued

```
ggt ccg att act tac aac agc aac aat ggc act ttc ggt ctc tct ata      3213
Gly Pro Ile Thr Tyr Asn Ser Asn Asn Gly Thr Phe Gly Leu Ser Ile
        420                 425                 430 ggc ccc gga atg tgg gta gac caa aac aga ctt cag gta aac cca ggc      3261
Gly Pro Gly Met Trp Val Asp Gln Asn Arg Leu Gln Val Asn Pro Gly
    435                 440                 445 gct ggt tta gtc ttc caa gga aac aac ctt gtc cca aac ctt gcg gat      3309
Ala Gly Leu Val Phe Gln Gly Asn Asn Leu Val Pro Asn Leu Ala Asp
450                 455                 460                 465 ccg ctg gct att tcc gac agc aaa att agt ctc agt ctc ggt ccc ggc      3357
Pro Leu Ala Ile Ser Asp Ser Lys Ile Ser Leu Ser Leu Gly Pro Gly
                470                 475                 480 ctg acc caa gct tcc aac gcc ctg act tta agt tta gga aac ggg ctt      3405
Leu Thr Gln Ala Ser Asn Ala Leu Thr Leu Ser Leu Gly Asn Gly Leu
            485                 490                 495 gaa ttc tcc aat caa gcc gtt gct ata aaa gcg ggc cgg ggc tta cgc      3453
Glu Phe Ser Asn Gln Ala Val Ala Ile Lys Ala Gly Arg Gly Leu Arg
        500                 505                 510 ttt gag tct tcc tca caa gct tta gag agc agc ctc aca gtc gga aat      3501
Phe Glu Ser Ser Ser Gln Ala Leu Glu Ser Ser Leu Thr Val Gly Asn
    515                 520                 525 ggc tta acg ctt acc gat act gtg atc cgc ccc aac cta ggg gac ggc      3549
Gly Leu Thr Leu Thr Asp Thr Val Ile Arg Pro Asn Leu Gly Asp Gly
530                 535                 540                 545 cta gag gtc aga gac aat aaa atc att gtt aag ctg ggc gcg aat ctt      3597
Leu Glu Val Arg Asp Asn Lys Ile Ile Val Lys Leu Gly Ala Asn Leu
                550                 555                 560 cgt ttt gaa aac gga gcc gta acc gcc ggc acc gtt aac cct tct gcg      3645
Arg Phe Glu Asn Gly Ala Val Thr Ala Gly Thr Val Asn Pro Ser Ala
            565                 570                 575 ccc gag gca cca cca act ctc act gca gaa cca ccc ctc cga gcc tcc      3693
Pro Glu Ala Pro Pro Thr Leu Thr Ala Glu Pro Pro Leu Arg Ala Ser
        580                 585                 590 aac tcc cat ctt caa ctg tcc cta tcg gag ggc ttg gtt gtg cat aac      3741
Asn Ser His Leu Gln Leu Ser Leu Ser Glu Gly Leu Val Val His Asn
    595                 600                 605 aac gcc ctt gct ctc caa ctg gga gac ggc atg gaa gta aat cag cac      3789
Asn Ala Leu Ala Leu Gln Leu Gly Asp Gly Met Glu Val Asn Gln His
610                 615                 620                 625 gga ctt act tta aga gta ggc tcg ggt ttg caa atg cgt gac ggc att      3837
Gly Leu Thr Leu Arg Val Gly Ser Gly Leu Gln Met Arg Asp Gly Ile
                630                 635                 640 tta aca gtt aca ccc agc ggc act cct att gag ccc aga ctg act gcc      3885
Leu Thr Val Thr Pro Ser Gly Thr Pro Ile Glu Pro Arg Leu Thr Ala
            645                 650                 655 cca ctg act cag aca gag aat gga atc ggg ctc gct ctc ggc gcc ggc      3933
Pro Leu Thr Gln Thr Glu Asn Gly Ile Gly Leu Ala Leu Gly Ala Gly
        660                 665                 670 ttg gaa tta gac gag agc gcg ctc caa gta aaa gtt ggg ccc ggc atg      3981
Leu Glu Leu Asp Glu Ser Ala Leu Gln Val Lys Val Gly Pro Gly Met
    675                 680                 685 cgc ctg aac cct gta gaa aag tat gta acc ctg ctc ctg ggt cct ggc      4029
Arg Leu Asn Pro Val Glu Lys Tyr Val Thr Leu Leu Leu Gly Pro Gly
690                 695                 700                 705 ctt agt ttt ggg cag ccg gcc aac agg aca aat tat gat gtg cgc gtt      4077
Leu Ser Phe Gly Gln Pro Ala Asn Arg Thr Asn Tyr Asp Val Arg Val
                710                 715                 720
```

| | |
|---|---|
| tct gtg gag ccc ccc atg gtt ttc gga cag cgt ggt cag ctc aca ttt<br>Ser Val Glu Pro Pro Met Val Phe Gly Gln Arg Gly Gln Leu Thr Phe<br>              725                        730                        735 | 4125 |
| tta gtg ggt cac gga cta cac att caa aat tcc aaa ctt cag ctc aat<br>Leu Val Gly His Gly Leu His Ile Gln Asn Ser Lys Leu Gln Leu Asn<br>        740                        745                        750 | 4173 |
| ttg gga caa ggc ctc aga act gac ccc gtc acc aac cag ctg gaa gtg<br>Leu Gly Gln Gly Leu Arg Thr Asp Pro Val Thr Asn Gln Leu Glu Val<br>755                        760                        765 | 4221 |
| ccc ctc ggt caa ggt ttg gaa att gca gac gaa tcc cag gtt agg gtt<br>Pro Leu Gly Gln Gly Leu Glu Ile Ala Asp Glu Ser Gln Val Arg Val<br>770                    775                        780                        785 | 4269 |
| aaa ttg ggc gat ggc ctg cag ttt gat tca caa gct cgc atc act acc<br>Lys Leu Gly Asp Gly Leu Gln Phe Asp Ser Gln Ala Arg Ile Thr Thr<br>                    790                        795                        800 | 4317 |
| gct cct aac atg gtc act gaa act ctg tgg acc gga aca ggc agt aat<br>Ala Pro Asn Met Val Thr Glu Thr Leu Trp Thr Gly Thr Gly Ser Asn<br>             805                        810                        815 | 4365 |
| gct aat gtt aca tgg cgg ggc tac act gcc ccc ggc agc aaa ctc ttt<br>Ala Asn Val Thr Trp Arg Gly Tyr Thr Ala Pro Gly Ser Lys Leu Phe<br>        820                        825                        830 | 4413 |
| ttg agt ctc act cgg ttc agc act ggt cta gtt tta gga aac atg act<br>Leu Ser Leu Thr Arg Phe Ser Thr Gly Leu Val Leu Gly Asn Met Thr<br>835                        840                        845 | 4461 |
| att gac agc aat gca tcc ttt ggg caa tac att aac gcg gga cac gaa<br>Ile Asp Ser Asn Ala Ser Phe Gly Gln Tyr Ile Asn Ala Gly His Glu<br>850                    855                        860                        865 | 4509 |
| cag atc gaa tgc ttt ata ttg ttg gac aat cag ggt aac cta aaa gaa<br>Gln Ile Glu Cys Phe Ile Leu Leu Asp Asn Gln Gly Asn Leu Lys Glu<br>                  870                        875                        880 | 4557 |
| gga tct aac ttg caa ggc act tgg gaa gtg aag aac aac ccc tct gct<br>Gly Ser Asn Leu Gln Gly Thr Trp Glu Val Lys Asn Asn Pro Ser Ala<br>              885                        890                        895 | 4605 |
| tcc aaa gct gct ttt ttg cct tcc acc gcc cta tac ccc atc ctc aac<br>Ser Lys Ala Ala Phe Leu Pro Ser Thr Ala Leu Tyr Pro Ile Leu Asn<br>900                        905                        910 | 4653 |
| gaa agc cga ggg agt ctt cct gga aaa aat ctt gtg ggc atg caa gcc<br>Glu Ser Arg Gly Ser Leu Pro Gly Lys Asn Leu Val Gly Met Gln Ala<br>915                        920                        925 | 4701 |
| ata ctg gga ggc ggg ggc act tgc act gtg ata gcc acc ctc aat ggc<br>Ile Leu Gly Gly Gly Gly Thr Cys Thr Val Ile Ala Thr Leu Asn Gly<br>930                    935                        940                        945 | 4749 |
| aga cgc agc aac aac tat ccc gcg ggc cag tcc ata att ttc gtg tgg<br>Arg Arg Ser Asn Asn Tyr Pro Ala Gly Gln Ser Ile Ile Phe Val Trp<br>                  950                        955                        960 | 4797 |
| caa gaa ttc aac acc ata gcc cgc caa cct ctg aac cac tct aca ctt<br>Gln Glu Phe Asn Thr Ile Ala Arg Gln Pro Leu Asn His Ser Thr Leu<br>        965                        970                        975 | 4845 |
| act ttt tct tac tgg act taaataagtt ggaaataaag agttaaactg<br>Thr Phe Ser Tyr Trp Thr<br>        980 | 4893 |
| aatgtttaag tgcaacagac ttttattggt tttggctcac aacaaattac aacagcatag | 4953 |
| acaagtcata ccggtcaaac aacacaggct ctcgaaaacg ggctaaccgc tccaagaatc | 5013 |
| tgtcacgcag acgagcaagt cctaaatgtt ttttcactct cttcggggcc aagttcagca | 5073 |
| tgtatcggat tttctgctta caccttt | 5100 |

<210> SEQ ID NO 26
<211> LENGTH: 983

<210> TYPE: PRT
<213> ORGANISM: Bovine adenovirus type 3

<400> SEQUENCE: 26

```
Ser His Pro Pro Val Asn Ile Met Lys Arg Ser Val Pro Gln Asp Phe
 1               5                  10                  15
Asn Leu Val Tyr Pro Tyr Lys Ala Lys Arg Pro Asn Ile Met Pro Pro
            20                  25                  30
Phe Phe Asp Arg Asn Gly Phe Val Glu Asn Gln Glu Ala Thr Leu Ala
        35                  40                  45
Met Leu Val Glu Lys Pro Leu Thr Phe Asp Lys Glu Gly Ala Leu Thr
    50                  55                  60
Leu Gly Val Gly Arg Gly Ile Arg Ile Asn Pro Ala Gly Leu Leu Glu
65                  70                  75                  80
Thr Asn Asp Leu Ala Ser Ala Val Phe Pro Leu Ala Ser Asp Glu
                85                  90                  95
Ala Gly Asn Val Thr Leu Asn Met Ser Asp Gly Leu Tyr Thr Lys Asp
            100                 105                 110
Asn Lys Leu Ala Val Lys Val Gly Pro Gly Leu Ser Leu Asp Ser Asn
        115                 120                 125
Asn Ala Leu Gln Val His Thr Gly Asp Gly Leu Thr Val Thr Asp Asp
    130                 135                 140
Lys Val Ser Leu Asn Thr Gln Ala Pro Leu Ser Thr Ser Ala Gly
145                 150                 155                 160
Leu Ser Leu Leu Leu Gly Pro Ser Leu His Leu Gly Glu Glu Arg
                165                 170                 175
Leu Thr Val Asn Thr Gly Ala Gly Leu Gln Ile Ser Asn Asn Ala Leu
            180                 185                 190
Ala Val Lys Val Gly Ser Gly Ile Thr Val Asp Ala Gln Asn Gln Leu
        195                 200                 205
Ala Ala Ser Leu Gly Asp Gly Leu Glu Ser Arg Asp Asn Lys Thr Val
    210                 215                 220
Val Lys Ala Gly Pro Gly Leu Thr Ile Thr Asn Gln Ala Leu Thr Val
225                 230                 235                 240
Ala Thr Gly Asn Gly Leu Gln Val Asn Pro Glu Gly Gln Leu Gln Leu
                245                 250                 255
Asn Ile Thr Ala Gly Gln Gly Leu Asn Phe Ala Asn Asn Ser Leu Ala
            260                 265                 270
Val Glu Leu Gly Ser Gly Leu His Phe Pro Pro Gly Gln Asn Gln Val
        275                 280                 285
Ser Leu Tyr Pro Gly Asp Gly Ile Asp Ile Arg Asp Asn Arg Val Thr
    290                 295                 300
Val Pro Ala Gly Pro Gly Leu Arg Met Leu Asn His Gln Leu Ala Val
305                 310                 315                 320
Ala Ser Gly Asp Gly Leu Glu Val His Ser Asp Thr Leu Arg Leu Lys
                325                 330                 335
Leu Ser His Gly Leu Thr Phe Glu Asn Gly Ala Val Arg Ala Lys Leu
            340                 345                 350
Gly Pro Gly Leu Gly Thr Asp Asp Ser Gly Arg Ser Val Val Arg Thr
        355                 360                 365
Gly Arg Gly Leu Arg Val Ala Asn Gly Gln Val Gln Ile Phe Ser Gly
    370                 375                 380
Arg Gly Thr Ala Ile Gly Thr Asp Ser Ser Leu Thr Leu Asn Ile Arg
385                 390                 395                 400
```

```
Ala Pro Leu Gln Phe Ser Gly Pro Ala Leu Thr Ala Ser Leu Gln Gly
                405                 410                 415
Ser Gly Pro Ile Thr Tyr Asn Ser Asn Asn Gly Thr Phe Gly Leu Ser
            420                 425                 430
Ile Gly Pro Gly Met Trp Val Asp Gln Asn Arg Leu Gln Val Asn Pro
            435                 440                 445
Gly Ala Gly Leu Val Phe Gln Gly Asn Asn Leu Val Pro Asn Leu Ala
450                 455                 460
Asp Pro Leu Ala Ile Ser Asp Ser Lys Ile Ser Leu Ser Leu Gly Pro
465                 470                 475                 480
Gly Leu Thr Gln Ala Ser Asn Ala Leu Thr Leu Ser Leu Gly Asn Gly
                485                 490                 495
Leu Glu Phe Ser Asn Gln Ala Val Ala Ile Lys Ala Gly Arg Gly Leu
                500                 505                 510
Arg Phe Glu Ser Ser Ser Gln Ala Leu Glu Ser Ser Leu Thr Val Gly
            515                 520                 525
Asn Gly Leu Thr Leu Thr Asp Thr Val Ile Arg Pro Asn Leu Gly Asp
            530                 535                 540
Gly Leu Glu Val Arg Asp Asn Lys Ile Ile Val Lys Leu Gly Ala Asn
545                 550                 555                 560
Leu Arg Phe Glu Asn Gly Ala Val Thr Ala Gly Thr Val Asn Pro Ser
                565                 570                 575
Ala Pro Glu Ala Pro Thr Leu Thr Ala Glu Pro Pro Leu Arg Ala
                580                 585                 590
Ser Asn Ser His Leu Gln Leu Ser Leu Ser Gly Leu Val Val His
            595                 600                 605
Asn Asn Ala Leu Ala Leu Gln Leu Gly Asp Gly Met Glu Val Asn Gln
            610                 615                 620
His Gly Leu Thr Leu Arg Val Gly Ser Gly Leu Gln Met Arg Asp Gly
625                 630                 635                 640
Ile Leu Thr Val Thr Pro Ser Gly Thr Pro Ile Glu Pro Arg Leu Thr
                645                 650                 655
Ala Pro Leu Thr Gln Thr Glu Asn Gly Ile Gly Leu Ala Leu Gly Ala
                660                 665                 670
Gly Leu Glu Leu Asp Glu Ser Ala Leu Gln Val Lys Val Gly Pro Gly
            675                 680                 685
Met Arg Leu Asn Pro Val Glu Lys Tyr Val Thr Leu Leu Leu Gly Pro
            690                 695                 700
Gly Leu Ser Phe Gly Gln Pro Ala Asn Arg Thr Asn Tyr Asp Val Arg
705                 710                 715                 720
Val Ser Val Glu Pro Pro Met Val Phe Gly Gln Arg Gly Gln Leu Thr
                725                 730                 735
Phe Leu Val Gly His Gly Leu His Ile Gln Asn Ser Lys Leu Gln Leu
                740                 745                 750
Asn Leu Gly Gln Gly Leu Arg Thr Asp Pro Val Thr Asn Gln Leu Glu
            755                 760                 765
Val Pro Leu Gly Gln Gly Leu Glu Ile Ala Asp Glu Ser Gln Val Arg
            770                 775                 780
Val Lys Leu Gly Asp Gly Leu Gln Phe Asp Ser Gln Ala Arg Ile Thr
785                 790                 795                 800
Thr Ala Pro Asn Met Val Thr Glu Thr Leu Trp Thr Gly Thr Gly Ser
                805                 810                 815
```

```
Asn Ala Asn Val Thr Trp Arg Gly Tyr Thr Ala Pro Gly Ser Lys Leu
            820                 825                 830

Phe Leu Ser Leu Thr Arg Phe Ser Thr Gly Leu Val Leu Gly Asn Met
            835                 840                 845

Thr Ile Asp Ser Asn Ala Ser Phe Gly Gln Tyr Ile Asn Ala Gly His
    850                 855                 860

Glu Gln Ile Glu Cys Phe Ile Leu Leu Asp Asn Gln Gly Asn Leu Lys
865                 870                 875                 880

Glu Gly Ser Asn Leu Gln Gly Thr Trp Glu Val Lys Asn Asn Pro Ser
                885                 890                 895

Ala Ser Lys Ala Ala Phe Leu Pro Ser Thr Ala Leu Tyr Pro Ile Leu
            900                 905                 910

Asn Glu Ser Arg Gly Ser Leu Pro Gly Lys Asn Leu Val Gly Met Gln
            915                 920                 925

Ala Ile Leu Gly Gly Gly Thr Cys Thr Val Ile Ala Thr Leu Asn
            930                 935                 940

Gly Arg Arg Ser Asn Asn Tyr Pro Ala Gly Gln Ser Ile Ile Phe Val
945                 950                 955                 960

Trp Gln Glu Phe Asn Thr Ile Ala Arg Gln Pro Leu Asn His Ser Thr
                965                 970                 975

Leu Thr Phe Ser Tyr Trp Thr
            980

<210> SEQ ID NO 27
<211> LENGTH: 227
<212> TYPE: PRT
<213> ORGANISM: Human adenovirus type 2

<400> SEQUENCE: 27

Met Ser Lys Glu Ile Pro Thr Pro Tyr Met Trp Ser Tyr Gln Pro Gln
  1               5                  10                  15

Met Gly Leu Ala Ala Gly Ala Ala Gln Asp Tyr Ser Thr Arg Ile Asn
                20                  25                  30

Tyr Met Ser Ala Gly Pro His Met Ile Ser Arg Val Asn Gly Ile Arg
            35                  40                  45

Ala His Arg Asn Arg Ile Leu Leu Glu Gln Ala Ala Ile Thr Thr Thr
    50                  55                  60

Pro Arg Asn Asn Leu Asn Pro Arg Ser Trp Pro Ala Ala Leu Val Tyr
65                  70                  75                  80

Gln Glu Ser Pro Ala Pro Thr Thr Val Val Leu Pro Arg Asp Ala Gln
                85                  90                  95

Ala Glu Val Gln Met Thr Asn Ser Gly Ala Gln Leu Ala Gly Gly Phe
            100                 105                 110

Arg His Arg Val Arg Ser Pro Gly Gln Gly Ile Thr His Leu Lys Ile
            115                 120                 125

Arg Gly Arg Gly Ile Gln Leu Asn Asp Glu Ser Val Ser Ser Ser Leu
130                 135                 140

Gly Leu Arg Pro Asp Gly Thr Phe Gln Ile Gly Gly Ala Gly Arg Ser
145                 150                 155                 160

Ser Phe Thr Pro Arg Gln Ala Ile Leu Thr Leu Gln Thr Ser Ser Ser
                165                 170                 175

Glu Pro Arg Ser Gly Gly Ile Gly Thr Leu Gln Phe Ile Glu Glu Phe
            180                 185                 190

Val Pro Ser Val Tyr Phe Asn Pro Phe Ser Gly Pro Pro Gly His Tyr
            195                 200                 205
```

-continued

```
Pro Asp Gln Phe Ile Pro Asn Phe Asp Ala Val Lys Asp Ser Ala Asp
    210                 215                 220

Gly Tyr Asp
225

<210> SEQ ID NO 28
<211> LENGTH: 128
<212> TYPE: PRT
<213> ORGANISM: Human adenovirus type 5

<400> SEQUENCE: 28

Met Thr Asp Thr Leu Asp Leu Glu Met Asp Gly Ile Ile Thr Glu Gln
  1               5                  10                  15

Arg Leu Leu Glu Arg Arg Arg Ala Ala Glu Gln Gln Arg Met Asn
             20                  25                  30

Gln Glu Leu Gln Asp Met Val Asn Leu His Gln Cys Lys Arg Gly Ile
         35                  40                  45

Phe Cys Leu Val Lys Gln Ala Lys Val Thr Tyr Asp Ser Asn Thr Thr
     50                  55                  60

Gly His Arg Leu Ser Tyr Lys Leu Pro Thr Lys Arg Gln Lys Leu Val
 65                  70                  75                  80

Val Met Val Gly Glu Lys Pro Ile Thr Ile Thr Gln His Ser Val Glu
                 85                  90                  95

Thr Glu Gly Cys Ile His Ser Pro Cys Gln Gly Pro Glu Asp Leu Cys
            100                 105                 110

Thr Leu Ile Lys Thr Leu Cys Gly Leu Lys Asp Leu Ile Pro Phe Asn
        115                 120                 125

<210> SEQ ID NO 29
<211> LENGTH: 582
<212> TYPE: PRT
<213> ORGANISM: Human adenovirus type 2

<400> SEQUENCE: 29

Met Lys Arg Ala Arg Pro Ser Glu Asp Thr Phe Asn Pro Val Tyr Pro
  1               5                  10                  15

Tyr Asp Thr Glu Thr Gly Pro Pro Thr Val Pro Phe Leu Thr Pro Pro
             20                  25                  30

Phe Val Ser Pro Asn Gly Phe Gln Glu Ser Pro Pro Gly Val Leu Ser
         35                  40                  45

Leu Arg Val Ser Glu Pro Leu Asp Thr Ser His Gly Met Leu Ala Leu
     50                  55                  60

Lys Met Gly Ser Gly Leu Thr Leu Asp Lys Ala Gly Asn Leu Thr Ser
 65                  70                  75                  80

Gln Asn Val Thr Thr Val Thr Gln Pro Leu Lys Lys Thr Lys Ser Asn
                 85                  90                  95

Ile Ser Leu Asp Thr Ser Ala Pro Leu Thr Ile Thr Ser Gly Ala Leu
            100                 105                 110

Thr Val Ala Thr Thr Ala Pro Leu Ile Val Thr Ser Gly Ala Leu Ser
        115                 120                 125

Val Gln Ser Gln Ala Pro Leu Thr Val Gln Asp Ser Lys Leu Ser Ile
    130                 135                 140

Ala Thr Lys Gly Pro Ile Thr Val Ser Asp Gly Lys Leu Ala Leu Gln
145                 150                 155                 160

Thr Ser Ala Pro Leu Ser Gly Ser Asp Ser Asp Thr Leu Thr Val Thr
                165                 170                 175
```

-continued

```
Ala Ser Pro Pro Leu Thr Thr Ala Thr Gly Ser Leu Gly Ile Asn Met
            180                 185                 190
Glu Asp Pro Ile Tyr Val Asn Asn Gly Lys Ile Gly Ile Lys Ile Ser
            195                 200                 205
Gly Pro Leu Gln Val Ala Gln Asn Ser Asp Thr Leu Thr Val Val Thr
            210                 215                 220
Gly Pro Gly Val Thr Val Glu Gln Asn Ser Leu Arg Thr Lys Val Ala
225                 230                 235                 240
Gly Ala Ile Gly Tyr Asp Ser Ser Asn Asn Met Glu Ile Lys Thr Gly
                245                 250                 255
Gly Gly Met Arg Ile Asn Asn Asn Leu Leu Ile Leu Asp Val Asp Tyr
            260                 265                 270
Pro Phe Asp Ala Gln Thr Lys Leu Arg Leu Lys Leu Gly Gln Gly Pro
            275                 280                 285
Leu Tyr Ile Asn Ala Ser His Asn Leu Asp Ile Asn Tyr Asn Arg Gly
            290                 295                 300
Leu Tyr Leu Phe Asn Ala Ser Asn Thr Lys Lys Leu Glu Val Ser
305                 310                 315                 320
Ile Lys Lys Ser Ser Gly Leu Asn Phe Asp Asn Thr Ala Ile Ala Ile
                325                 330                 335
Asn Ala Gly Lys Gly Leu Glu Phe Asp Thr Asn Thr Ser Glu Ser Pro
            340                 345                 350
Asp Ile Asn Pro Ile Lys Thr Lys Ile Gly Ser Gly Ile Asp Tyr Asn
            355                 360                 365
Glu Asn Gly Ala Met Ile Thr Lys Leu Gly Ala Gly Leu Ser Phe Asp
            370                 375                 380
Asn Ser Gly Ala Ile Thr Ile Gly Asn Lys Asn Asp Asp Lys Leu Thr
385                 390                 395                 400
Leu Trp Thr Thr Pro Asp Pro Ser Pro Asn Cys Arg Ile His Ser Asp
                405                 410                 415
Asn Asp Cys Lys Phe Thr Leu Val Leu Thr Lys Cys Gly Ser Gln Val
            420                 425                 430
Leu Ala Thr Val Ala Ala Leu Ala Val Ser Gly Asp Leu Ser Ser Met
            435                 440                 445
Thr Gly Thr Val Ala Ser Val Ser Ile Phe Leu Arg Phe Asp Gln Asn
            450                 455                 460
Gly Val Leu Met Glu Asn Ser Ser Leu Lys Lys His Tyr Trp Asn Phe
465                 470                 475                 480
Arg Asn Gly Asn Ser Thr Asn Ala Asn Pro Tyr Thr Asn Ala Val Gly
                485                 490                 495
Phe Met Pro Asn Leu Leu Ala Tyr Pro Lys Thr Gln Ser Gln Thr Ala
            500                 505                 510
Lys Asn Asn Ile Val Ser Gln Val Tyr Leu His Gly Asp Lys Thr Lys
            515                 520                 525
Pro Met Ile Leu Thr Ile Thr Leu Asn Gly Thr Ser Glu Ser Thr Glu
            530                 535                 540
Thr Ser Glu Val Ser Thr Tyr Ser Met Ser Phe Thr Trp Ser Trp Glu
545                 550                 555                 560
Ser Gly Lys Tyr Thr Thr Glu Thr Phe Ala Thr Asn Ser Tyr Thr Phe
                565                 570                 575
Ser Tyr Ile Ala Gln Glu
            580
```

<210> SEQ ID NO 30
<211> LENGTH: 21
<212> TYPE: PRT
<213> ORGANISM: Artificial
<220> FEATURE:
<221> NAME/KEY: Modified-sites
<222> LOCATION: 2, 3, 5-17, 19-20
<223> OTHER INFORMATION: Xaa can be any amino acid; consensus
      metal-binding sequence

<400> SEQUENCE: 30

Cys Xaa Xaa Cys Xaa Xaa Xaa Xaa Xaa Xaa Xaa Xaa Xaa Xaa Xaa
 1               5                  10                  15

Xaa Cys Xaa Xaa Cys
            20

<210> SEQ ID NO 31
<211> LENGTH: 7
<212> TYPE: PRT
<213> ORGANISM: Bovine adenovirus type 3; human adenovirus type 5
<220> FEATURE:
<221> NAME/KEY: Modified-site
<222> LOCATION: (4)
<223> OTHER INFORMATION: Xaa can be any amino acid; region of homology

<400> SEQUENCE: 31

Gln Ser Ser Xaa Ser Thr Ser
 1               5

<210> SEQ ID NO 32
<211> LENGTH: 27
<212> TYPE: PRT
<213> ORGANISM: Bovine adenovirus type 3

<400> SEQUENCE: 32

Pro Leu Leu Phe Ala Phe Val Leu Cys Thr Gly Cys Ala Val Leu Leu
 1               5                  10                  15

Thr Ala Phe Gly Pro Ser Ile Leu Ser Gly Thr
            20                  25

<210> SEQ ID NO 33
<211> LENGTH: 57
<212> TYPE: PRT
<213> ORGANISM: Bovine adenovirus type 3

<400> SEQUENCE: 33

Glu Glu Val Thr Ser His Phe Phe Leu Asp Cys Pro Glu Asp Pro Ser
 1               5                  10                  15

Arg Glu Cys Ser Ser Cys Gly Phe His Gln Ala Gln Ser Gly Ile Pro
            20                  25                  30

Gly Ile Met Cys Ser Leu Cys Tyr Met Arg Gln Thr Tyr His Cys Ile
        35                  40                  45

Tyr Ser Pro Val Ser Glu Glu Glu Met
    50                  55

<210> SEQ ID NO 34
<211> LENGTH: 12
<212> TYPE: PRT
<213> ORGANISM: Bovine adenovirus type 3

<400> SEQUENCE: 34

Val Asp Leu Glu Cys His Glu Val Leu Pro Pro Ser
 1               5                  10

-continued

<210> SEQ ID NO 35
<211> LENGTH: 34446
<212> TYPE: DNA
<213> ORGANISM: Bovine adenovirus type 3

<400> SEQUENCE: 35

| | | | | | |
|---|---|---|---|---|---|
| catcatcaat | aatctacagt | acactgatgg | cagcggtcca | actgccaatc | attttttgcca | 60 |
| cgtcatttat | gacgcaacga | cggcgagcgt | ggcgtgctga | cgtaactgtg | gggcggagcg | 120 |
| cgtcgcggag | gcggcggcgc | tgggcggggc | tgagggcggc | gggggcggcg | cgcggggcgg | 180 |
| cgcgcgggc | ggggcgaggg | gcggagttcc | gcacccgcta | cgtcattttc | agacattttt | 240 |
| tagcaaattt | gcgccttttg | caagcatttt | tctcacattt | caggtattta | gagggcggat | 300 |
| ttttggtgtt | cgtacttccg | tgtcacatag | ttcactgtca | atcttcatta | cggcttagac | 360 |
| aaattttcgg | cgtcttttcc | gggtttatgt | ccccggtcac | ctttatgact | gtgtgaaaca | 420 |
| cacctgccca | ttgtttaccc | ttggtcagtt | ttttcgtctc | ctagggtggg | aacatcaaga | 480 |
| acaaatttgc | cgagtaattg | tgcaccttt | tccgcgttag | gactgcgttt | cacacgtaga | 540 |
| cagacttttt | ctcattttct | cacactccgt | cgtccgcttc | agagctctgc | gtcttcgctg | 600 |
| ccaccatgaa | gtacctggtc | ctcgttctca | acgacggcat | gagtcgaatt | gaaaaagctc | 660 |
| tcctgtgcag | cgatggtgag | gtggatttag | agtgtcatga | ggtacttccc | ccttctcccg | 720 |
| cgcctgtccc | cgcttctgtg | tcacccgtga | ggagtcctcc | tcctctgtct | ccggtgtttc | 780 |
| ctccgtctcc | gccagccccg | cttgtgaatc | cagaggcgag | ttcgctgctg | cagcagtatc | 840 |
| ggagagagct | gttagagagg | agcctgctcc | gaacggccga | aggtcagcag | cgtgcagtgt | 900 |
| gtccatgtga | gcggttgccc | gtggaagagg | atgagtgtct | gaatgccgta | aatttgctgt | 960 |
| ttcctgatcc | ctggctaaat | gcagctgaaa | tgggggtga | tatttttaag | tctccggcta | 1020 |
| tgtctccaga | accgtggata | gatttgtcta | gctacgatag | cgatgtagaa | gaggtgacta | 1080 |
| gtcacttttt | tctggattgc | cctgaagacc | ccagtcggga | gtgttcatct | tgtgggtttc | 1140 |
| atcaggctca | aagcggaatt | ccaggcatta | tgtgcagttt | gtgctacatg | cgccaaacct | 1200 |
| accattgcat | ctatagtaag | tacattctgt | aaaagaacat | cttggtgatt | tctaggtatt | 1260 |
| gtttagggat | taactgggtg | gagtgatctt | aatccggcat | aaccaaatac | atgttttcac | 1320 |
| aggtccagtt | tctgaagagg | aaatgtgagt | catgttgact | ttggcgcgca | agaggaaatg | 1380 |
| tgagtcatgt | tgactttggc | gcgccctacg | gtgactttaa | agcaatttga | ggatcacttt | 1440 |
| tttgttagtc | gctataaagt | agtcacggag | tcttcatgga | tcacttaagc | gttcttttgg | 1500 |
| atttgaagct | gcttcgctct | atcgtagcgg | gggcttcaaa | tcgcactgga | gtgtggaaga | 1560 |
| ggcggctgtg | gctgggacgc | ctgactcaac | tggtccatga | tacctgcgta | gagaacgaga | 1620 |
| gcatatttct | caattctctg | ccagggaatg | aagcttttt | aaggttgctt | cggagcggct | 1680 |
| attttgaagt | gtttgacgtg | tttgtggtgc | ctgagctgca | tctggacact | ccgggtcgag | 1740 |
| tggtcgccgc | tcttgctctg | ctggtgttca | tcctcaacga | tttagacgct | aattctgctt | 1800 |
| cttcaggctt | tgattcaggt | tttctcgtgg | accgtctctg | cgtgccgcta | tggctgaagg | 1860 |
| ccagggcgtt | caagatcacc | cagagctcca | ggagcacttc | gcagccttcc | tcgtcgcccg | 1920 |
| acaagacgac | ccagactacc | agccagtaga | cggggacagc | ccaccccggg | ctagcctgga | 1980 |
| ggaggctgaa | cagagcagca | ctcgtttcga | gcacatcagt | taccgagacg | tggtggatga | 2040 |
| cttcaataga | tgccatgatg | ttttttatga | gaggtacagt | tttgaggaca | taagagcta | 2100 |
| cgaggctttg | cctgaggaca | atttggagca | gctcatagct | atgcatgcta | aaatcaagct | 2160 |

-continued

```
gctgcccggt cgggagtatg agttgactca acctttgaac ataacatctt gcgcctatgt      2220
gctcggaaat ggggctacta ttagggtaac aggggaagcc tccccggcta ttagagtggg      2280
ggccatggcc gtgggtccgt gtgtaacagg aatgactggg gtgactttg tgaattgtag      2340 gtttgagaga gagtcaacaa ttaggggtc cctgatacga gcttcaactc acgtgctgtt      2400
tcatggctgt tattttatgg gaattatggg cacttgtatt gaggtggggg cgggagctta      2460
cattcggggt tgtgagtttg tgggctgtta ccggggaatc tgttctactt ctaacagaga      2520
tattaaggtg aggcagtgca actttgacaa atgcttactg ggtattactt gtaaggggga      2580
ctatcgtctt tcgggaaatg tgtgttctga gactttctgc tttgctcatt tagagggaga      2640
gggtttggtt aaaaacaaca cagtcaagtc ccctagtcgc tggaccagcg agtctggctt      2700
ttccatgata acttgtgcag acggcagggt tacgcctttg ggttccctcc acattgtggg      2760
caaccgttgt aggcgttggc caaccatgca ggggaatgtg tttatcatgt ctaaactgta      2820
tctgggcaac agaataggga ctgtagccct gccccagtgt gctttctaca agtccagcat      2880
ttgtttggag gagagggcga caaacaagct ggtcttggct tgtgcttttg agaataatgt      2940
actggtgtac aaagtgctga gacgggagag tccctcaacc gtgaaaatgt gtgtttgtgg      3000
gacttctcat tatgcaaagc cttgtacact ggcaattatt tcttcagata ttcgggctaa      3060
tcgatacatg tacactgtgg actcaacaga gttcacttct gacgaggatt aaaagtgggc      3120
ggggccaaga ggggtataaa taggtgggga ggttgagggg agccgtagtt tctgtttttc      3180
ccagactggg ggggacaaca tggccgagga agggcgcatt tatgtgcctt atgtaactgc      3240
ccgcctgccc aagtggtcgg gttcggtgca ggataagacg ggctcgaaca tgttgggggg      3300
tgtggtactc cctcctaatt cacaggcgca ccggacggag accgtgggca ctgaggccac      3360
cagagacaac ctgcacgccg agggagcgcg tcgtcctgag gatcagacgc cctacatgat      3420
cttggtggag gactctctgg gaggtttgaa gaggcgaatg gacttgctgg aagaatctaa      3480
tcagcagctg ctggcaactc tcaaccgtct ccgtacagga ctcgctgcct atgtgcaggc      3540
taaccttgtg ggcggccaag ttaaccccctt tgtttaaata aaaatacact catacagttt      3600
attatgctgt caataaaatt ctttattttt cctgtgataa taccgtgtcc agcgtgctct      3660
gtcaataagg gtcctatgca tcctgagaag ggcctcatat accatggcat gaatattaag      3720
atacatgggc ataaggcccct cagaagggtt gaggtagagc cactgcagac tttcgtgggg      3780
aggtaaggtg ttgtaaataa tccagtcata ctgactgtgc tgggcgtgga aggaaaagat      3840 gtctttttaga agaagggtga ttggcaaagg gaggctctta gtgtaggtat tgataaatct      3900
gttcagttgg gagggatgca ttcgggggct aataaggtgg agtttagcct gaatcttaag      3960
gttggcaatg ttgcccccta ggtctttgcg aggattcatg ttgtgcagta ccacaaaaac      4020
agagtagcct gtgcatttgg ggaatttatc atgaagcttg gaggggaagg catgaaaaaa      4080
ttttgagatg gctttatggc gccccaggtc ttccatgcat tcgtccataa taatagcaat      4140
aggcccggtt ttggctgcct gggcaaacac gttctgaggg tgggcgacat catagttgta      4200
gtccatggtc aggtcttcat aggacatgat cttaaaggca ggttttaggg tgctgctttg      4260
aggaaccaga gttcctgtgg ggccgggggt gtagttccct tcacagattt gggtctccca      4320
agcaagcagt tcttgcgggg gtatcatgtc aacttggggg actataaaaa aaacagtttc      4380
gggaggtggt tgaatgaggc ccgtagacat aaggtttctg aggagctggg atttccaca      4440 accggttggt ccgtagacca ccccaataac gggttgcatg gtaaagttta aagatttgca      4500
```

```
tgaaccgtca gggcgcagat atggcatggt ggcattcatg gcatctctta tcgcctgatt    4560
atagtctgag agggcattga gtagggtggc gcccccata gccagtagct cgtccaagga    4620
agaaaagtgt ctaagaggtt tgaggccttc agccatgggc atggactcta agcactgttg    4680
catgagagca catttgtccc aaagctcaga gacgtggtct agtacatctc catccagcat    4740
agctctttgt ttcttgggtt ggggtggctg ttgctgtagg gggcgagacg gtgacggtcg    4800
atggcccgca gggtgcggtc tttccagggc ctgagcgtcc tcgccagggt cgtctcggtg    4860
accgtgaagg gctgctgatg cgtctgtctg ctgaccagcg agcgcctcag gctgagcctg    4920
ctggtgccga acttttcgtc gcctagctgt tcagtggaat aataacaagt caccagaagg    4980
tcgtaggaga gttgtgaggt ggcatggcct ttgctcgaag tttgccagaa ctctcggcgg    5040
cggcagcttg ggcagtagat gttttttaagg gcatatagtt tgggggctaa aagacagat    5100 tcctggctgt gggcgtctcc gtggcagcgg ggcactggg tctcgcattc cacaagccaa    5160
gtcagctgag ggttggtggg atcaaagacc agaggacggt tattacctttt caggcggtgc    5220 ttgcctcggg tgtccatgag ttcctttccc ctttgggtga gaaacatgct gtccgtgtct    5280
ccgtagacaa atttgagaat ccggtcttct aggggagtgc ctctgtcttc taaatagagg    5340
atgtctgccc attcagagac aaaggctcta gtccacgcga ggacaaatga agctatgtgt    5400 gagggtatc tgttattaaa tatgagagag gattttttt gcaaagtatg caggcacagg    5460
gctgagtcat cagcttccag aaaggtgatt ggtttgtaag tgtatgtcac gtgatggttc    5520
tgggggtctc ccagggtata aaaggggggcg tcttcgtctg aggagctatt gctagtgggt    5580
gtgcactgac ggtgcttccg cgtggcatcc gtttgctgct tgacgggtga gtaggtgatt    5640
tttagctctg ccatgacaga ggagctcagg ttgtcagttt ccacgaaggc ggtgcttttg    5700
atgtcgtagg tgccgtctga aatgcctcta acatatttgt cttccatttg gtcagaaaag    5760
acagtgactc tgttgtctag cttagtggca aagctgccat acagggcatt ggacagcagt    5820
ttggcaatgc ttctgagagt ttggttttt ctttatccg ccctttcctt gggcgcaatg    5880
ttaagttgca cgtagtctct agccagacac tcccactggg gaaatactgt ggtgcggggg    5940
tcgttgagaa tttggactct ccagccgcgg ttatgaagcg tgatggcatc caaacaagtt    6000
accacttccc cccgtagtgt ctcgttggtc cagcagaggc gacctccttt tctggagcag    6060
aagggcggta taacgtccaa gaatgcttct gggggtgggt ctgcatcaat ggtgaatatc    6120
gcgggcagta gggtgcgatc aaaatagtca atgggtctgt gcaactgggt taggcggtct    6180
tgccagtttt taattgcaag cgctcgatca aagggggttca aaggttttcc cgctgggaaa    6240
ggatgggtga gggcgctggc atacatgccg cagatgtcat acacatagat ggcttctgtt    6300
aggacgccta tgtaggtagg atagcatcgg ccgccccgaa tactttctct aacgtaatca    6360
tacatttcat tggaaggggc tagtagaaag ttgcccagag agctcctgtt gggacgctgg    6420
gatcggtaga ctacctgtct gaagatggca tgggaattgg agctgatggt gggcctttgg    6480
aggacattga aattgcagtg gggcagcccc actgacgtgt gaacaaagtc caataagat    6540 gcttggagtt ttttaaccaa ttcggccgta accagcacgt ccatagcaca gtagtccaag    6600
gtgcgttgca caatatcata ggcacctgaa ttctcttgca gccagagact cttattgaga    6660
aggtactcct cgtcgctgga ccagtagtcc ctctgaggaa aagaatctgc gtcggttcgg    6720
taggtaccta acatgtaaaa ttcatttaca gctttgtaag ggcagcagcc ttttttccacg    6780 ggtaaagcgt aagcggcagc tgcgttcctg agactcgtgt gcgtgagagc aaaggtatct    6840
cggaccatga acttcacaaa ctgaaattta tagtctgctg aggtgggagt gccttcctcc    6900
```

-continued

```
cagtctttga agtcttttcg agcagcatgt gtggggttag gcagagcaaa agttaagtca      6960
ttgaaaagaa tcttgccaca acgaggcatg aaatttctac tgactttaaa agcagctgga      7020
ataccttgtt tgttgttaat gacttgtgcg gctagaacaa tctcatcaaa gccgtttatg      7080
ttgtgcccta cgacatagac ttccaagaaa gtcggttgcc ctttgagttc aagcgtacac      7140
agttcctcga aaggaatgtc gctggcatgg acatagccca gtttgaggca gaggttttct      7200
aagcacggat tatctgccag gaactggcgc aaagcaaag tgctggcagc ttcttgaagg       7260
gcatcccgat actgtttaaa caagctgcct actttgtttc tttgcgggtt gaggtagtag      7320
aaggtatttg cttgctttgg ccagcttgac cacttttgct ttttagctat gttaacagcc      7380
tgttcgcata gctgcgcgtc accaaacaaa gtaaacacga gcataaaagg catgagttgc      7440
ttgccaaagc taccgtgcca agtgtatgtt tccacatcat agacgacaaa gaggcgccgg      7500
gtgtcgggt gagcggccca ggggaaaaac tttatttctt cccaccagtc cgaagattgg       7560
gtgtttatgt ggtgaaagta aaagtcccgg cggcgagtgc tgcaggtgtg cgtctgctta      7620
aaatacgaac cgcagtcggc acatcgctgg acctctgcga tggtgtctat gagatagagc      7680
tttctcttgt gaataagaaa gttgaggggg aagggaaggc gcggcctgtc agcgcgggcc      7740
gggatgcttg taattttcag cttccccttg tatgttttgt aaacgcacat atttgcgttg      7800
cagaaccgga cgagcgtgtc ttggaatgaa aggatatttt ctggttttaa atcaaatggg      7860
cagtgctcca agtgcagttc aaaaaggttt cggagactgc tggaaacgtc tgcgtgatac      7920
ttgacttcca gggtggtccc gtcttcagtc tgaccgtgca gccgtagggt actgcgtttg      7980
gcgaccaggg gccccttgg ggctttcttt aaaggggacg tcgagggccg aggggcggcc       8040
tttgcctttc gggcctgagg ggcggtagct ggaccggatc gttgagttcg ggcatgggtt      8100
gcagctgttg gcgcaggtct gatgcgtgct gcacgactct gcggttgatt ctctgaatct      8160
ccgggtgttg ggtgaatgct actggccccg tcactttgaa cctgaaagag aggtcgacag      8220
agttaataga tgcatcgtta agctccgcct gtctaataat ttcttccacg tcaccgctgt      8280
ggtctcggta agcaatgtct gtcataaacc gttcgatctc ttcctcgtcc agttctccgc      8340
gaccagctcg gtgaccgtg gctgccaagt ccgtgctaat gcgtcgcatg agctgggaaa       8400
aggcattggt tcccggttca ttccacactc tgctgtatat aacagcgcca tcttcgtctc      8460
gggctcgcat gaccacctgg cccaagttta gctccacgtg gcgagcaaag acggggctga      8520
ggcggaggtg gtggtgcaga taattgagag tggtggctat gtgctccacg atgaagaagt     8580
agatgaccca tctgcggatg gtcgactcgt taatgttgcc ctctcgctcc agcatgttta     8640
tggcttcgta aaagtccaca gcgaagttaa aaaactgctc gttgcgggcg gagactgtca     8700
gctcttcttg caggagacga atgacttcgg ctacggcggc gcggacttct tcggcaaagg     8760
agcgcggcg cacgtcctcc tcctcctctt cttccccctc cagcgggggc atctccagct     8820
ctaccggttc cgggctgggg gacagggaag gcggtgcggg ccgaacgacc cgtcggcgtc    8880
gggtgggcaa ggggagactc tctatgaatc gctgcaccat ctcgccccgg cgtatccgca    8940
tctcctgggt aacggcacgc ccgtgttctc ggggtcggag ctcaaaagct ccgccccgca    9000
gttcggtcag aggccgcgcc gcgggctggg gcaggctgag tgcgtcaata acatgcgcca    9060
ccactctctc cgtagaggcg gctgtttcga accgaagaga ctgagcatcc acgggatcgc    9120
tgaagcgttg cacaaaagct tctaaccagt cgcagtcaca aggtaggctg agcataggtg    9180
aggctcgctc ggtgttgttt ctgtttggcg gcgggtggct gaggagaaaa ttaaagtacg    9240
```

-continued

```
cgcaccgcag gcgccggatg gttgtcagta tgatgagatc cctgcgaccc gcttgttgga    9300
ttctgatgcg gtttgcaaag ccccaggctt ggtcttggca tcgcccaggt tcatgcactg    9360
ttcttggagg aatctctcta cgggcacgtt gcggcgctgc gggggcaggg tcagccattt    9420
cggtgcgtcc aaacccacgc aatggttgga tgagagccaa gtccgctact acgcgctctg    9480
ctaggacggg ttgctggatc tgccgcagcg tttcatcaaa gttttccaag tcaatgaagc    9540
ggtcgtaggg gcccgcgttt atggtgtagg agcagtttgc catggtggac cagtccacaa    9600
tctgctgatc tacccgcacc gtttctcggt acaccagtcg gctataggct cgcgtctcga    9660
aaacatagtc gttgcaaacg cgcaccacgt attggtagcc gattaggaag tgcggcggcg    9720
ggtataagta gagcggccag ttttgcgtgg ccggctgtct ggcgcccaga ttccgtagca    9780
tgagtgtggg gtatcggtac acgtgacgcg acatccagga gatgcccgcg gccgaaatgg    9840
cggccctggc gtactcccgg gcccggttcc atatattcct gagaggacga aagattccat    9900
ggtgtgcagg gtctgcccg taagacgcgc gcaatctctc gcgctctgca aaaacatac    9960 agatgaaaca ttttttgggc ttttcagatg atgcatcccg ctttacggca aatgaagccc    10020
agatccgcgg cagtggcggg ggttcctgct gcggccgccg gcgcgagcgt tgactcaggc    10080
ggtactaccg cgcccctgg tgtcgagtgc ggcgagggg aagggttagc tcggctgtac    10140
gcgcacccgg acacacaccc gcgcgtgtgc gtgaagcgcg atgcggcgga ggcgtacgtt    10200
ccccgggaga acttattccg cgaccgcagc ggggaggaac ccgaagggag ccgagaccta    10260
aagtacaagg ccggtcggca gttgcgcgcc ggcatgcccc gaaagcgggt gctgaccgaa    10320
ggggactttg aggtggatga gcgcactggc atcagctcag ccaaagccca catggaggcg    10380
gccgatctag tgcgggctta cgagcaaacg gtgaagcaag aggctaattt tcaaaagtca    10440
tttaataacc acgtgcggac actgatctcc cgcgaggaga ccaccctggg tttgatgcac    10500
ttgtgggact tgcggaggc atacgcgcag aaccccggca gcaagaccct tacggcccaa    10560
gtctttctca tcgtgcagca cttgcaagat gagggcattt ttggggaagc tttcttaagc    10620
atagcagagc ccgaggacg atggatgcta gatctgctaa acatattgca gtccattgtg    10680
gtgcaagagc gccagctttc gctatctgaa aaggtagccg cggtgaacta ctccgtagtt    10740
accctgggca aacattatgc ccgcaagatc tttaagagcc cctttgtgcc gcttgacaag    10800
gaggtgaaga tcagtacatt ttatatgcgc gcggtgctta aggtcctggg tctaagtcac    10860
gacctgggca tgtacagaaa cgaaaaggtg gagaagctag ctagcatagg caggcgttcg    10920
ggagatgagc gacgcggagc tgctgttcaa cctccgccgc gcactaacca ctggcgattc    10980
tgaagcattc gatgaaggcg gggactttac ctgggctccg ccaactcgcg cgaccgcggc    11040
ggccgctttg ccggggcccg agtttgagag tgaagagacg gacgatgaag tcgacgaatg    11100
agtgatgcgg accccgtat ctttcagctg gtcagtcggc aagagaccgt agccatggcc    11160
gaagcgcccc gaagcctggg ccccgcccct tccaatccta gtttgcaggc tttattccaa    11220
agccagccca gcgccgagca ggagtggcac ggcgtgctgg agagagtcat ggcccttaac    11280
aaaaatggag actttggctc gcagcccag gcgaaccggt ttggagccat cctcgaagcc    11340
gtggtgcccc cgcgctccga tcccacccat gaaaaagtgc tagctattgt gaatgcgctc    11400
ttggagactc aggccatccg tcgcgatgag gccggacaga tgtacaccgc gctgttgcag    11460
cgggtggcca gatacaacag tgtgaatgtg caggcaatt tggacaggct gattcaggac    11520
gtgaaggagg ctctggcgca gcgcgagcgc accgggccgg gggccggcct aggtctgtg    11580 gtagccttga atgccttcct gagcacacag ccagcggtgg tggagagggg ccaggagaac    11640
```

```
tatgtggcct tgtgagcgc cttaaaactc atggtgaccg aggcgccgca gtctgaggtt   11700
taccaggccg gacctagttt cttttttcaa accagccggc acggttcgca gacggtaaac   11760
ctcagtcagg cctttgataa cttgcgaccc ctctggggcg tgcgcgcgcc agtacacgag   11820
cgtactacca tctcctctct gctcacacca aacacccgct tgctcttgct cctcattgcg   11880 cccttttacgg acagcgtggg catatcccgg acagttacc tggggcatct gctgacccctt   11940 taccgggaga ccataggtaa cactcgagtt gatgagacca cgtacaacga gatcacggaa   12000
gtgagtcggg ccctgggcgc cgaagacgcg tctaacttgc aagccactct caactactta   12060
ctcacaaata agcagagcaa gttgccacag gagttttctc tgagtcccga agaggagcgg   12120
gtgctgcgct acgtgcagca atctgtcagt ttatttttaa tgcaggatgg acacacggcc   12180
accactgctc tagatcaggc tgcggccaac atagcgccct cgttttacgc gtcccaccgc   12240
gactttataa accgactgat ggactatttc cagcgagctg cggctatggc ccctgactac   12300
tttttacagg ctgttatgaa tccccactgg ctcccgccgc cgggtttctt tactcaggag   12360
tttgactttc cggagcccaa cgaaggcttc ctgtgggatg atttggacag cgcgctccta   12420
cgcgcgcacg taaaagaaga ggaggatcaa ggagctgtgg gcggcacgcc ggcggcttcg   12480
gcgcccgcgt ctcgcgcgca cacaccaccg ccgccgcccg tgccgcgga cctctttgct   12540 cctaacgcct tccgcaatgt gcaaaataac ggcgtggatg aacttattga cggcttaagc   12600
agatggaaga cttacgccca ggagaggcag gaagtcgttg agcggcacag gcgcagagag   12660
gcgcgtcgcc gggcgcgcga ggcgcgtcta gagtcgagcg atgatgacga cagcgaccta   12720
gggccgtttc tacggggcac ggggcacctc gttcacaacc agtttatgca tctgaagccc   12780
cggggtcccc gccagttttg gtaaccgcac tgtattaagc tgtaagtcct ctcatttgac   12840
acttaccaaa gccatggtct tgcttcgcct ctgacacttt ctctccccc acacgcggca   12900 ccctacagcc taggggcgat gctccagccc gaactgcagc caattccgct gtcccgccgc   12960
cggcttatga ggcggtggtg gctggggcct tccagacgct ttctcttcga cgagatccac   13020
gtcccgccgc gatatgctgc cgcgtctgcg gggagaaaca gtatccgtta ttccatgctg   13080
cccccgttgt atgacaccac gaagatatac cttatcgaca caaatcttc agacatccaa   13140 actctgaatt accaaaacga ccactcagat tacctcacta ccatcgtgca aacagcgac   13200 ttcacgcccc tggaggctag caaccacagc atcgagctag acgagcggtc ccgctggggc   13260
ggaaacctta aaaccatcct ttatacaaac ctgcctaata tcacccagca catgtttttct   13320 aactcttttc gggtaaagat gatggcctca aaaaaagacg gcgtgcccca gtacgagtgg   13380 ttcccctaa ggctgcccga gggtaacttt tctgagacta tggtcattga cctcatgaac   13440
aatgccatcg tagagctgta cttggctttg gggcgccagg agggcgtgaa ggaagaggac   13500
atcggggtaa agatcgatac gcgcaacttt agtctgggct atgacccgca gacccagtta   13560
gtgacgcccg gcgtatacac caatgaagct atgcatgcgg acatcgtgtt gctgccgggc   13620
tgtgctatag actttacgca ctcccgatta aacaacctct gggcatacg caagcgtttt   13680 ccgtaccaag agggcttcgt catctcctat gaggaccttta agggggtaa catccccgct   13740 ttgatggacg tggaggagtt taacaagagc aagacggttc gagctttgcg ggaggacccc   13800 aagggcgca gttatcacgt gggcgaagac ccagaagcca gagaaaacga aaccgcctac   13860
cgcagctggt acctggctta caattacggg gacccagaaa aaggggtgcg ggccaccaca   13920
ctgctgacta ccggcgacgt gacctgcggg gtggaacaga tctactggag cttgccggac   13980
```

-continued

```
atggcactgg acccagtcac tttcaaggct tcgctgaaaa ctagcaatta ccccgtggtg   14040
ggcacagaac ttttgccact ggtgccgcgt agcttttata acgctcaggc tgtgtactca   14100
cagtggatac aagaaaaaac taaccagacc cacgttttca atcgctttcc cgaaaatcag   14160
atcttggtgc ggcccctgc gcctaccatc acgtccataa gtgaaaataa gcccagcttg   14220
acagatcacg gaatcgtgcc gctccggaac cgcttggggg gcgtgcaacg tgtgactttg   14280
actgacgcgc ggcgaagatc ctgcccctac gtctacaaga gcttaggcat tgtgacgccg   14340
caagtgctat ctagccgcac gttttaagca gacaggggca cagcagccgt ttttttttt   14400 tttttttcgc tccaccaggg actgtcagga acatggccat tctaatctct cctagcaata   14460
acacgggctg gggcctggga tgcaataaga gtacggggg cgctcgcata cgttcagact   14520
tgcatccagt gaaggtgcgg tcgcattatc gggccgcctg gggcagccgc accggtcggg   14580
tgggtcgccg cgcaaccgca gctttagccg atgccgtcgc ggccaccggt gatccggtgg   14640
ccgacacaat cgaggcggtg gtggctgacg cccgccagta ccggcgccgc agacggcgag   14700
gggtgcgccg agtcagaagg ttgcgtcgga gccccgcac tgccctgcag cgacgggttc   14760
gtagcgtacg ccgacaagtg gcgagggccc gcaggtgggg ccggcgcgcg gccgctatcg   14820
cagcagacgc ggccatggcc atggcggcgc cagctcggcg acgccgtaac atctactggg   14880
tacgcgatgc ggcaaccgga gcccgcgttc cggtgacaac ccggcctacg gtcagcaaca   14940
ccgtttgaaa tgtctgctac tttttttgc ttcaataaaa gcccgccgac tgatcagcca   15000
caccttgtca cgcagaattc tttcaaacca ttgcgctctc agcgcgcgcg ccgataaacc   15060
cactgtgatg gcctcctctc ggttgattaa agaagaaatg ttagacatcg tggcgcctga   15120
gatttacaag cgcaaacggc ccaggcgaga acgcgcagca ccgtatgctg tgaagcagga   15180
ggagaagcct ttagtaaagg cggagcgcaa aattaagcgc ggctccagaa agcgggcctt   15240
gtcaggcgtt gacgttcctc tgcccgatga cggctttgag gacgacgagc cccacataga   15300
atttgtgtct gcgccgcgtc ggccctacca gtggaagggc aggcgggtgc gccgggtttt   15360
gcgtcccggc gtggccgtta gtttcacgcc cggcgcgcgc tccctccgtc cgagttccaa   15420
gcgggtgtat gacgaggtgt acgcagacga cgacttctta gaagcggccg cggcccgtga   15480
gggggagttt gcttacggaa agcggggacg cgaggcggcc caggcccagc tgctaccggc   15540
tgtggccgtg ccggaaccga cttacgtagt tttggatgag agcaaccccca ccccgagcta   15600 caagcctgta accgagcaga aagttattct ttcccgcaag cggggtgtgg ggaaggtaga   15660
gcctaccatc caggttttag ctagcaagaa gcggcgcatg gccgagaatg aggatgaccg   15720
cggggccggc tccgtggccg aagtgcagat gcgagaagtt aaaccggtaa ccgctgcctt   15780
gggtattcag accgtggatg ttagcgtgcc cgaccacagc actcccatgg aggtcgtgca   15840
gagtctcagt cgggcggctc aagtagctca acgcctgacc caacaacagg tgcggccttc   15900
ggctaagatt aaagtggagg ccatggatct ttctgctccc gtagacgcaa agcctcttga   15960
cttaaaaccc gtggacgtaa agccgacccc gaccttcgtc cttcccagct ttcgttcact   16020
cagcacccaa actgactctt tgcccgcggc agtggtcgtg ccgcgcaagc cccgcgtgca   16080
ccgtgctact aggcgtactg cgcgcggctt gctgccctat taccgcctgc atcctagcat   16140
cacgccgaca ccgggttacc gaggatctgt ctacacgagc tcgggtgtgc gcctgcccgc   16200 cgtccggggcg ccgccgtcgc cgccgtaccc gcagggcgac tccccgcctc agcgctgccg   16260
cggccgcggc gctgctgccc ggcgtgcgct atcaccctag catccgccaa gcggccacag   16320
taacccggct ccgccgttaa gcgctgtgaa actgcaacaa caacaacaaa aataaaaaaa   16380
```

-continued

```
agtctccgct ccactgtgca ccgttgtcca tcggctaata aagtcccgct ttgtgcgccg   16440
caggaaccac tatccgtaac ctgcgaaaat gagtcccgc ggaaatctga cttacagact   16500
gagaataccg gtcgccctca gtggccggcg ccggcgccga acaggcttgc gaggagggtc   16560
tgcgtacctg ctcggccgcc gcagaaggcg cgcgggcggc ggccgcctgc gcggggcgtt   16620
ccttcccctc ctggctccca tcattgcagc cgccatcggc gcaatccccg gcatcgcatc   16680
agtggccatt caggcggccc acaacaaata gggacagtgt aaagaaagct caatctcaat   16740
aaaacaaacc gctcgatgtg cataacgctc tcggcctgca acttctgctg cttacgtctt   16800
tgaccaaagt cactactgtt ttccttttac ccagagccgg cgccagcccc acacagcttg   16860
ttaacacgcc atggacgaat acaattacgc ggctcttgct ccccggcaag gctcccgacc   16920
catgctgagc cagtggtccg gcatcggcac gcacgaaatg cacggcggac gttttaatct   16980
gggcagtttg tggagcggga tcaggaatgt gggcagcgcg ttaagaactg gggctctcgg   17040
gcctggcaca gcaatgcggg caagcgttgc gcgcccagct gaaaaagacg ggcttgcaag   17100 aaagatatt gagggcgtta gcgccggtat ccacggagcc gtggatctgg gccgtcagca   17160
gctagagaaa gctattgagc agcgcctaga gcgtcgcccc accgctgccg gtgtggaaga   17220
ccttccgctt cccccgggaa cagtcttaga agctgatcgt ttaccgccct cctacgccga   17280
agcggtggct gagcgcccgc cgccggctga cgttctcctg cccgcatcct caaagccgcc   17340
ggtggcggtg gtgaccttgc ccccgaaaaa gagagtgtct gaagagcctg tggaggaagt   17400
tgtgattcgt tcctccgcac cgccgtcgta cgacgaggtt atggcaccgc agccgactct   17460
ggtagccgag cagggcgcca tgaaagcagt gcccgtgatt aagccggctc aaccttttac   17520
cccagctgtg cacgaaacgc aacgcatagt gaccaacttg ccaatcacca cagctgtgac   17580
acggcgacgc gggtggcagg gcactctgaa tgacatcgtg ggcctcggcg ttcgtaccgt   17640
gaagcgccgg cggtgctatt gagggggcgc gcagcggtaa taaagagaac ataaaaaagc   17700
aggattgtgt tttttgttta gcggccactg actctccctc tgtgtgacac gtcctccgcc   17760
agagcgtgat tgattgaccg agatggctac cccgtcgatg ctgccgcaat ggtcctactg   17820
cacatcgccg gtcaggacgc gtccgagtac ctgtcccccg gcttggtgca attcgcacaa   17880
gccaccgaat cctactttaa cattgggaac aagtttagaa accccaccgt cgccccgacg   17940
cacgatgtca ccacggagcg ttcgcagcgt ctgcagctcc gcttcgtgcc cgtagaccgg   18000
gaggacacac agtactccta caaaacccgc ttccagctag ccgtgggcga caaccgggtg   18060
ctggacatgg ccagcacgta ttttgacatc cgcggtacgc tggagagggg cgccagtttc   18120
aagccttaca gcggcacggc ctacaactcc tttgccccca acagtgcccc taacaatacg   18180
cagtttaggc aggccaacaa cggtcatcct gctcagacca tagctcaagc ttcttacgtg   18240
gctaccatcg gcggtgccaa caatgacttg caaatgggtg tggacgagcg tcagcagccg   18300
gtgtatgcga acactacgta ccagccggaa cctcagctcg gcattgaagg ttggacagct   18360
ggatccatgg cggtcatcga tcaagcaggc gggcgggttc tcaggaaccc tactcaaact   18420
ccctgctacg ggtcctatgc taagccgact aacgagcacg ggggcattac taaagcaaac   18480
actcaggtgg agaaaaagta ctacagaaca ggggacaacg gtaacccgga aacagtgttt   18540
tatactgaag aggctgacgt gctaacgccc gacacccacc ttgttcacgc ggtaccggcc   18600
gcggatcggc caaaggtgga ggggctatct cagcacgcag ctcccaacag gccgaacttt   18660
atcggctttc gggactgctt tgtaggcttg atgtattata acagcggggg caacctgggc   18720
```

```
gtcttagcgg gtcaatcctc tcagctgaat gccgtggtag acctgcaaga ccgcaacact   18780
gagctttcct atcagatgct tcttgcaaac acgacggaca gatcccgcta tttagcatg    18840 tggaaccaag ccatggactc gtacgacccg gaggtcaggg tgatagataa cgtgggcgta   18900
gaggacgaga tgcctaatta ctgctttccg ttgtcggggg ttcagattgg aaaccgtagc   18960
cacgaggttc aaagaaacca acaacagtgg caaaatgtag ctaatagtga caacaattac   19020
ataggcaagg ggaacctacc ggccatggag ataaatctag cggccaatct ctggcgttcc   19080
tttttgtaca gtaatgtggc gttgtacttg ccagacaacc ttaaattcac ccctcacaac   19140
attcaactcc cgcctaacac gaacacctac gagtacatga acgggcgaat ccccgttagc   19200
ggccttattg atacgtacgt aaatataggc acgcggtggt cgcccgatgt gatggacaac   19260
gtgaatccct ttaaccacca ccgcaactcg ggcctgcgtt accgctccca gctgctgggc   19320
aacggccgct tctgcgactt tcacattcag gtgccacaaa agttttttgc tattcgaaac   19380
ctgcttctcc tgcccggcac gtacacttac gagtggtcct ttagaaagga cgtaaacatg   19440
atccttcaga gcactctggg caatgatctg cgggtcgatg gggccactgt taatattacc   19500
agcgtcaacc tctacgccag cttctttccc atgtcacata acaccgcttc cactttggaa   19560
gctatgctcc gcaacgacac taatgaccag tcttttaatg actatctctc ggcggctaac   19620
atgttgtatc ccattccgcc caatgccacc caactgccca tcccctcacg caactgggca   19680
gcgttccgtg gctggagtct cacccggcta aaacagaggg agacaccggc gctgggtcc   19740 ccgttcgatc cctatttcac ctattcgggc accatcccgt acctggacgg cacttttac   19800 ctcagccaca ccttttcgcaa ggtggccatc cagtttgact cttctgtgac ctggcccggc   19860
aatgacaggc ttttaacccc taacgagttc gaaataaaaa taagtgtgga cggtgaaggc   19920
tacaacgtgg ctcagagcaa tatgactaag gactggttcc tggtgcagat gctagcgaat   19980
tacaacatag gctaccaggg atatcacctg ccccccggact acaaggacag gacattttcc  20040
ttcctgcata acttcatacc catgtgccga caggttccca acccagcaac cgagggctac   20100
tttggactag gcatagtgaa ccatagaaca actccggctt attggttcg attctgccgc   20160 gctccgcgcg agggccaccc ctacccccaa ctggccttac cccctcattg ggacccacgc   20220
catgccctcc gtgacccaga gagaaagttt ctctgcgacc gcaccctctg gcgaatcccc   20280
ttctcctcga acttcatgtc catggggtcc ctcacagatc tcggacagaa cctactgtat   20340
gccaatgccg cgcatgccct agacatgact tttgagatgg atcccatcaa tgagcccact   20400
ctgctgtacg ttctgttga ggtgtttgac gtggcccgcg ttcaccagcc ccacagaggc   20460
gtgatcgaag tggtgtactt gagaacgcca ttctcagccg gcaacgctac cacataagtg   20520
ccggcttccc tctcaggccc cgcgatgggt tctcgggaag aggagctgag attcatcctt   20580
cacgatctcg gtgtggggcc atacttcctc ggcactttcg ataaacactt ccgggggttc   20640
atctccaaag accgaatgag ctgtgccata gtcaacactg ccggacgcga aaccgggggc   20700
gtgcattggc tggccatggc ttggcaccca gcctcgcaga cctttttacat gtttgaccct   20760 ttcggttttct cggatcaaaa gctaaagcaa atttacaact ttgagtatca gggcctccta   20820
aagcgcagcg ccctgacttc cactgctgac cgctgcctga cccttattca aagcactcaa   20880
tctgtccagg gacccaacag cgccgcctgc ggtctgttct gctgcatgtt cctccacgcc   20940
tttgtccgct ggccgcttag ggccatggac aacaatccca ccatgaacct catccacgga   21000
gttcccaaca acatgttgga gagcccagc tcccaaaatg tgttttgag aaaccagcaa   21060 aatctgtacc gtttcctaag acgccactcc ccccattttg ttaagcatgc ggctcaaatt   21120
```

-continued

```
gaggctgaca ccgcctttga taaaatgtta acaaattaga ccgtgagcca tgattgcaga  21180
agcatgtcat ttttttttta ttgtttaaaa taaaaacaac acataacatc tgccgcctgt  21240
cctcccgtga tttcttctgc tttatttgca aatgggggc  accttaaaac aaagagtcat  21300
ctgcatcgta ctgatcgatg ggcagaataa cattctgatg ctggtactgc gggtcccagc  21360
ggaattcggg aatggtaatg gggggctct  gtttaaccag cgcggaccac atctgcttaa  21420
ccagctgcaa ggctgaaatc atatctggag ccgaaatctt gaaatcgcag tttcgctggg  21480
cattagcccg cgtctgccgg tacacagggt tacagcactg aaatactaac accgatgggt  21540
gttctacgct ggccaggagt ttgggatctt ctacgaggct cttatctacc gcagagcccg  21600
cgttgatatt aaagggcgtt atcttgcata cctgacggcc taggaggggc aattgggagt  21660
gaccccagtt acaatcacac tttaaaggca taagcagatg agttccggca ctttgcatcc  21720
tggggtaaca ggctttctga aaggtcatga tctgccagaa agcctgcaaa gccttgggcc  21780
cctcgctgaa aaacatacca caagactttg aggtaaagct gccggccggc aaagcggcgt  21840
caaagtgaca gcaagccgcg tcttcattct ttagctgcac tacgttcata ttccaccggt  21900
tggtggtgat ctttgtctta tgcggggtct cttttaaagc ccgctgccca ttttcgctgt  21960
tcacatccat ctctatcact tggtcttttgg taagcatagg caggccatgc aggcagtgaa  22020
gggccccgtc tcccccctcg gtacactggt ggcgccagac cacacagccc gtggggctcc  22080
acgaggtcgt ccccaggcct gcgacttttta acacaaaatc atacaagaag cggcccataa  22140
tagttagcac ggtttttctga gtactgaaag taagaggcag gtacacttta gactcattaa  22200
gccaagcttg tgcaaccttc ctaaaacact cgagcgtgcc agtgtcgggc agcaaggtta  22260
agttttttaat atccactttc aaaggcacac acagccccac tgctaattcc atggcccgct  22320
gccaagcaac ttcgtcggct tccagcaagg cccggctggc cgccggcagg gcgggagcgg  22380
cggcctcagc ggctggggct gaaggtttga aaatcttggc gcgcttaacg gctgtgacat  22440
cttcggcggg gggctcagcg atcggcgcgc gccgtttgcg gctgactttt ttccggggcg  22500
tctcatctat cactaagggg ttctcgtccc cgctgctgtc agccgaactc gtggctcgcg  22560
ttaagtcacc gctgcgattc attattctct cctagataac gacaacaaat ggcagagaaa  22620
ggcagtgaaa atcagcggcc agagaacgac actgagctag cagcggtttc agaagcccta  22680
ggcgcggccg cttcggcccc ctcacgtaac tccccgactg acacggattc aggggtggaa  22740
atgacgccca ccagcagccc cgagccgccc gccgctcccc caagttcgcc tgccgcagca  22800
cctgcccctc agaagaacca ggaggagctc tcttcccccg agcccgcggt agcagcagcg  22860
gagccagaag ccgcttcgcg gcccagacca cccacaccca ccgttcaggt cccgcgggag  22920
ccgagcgagg atcaacctga cggacccgcg acgaggcctt cgtacgtgag cgaggattgc  22980
ctcatccgcc atatctctcg ccaggctaac attgttagag acagcctggc agaccgctgg  23040
gagttagagc ccaccgtgtc ggctctctcc gaggcttacg aaaagctcct cttttgtccc  23100
aaggtaccac ccaagaagca agagaatggc acttgcgaac ctgaacctcg cgttaatttt  23160
ttccccacct ttgtagtgcc cgaaactttta gccacgtacc acatcttttt ccaaaaccaa  23220
aaaatccccc tgtcttgtcg cgccaaccgc acccacacag acaccatcat gcacctctac  23280
tcggggact  ccttaccgtg cttccccacg ctgcagctgg tcaacaaaat ctttgaaggc  23340
ttgggctcag aggagcggcg cgcagccaac tcgctgaaaa atcaagagga taacagcgcg  23400
ttagttgagc tcgaagggga cagtccccga ctggctgtgg ttaagcgcac actgtctttg  23460
```

-continued

```
acacatttcg cctaccctgc cataacacta ccgcctaagg tgatggcagc tgtcactggc    23520
agcctcattc atgaatcagc agcgaccgcc gaaccggaag ctgaggcgct gccagaagcc    23580
gaggagcccg tggttagtga ccctgaactt gctcgctggt tggggctcaa cttacaacag    23640
gagcccgagg ccacggccca ggctttggaa gaaagacgca agattatgtt ggcagtatgc    23700
ttagtcacac ttcagctcga gtgcctgcac aagttttttt cttcagagga tgtcatcaaa    23760
aagctgggag agagcctcca ctacgccttt cgccacggct acgtgcgcca agcctgctcc    23820
atttctaacg tggaactaac gaacatcgtc tcatacctgg gtatcttgca cgaaaaccgc    23880
ttgggacaga gtaccctaca cgccacccct aaagacgaga accgcagaga ctacatcaga    23940
gacacagtct ttctctttct ggtttatact tggcagactg ccatgggcat ttggcagcag    24000
tgcctcgaga ctgagaacgt aaaagaactt gaaaagctct tgcaaaaaag caagagggct    24060
ctctggacgg gcttcgacga gctcaccata gctcaagacc tagctgacat agtgttcccc    24120
cccaaattct tgcacaccct gcaagccggc ctgccagacc ttacatccca gagtctcctt    24180
cacaactttc gctccttcat tttcgaacgc tcgggcattc tacccgccat gtgcaatgca    24240
ctgcccaccg acttcatccc tatcagctac cgggagtgcc ctccaacttt ctgggcctac    24300
acctacctct ttaaactggc caattacctc atgtttcact ccgacatcgc ttacgatcgg    24360
agcggccccg gtctcatgga atgctactgt cgctgcaacc tgtgcagtcc tcaccgctgc    24420
ttggcgacca accccgccct gctcagcgag acccaagtta tcggtacctt cgagattcag    24480
ggccctcctg ctcaagacgg acagccgacc aaaccgcccc tcaggctgac tgcaggtctc    24540
tggacttccg cctacctgcg caaatttgta ccgcaagact tcaacgccca caaaatagcc    24600
ttctacgaag accaatccaa aaagccgaaa gtgaccccca gcgcttgtgt catcactgaa    24660
gaaaagtttt agcccaatt gcatgaaatt aaaaagcgc gggaagactt tcctcttaaa     24720
aaggggcacg gagtgtatct ggaccctcag accggcgagg agctgaacgg accgcaccc    24780 tccgcagcta ggaatgaaac cccgcagcat gtcggcagcc gggccttccg cggctcaggc    24840
ttcggagggc aacagctgc cgccacagac agcggggctg cagccgagca agagggctgt    24900
gaggaaggta gtagcttctc tgaatcccac cgccgccctg gaagacatat ccgagggga    24960 ggaaggcttc cccctgacgg acgaggaaga cggggacacc ctggagagcg atttcagcga    25020
cttcacggac gaagacgtcg aggaggagga tatgatttcg ataccccgcg accaggggca    25080
ctccggcgag ctcgaggagg gcgaaattcc cgcaacggta gcggcgacgg cggtcaagaa    25140
gggccagggc aagaagagta ggtgggacca gcaggtccgc tccacagcgc ctctaaaggg    25200
cgctagaggt aagaggagct acagtcctg gaaacccctc aagcccacta tccttttcatg    25260 cttactgcag agctccggca gcactgcctt cactcgccgc tatctgcttt ttcgccatgg    25320
cgtgtccgtt ccctccaggg taattcatta ctataattct tactgcagac ccgaagctga    25380
ccaaaaccgc cactcagagc aaaaagagcc gccggagtgc cagcgcggcg cgccctcgcc    25440
ctcctcctct tcctcccaag cgtgctcggg cgcccccgcc ccccaaaggc cagcgccatc    25500
aggccgacga cgcaagcacc gagggccgcg acaagcttcg ggagctgatc tttcccactc    25560
tctatgccat attccaacaa agtcgcgctc agcggtgtca cctcaaagtg aaaaatagat    25620
ccttacgttc actgacgcgc agctgcctct accacaacaa ggaggaacag ctccagcgaa    25680
ccctagcaga ctccgaggcg cttctcagta aatactgctc tgcagctccg acacgattct    25740
cgccgccctc ttataccgag tctcccgcca aggacgaatc cggaccgcc taaactctca    25800 gcatgagcaa agaaattccc acaccttatg tttggacctt tcaacctcag atgggagcgg    25860
```

```
ccgcaggtgc cagtcaagat tactcgaccc gcatgaattg gttcagcgcg ggacctgata      25920
tgatccacga cgttaacaac attcgtgacg cccaaaaccg catccttatg actcagtcgg      25980
ccattaccgc cactcccagg aatctgattg atcccagaca gtgggccgcc cacctcatca      26040
aacaacccgt ggtgggcacc acccacgtgg aaatgcctcg caacgaagtc ctagaacaac      26100
atctgacctc acatggcgct caaatcgcgg gcggaggcgc tgcgggcgat tactttaaaa      26160
gccccacttc agctcgaacc cttatcccgc tcaccgcctc ctgcttaaga ccagatggag      26220
tctttcaact aggaggaggc tcgcgttcat ctttcaaccc cctgcaaaca gattttgcct      26280
tccacgccct gccctccaga ccgcgccacg ggggcatagg atccaggcag tttgtagagg      26340
aatttgtgcc cgccgtctac ctcaacccct actcgggacc gccggactct tatccggacc      26400
agtttatacg ccactacaac gtgtacagca actctgtgag cggttatagc tgagattgta      26460
agactctcct atctgtctct gtgctgcttt tccgcttcaa gccccacaag catgaagggg      26520
tttctgctca tcttcagcct gcttgtgcat tgtcccctaa ttcatgttgg gaccattagc      26580
ttctatgctg caaggcccgg gtctgagcct aacgcgactt atgtttgtga ctatggaagc      26640
gagtcagatt acaaccccac cacggttctg tggttggctc gagagaccga tggctcctgg      26700
atctctgttc ttttccgtca caacggctcc tcaactgcag cccccggggt cgtcgcgcac      26760
tttactgacc acaacagcag cattgtggtg ccccagtatt acctcctcaa caactcactc      26820
tctaagctct gctgctcata ccggcacaac gagcgttctc agtttacctg caaacaagct      26880
gacgtcccta cctgtcacga gcccggcaag ccgctcaccc tccgcgtctc ccccgcgctg      26940
ggaactgccc accaagcagt cacttggttt tttcaaaatg tacccatagc tactgtttac      27000
cgaccttggg gcaatgtaac ttggttttgt cctcccttca tgtgtacctt taatgtcagc      27060
ctgaactccc tacttattta caacttttct gacaaaaccg gggggcaata cacagctctc      27120
atgcactccg gacctgcttc cctctttcag ctctttaagc caacgacttg tgtcaccaag      27180
gtggaggacc cgccgtatgc caacgacccg gcctcgcctg tgtggcgccc actgcttttt      27240
gccttcgtcc tctgcaccgg ctgcgcggtg ttgttaaccg ccttcggtcc atcgattcta      27300
tccggtaccc gaaagcttat ctcagcccgc ttttggagtc ccgagcccta taccaccctc      27360
cactaacagt cccccccatgg agccagacgg agttcatgcc gagcagcagt ttatcctcaa      27420
tcagatttcc tgcgccaaca ctgccctcca gcgtcaaagg gaggaactag cttcccttgt      27480
catgttgcat gcctgtaagc gtggcctctt ttgtccagtc aaaacttaca agctcagcct      27540
caacgcctcg gccagcgagc acagcctgca ctttgaaaaa agtccctccc gattcaccct      27600
ggtcaacact cacgccggag cttctgtgcg agtggcccta caccaccagg gagcttccgg      27660
cagcatccgc tgttcctgtt cccacgccga gtgcctcccc gtcctcctca agaccctctg      27720
tgcctttaac tttttagatt agctgaaagc aaatataaaa tggtgtgctt accgtaattc      27780
tgttttgact tgtgtgcttg atttctcccc ctgcgccgta atccagtgcc cctcttcaaa      27840
actctcgtac cctatgcgat tcgcataggc atattttcta aaagctctga agtcaacatc      27900
actctcaaac acttctccgt tgtaggttac tttcatctac agataaagtc atccaccggt      27960
taacatcatg aagagaagtg tgcccaggga cttttaatctt gtgtatccgt acaaggctaa      28020
gaggcccaac atcatgccgc cctttttttga ccgcaatggc tttgttgaaa accaagaagc      28080
cacgctagcc atgcttgtgg aaaagccgct cacgttcgac aaggaaggtg cgctgaccct      28140
gggcgtcgga cgcggcatcc gcattaaccc cgcggggctt ctggagacaa acgacctcgc      28200
```

-continued

```
gtccgctgtc ttcccaccgc tggcctccga tgaggccggc aacgtcacgc tcaacatgtc   28260
tgacgggcta tatactaagg acaacaagct agctgtcaaa gtaggtcccg ggctgtccct   28320
cgactccaat aatgctctcc aggtccacac aggcgacggg ctcacggtaa ccgatgacaa   28380
ggtgtctcta aatacccaag ctcccctctc gaccaccagc gcgggcctct ccctacttct   28440
gggtcccagc ctccacttag gtgaggagga acgactaaca gtaaacaccg gagcgggcct   28500
ccaaattagc aataacgctc tggccgtaaa agtaggttca ggtatcaccg tagatgctca   28560
aaaccagctc gctgcatccc tggggacgg tctagaaagc agagataata aaactgtcgt   28620
taaggctggg cccggactta caataactaa tcaagctctt actgttgcta ccgggaacgg   28680
ccttcaggtc aacccggaag ggcaactgca gctaaacatt actgccggtc agggcctcaa   28740
ctttgcaaac aacagcctcg ccgtggagct gggctcgggc ctgcattttc ccctggcca   28800 aaaccaagta agcctttatc ccggagatgg aatagacatc cgagataata gggtgactgt   28860
gcccgctggg ccaggcctga gaatgctcaa ccaccaactt gccgtagctt ccggagacgg   28920
tttagaagtc cacagcgaca ccctccggtt aaagctctcc cacggcctga catttgaaaa   28980
tggcgccgta cgagcaaaac taggaccagg acttggcaca gacgactctg gtcggtccgt   29040
ggttcgcaca gtcgaggac ttagagttgc aaacggccaa gtccagatct tcagcggaag   29100
aggcaccgcc atcggcactg atagcagcct cactctcaac atccgggcgc ccctacaatt   29160
ttctggaccc gccttgactg ctagtttgca aggcagtggt ccgattactt acaacagcaa   29220
caatggcact ttcggtctct ctataggccc cggaatgtgg gtagaccaaa acagacttca   29280
ggtaaaccca ggcgctggtt tagtcttcca aggaaacaac cttgtcccaa accttgcgga   29340
tccgctggct atttccgaca gcaaaattag tctcagtctc ggtcccggcc tgacccaagc   29400
ttccaacgcc ctgactttaa gtttaggaaa cgggcttgaa ttctccaatc aagccgttgc   29460
tataaaagcg ggccggggct tacgctttga gtcttcctca caagctttag agagcagcct   29520
cacagtcgga aatggcttaa cgcttaccga tactgtgatc cgccccaacc taggggacgg   29580
cctagaggtc agagacaata aaatcattgt taagctgggc gcgaatcttc gttttgaaaa   29640
cggagccgta accgccggca ccgttaaccc ttctgcgccc gaggcaccac caactctcac   29700
tgcagaacca cccctccgag cctccaactc ccatcttcaa ctgtccctat cggagggctt   29760
ggttgtgcat aacaacgccc ttgctctcca actgggagac ggcatggaag taaatcagca   29820
cggacttact ttaagagtag gctcgggttt gcaaatgcgt gacggcattt taacagttac   29880
acccagcggc actcctattg agcccagact gactgcccca ctgactcaga cagagaatgg   29940
aatcgggctc gctctcggcg ccggcttgga attagacgag agcgcgctcc aagtaaaagt   30000
tgggcccggc atgcgcctga accctgtaga aaagtatgta accctgctcc tgggtcctgg   30060
ccttagtttt gggcagccgg ccaacaggac aaattatgat gtgcgcgttt ctgtggagcc   30120
ccccatggtt ttcggacagc gtggtcagct cacattttta gtgggtcacg gactacacat   30180
tcaaaattcc aaacttcagc tcaatttggg acaaggcctc agaactgacc ccgtcaccaa   30240
ccagctggaa gtgcccctcg gtcaaggttt ggaaattgca gacgaatccc aggttagggt   30300
taaattgggc gatggcctgc agtttgattc acaagctcgc atcactaccg ctcctaacat   30360
ggtcactgaa actctgtgga ccggaacagg cagtaatgct aatgttacat ggcggggcta   30420
cactgccccc ggcagcaaac tctttttgag tctcactcgg ttcagcactg gtctagtttt   30480
aggaaacatg actattgaca gcaatgcatc ctttgggcaa tacattaacg cggacacga   30540 acagatcgaa tgctttatat tgttggacaa tcagggtaac ctaaaagaag gatctaactt   30600
```

```
gcaaggcact tgggaagtga agaacaaccc ctctgcttcc aaagctgctt ttttgccttc   30660
caccgcccta taccccatcc tcaacgaaag ccgagggagt cttcctggaa aaaatcttgt   30720
gggcatgcaa gccatactgg gaggcggggg cacttgcact gtgatagcca ccctcaatgg   30780
cagacgcagc aacaactatc ccgcgggcca gtccataatt ttcgtgtggc aagaattcaa   30840
caccatagcc cgccaacctc tgaaccactc tacacttact ttttcttact ggacttaaat   30900
aagttggaaa taaagagtta aactgaatgt ttaagtgcaa cagacttttta ttggttttgg   30960 ctcacaacaa attacaacag catagacaag tcataccggt caaacaacac aggctctcga   31020
aaacgggcta accgctccaa gaatctgtca cgcagacgag caagtcctaa atgttttttc   31080
actctcttcg gggccaagtt cagcatgtat cggattttct gcttacacct ttttagacag   31140
cagtttacac tcatttccgt taaaggatta caactgcggc atatgagaat taagtatata   31200
caactattgc ccttttaccca caaacactcc ccccacgggg tgcacctgat gtagctgccc   31260
tcctcaatca tgaaagtgct attaaagtaa attaaatgaa cattattcac atacacgctt   31320
cccacatagg ccaaaaaaac agaggacaac tttgacagct cccgcctgaa ataccaatac   31380
actctatcaa actgcgcacc gtgcacgcac tgctttacca ggccttgaaa gtaaacagcg   31440
gcggaccgac actgcaagct tctaggcttt gggcagtggc agtgaatata tagccactcc   31500
tccccatgca cgtagtagga acgccgcttc ccgggaatca caaatgacaa gcagtagtca   31560
cagaggcaac tagtcaagtg agcgtcctcc tgaggcatga ttaccttcca tggaatgggc   31620
cagtgaatca tagtggcaaa gccagctgca tctggagcgc tgcgaacctt ggctacatgt   31680
ggtgattggc gacgcagatg gagacaggac cttgcattct gaagaccact gcaacagctt   31740
ctgcgtacgc ttgtatttac agtacataaa aaagcacttt tgccacagag cggtcttact   31800
caaccgacag ctttttttctt tctgacgctg ccttctgcta ctcaggtagt acaagtccaa   31860
aagagccaaa cggacactca aatccgggtt atctcgatgc tgaagccaga gtccaaaagt   31920
aaccacgcta aaagcctgca tccatatttt gtaactgctg taactccatc ccagagccgg   31980
gcaccgcact tggtccacca tagctgcaaa caaacgggac aattaaggaa agtaaaatga   32040
gcgctggggg cggactcttc tcccgttcgt aggaaacagc cacgtatcaa acacccttttt  32100 caacactggc tctccagccg ctactcgttg aattaatttg tccctgtgct caaacaaccc   32160
acactggtaa cggtggtcgc taggcaaaca tgtcaaatag cacataatca tttccttcac   32220
tttaagcaaa catcgactag cagacacttc acttaattca gcacagtcat agcaaggaat   32280
gattatacac ttgtcatcta atccactgcc catgtacaca ttgccccagg caaagtggg    32340 cagggacttt aagagctgat tgctcgcccc gacatagttg gtaaaataca gcaaatgcac   32400
cttgttaaca tacacactcc ccacatagta aatataccga gtagacagct tagaaagctc   32460
cctccgaaaa aatgggaaca tggtatcaaa ggcagtgccc gcaacacaca tcttgaacag   32520
atccatcagg atagtagctc gacacagccc ctgcagactt tggtcagctt gcttgctgca   32580
gcagtacact ctccacgtag catctccgct gatgaagtat tcgctatcgc agcgaccaaa   32640
aatacagcaa tcacaaggca gacgcaacag tctttcatcc agactgttca tgagaggctt   32700
tagaggtatg ggaaaaaatc caaagtgctc aaaataagca gcgctgggct cattctgaca   32760
ttcccccaac atgctgagtc gaaccatagc acagtcatac aaactcagct gtcggaattg   32820
atcttccatg attgagtttc tactgagata ttatctcaaa cttaaaactg ttgctcacca   32880
actctatgcg aacttgctca agaagctctt ggtttagggc gacctcttct ggtcgtcgga   32940
```

-continued

```
agttactgat ggaacaacaa gcgccgccca acttcaaatt tccagccgac ccaatccagt    33000
ggtctctcaa ctcacgcgca caagctacta tgcagtcctc actttcgtca aagtcagcag    33060
cgcctataga aatcaacaca ctgagtccac catcttcagc ttttaaggga taacagctga    33120
tagcaaactg gttctgagac cacggcaaag cacgtaggaa ttgctgttaa gttaatttcc    33180
aaacaccgct gaagcagctc tatggttgct ggacatatgt cctctgcata gaagctttga    33240
acataactta agacagggcc gggcacatga aacacaaaca gagaactata cacaatctgg    33300
gccatgatca ctcacattta aatagcagct gaaaagtggc tttcttcact tgggagcaaa    33360
attagcgaag actgtgccag aatgctcacg tcgaaaggcg gtgggtctcg cagaggcagg    33420
ttcggagctc taattaaaca caggtgggta atccagtcaa cgatgaggac cagctgaaaa    33480
gtggctttct tcacttggga gcaaaattag cgaagactgt gccagaatgc tcacgtcgaa    33540
aggcggtggg tctcgcagag gcaggttcgg agctctaatt aaacacaggt gggtaatcca    33600
gtcaacgatg aggacttta aaaactgtc taaaactgaa gcagttaagt tagaggcaga    33660
cacagaaaaa actacagtta aactatcagt tgctgaaatt gaaaagcacc caataattat    33720
gcgcgagggc acaggcaata aaagtgttag cccctcggct aacgcgtcag ctaaaaaatc    33780
tttagctaaa gtatctactg gccgcgtggt aaaagtttga atataattta cgacaggagc    33840
tggcaagtga aactccacaa aaaagtaaa tggctgcaca cacgccatta ttttgaaaat    33900
aagaagtact cacaaaatca gctggagctg ccgcaagtga aaaagaccag ctgaagtctt    33960
attttaaact gtaaaatata aaaaaaaaaa tagggcgtga acaaaaatga gaaataata    34020 ccggatatga ctattaaggg cgtacactga aactgggtaa tatttgagaa aaagattaag    34080
ataatagctg aacaatgtt gtgtgcagaa cacggaacaa tggtggcgaa aaaaaaaac    34140 agtgtaagca catggcgcgc acgtacttcc gtgagaaaaa ttaaaaaaat ttacccagta    34200
taaggtgcgt cattagaccc gccttgtggc gcggttgtag ccctgccctt tgccccgccc    34260
cgcgcgccgc cccgcgcgcc gccccgccg ccctcagccc cgcccagcgc cgccgcctcc    34320
gcgacgcgct ccgccccaca gttacgtcag cacgccacgc tcgccgtcgt tgcgtcataa    34380
atgacgtggc aaaaatgatt ggcagttgga ccgctgccat cagtgtactg tagattattg    34440
atgatg                                                              34446
```

<210> SEQ ID NO 36
<211> LENGTH: 19
<212> TYPE: DNA
<213> ORGANISM: Bovine adenovirus type 3

<400> SEQUENCE: 36
acgcgtcgac tcctcctca                                                    19

<210> SEQ ID NO 37
<211> LENGTH: 18
<212> TYPE: DNA
<213> ORGANISM: Bovine adenovirus type 3

<400> SEQUENCE: 37
ttgacagcta gcttgttc                                                     18

<210> SEQ ID NO 38
<211> LENGTH: 17
<212> TYPE: DNA
<213> ORGANISM: Bovine adenovirus type 3

<400> SEQUENCE: 38

-continued

```
<210> SEQ ID NO 39
<211> LENGTH: 25
<212> TYPE: DNA
<213> ORGANISM: Bovine adenovirus type 3

<400> SEQUENCE: 39
ggcgatatct cagctataac cgctc                                          25

<210> SEQ ID NO 40
<211> LENGTH: 12
<212> TYPE: DNA
<213> ORGANISM: Bovine adenovirus type 3

<400> SEQUENCE: 40
ttgcccgggc tt                                                        12
```